US010314926B2

(12) United States Patent
Merenick et al.

(10) Patent No.: US 10,314,926 B2
(45) Date of Patent: Jun. 11, 2019

(54) THERAPEUTIC GENE-SWITCH CONSTRUCTS AND BIOREACTORS FOR THE EXPRESSION OF BIOTHERAPEUTIC MOLECULES, AND USES THEREOF

(71) Applicant: Intrexon Corporation, Blacksburg, VA (US)

(72) Inventors: Bethany Lynn Merenick, Christiansburg, VA (US); Robert P. Beech, Cincinnati, OH (US); Thomas D. Reed, Blacksburg, VA (US); Anna P. Tretiakova, Royersford, PA (US); Richard E. Peterson, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 15/637,624

(22) Filed: Jun. 29, 2017

(65) Prior Publication Data

US 2018/0126007 A1 May 10, 2018

Related U.S. Application Data

(60) Division of application No. 14/864,265, filed on Sep. 24, 2015, now Pat. No. 9,724,430, which is a continuation of application No. 12/241,018, filed on Sep. 29, 2008, now abandoned.

(60) Provisional application No. 61/047,899, filed on Apr. 25, 2008, provisional application No. 60/975,986, filed on Sep. 28, 2007.

(51) Int. Cl.

| | |
|---|---|
| *C07H 21/04* | (2006.01) |
| *C12N 15/00* | (2006.01) |
| *A61K 48/00* | (2006.01) |
| *A61K 31/7088* | (2006.01) |
| *C12N 15/85* | (2006.01) |
| *C12N 15/63* | (2006.01) |
| *A01K 67/00* | (2006.01) |
| *A61K 35/12* | (2015.01) |

(52) U.S. Cl.

CPC ...... *A61K 48/0066* (2013.01); *A61K 31/7088* (2013.01); *C12N 15/635* (2013.01); *C12N 15/85* (2013.01); *A61K 35/12* (2013.01); *C12N 2510/02* (2013.01); *C12N 2830/002* (2013.01); *C12N 2830/15* (2013.01)

(58) Field of Classification Search

CPC ............ A61K 48/0066; A61K 31/7088; C12N 15/85; C12N 15/635

See application file for complete search history.

(56) References Cited

U.S. PATENT DOCUMENTS

| | | | | |
|---|---|---|---|---|
| 2003/0022870 A1* | 1/2003 | Dzau | A61K 31/436 | 514/152 |
| 2005/0191659 A1* | 9/2005 | Voellmy | C07K 14/47 | 435/6.16 |
| 2006/0020146 A1* | 1/2006 | Hormann | C07C 243/24 | 564/123 |

OTHER PUBLICATIONS

Karzenowski et al. Inducible control of transgene expression with ecdysone receptor: gene switches with high sensitivity, robust expression, and reduced size. BioTechniques 39:191-200, (Year: 2005).*

* cited by examiner

*Primary Examiner* — Quang Nguyen

(74) *Attorney, Agent, or Firm* — Sterne, Kessler, Goldstein & Fox P.L.L.C.

(57) ABSTRACT

The present invention relates to methods and compositions for treating, ameliorating or preventing a disease or disorder in a subject by introducing into cells of the subject a therapeutic gene switch construct that controls expression of one or more therapeutic products.

4 Claims, 17 Drawing Sheets

Specification includes a Sequence Listing.

Sequence from (9861bp)

Sequence from (10361bp)

Sequence from (17505bp)

Sequence from (16379bp)

SEQUENCE LISTING

<160> NUMBER OF SEQ ID NOS: 26

<210> SEQ ID NO 1
<211> LENGTH: 17
<212> TYPE: DNA
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (9)..(9)
<223> OTHER INFORMATION: n is a, c, g, or t

<400> SEQUENCE: 1
rrggttcant gacacyy 17

<210> SEQ ID NO 2
<211> LENGTH: 13
<212> TYPE: DNA
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (7)..(7)
<223> OTHER INFORMATION: n is a, c, g, or t

<400> SEQUENCE: 2
aggtcanagg tca 13

<210> SEQ ID NO 3
<211> LENGTH: 15
<212> TYPE: DNA
<213> ORGANISM: Artificial Sequence
<220> FEATURE:
<223> OTHER INFORMATION: Synthetic ecdysone receptor response element

<400> SEQUENCE: 3
gggttgaatg aattt 15

<210> SEQ ID NO 4
<211> LENGTH: 18
<212> TYPE: DNA
<213> ORGANISM: Artificial Sequence
<220> FEATURE:
<223> OTHER INFORMATION: Synthetic I-SceI homing endonuclease restriction site

<400> SEQUENCE: 4
tagggataac agggtaat 18

<210> SEQ ID NO 5
<211> LENGTH: 878
<212> TYPE: PRT
<213> ORGANISM: Drosophila melanogaster
<220> FEATURE:
<223> OTHER INFORMATION: Ecdysone receptor

<400> SEQUENCE: 5

```
Met Lys Arg Arg Trp Ser Asn Asn Gly Gly Phe Met Arg Leu Pro Glu
1               5                   10                  15

Glu Ser Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Gln Asp Leu Trp Leu Cys Gly Asn Glu Ser Gly Ser Phe Gly Gly
```

-continued

```
    50                  55                  60

Ser Asn Gly His Gly Leu Ser Gln Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Gly Ser Thr Asn Gly Gln
            100                 105                 110

Tyr Val Pro Gly Ala Thr Asn Leu Gly Ala Leu Ala Asn Gly Met Leu
        115                 120                 125

Asn Gly Gly Phe Asn Gly Met Gln Gln Gln Ile Gln Asn Gly His Gly
    130                 135                 140

Leu Ile Asn Ser Thr Thr Pro Ser Thr Pro Thr Thr Pro Leu His Leu
145                 150                 155                 160

Gln Gln Asn Leu Gly Gly Ala Gly Gly Gly Gly Ile Gly Gly Met Gly
                165                 170                 175

Ile Leu His His Ala Asn Gly Thr Pro Asn Gly Leu Ile Gly Val Val
            180                 185                 190

Gly Gly Gly Gly Gly Val Gly Leu Gly Val Gly Gly Gly Gly Val Gly
        195                 200                 205

Gly Leu Gly Met Gln His Thr Pro Arg Ser Asp Ser Val Asn Ser Ile
    210                 215                 220

Ser Ser Gly Arg Asp Asp Leu Ser Pro Ser Ser Ser Leu Asn Gly Tyr
225                 230                 235                 240

Ser Ala Asn Glu Ser Cys Asp Ala Lys Lys Ser Lys Lys Gly Pro Ala
                245                 250                 255

Pro Arg Val Gln Glu Glu Leu Cys Leu Val Cys Gly Asp Arg Ala Ser
            260                 265                 270

Gly Tyr His Tyr Asn Ala Leu Thr Cys Glu Gly Cys Lys Gly Phe Phe
        275                 280                 285

Arg Arg Ser Val Thr Lys Ser Ala Val Tyr Cys Cys Lys Phe Gly Arg
    290                 295                 300

Ala Cys Glu Met Asp Met Tyr Met Arg Arg Lys Cys Gln Glu Cys Arg
305                 310                 315                 320

Leu Lys Lys Cys Leu Ala Val Gly Met Arg Pro Glu Cys Val Val Pro
                325                 330                 335

Glu Asn Gln Cys Ala Met Lys Arg Arg Glu Lys Lys Ala Gln Lys Glu
            340                 345                 350

Lys Asp Lys Met Thr Thr Ser Pro Ser Ser Gln His Gly Gly Asn Gly
        355                 360                 365

Ser Leu Ala Ser Gly Gly Gly Gln Asp Phe Val Lys Lys Glu Ile Leu
    370                 375                 380

Asp Leu Met Thr Cys Glu Pro Pro Gln His Ala Thr Ile Pro Leu Leu
385                 390                 395                 400

Pro Asp Glu Ile Leu Ala Lys Cys Gln Ala Arg Asn Ile Pro Ser Leu
                405                 410                 415

Thr Tyr Asn Gln Leu Ala Val Ile Tyr Lys Leu Ile Trp Tyr Gln Asp
            420                 425                 430

Gly Tyr Glu Gln Pro Ser Glu Glu Asp Leu Arg Arg Ile Met Ser Gln
        435                 440                 445

Pro Asp Glu Asn Glu Ser Gln Thr Asp Val Ser Phe Arg His Ile Thr
    450                 455                 460

Glu Ile Thr Ile Leu Thr Val Gln Leu Ile Val Glu Phe Ala Lys Gly
465                 470                 475                 480
```

```
Leu Pro Ala Phe Thr Lys Ile Pro Gln Glu Asp Gln Ile Thr Leu Leu
                485                 490                 495

Lys Ala Cys Ser Ser Glu Val Met Met Leu Arg Met Ala Arg Arg Tyr
            500                 505                 510

Asp His Ser Ser Asp Ser Ile Phe Phe Ala Asn Asn Arg Ser Tyr Thr
        515                 520                 525

Arg Asp Ser Tyr Lys Met Ala Gly Met Ala Asp Asn Ile Glu Asp Leu
    530                 535                 540

Leu His Phe Cys Arg Gln Met Phe Ser Met Lys Val Asp Asn Val Glu
545                 550                 555                 560

Tyr Ala Leu Leu Thr Ala Ile Val Ile Phe Ser Asp Arg Pro Gly Leu
                565                 570                 575

Glu Lys Ala Gln Leu Val Glu Ala Ile Gln Ser Tyr Tyr Ile Asp Thr
            580                 585                 590

Leu Arg Ile Tyr Ile Leu Asn Arg His Cys Gly Asp Ser Met Ser Leu
        595                 600                 605

Val Phe Tyr Ala Lys Leu Leu Ser Ile Leu Thr Glu Leu Arg Thr Leu
    610                 615                 620

Gly Asn Gln Asn Ala Glu Met Cys Phe Ser Leu Lys Leu Lys Asn Arg
625                 630                 635                 640

Lys Leu Pro Lys Phe Leu Glu Glu Ile Trp Asp Val His Ala Ile Pro
                645                 650                 655

Pro Ser Val Gln Ser His Leu Gln Ile Thr Gln Glu Glu Asn Glu Arg
            660                 665                 670

Leu Glu Arg Ala Glu Arg Met Arg Ala Ser Val Gly Gly Ala Ile Thr
        675                 680                 685

Ala Gly Ile Asp Cys Asp Ser Ala Ser Thr Ser Ala Ala Ala Ala Ala
    690                 695                 700

Ala Gln His Gln Pro Gln Pro Gln Pro Gln Pro Gln Pro Ser Ser Leu
705                 710                 715                 720

Thr Gln Asn Asp Ser Gln His Gln Thr Gln Pro Gln Leu Gln Pro Gln
                725                 730                 735

Leu Pro Pro Gln Leu Gln Gly Gln Leu Gln Pro Gln Leu Gln Pro Gln
            740                 745                 750

Leu Gln Thr Gln Leu Gln Pro Gln Ile Gln Pro Gln Pro Gln Leu Leu
        755                 760                 765

Pro Val Ser Ala Pro Val Pro Ala Ser Val Thr Ala Pro Gly Ser Leu
    770                 775                 780

Ser Ala Val Ser Thr Ser Ser Glu Tyr Met Gly Gly Ser Ala Ala Ile
785                 790                 795                 800

Gly Pro Ile Thr Pro Ala Thr Thr Ser Ser Ile Thr Ala Ala Val Thr
                805                 810                 815

Ala Ser Ser Thr Thr Ser Ala Val Pro Met Gly Asn Gly Val Gly Val
            820                 825                 830

Gly Val Gly Val Gly Gly Asn Val Ser Met Tyr Ala Asn Ala Gln Thr
        835                 840                 845

Ala Met Ala Leu Met Gly Val Ala Leu His Ser His Gln Glu Gln Leu
    850                 855                 860

Ile Gly Gly Val Ala Val Lys Ser Glu His Ser Thr Thr Ala
865                 870                 875
```

<210> SEQ ID NO 6
<211> LENGTH: 605

```
<212> TYPE: PRT
<213> ORGANISM: Streptomyces sp.
<220> FEATURE:
<223> OTHER INFORMATION: Streptomyces phage phiC31 integrase

<400> SEQUENCE: 6

Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60

Thr Ala Glu Arg Pro Glu Phe Glu Arg Ile Leu Asn Glu Cys Arg Ala
65                  70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
            100                 105                 110

Gly Val Thr Ile Val Ser Thr Gln Glu Gly Val Phe Arg Gln Gly Asn
        115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
            180                 185                 190

Val Val Ile Asn Lys Leu Ala His Ser Thr Thr Pro Leu Thr Gly Pro
        195                 200                 205

Phe Glu Phe Glu Pro Asp Val Ile Arg Trp Trp Trp Arg Glu Ile Lys
    210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
            260                 265                 270

Asp Pro Ala Thr Val Met Arg Ile Leu Arg Asp Pro Arg Ile Ala Gly
        275                 280                 285

Phe Ala Ala Glu Val Ile Tyr Lys Lys Lys Pro Asp Gly Thr Pro Thr
    290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
            340                 345                 350

Arg Gly Gln Ala Ile Leu Ser Ala Met Asp Lys Leu Tyr Cys Glu Cys
        355                 360                 365

Gly Ala Val Met Thr Ser Lys Arg Gly Glu Glu Ser Ile Lys Asp Ser
    370                 375                 380
```

```
Tyr Arg Cys Arg Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415

Ala Glu Arg Ile Phe Asn Lys Ile Arg His Ala Glu Gly Asp Glu Glu
            420                 425                 430

Thr Leu Ala Leu Leu Trp Glu Ala Ala Arg Arg Phe Gly Lys Leu Thr
        435                 440                 445

Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480

Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Glu Arg Leu Ala Glu
            500                 505                 510

Leu Glu Ala Ala Glu Ala Pro Lys Leu Pro Leu Asp Gln Trp Phe Pro
        515                 520                 525

Glu Asp Ala Asp Ala Asp Pro Thr Gly Pro Lys Ser Trp Trp Gly Arg
    530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
            580                 585                 590

Glu Asp Asp Ala Gln Asp Gly Thr Glu Asp Val Ala Ala
        595                 600                 605
```

```
<210> SEQ ID NO 7
<211> LENGTH: 9861
<212> TYPE: DNA
<213> ORGANISM: Artificial Sequence
<220> FEATURE:
<223> OTHER INFORMATION: Synthetic hypoxia-inducible gene switch
      constructor expressing IGF-1

<400> SEQUENCE: 7
taaacaaata ggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gcgggtgtcg gggatttagg tgacactata ggctgagcgc     180
cgcacaggca tctagaggct atggcagggc ctgccgcccc gacgttggct gcgagccctg     240
ggccttcacc cgaacttggg gggtggggtg gggaaaagga agaaacgcgg gcgtattggc     300
cccaatgggg tctcggtggg gtatcgacag agtgccagcc ctgggaccga accccgcgtt     360
tatgaacaaa cgacccaaca ccgtgcgttt tattctgtct ttttattgcc gtcatagcgc     420
gggttccttc cggtattgtc tccttccgtg tttcaatcga ttcaaaagaa ctcgtccagc     480
agacggtaaa aagcaatgcg ttgagaatcc ggtgcagcaa tgccatacag caccagaaag     540
cgatcagccc attcaccgcc cagttcttca gcaatgtcac gggttgccag tgcgatgtcc     600
tgatagcgat cagccacgcc caggcgaccg cagtcgataa agccggagaa acggccgttt     660
tccaccataa tgtttggcag acaagcatcg ccgtgggtca caaccaggtc ctcgccatct     720
ggcatacgtg ctttcaggcg tgcgaacagt tctgccggtg ccagaccctg atgttcctcg     780
```

-continued

```
tccaggtcat cctgatcaac caggccagct tccatgcgag tgcgtgcgcg ctcgatacgg    840
tgtttagctt ggtgatcgaa tgggcaagta gctgggtcca gggtatgcag acggcgcata    900
gcatcagcca tgatggaaac cttttctgcc ggtgccagat gagaggacag cagatcctgg    960
cctggaacct cgcccagcag cagccagtcg cggccagcct cggtcacaac atccagcaca   1020
gctgcgcatg gaacgccggt agtagccagc caggacagac gagctgcttc atcttgcagt   1080
tcgttcagtg cgccggacag atcggtctta acaaacagca ccggacggcc ttgagcggac   1140
agacggaaca cagctgcgtc ggagcaaccg atagtctgtt gagcccagtc atagccaaac   1200
agacgttcca cccaagcagc cggagaacca gcgtgcagac cgtcttgttc aatcatggtg   1260
gcaattgggt gtctgagcga tgtggctcgg ctggcgacgc aaaagaagat gcggctgact   1320
gtcgaacagg aggagcagag agcgaagcgg gaggctgcgg gctcaatttg catgctttag   1380
ttcctcacct tgtcgtatta tactatgccg atatactatg ccgatgatta attgtcaacg   1440
tatacggaat agctctgagg ccgaggcagc ttcggcctct gcataaataa aaaaaattag   1500
tcagccatgg ggcggagaat gggcggaact gggcggagtt aggggcggga tgggcggagt   1560
taggggcggg actatggttg ctgactaatt gagatgcttg ctttgcatac ttctgcctgc   1620
tggggagcct ggggactttc cacacctggt tgctgactaa ttgagatgct tgctttgcat   1680
acttctgcct gctggggagc ctggggactt tccacaccct aacctcgagg ccatcgtggc   1740
acgccagggt tttcccagtc acgacgttgt aaaacgacgg ccagtgctct tctccccccgc  1800
gggaggtttt ataaatccga ctgtctagat accacatttg tagaggtttt acttgcttta   1860
aaaaacctcc cacatctccc cctgaacctg aaacataaaa tgaatgcaaa tgttttatta   1920
acttgtttat tgcagcttat aatggttaca aattaagcaa tagcatcaca aatttcacaa   1980
attaagcatt tttttcactg cattctagtt gtggtttgtc caaactcatc aatgtatctt   2040
atcatgtcta atcgattcac aggttggtgg ggctctccag gatgggggg ggctgggtgt   2100
ggctcatgtc ggccacgtcc caaatctcct ccaggaaggg gggcagcttc ctgttcttca   2160
gcttcaggct gatacacata ttgctgttct gcattcccag ggtcctcagc tcgctcagga   2220
tgctcaggat cttgccgtag atcacgctgc tcctggcgct gccgctcagc tggttcagga   2280
tgtagatcct cagggtgttc aggtagtacc tctggatctc ctccaccagc tggggctgct   2340
ccaggccggg cctgtcgctg aagatcacca cggcggtcag cagggcgtag tggatgttgt   2400
ccagggccat gctgtacata catctgcaga agtgcaggag gtcctcgatc acctcggcca   2460
tgccagcctt cctgtagttg tccctggtgt aagcctggtt gttggcgaac aggatgctgt   2520
cgctggcggc gtcgtacctc ctggccaccc tcagcatcat cacctcgctg ctgcaagcct   2580
tcagcagggt gatctggtcg ggctggctga tcttggcgaa tccgggcagg cccttggcga   2640
actccacgat cagctgcacg gtcaggatgg tcatctcggt gatctgcctg aagggggtgt   2700
cgctctcctc gttctcgtcg tcggcctgct gccaggtctg ggtgatcctt ttcaggtcct   2760
cgtcgctggg ctgctcgtag ccgtcctgat accagatcag cctggcgatc aggaactgct   2820
ggttggcggt cagctggggg atgttcttct gcctgttggt caccagcagc ttgtcgctca   2880
ggaacctggg cacgacctcg tgaatcctgg cggcctcggg ggggggggc tcgcactgca   2940
tgatgggggg catgtggtca tcgacggtgg tggtgctcac gggcagcttg tccttctcct   3000
tctgggcctt cttctccttc cttttcatgg cgcactgggt ctcgggcacc acgcactcgg   3060
gcctgatccc gggaaactcg gggctcacgg tcagctgcct ctggcccttg ttgctgctct   3120
cctcgctgct gctggtggcg ctgatcctgt gctgcctcag ggtcaggggc atgtcggtct   3180
```

-continued

```
ccacgctggc cagcctgtcg gtcacggcgt ccttgttcac gttgtcctgc acgaacaggc   3240
cggtcagcag ggccttgatg tcttgcaggc tgtccatctt caggatcatg tccaggtcct   3300
ccctggggaa gatcagcagg aacagctgct ccagcctctc cagcctgctc tccacctcgg   3360
tcaggtgggc cctggtcagg gggctcctct tggtcttggg gctgtatctg cactcccagt   3420
tgttcttcag gcacttggcg cacttgggct tctccttgct gcacttcagc ttcttcagcc   3480
tgcagatgtc gcaagcctgc tcgatgctgc tcagcagctt catggtggca gatctggtcg   3540
cgggaggctg ctggttttcc actacccgaa aaaaatccag cgtctaagca gctgcaagga   3600
gagcctttca gagaagcggg tcctggcagc ggcggggaag tgtccccaaa tgggcagaat   3660
agcctccccg cgtcgggaga gtcgcgtcct tgctcgggtg ttgtaagttc cagtgcaaag   3720
tgcccgcccg ctgctatggg caaagtttcg tggatgcggc tagggttgcg caccgctggc   3780
tgggggatca gcgggagggc tgggccagag gcgaagcccc ctattcgctc cggatctccc   3840
ttcccaggac gcccgcagcg cagctctgct cgccgggctc ctccacccta gcccgccgcc   3900
cgctcgctcc ctctgcctct cgctggaatt actacagcga gttgccggct cagctgtcgc   3960
tggggctctc cagcatctcc atcaggaagg tgtcgatggg cacgtcgccg atcagcctga   4020
agaagaacag gtgctccagg cacttcaggc cgatgctcct caggctgggc agcctcagca   4080
gcagcttggc gaatctgccg ggctcgtcgg ggtgggtggt cctggtgtac tcctccaggg   4140
cggcgtacac cttctccctc agcagctcca cctcctgggc gcttttcagg cccctcacct   4200
cggggttgaa caggatgatg gccctcaggc agcccagctc ggtcttgtcc atcctcatgt   4260
ccctcatctt gctcaccagc tcggtcagca ccctgtcgaa gatggcgccc actccggcgc   4320
tgtgggcgct gttcctatgg acgtgcaggc cggtggccag caggatgccg tccctcacgt   4380
cgatgctcct gtggctgaag ctggcgatca gcagctcgtt ccatccggcc ctcagcagga   4440
tcacctggtc gtccaggggc aggctgctga agtggggaat cctcttggcc cactccacca   4500
gggtgaacag ctgcttgtcg gcggcctggc agatgttggt cacggggtcg ttggggctgc   4560
tgccgctgcc gccggttccg ccggggccct ccacgccctg gtcgcttttc tgctccacgg   4620
cgagttcggc ctccagaatc ctgtccacgg gcatctccat atggccgccg tactcgtcga   4680
tgcccagggc gtcggtgaac atctgctcga actcgaagtc ggccatgtcc agggcgccgt   4740
agggggcgct gtcgtggggg gtgaagccgg ggccggggct gtcgccgtcg cccagcatgt   4800
ccaggtcgaa gtcgtccagg gcgtcggcgt gggccatggc cacgtcctcg ccgtccaggt   4860
gcagctcgtc gcccaggctc acgtcggtgg ggggggccac cttccttttc ttcttggggc   4920
ccatggtggc caattgcccc cccccccccc cgcatgcggc tggctgctgc ctctgaagaa   4980
ttcaaggagc ctgctggtcg gcccctgctg tggaacaata aatacctctt ccctggggtt   5040
aaaaataacc ccatgaccac ttttggcagt tgtaggtgag gcagaggcca cctaagcccc   5100
cccaccccat gccgttcttc tgaagtaaga gccgttcaaa gtccgacacc cgcctgggtg   5160
gacacgtgag acccaaaaat gccttcaagg ttaaagagac agtggctggg gcctggcctg   5220
ggaacgatgc tctgtgctct gggtcctgcc attgccgaca ggcgctgtgt gagacagcac   5280
gtagggcgac aggcgctgtg tgagacagca cgtagggcga caggcgctgt gtgagacagc   5340
acgtagggcg acaggcgctg tgtgagacag cacgtagggc gacaggcgct gtgtgagaca   5400
gcacgtaggg cgacaggcgc tgtgtgagac agcacgtagg gcgacaggcg ctgtgtgaga   5460
cagcacgtag ggcgacaggc gctgtgtgag acagcacgta gggcgacagg cgctgtgtga   5520
```

-continued gacagcacgt agggcctcga gtaggcgaga ccaatgggtg cgccatgggc tcttccaaaa 5580
atttaggtga cactataggg caccgctcgc acctgcgcac aggcataagc caaatggaac 5640
tacgagacct gcatcgtggt gtaactataa cggtcctaag gtagcgaccg cggagactag 5700
gtgtatttat ctaagcgatc gcttaattaa ggccggccgc cgcaataaaa tatctttatt 5760
ttcattacat ctgtgtgttg gttttttgtg tgaatccata gtactaacat acgctctcca 5820
tcaaaacaaa acgaaacaaa acaaactagc aaaataggct gtccccagtg caagtccagg 5880
tgccagaaca tttctctatc cataatgcag gggtaccggg tgatgacggt gaaaacctcc 5940
aattgcggag tactgtcctc cgagcggagt actgtcctcc gagcggagta ctgtcctccg 6000
agcggagtac tgtcctccga gcggagtact gtcctccgag cggagtactg tcctccgagc 6060
ggagagtccc cggggaccta gagggtatat aatgggtgcc ttagctggtg tgtgacctca 6120
tcttcctgta cgcccctgca ggggcgcgcc acgcgtcgaa gaaggtgagt aatcttaaca 6180
tgctcttttt tttttttttt gctaatccct tttgtgtgct gatgttagga tgacatttac 6240
aacaaatgtt tgttcctgac aggaaaaacc ttgctgggta ccttcgttgc cggacacttc 6300
ttgtcctcta ctttggaaaa aaggaattga gagccgctag cgccaccatg ggaaaaatca 6360
gcagcctgcc cacccaatta tttaagtgct gcttttgtga tttcttgaag gtgaagatgc 6420
acaccatgtc ctcctcgcat ctgttctacc tggcgctgtg cctgctgacc ttcaccagct 6480
ctgccacggc tggaccggag accctctgcg gggccgagct ggtggatgcc ctgcaattcg 6540
tgtgtggaga caggggcttc tacttcaaca agcccacagg gtatggctcc agcagtcgga 6600
gagcccccca gacaggcatc gtggatgagt gctgcttcag aagctgtgat ctaaggaggc 6660
tggagatgta ttgcgcaccc ctcaagcctg ccaagtcagc tcgctctgtc cgtgcccagc 6720
gccacaccga catgcccaag acccagaagt atcagccccc atctaccaac aagaacacga 6780
agtctcagag aaggaaagga agtacatttg aagaacgcaa gtagatcgat tgcgcaaagc 6840
tttcgcgata ggcgagacca atgggtgtgt acgtagcggc cgcgtcgacg atagcttgat 6900
gggtggcatc cctgtgaccc ctccccagtg cctctcctgg ccctggaagt tgccactcca 6960
gtgcccacca gccttgtcct aataaaatta agttgcatca ttttgtctga ctaggtgtcc 7020
ttctataata ttatggggtg gaggggggtg gtatggagca aggggcaagt tgggaagaca 7080
acctgtaggg cctgcggggt ctattgggaa ccaagctgga gtgcagtggc acaatcttgg 7140
ctcactgcaa tctccgcctc ctgggttcaa gcgattctcc tgcctcagcc tcccgagttg 7200
ttgggattcc aggcatgcat gaccaggctc agctaatttt tgttttttttg gtagagacgg 7260
ggtttcacca tattggccag gctggtctcc aactcctaat ctcaggtgat ctacccacct 7320
tggcctccca aattgctggg attacaggcg tgaaccactg ctcccttccc tgtccttctg 7380
attttaaaat aactatacca gcaggaggac gtccagacac agcataggct acctggccat 7440
gcccaaccgg tgggacattt gagttgcttg cttggcactg tcctctcatg cgttgggtcc 7500
actcagtaga tgcctgttga attctgattt aaatcggtcc gcgtacggcg tggtaggtcc 7560
gaacgaatcc atggattacc ctgttatccc tactcaagga catcatccct ttagtgaggg 7620
ttaattcacg cagtgggtac ggaactaaag gcagcacaca tcgtgtaatc atggtcatag 7680
ctgtttcctg tgtgaaattg ttatccgcta cgtctctccc ccgcagtaag ggctagatta 7740
actcgtctcg tgaatatccg gaactccctt tagtgagggt taattgcgtt gcgctcactg 7800
cccgctttcc agtcgggaaa cctgtcgtgc cagcttaatc atggtcatag ctgtttcctg 7860
tgtgaaattg ttatccgcta ccggaaacgc ttccttcatg tgagcaaaag gccagcaaaa 7920
ggccaggaac cgtaaaaagg ccgcgttgct ggcgtttttc cataggctcc gcccccctga 7980
cgagcatcac aaaaatcgac gctcaagtca gaggtggcga aacccgacag gactataaag 8040
ataccaggcg tttccccctg gaagctccct cgtgcgctct cctgttccga ccctgccgct 8100
taccggatac ctgtccgcct ttctcccttc gggaagcgtg gcgctttctc atagctcacg 8160
ctgtaggtat ctcagttcgg tgtaggtcgt tcgctccaag ctgggctgtg tgcacgaacc 8220
ccccgttcag cccgaccgct gcgccttatc cggtaactat cgtcttgagt ccaacccggt 8280
aagacacgac ttatcgccac tggcagcagc cactggtaac aggattagca gagcgaggta 8340
tgtaggcggt gctacagagt tcttgaagtg gtggcctaac tacggctaca ctagaagaac 8400
agtatttggt atctgcgctc tgctgaagcc agttaccttc ggaaaaagag ttggtagctc 8460
ttgatccggc aaacaaacca ccgctggtag cggtggtttt tttgtttgca agcagcagat 8520
tacgcgcaga aaaaaaggat ctcaagaaga tcctttgatc ttttctacgg ggtctgacgc 8580
tcagtggaac gaaaactcac gttaagggat tttggtcatg cctaggacga aaggaggtcg 8640
tgaaatggat aaaaaaatac agcgtttttc atgtacaact atactagttg tagtgcctaa 8700
ataatgcttt taaaacttaa aaataatcta tgtcgggtgc ggagaaagag gtaatgaaat 8760
ggcaaatcaa tgtcctcagc gaaatggcat acgagtaaac ttggtctgac accgctgcat 8820
gagattatca aaaaggatct tcacctagat ccttttaaat taaaaatgaa gttttaaatc 8880
aatctaaagt atatatgagt aaacttggtc tgacagttac caatgcttaa tcagtgaggc 8940
acctatctca gcgatctgtc tatttcgttc atccatagtt gcctgactcc ccgtcgtgta 9000
gataactacg atacgggagg gcttaccatc tggccccagt gctgcaatga taccgcgaga 9060
cccacgctca ccggctccag atttatcagc aataaaccag ccagccggaa gcgccgagcg 9120
cagaagtggt cctgcaactt tatccgcctc catccagtct attaactgtt gccgggaagc 9180
tagagtaagt agttcgccag ttaatagttt gcggagcgtt gttgccattg ctacaggcat 9240
cgtggtgtca cgctcgtcgt ttggtatggc ttcattcagc tccggttccc aacgatcaag 9300
gcgagttaca tgatccccca tgttgtgcaa aaaagcggtt agctccttcg gtcctccgat 9360
ggttgtcaga agtaagttgg ccgcagtgtt atcactcatg gttatggcag cactgcataa 9420
ttctcttact gtcatgccat ccgtaagatg cttttctgtg actggtgagt attcaaccaa 9480
gtcattctga gaatagtgta tgcggcgacc gagttgctct tgcccggcgt caatacggga 9540
taataccgcg ccacatagca gaactttaaa agtgctcatc attgggaagc gttcttcggg 9600
gcgaaaactc tcaaggatct taccgctgtt gagatccagt tcgatgtaac ccacacgagc 9660
acccaactga tcttcagcat cttttacttt caccagcgtt tctgggtgag caaaaacagg 9720
aaggcaaaat gccgcaaaaa agggaataag ggcgacacgg aaatgttgaa tactcatacg 9780
cttccttttt caatagtatt gaagcattta tcagggttat tgtctcggga gcgaatacat 9840
atttgaatgt atttagaaaa a 9861

<210> SEQ ID NO 8
<211> LENGTH: 10823
<212> TYPE: DNA
<213> ORGANISM: Artificial Sequence
<220> FEATURE:
<223> OTHER INFORMATION: Synthetic ubiquitous and hypoxia inducible promoter gene switch construct expressing bFGF

<400> SEQUENCE: 8
taaacaaata ggggttccgc gcacatttcc ccgaaaagtg ccacctgacg tactgaggac 60

```
gccagggttt tcccagtcac gacgttgtaa aacgacggcc agtagcagac aagcccgtca    120
gggcgcgtca gcgggtgttg gccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg ggctctcca    2040 gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca    2280 ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
```

-continued

```
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag gggcgctgt    2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccgtct aacaaaaaag ccaaaaacgg ccagaattta   3060
gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
gcctgttccg ctctctggaa agaaaaccag tgccctagag tcacccaagt cccgtcctaa   3420
aatgtccttc tgctgatact ggggttctaa ggccgagtct tatgagcagc gggccgctgt   3480
cctgagcgtc cgggcggaag gatcaggacg ctcgctgcgc ccttcgtctg acgtggcagc   3540
gctcgccgtg aggagggggg cgcccgcggg aggcgccaaa acccggcgcg gaggccctcg   3600
agtaggcgag accaatgggt gcgccatggg ctcttccaaa aatttaggtg acactatagg   3660
gcaccgctcg cacctgcgca caggcccgcg gctacaaact acgaacgatc attctagata   3720
ccacatttgt agaggtttta cttgctttaa aaaacctccc acatctcccc ctgaacctga   3780
aacataaaat gaatgcaaat gttttattaa cttgtttatt gcagcttata atggttacaa   3840
attaagcaat agcatcacaa atttcacaaa ttaagcattt ttttcactgc attctagttg   3900
tggtttgtcc aaactcatca atgtatctta tcatgtctaa tcgattcaca ggttggtggg   3960
gctctccagg atgggggggg gctgggtgtg gctcatgtcg gccacgtccc aaatctcctc   4020
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
cctggcgctg ccgctcagct ggttcaggat gtagatcctc agggtgttca ggtagtacct   4200
ctggatctcc tccaccagct ggggctgctc caggccgggc ctgtcgctga agatcaccac   4260
ggcggtcagc agggcgtagt ggatgttgtc cagggccatg ctgtacatac atctgcagaa   4320
gtgcaggagg tcctcgatca cctcggccat gccagccttc ctgtagttgt ccctggtgta   4380
agcctggttg ttggcgaaca ggatgctgtc gctggcggcg tcgtacctcc tggccaccct   4440
cagcatcatc acctcgctgc tgcaagcctt cagcagggtg atctggtcgg gctggctgat   4500
cttggcgaat ccgggcaggc ccttggcgaa ctccacgatc agctgcacgg tcaggatggt   4560
catctcggtg atctgcctga agggggtgtc gctctcctcg ttctcgtcgt cggcctgctg   4620
ccaggtctgg gtgatccttt tcaggtcctc gtcgctgggc tgctcgtagc cgtcctgata   4680
ccagatcagc ctggcgatca ggaactgctg gttggcggtc agctggggga tgttcttctg   4740
cctgttggtc accagcagct tgtcgctcag gaacctgggc acgacctcgt gaatcctggc   4800
```

```
ggcctcgggg ggggggggct cgcactgcat gatggggggc atgtggtcat cgacggtggt   4860
ggtgctcacg ggcagcttgt ccttctcctt ctgggccttc ttctccttcc ttttcatggc   4920
gcactgggtc tcgggcacca cgcactcggg cctgatcccg ggaaactcgg ggctcacggt   4980
cagctgcctc tggcccttgt tgctgctctc ctcgctgctg ctggtggcgc tgatcctgtg   5040
ctgcctcagg gtcaggggca tgtcggtctc cacgctggcc agcctgtcgg tcacggcgtc   5100
cttgttcacg ttgtcctgca cgaacaggcc ggtcagcagg gccttgatgt cttgcaggct   5160
gtccatcttc aggatcatgt ccaggtcctc cctggggaag atcagcagga acagctgctc   5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc cccccccccg catgcacagg aagatgagct   5460
cacacaccag ctaaggcacc cattatatac cctctaggtc ttcgcggacg tgcgggaacc   5520
cacgtggggg ctccgtcacg tactccgagt cccgcacgca ctcagcgtcg ctctggggcc   5580
ccacgtccgg ccctgacgtg cggcttcgtt tgtcacgtcg cggacgtgcg ggaacccacg   5640
tgggggctcc gtcacgtact ccgagtcccg cacgcactca gcgtcgctct ggggccccac   5700
gtccggccct gacgtgcggc ttcgtttgtc acgtcgcgga cgtgcgggaa cccacgtggg   5760
ggctccgtca cgtactccga gtcccgcacg cactcagcgt cgctctgggg ccccacgtcc   5820
ggccctgacg tgcggcttcg tttgtcacgt cgcggacgtg cgggaaccca cgtgggggct   5880
ccgtcacgta ctccgagtcc cgcacgcact cagcgtcgct ctggggcccc acgtccggcc   5940
ctgacgtgcg gcttcgtttg tcacgtcgcg gacgtgcggg aacccacgtg ggggctccgt   6000
cacgtactcc gagtcccgca cgcactcagc gtcgctctgg ggccccacgt ccggccctga   6060
cgtgcggctt cgtttgtcac gtcgcggacg tgcgggaacc cacgtggggg ctccgtcacg   6120
tactccgagt cccgcacgca ctcagcgtcg ctctggggcc ccacgtccgg ccctgacgtg   6180
cggcttcgtt tgtcacgtcg cggacgtgcg ggaacccacg tgggggctcc gtcacgtact   6240
ccgagtcccg cacgcactca gcgtcgctct ggggccccac gtccggccct gacgtgcggc   6300
ttcgtttgtc acgtcctcga gtggtaatac aatggccggt tcccatggac ctgcatcgtg   6360
gtgtaactat aacggtccta aggtagcgac cgcggagact aggtgtattt atctaagcga   6420
tcgcttaatt aaggccggcc gccgcaataa aatatcttta ttttcattac atctgtgtgt   6480
tggttttttg tgtgaatcca tagtactaac atacgctctc catcaaaaca aaacgaaaca   6540
aaacaaacta gcaaaatagg ctgtccccag tgcaagtcca ggtgccagaa catttctcta   6600
tccataatgc aggggtaccg ggtgatgacg gtgaaaacct ccaattgcgg agtactgtcc   6660
tccgagcgga gtactgtcct ccgagcggag tactgtcctc cgagcggagt actgtcctcc   6720
gagcggagta ctgtcctccg agcggagtac tgtcctccga gcggagagtc cccggggacc   6780
tagagggtat ataatgggtg ccttagctgg tgtgtgacct catcttcctg tacgcccctg   6840
caggggcgcg ccacgcgtcg aagaaggtga gtaatcttaa catgctcttt tttttttttt   6900
ttgctaatcc cttttgtgtg ctgatgttag gatgacattt acaacaaatg tttgttcctg   6960
acaggaaaaa ccttgctggg taccttcgtt gccggacact tcttgtcctc tactttggaa   7020
aaaaggaatt gagagccgct agcgccacca tggtgggtgt ggggggtgga gatgtagaag   7080
atgtgacgcc caggcccggc gggtgccaga ttagcggacg cggtgccaga ggctgcaacg   7140
```

-continued

```
gcatccccgg cgcagccgcc tgggaagccg ctctccccag gcggcgtccc agaaggcacc   7200
catccgtgaa ccccaggagc agagccgccg gatcgccgcg caccaggggc agaagaacag   7260
aggaacggcc gagcggcagc agactggggg acagaggcag aggcagagcg ctgccgggcg   7320
ggaggctggg gggccggggc cggggccgtg ccccggagcg ggtcggaggc cggggccggg   7380
gccgggggac ggcggctccc cgcgcggctc cagcggctcg ggctccaga cccggccccg   7440
cagggacaat ggccgccggg agcatcacca cgctgcccgc cttgcccgag gatggcggca   7500
gcggcgcttt cccgcccggc cacttcaagg accccaagcg gctgtactgc aaaaacgggg   7560
gcttcttcct gcgcatccac cccgacggcc gagttgacgg ggtccgggag aagtccgacc   7620
ctcacatcaa gctacaactt caagcagagg agagaggagt tgtgtctatc aaaggagtgt   7680
gtgctaaccg ttacctggct atgaaggaag atggaagatt actggcttct aaatgtgtta   7740
cggatgagtg tttctttttt gaacgattgg aatctaataa ctacaatact tacagaagca   7800
ggaaatacac cagttggtat gtggcactga aacgaactgg gcagtataaa cttggcagca   7860
aaacaggacc tgggcagaaa gctatacttt ttcttccaat gtctgctaag agctgaatcg   7920
attgcgcaaa gctttcgcga taggcgagac caatgggtgt gtacgtagcg gccgcgtcga   7980
cgatagcttg atgggtggca tccctgtgac ccctccccag tgcctctcct ggccctggaa   8040
gttgccactc cagtgcccac cagccttgtc ctaataaaat taagttgcat cattttgtct   8100
gactaggtgt ccttctataa tattatgggg tggagggggg tggtatggag caaggggcaa   8160
gttgggaaga caacctgtag ggcctgcggg gtctattggg aaccaagctg gagtgcagtg   8220
gcacaatctt ggctcactgc aatctccgcc tcctgggttc aagcgattct cctgcctcag   8280
cctcccgagt tgttgggatt ccaggcatgc atgaccaggc tcagctaatt tttgtttttt   8340
tggtagagac ggggtttcac catattggcc aggctggtct ccaactccta atctcaggtg   8400
atctacccac cttggcctcc caaattgctg ggattacagg cgtgaaccac tgctcccttc   8460
cctgtccttc tgattttaaa ataactatac cagcaggagg acgtccagac acagcatagg   8520
ctacctggcc atgcccaacc ggtgggacat ttgagttgct tgcttggcac tgtcctctca   8580
tgcgttgggt ccactcagta gatgcctgtt gaattctgat ttaaatcggt ccgcgtacgg   8640
cgtggtaggt ccgaacgaat ccatggatta ccctgttatc cctactcaag gacatcatcc   8700
ctttagtgag ggttaattca cgcagtgggt acggaactaa aggcagcaca catcgtgtaa   8760
tcatggtcat agctgtttcc tgtgtgaaat tgttatccgc tacgtctctc ccccgcagta   8820
agggctagat taactcgtct cgtgaatatc cggaactccc tttagtgagg gttaattgcg   8880
ttgcgctcac tgcccgcttt ccagtcggga aacctgtcgt gccagcttaa tcatggtcat   8940
agctgtttcc tgtgtgaaat tgttatccgc taccggaaac gcttccttca tgtgagcaaa   9000
aggccagcaa aaggccagga accgtaaaaa ggccgcgttg ctggcgtttt tccataggct   9060
ccgcccccct gacgagcatc acaaaaatcg acgctcaagt cagaggtggc gaaacccgac   9120
aggactataa agataccagg cgtttccccc tggaagctcc ctcgtgcgct ctcctgttcc   9180
gaccctgccg cttaccggat acctgtccgc ctttctccct tcgggaagcg tggcgctttc   9240
tcatagctca cgctgtaggt atctcagttc ggtgtaggtc gttcgctcca agctgggctg   9300
tgtgcacgaa ccccccgttc agcccgaccg ctgcgcctta tccggtaact atcgtcttga   9360
gtccaacccg gtaagacacg acttatcgcc actggcagca gccactggta acaggattag   9420
cagagcgagg tatgtaggcg gtgctacaga gttcttgaag tggtggccta actacggcta   9480
cactagaaga acagtatttg gtatctgcgc tctgctgaag ccagttacct tcggaaaaag   9540
```

```
agttggtagc tcttgatccg gcaaacaaac caccgctggt agcggtggtt tttttgtttg   9600
caagcagcag attacgcgca gaaaaaaagg atctcaagaa gatcctttga tcttttctac   9660
ggggtctgac gctcagtgga acgaaaactc acgttaaggg attttggtca tgatctatgt   9720
cgggtgcgga gaaagaggta atgaaatggc atacgagtaa acttggtctg acaccgctgc   9780
atgagattat caaaaaggat cttcacctag atccttttaa attaaaaatg aagttttaaa   9840
tcaatctaaa gtatatatga gtaaacttgg tctgacagtt accaatgctt aatcagtgag   9900
gcacctatct cagcgatctg tctatttcgt tcatccatag ttgcctgact ccccgtcgtg   9960
tagataacta cgatacggga gggcttacca tctggcccca gtgctgcaat gataccgcga  10020
gacccacgct caccggctcc agatttatca gcaataaacc agccagccgg aagcgccgag  10080
cgcagaagtg gtcctgcaac tttatccgcc tccatccagt ctattaactg ttgccgggaa  10140
gctagagtaa gtagttcgcc agttaatagt ttgcggagcg ttgttgccat tgctacaggc  10200
atcgtggtgt cacgctcgtc gtttggtatg gcttcattca gctccggttc ccaacgatca  10260
aggcgagtta catgatcccc catgttgtgc aaaaaagcgg ttagctcctt cggtcctccg  10320
atggttgtca gaagtaagtt ggccgcagtg ttatcactca tggttatggc agcactgcat  10380
aattctctta ctgtcatgcc atccgtaaga tgcttttctg tgactggtga gtattcaacc  10440
aagtcattct gagaatagtg tatgcggcga ccgagttgct cttgcccggc gtcaatacgg  10500
gataataccg cgccacatag cagaacttta aaagtgctca tcattggaaa gcgttcttcg  10560
gggcgaaaac tctcaaggat cttaccgctg ttgagatcca gttcgatgta acccacacga  10620
gcacccaact gatcttcagc atcttttact ttcaccagcg tttctgggtg agcaaaaaca  10680
ggaaggcaaa atgccgcaaa aaagggaata agggcgacac ggaaatgttg aatactcata  10740
cgcttccttt ttcaatagta ttgaagcatt tatcagggtt attgtctcgg gagcgaatac  10800
atatttgaat gtatttagaa aaa                                          10823
```

<210> SEQ ID NO 9
<211> LENGTH: 10538
<212> TYPE: DNA
<213> ORGANISM: Artificial Sequence
<220> FEATURE:
<223> OTHER INFORMATION: Synthetic ubiquitous and hypoxia inducible gene switch construct expressing EPO

<400> SEQUENCE: 9

```
taaacaaata ggggttccgc gcacatttcc ccgaaaagtg ccacctgacg tactgaggac     60
gccagggttt tcccagtcac gacgttgtaa aacgacggcc agtagcagac aagcccgtca    120
gggcgcgtca gcgggtgttg gccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
```

```
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctccccg   1920
cgggaggttt tataaatccg actgtctaga ttgttgttaa atcacacaaa aaaccaacac   1980
acagatgtaa tgaaaataaa gatattttat tatcgattca gctgtcgctg ggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820
cgtgggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccgtct aacaaaaaag ccaaaaacgg ccagaattta   3060
```
gcggacaatt tactagtcta acactgaaaa ttacatattg acccaaatga ttacatttca 3120
aaaggtgcct aaaaaacttc acaaaacaca ctcgccaacc ccgagcgcac gtacccagcc 3180
cagcagcccg ctactcacca agtgacgatc acagcgatcc acaaacaaga accgcgaccc 3240
aaatcccggc tgcgacggaa ctagctgtgc cacacccggc gcgtccttat ataatcatcg 3300
gcgttcaccg ccccacggag atccctccgc agaatcgccg agaagggact acttttcctc 3360
gcctgttccg ctctctggaa agaaaaccag tgccctagag tcacccaagt cccgtcctaa 3420
aatgtccttc tgctgatact ggggttctaa ggccgagtct tatgagcagc gggccgctgt 3480
cctgagcgtc cgggcggaag gatcaggacg ctcgctgcgc ccttcgtctg acgtggcagc 3540
gctcgccgtg aggagggggg cgcccgcggg aggcgccaaa acccggcgcg gaggccctcg 3600
agtaggcgag accaatgggt gcgccatggg ctcttccaaa aatttaggtg acactatagg 3660
gcaccgctcg cacctgcgca caggcccgcg gctacaaact acgaacgatc attctagata 3720
ccacatttgt agaggtttta cttgctttaa aaaacctccc acatctcccc ctgaacctga 3780
aacataaaat gaatgcaaat gttttattaa cttgtttatt gcagcttata atggttacaa 3840
attaagcaat agcatcacaa atttcacaaa ttaagcattt ttttcactgc attctagttg 3900
tggtttgtcc aaactcatca atgtatctta tcatgtctaa tcgattcaca ggttggtggg 3960
gctctccagg atgggggggg gctgggtgtg gctcatgtcg gccacgtccc aaatctcctc 4020
caggaagggg ggcagcttcc tgttcttcag cttcaggctg atacacatat tgctgttctg 4080
cattcccagg gtcctcagct cgctcaggat gctcaggatc ttgccgtaga tcacgctgct 4140
cctggcgctg ccgctcagct ggttcaggat gtagatcctc agggtgttca ggtagtacct 4200
ctggatctcc tccaccagct ggggctgctc caggccgggc ctgtcgctga agatcaccac 4260
ggcggtcagc agggcgtagt ggatgttgtc cagggccatg ctgtacatac atctgcagaa 4320
gtgcaggagg tcctcgatca cctcggccat gccagccttc ctgtagttgt ccctggtgta 4380
agcctggttg ttggcgaaca ggatgctgtc gctggcggcg tcgtacctcc tggccaccct 4440
cagcatcatc acctcgctgc tgcaagcctt cagcagggtg atctggtcgg gctggctgat 4500
cttggcgaat ccgggcaggc ccttggcgaa ctccacgatc agctgcacgg tcaggatggt 4560
catctcggtg atctgcctga agggggtgtc gctctcctcg ttctcgtcgt cggcctgctg 4620
ccaggtctgg gtgatccttt tcaggtcctc gtcgctgggc tgctcgtagc cgtcctgata 4680
ccagatcagc ctggcgatca ggaactgctg gttggcggtc agctggggga tgttcttctg 4740
cctgttggtc accagcagct tgtcgctcag gaacctgggc acgacctcgt gaatcctggc 4800
ggcctcgggg ggggggggct cgcactgcat gatggggggc atgtggtcat cgacggtggt 4860
ggtgctcacg ggcagcttgt ccttctcctt ctgggccttc ttctccttcc ttttcatggc 4920
gcactgggtc tcgggcacca cgcactcggg cctgatcccg ggaaactcgg ggctcacggt 4980
cagctgcctc tggcccttgt tgctgctctc ctcgctgctg ctggtggcgc tgatcctgtg 5040
ctgcctcagg gtcaggggca tgtcggtctc cacgctggcc agcctgtcgg tcacggcgtc 5100
cttgttcacg ttgtcctgca cgaacaggcc ggtcagcagg gccttgatgt cttgcaggct 5160
gtccatcttc aggatcatgt ccaggtcctc cctggggaag atcagcagga acagctgctc 5220
cagcctctcc agcctgctct ccacctcggt caggtgggcc ctggtcaggg ggctcctctt 5280
ggtcttgggg ctgtatctgc actcccagtt gttcttcagg cacttggcgc acttgggctt 5340
ctccttgctg cacttcagct tcttcagcct gcagatgtcg caagcctgct cgatgctgct 5400
cagcagcttc atggtggcca attgcccccc cccccccccg catgcacagg aagatgagct 5460

```
cacacaccag ctaaggcacc cattatatac cctctaggtc ttcgcggacg tgcgggaacc   5520
cacgtggggg ctccgtcacg tactccgagt cccgcacgca ctcagcgtcg ctctggggcc   5580
ccacgtccgg ccctgacgtg cggcttcgtt tgtcacgtcg cggacgtgcg ggaacccacg   5640
tgggggctcc gtcacgtact ccgagtcccg cacgcactca gcgtcgctct ggggccccac   5700
gtccggccct gacgtgcggc ttcgtttgtc acgtcgcgga cgtgcgggaa cccacgtggg   5760
ggctccgtca cgtactccga gtcccgcacg cactcagcgt cgctctgggg ccccacgtcc   5820
ggccctgacg tgcggcttcg tttgtcacgt cgcggacgtg cgggaaccca cgtgggggct   5880
ccgtcacgta ctccgagtcc cgcacgcact cagcgtcgct ctggggcccc acgtccggcc   5940
ctgacgtgcg gcttcgtttg tcacgtcgcg gacgtgcggg aacccacgtg ggggctccgt   6000
cacgtactcc gagtcccgca cgcactcagc gtcgctctgg ggccccacgt ccggccctga   6060
cgtgcggctt cgtttgtcac gtcgcggacg tgcgggaacc cacgtggggg ctccgtcacg   6120
tactccgagt cccgcacgca ctcagcgtcg ctctggggcc ccacgtccgg ccctgacgtg   6180
cggcttcgtt tgtcacgtcg cggacgtgcg ggaacccacg tgggggctcc gtcacgtact   6240
ccgagtcccg cacgcactca gcgtcgctct ggggccccac gtccggccct gacgtgcggc   6300
ttcgtttgtc acgtcctcga gtggtaatac aatggccggt tcccatggac ctgcatcgtg   6360
gtgtaactat aacggtccta aggtagcgac cgcggagact aggtgtattt atctaagcga   6420
tcgcttaatt aaggccggcc gccgcaataa aatatcttta ttttcattac atctgtgtgt   6480
tggttttttg tgtgaatcca tagtactaac atacgctctc catcaaaaca aaacgaaaca   6540
aaacaaacta gcaaaatagg ctgtccccag tgcaagtcca ggtgccagaa catttctcta   6600
tccataatgc aggggtaccg ggtgatgacg gtgaaaacct ccaattgcgg agtactgtcc   6660
tccgagcgga gtactgtcct ccgagcggag tactgtcctc cgagcggagt actgtcctcc   6720
gagcggagta ctgtcctccg agcggagtac tgtcctccga gcggagagtc cccggggacc   6780
tagagggtat ataatgggtg ccttagctgg tgtgtgacct catcttcctg tacgcccctg   6840
caggggcgcg ccacgcgtcg aagaaggtga gtaatcttaa catgctcttt tttttttttt   6900
ttgctaatcc cttttgtgtg ctgatgttag gatgacattt acaacaaatg tttgttcctg   6960
acaggaaaaa ccttgctggg taccttcgtt gccggacact tcttgtcctc tactttggaa   7020
aaaaggaatt gagagccgct agcgccacca tgggggtgca tgaatgtcct gcctggctgt   7080
ggcttctcct gtccctgctg tcgctccctc tgggcctccc agtcctgggc gctccaccac   7140
gcctcatctg tgacagccga gtcctggaga gatacctgtt ggaggccaag gaagccgaga   7200
atatcacgac gggctgtgct gaacactgct ccttgaatga gaatatcact gtcccagaca   7260
ccaaagttaa tttctatgcc tggaagcgga tggaggtcgg gcagcaggcc gtagaagtct   7320
ggcagggcct ggccctgctg tcggaagctg tcctgcgggg ccaggccctg ttggtcaaca   7380
gcagccagcc gtgggagccc ctgcaactgc atgtggataa agccgtcagt ggccttcgca   7440
gcctcaccac tctgcttcgg gctctgcgag cccagaagga agccatctcc cctccagatg   7500
cggccagcgc cgctccactc cgaacaatca ctgctgacac tttccgcaaa ctgttccgag   7560
tctactccaa tttcctccgg ggaaagctga agctgtacac aggggaggct tgcaggacag   7620
gggacagatg aatcgattgc gcaaagcttt cgcgataggc gagaccaatg ggtgtgtacg   7680
tagcggccgc gtcgacgata gcttgatggg tggcatccct gtgacccctc cccagtgcct   7740
ctcctggccc tggaagttgc cactccagtg cccaccagcc ttgtcctaat aaaattaagt   7800
```

-continued

```
tgcatcattt tgtctgacta ggtgtccttc tataatatta tggggtggag gggggtggta   7860
tggagcaagg ggcaagttgg gaagacaacc tgtagggcct gcggggtcta ttgggaacca   7920
agctggagtg cagtggcaca atcttggctc actgcaatct ccgcctcctg ggttcaagcg   7980
attctcctgc ctcagcctcc cgagttgttg ggattccagg catgcatgac caggctcagc   8040
taatttttgt ttttttggta gagacggggt ttcaccatat tggccaggct ggtctccaac   8100
tcctaatctc aggtgatcta cccaccttgg cctcccaaat tgctgggatt acaggcgtga   8160
accactgctc ccttccctgt ccttctgatt ttaaaataac tataccagca ggaggacgtc   8220
cagacacagc ataggctacc tggccatgcc caaccggtgg gacatttgag ttgcttgctt   8280
ggcactgtcc tctcatgcgt tgggtccact cagtagatgc ctgttgaatt ctgatttaaa   8340
tcggtccgcg tacggcgtgg taggtccgaa cgaatccatg gattaccctg ttatccctac   8400
tcaaggacat catcccttta gtgagggtta attcacgcag tgggtacgga actaaaggca   8460
gcacacatcg tgtaatcatg gtcatagctg tttcctgtgt gaaattgtta tccgctacgt   8520
ctctcccccg cagtaagggc tagattaact cgtctcgtga atatccggaa ctccctttag   8580
tgagggttaa ttgcgttgcg ctcactgccc gctttccagt cgggaaacct gtcgtgccag   8640
cttaatcatg gtcatagctg tttcctgtgt gaaattgtta tccgctaccg gaaacgcttc   8700
cttcatgtga gcaaaaggcc agcaaaaggc caggaaccgt aaaaaggccg cgttgctggc   8760
gtttttccat aggctccgcc cccctgacga gcatcacaaa aatcgacgct caagtcagag   8820
gtggcgaaac ccgacaggac tataaagata ccaggcgttt ccccctggaa gctccctcgt   8880
gcgctctcct gttccgaccc tgccgcttac cggatacctg tccgcctttc tcccttcggg   8940
aagcgtggcg ctttctcata gctcacgctg taggtatctc agttcggtgt aggtcgttcg   9000
ctccaagctg ggctgtgtgc acgaaccccc cgttcagccc gaccgctgcg ccttatccgg   9060
taactatcgt cttgagtcca acccggtaag acacgactta tcgccactgg cagcagccac   9120
tggtaacagg attagcagag cgaggtatgt aggcggtgct acagagttct tgaagtggtg   9180
gcctaactac ggctacacta gaagaacagt atttggtatc tgcgctctgc tgaagccagt   9240
taccttcgga aaaagagttg gtagctcttg atccggcaaa caaaccaccg ctggtagcgg   9300
tggttttttt gtttgcaagc agcagattac gcgcagaaaa aaaggatctc aagaagatcc   9360
tttgatcttt tctacggggt ctgacgctca gtggaacgaa aactcacgtt aagggatttt   9420
ggtcatgatc tatgtcgggt gcggagaaag aggtaatgaa atggcatacg agtaaacttg   9480
gtctgacacc gctgcatgag attatcaaaa aggatcttca cctagatcct tttaaattaa   9540
aaatgaagtt ttaaatcaat ctaaagtata tatgagtaaa cttggtctga cagttaccaa   9600
tgcttaatca gtgaggcacc tatctcagcg atctgtctat ttcgttcatc catagttgcc   9660
tgactccccg tcgtgtagat aactacgata cgggagggct taccatctgg ccccagtgct   9720
gcaatgatac cgcgagaccc acgctcaccg gctccagatt tatcagcaat aaaccagcca   9780
gccggaagcg ccgagcgcag aagtggtcct gcaactttat ccgcctccat ccagtctatt   9840
aactgttgcc gggaagctag agtaagtagt tcgccagtta atagtttgcg gagcgttgtt   9900
gccattgcta caggcatcgt ggtgtcacgc tcgtcgtttg gtatggcttc attcagctcc   9960
ggttcccaac gatcaaggcg agttacatga tcccccatgt tgtgcaaaaa agcggttagc  10020
tccttcggtc ctccgatggt tgtcagaagt aagttggccg cagtgttatc actcatggtt  10080
atggcagcac tgcataattc tcttactgtc atgccatccg taagatgctt ttctgtgact  10140
ggtgagtatt caaccaagtc attctgagaa tagtgtatgc ggcgaccgag ttgctcttgc  10200
```
ccggcgtcaa tacgggataa taccgcgcca catagcagaa ctttaaaagt gctcatcatt 10260
gggaagcgtt cttcggggcg aaaactctca aggatcttac cgctgttgag atccagttcg 10320
atgtaaccca cacgagcacc caactgatct tcagcatctt ttactttcac cagcgtttct 10380
gggtgagcaa aaacaggaag gcaaaatgcc gcaaaaaagg gaataagggc gacacggaaa 10440
tgttgaatac tcatacgctt cctttttcaa tagtattgaa gcatttatca gggttattgt 10500
ctcgggagcg aatacatatt tgaatgtatt tagaaaaa 10538

<210> SEQ ID NO 10
<211> LENGTH: 10361
<212> TYPE: DNA
<213> ORGANISM: Artificial Sequence
<220> FEATURE:
<223> OTHER INFORMATION: Synthetic ubiquitous and hypoxia inducible gene switch construct expressing BNP

<400> SEQUENCE: 10
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gccctaggac gaaaggaggt cgtgaaatgg ataaaaaaat 180
acagcgtttt tcatgtacaa ctatactagt tgtagtgcct aaataatgct tttaaaactt 240
aaaaataatc aatgtcctca gcggggtgtc ggggatttag gtgacactat aggctgagcg 300
ccgcacaggc atctagaggc tatggcaggg cctgccgccc cgacgttggc tgcgagccct 360
gggccttcac ccgaacttgg ggggtggggt ggggaaaagg aagaaacgcg ggcgtattgg 420
ccccaatggg gtctcggtgg ggtatcgaca gagtgccagc cctgggaccg aaccccgcgt 480
ttatgaacaa acgacccaac accgtgcgtt ttattctgtc tttttattgc cgtcatagcg 540
cgggttcctt ccggtattgt ctccttccgt gtttcaatcg attcaaaaga actcgtccag 600
cagacggtaa aaagcaatgc gttgagaatc cggtgcagca atgccataca gcaccagaaa 660
gcgatcagcc cattcaccgc ccagttcttc agcaatgtca cgggttgcca gtgcgatgtc 720
ctgatagcga tcagccacgc ccaggcgacc gcagtcgata aagccggaga aacggccgtt 780
ttccaccata atgtttggca gacaagcatc gccgtgggtc acaaccaggt cctcgccatc 840
tggcatacgt gctttcaggc gtgcgaacag ttctgccggt gccagaccct gatgttcctc 900
gtccaggtca tcctgatcaa ccaggccagc ttccatgcga gtgcgtgcgc gctcgatacg 960
gtgtttagct tggtgatcga atgggcaagt agctgggtcc agggtatgca gacggcgcat 1020
agcatcagcc atgatggaaa cctttttctgc cggtgccaga tgagaggaca gcagatcctg 1080
gcctggaacc tcgcccagca gcagccagtc gcggccagcc tcggtcacaa catccagcac 1140
agctgcgcat ggaacgccgg tagtagccag ccaggacaga cgagctgctt catcttgcag 1200
ttcgttcagt gcgccggaca gatcggtctt aacaaacagc accggacggc cttgagcgga 1260
cagacggaac acagctgcgt cggagcaacc gatagtctgt tgagcccagt catagccaaa 1320
cagacgttcc acccaagcag ccggagaacc agcgtgcaga ccgtcttgtt caatcatggt 1380
ggcaattggg tgtctgagcg atgtggctcg gctggcgacg caaaagaaga tgcggctgac 1440
tgtcgaacag gaggagcaga gagcgaagcg ggaggctgcg ggctcaattt gcatgcttta 1500
gttcctcacc ttgtcgtatt atactatgcc gatatactat gccgatgatt aattgtcaac 1560
gtatacggaa tagctctgag gccgaggcag cttcggcctc tgcataaata aaaaaaatta 1620
gtcagccatg ggcggagaa tgggcggaac tgggcggagt taggggcggg atgggcggag 1680

```
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag gggcgctgt   2820
cgtgggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccgtct aacaaaaaag ccaaaaacgg ccagaattta   3060
gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
gcctgttccg ctctctggaa agaaaaccag tgccctagag tcacccaagt cccgtcctaa   3420
aatgtccttc tgctgatact ggggttctaa ggccgagtct tatgagcagc gggccgctgt   3480
cctgagcgtc cgggcggaag gatcaggacg ctcgctgcgc ccttcgtctg acgtggcagc   3540
gctcgccgtg aggaggggg cgcccgcggg aggcgccaaa acccggcgcg gaggccctcg   3600
agtaggcgag accaatgggt gcgccatggg ctcttccaaa aatttaggtg acactatagg   3660
gcaccgctcg cacctgcgca caggcccgcg gctacaaact acgaacgatc attctagata   3720
ccacatttgt agaggtttta cttgctttaa aaaacctccc acatctcccc ctgaacctga   3780
aacataaaat gaatgcaaat gttttattaa cttgtttatt gcagcttata atggttacaa   3840
attaagcaat agcatcacaa atttcacaaa ttaagcattt ttttcactgc attctagttg   3900
tggtttgtcc aaactcatca atgtatctta tcatgtctaa tcgattcaca ggttggtggg   3960
gctctccagg atgggggggg gctgggtgtg gctcatgtcg gccacgtccc aaatctcctc   4020
```

```
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
cctggcgctg ccgctcagct ggttcaggat gtagatcctc agggtgttca ggtagtacct   4200
ctggatctcc tccaccagct ggggctgctc caggccgggc ctgtcgctga agatcaccac   4260
ggcggtcagc agggcgtagt ggatgttgtc cagggccatg ctgtacatac atctgcagaa   4320
gtgcaggagg tcctcgatca cctcggccat gccagccttc ctgtagttgt ccctggtgta   4380
agcctggttg ttggcgaaca ggatgctgtc gctggcggcg tcgtacctcc tggccaccct   4440
cagcatcatc acctcgctgc tgcaagcctt cagcagggtg atctggtcgg gctggctgat   4500
cttggcgaat ccgggcaggc ccttggcgaa ctccacgatc agctgcacgg tcaggatggt   4560
catctcggtg atctgcctga agggggtgtc gctctcctcg ttctcgtcgt cggcctgctg   4620
ccaggtctgg gtgatccttt tcaggtcctc gtcgctgggc tgctcgtagc cgtcctgata   4680
ccagatcagc ctggcgatca ggaactgctg gttggcggtc agctggggga tgttcttctg   4740
cctgttggtc accagcagct tgtcgctcag gaacctgggc acgacctcgt gaatcctggc   4800
ggcctcgggg gggggggct cgcactgcat gatgggggc atgtggtcat cgacggtggt   4860
ggtgctcacg ggcagcttgt ccttctcctt ctgggccttc ttctccttcc ttttcatggc   4920
gcactgggtc tcgggcacca cgcactcggg cctgatcccg ggaaactcgg ggctcacggt   4980
cagctgcctc tggcccttgt tgctgctctc ctcgctgctg ctggtggcgc tgatcctgtg   5040
ctgcctcagg gtcaggggca tgtcggtctc cacgctggcc agcctgtcgg tcacggcgtc   5100
cttgttcacg ttgtcctgca cgaacaggcc ggtcagcagg gccttgatgt cttgcaggct   5160
gtccatcttc aggatcatgt ccaggtcctc cctggggaag atcagcagga acagctgctc   5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc cccccccccg catgcacagg aagatgagct   5460
cacacaccag ctaaggcacc cattatatac cctctaggtc ttcgcggacg tgcgggaacc   5520
cacgtggggg ctccgtcacg tactccgagt cccgcacgca ctcagcgtcg ctctggggcc   5580
ccacgtccgg ccctgacgtg cggcttcgtt tgtcacgtcg cggacgtgcg ggaacccacg   5640
tgggggctcc gtcacgtact ccgagtcccg cacgcactca gcgtcgctct ggggccccac   5700
gtccggccct gacgtgcggc ttcgtttgtc acgtcgcgga cgtgcgggaa cccacgtggg   5760
ggctccgtca cgtactccga gtcccgcacg cactcagcgt cgctctgggg ccccacgtcc   5820
ggccctgacg tgcggcttcg tttgtcacgt cgcggacgtg cgggaaccca cgtgggggct   5880
ccgtcacgta ctccgagtcc cgcacgcact cagcgtcgct ctggggcccc acgtccggcc   5940
ctgacgtgcg gcttcgtttg tcacgtcgcg gacgtgcggg aacccacgtg ggggctccgt   6000
cacgtactcc gagtcccgca cgcactcagc gtcgctctgg ggccccacgt ccggccctga   6060
cgtgcggctt cgtttgtcac gtcgcggacg tgcgggaacc cacgtggggg ctccgtcacg   6120
tactccgagt cccgcacgca ctcagcgtcg ctctggggcc ccacgtccgg ccctgacgtg   6180
cggcttcgtt tgtcacgtcg cggacgtgcg ggaacccacg tgggggctcc gtcacgtact   6240
ccgagtcccg cacgcactca gcgtcgctct ggggccccac gtccggccct gacgtgcggc   6300
ttcgtttgtc acgtcctcga gtggtaatac aatggccggt tcccatggac ctgcatcgtg   6360
gtgtaactat aacggtccta aggtagcgac cgcggagact aggtgtattt atctaagcga   6420
```

```
tcgcttaatt aaggccggcc gccgcaataa aatatcttta ttttcattac atctgtgtgt   6480
tggtttttttg tgtgaatcca tagtactaac atacgctctc catcaaaaca aaacgaaaca   6540
aaacaaacta gcaaaatagg ctgtccccag tgcaagtcca ggtgccagaa catttctcta   6600
tccataatgc aggggtaccg ggtgatgacg gtgaaaacct ccaattgcgg agtactgtcc   6660
tccgagcgga gtactgtcct ccgagcggag tactgtcctc cgagcggagt actgtcctcc   6720
gagcggagta ctgtcctccg agcggagtac tgtcctccga gcggagagtc cccggggacc   6780
tagagggtat ataatgggtg ccttagctgg tgtgtgacct catcttcctg tacgcccctg   6840
caggggcgcg ccacgcgtcg aagaaggtga gtaatcttaa catgctcttt tttttttttt   6900
ttgctaatcc cttttgtgtg ctgatgttag gatgacattt acaacaaatg tttgttcctg   6960
acaggaaaaa ccttgctggg taccttcgtt gccggacact tcttgtcctc tactttggaa   7020
aaaaggaatt gagagccgct agcgccacca tggacccccca gacagcacct agcagagccc   7080
tcctgctcct gctgttcttg catctggctt tcctgggagg tcgttcccac ccgctgggca   7140
gccccggttc agcctcggac ttggaaacgt ccgggttaca ggagcagcgc aaccatttgc   7200
agggcaaact gtcggagctg caagtggagc agacatccct ggagcccctc caggagagcc   7260
cccgtcccac aggtgtctgg aagtccagag aggtagccac cgagggcatc cgtgggcacc   7320
gcaaaatggt cctctacacc ctgcgggcac cacgaagccc caagatggtg caagggtctg   7380
gctgctttgg gaggaagatg gaccggatca gctccagcag cggcctgggc tgcaaagtgc   7440
tgagaaggca ctaaatcgat tgcgcaaagc tttcgcgata ggcgagacca atgggtgtgt   7500
acgtagcggc cgcgtcgacg atagcttgat gggtggcatc cctgtgaccc ctccccagtg   7560
cctctcctgg ccctggaagt tgccactcca gtgcccacca gccttgtcct aataaaatta   7620
agttgcatca ttttgtctga ctaggtgtcc ttctataata ttatggggtg gaggggggtg   7680
gtatggagca aggggcaagt tgggaagaca acctgtaggg cctgcggggt ctattgggaa   7740
ccaagctgga gtgcagtggc acaatcttgg ctcactgcaa tctccgcctc ctgggttcaa   7800
gcgattctcc tgcctcagcc tcccgagttg ttgggattcc aggcatgcat gaccaggctc   7860
agctaatttt tgtttttttg gtagagacgg ggtttcacca tattggccag gctggtctcc   7920
aactcctaat ctcaggtgat ctacccacct tggcctccca aattgctggg attacaggcg   7980
tgaaccactg ctcccttccc tgtccttctg attttaaaat aactatacca gcaggaggac   8040
gtccagacac agcataggct acctggccat gcccaaccgg tgggacattt gagttgcttg   8100
cttggcactg tcctctcatg cgttgggtcc actcagtaga tgcctgttga attctgattt   8160
aaatcggtcc gcgtacggcg tggtaggtcc gaacgaatcc atggattacc ctgttatccc   8220
tactcaagga catcatccct ttagtgaggg ttaattcacg cagtgggtac ggaactaaag   8280
gcagcacaca tcgtgtaatc atggtcatag ctgtttcctg tgtgaaattg ttatccgcta   8340
cgtctctccc ccgcagtaag ggctagatta actcgtctcg tgaatatccg gaactccctt   8400
tagtgagggt taattgcgtt gcgctcactg cccgctttcc agtcgggaaa cctgtcgtgc   8460
cagcttaatc atggtcatag ctgtttcctg tgtgaaattg ttatccgcta ccggaaacgc   8520
ttccttcatg tgagcaaaag gccagcaaaa ggccaggaac cgtaaaaagg ccgcgttgct   8580
ggcgtttttc cataggctcc gcccccctga cgagcatcac aaaaatcgac gctcaagtca   8640
gaggtggcga aacccgacag gactataaag ataccaggcg tttccccctg gaagctccct   8700
cgtgcgctct cctgttccga ccctgccgct taccggatac ctgtccgcct ttctcccttc   8760
```
gggaagcgtg gcgctttctc atagctcacg ctgtaggtat ctcagttcgg tgtaggtcgt 8820
tcgctccaag ctgggctgtg tgcacgaacc ccccgttcag cccgaccgct gcgccttatc 8880
cggtaactat cgtcttgagt ccaacccggt aagacacgac ttatcgccac tggcagcagc 8940
cactggtaac aggattagca gagcgaggta tgtaggcggt gctacagagt tcttgaagtg 9000
gtggcctaac tacggctaca ctagaagaac agtatttggt atctgcgctc tgctgaagcc 9060
agttaccttc ggaaaaagag ttggtagctc ttgatccggc aaacaaacca ccgctggtag 9120
cggtggtttt tttgtttgca agcagcagat tacgcgcaga aaaaaaggat ctcaagaaga 9180
tcctttgatc ttttctacgg ggtctgacgc tcagtggaac gaaaactcac gttaagggat 9240
tttggtcatg atctatgtcg ggtgcggaga aagaggtaat gaaatggcat acgagtaaac 9300
ttggtctgac accgctgcat gagattatca aaaaggatct tcacctagat ccttttaaat 9360
taaaaatgaa gttttaaatc aatctaaagt atatatgagt aaacttggtc tgacagttac 9420
caatgcttaa tcagtgaggc acctatctca gcgatctgtc tatttcgttc atccatagtt 9480
gcctgactcc ccgtcgtgta gataactacg atacgggagg gcttaccatc tggccccagt 9540
gctgcaatga taccgcgaga cccacgctca ccggctccag atttatcagc aataaaccag 9600
ccagccggaa gcgccgagcg cagaagtggt cctgcaactt tatccgcctc catccagtct 9660
attaactgtt gccgggaagc tagagtaagt agttcgccag ttaatagttt gcggagcgtt 9720
gttgccattg ctacaggcat cgtggtgtca cgctcgtcgt ttggtatggc ttcattcagc 9780
tccggttccc aacgatcaag gcgagttaca tgatccccca tgttgtgcaa aaaagcggtt 9840
agctccttcg gtcctccgat ggttgtcaga agtaagttgg ccgcagtgtt atcactcatg 9900
gttatggcag cactgcataa ttctcttact gtcatgccat ccgtaagatg cttttctgtg 9960
actggtgagt attcaaccaa gtcattctga gaatagtgta tgcggcgacc gagttgctct 10020
tgcccggcgt caatacggga taataccgcg ccacatagca gaactttaaa agtgctcatc 10080
attgggaagc gttcttcggg gcgaaaactc tcaaggatct taccgctgtt gagatccagt 10140
tcgatgtaac ccacacgagc acccaactga tcttcagcat cttttacttt caccagcgtt 10200
tctgggtgag caaaaacagg aaggcaaaat gccgcaaaaa agggaataag ggcgacacgg 10260
aaatgttgaa tactcatacg cttccttttt caatagtatt gaagcattta tcagggttat 10320
tgtctcggga gcgaatacat atttgaatgt atttagaaaa a 10361

<210> SEQ ID NO 11
<211> LENGTH: 11545
<212> TYPE: DNA
<213> ORGANISM: Artificial Sequence
<220> FEATURE:
<223> OTHER INFORMATION: Synthetic ubiquitous and Plexin D1 inducible gene switch expressing tPA

<400> SEQUENCE: 11
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gccctaggac gaaaggaggt cgtgaaatgg ataaaaaaat 180
acagcgtttt tcatgtacaa ctatactagt tgtagtgcct aaataatgct tttaaaactt 240
aaaaataatc aatgtcctca gcggggtgtc ggggatttag gtgacactat aggctgagcg 300
ccgcacaggc atctagaggc tatggcaggg cctgccgccc cgacgttggc tgcgagccct 360
gggccttcac ccgaacttgg ggggtggggt ggggaaaagg aagaaacgcg ggcgtattgg 420

-continued

```
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg ggctctcca    2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggggttgaaca  2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag gggcgctgt    2820
```
cgtggggggt gaagccgggg ccggggctgt cgccgtcgcc cagcatgtcc aggtcgaagt 2880
cgtccagggc gtcggcgtgg gccatggcca cgtcctcgcc gtccaggtgc agctcgtcgc 2940
ccaggctcac gtcggtgggg ggggccacct tccttttctt cttggggccc atggtggcca 3000
attgcccccc cccccccccg catgccgtct aacaaaaaag ccaaaaacgg ccagaattta 3060
gcggacaatt tactagtcta acactgaaaa ttacatattg acccaaatga ttacatttca 3120
aaaggtgcct aaaaaacttc acaaaacaca ctcgccaacc ccgagcgcac gtacccagcc 3180
cagcagcccg ctactcacca agtgacgatc acagcgatcc acaaacaaga accgcgaccc 3240
aaatcccggc tgcgacggaa ctagctgtgc cacacccggc gcgtccttat ataatcatcg 3300
gcgttcaccg ccccacggag atccctccgc agaatcgccg agaagggact acttttcctc 3360
gcctgttccg ctctctggaa agaaaaccag tgccctagag tcacccaagt cccgtcctaa 3420
aatgtccttc tgctgatact ggggttctaa ggccgagtct tatgagcagc gggccgctgt 3480
cctgagcgtc cgggcggaag gatcaggacg ctcgctgcgc ccttcgtctg acgtggcagc 3540
gctcgccgtg aggagggggg cgcccgcggg aggcgccaaa acccggcgcg gaggccctcg 3600
agtaggcgag accaatgggt gcgccatggg ctcttccaaa aatttaggtg acactatagg 3660
gcaccgctcg cacctgcgca caggcccgcg gctacaaact acgaacgatc attctagata 3720
ccacatttgt agaggtttta cttgctttaa aaaacctccc acatctcccc ctgaacctga 3780
aacataaaat gaatgcaaat gttttattaa cttgtttatt gcagcttata atggttacaa 3840
attaagcaat agcatcacaa atttcacaaa ttaagcattt ttttcactgc attctagttg 3900
tggtttgtcc aaactcatca atgtatctta tcatgtctaa tcgattcaca ggttggtggg 3960
gctctccagg atgggggggg gctgggtgtg gctcatgtcg gccacgtccc aaatctcctc 4020
caggaagggg ggcagcttcc tgttcttcag cttcaggctg atacacatat tgctgttctg 4080
cattcccagg gtcctcagct cgctcaggat gctcaggatc ttgccgtaga tcacgctgct 4140
cctggcgctg ccgctcagct ggttcaggat gtagatcctc agggtgttca ggtagtacct 4200
ctggatctcc tccaccagct ggggctgctc caggccgggc ctgtcgctga agatcaccac 4260
ggcggtcagc agggcgtagt ggatgttgtc cagggccatg ctgtacatac atctgcagaa 4320
gtgcaggagg tcctcgatca cctcggccat gccagccttc ctgtagttgt ccctggtgta 4380
agcctggttg ttggcgaaca ggatgctgtc gctggcggcg tcgtacctcc tggccaccct 4440
cagcatcatc acctcgctgc tgcaagcctt cagcagggtg atctggtcgg gctggctgat 4500
cttggcgaat ccgggcaggc ccttggcgaa ctccacgatc agctgcacgg tcaggatggt 4560
catctcggtg atctgcctga agggggtgtc gctctcctcg ttctcgtcgt cggcctgctg 4620
ccaggtctgg gtgatccttt tcaggtcctc gtcgctgggc tgctcgtagc cgtcctgata 4680
ccagatcagc ctggcgatca ggaactgctg gttggcggtc agctggggga tgttcttctg 4740
cctgttggtc accagcagct tgtcgctcag gaacctgggc acgacctcgt gaatcctggc 4800
ggcctcgggg gggggggct cgcactgcat gatgggggc atgtggtcat cgacggtggt 4860
ggtgctcacg ggcagcttgt ccttctcctt ctgggccttc ttctccttcc ttttcatggc 4920
gcactgggtc tcgggcacca cgcactcggg cctgatcccg ggaaactcgg ggctcacggt 4980
cagctgcctc tggcccttgt tgctgctctc ctcgctgctg ctggtggcgc tgatcctgtg 5040
ctgcctcagg gtcaggggca tgtcggtctc cacgctggcc agcctgtcgg tcacggcgtc 5100
cttgttcacg ttgtcctgca cgaacaggcc ggtcagcagg gccttgatgt cttgcaggct 5160

```
gtccatcttc aggatcatgt ccaggtcctc cctggggaag atcagcagga acagctgctc   5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc cccccccccg catgccccgg aggcggcggg   5460
aggcgggggg cgggtccggg ccacgatgcg cttcctgccc gcgccagccg cccccgaccc   5520
cggcgtccgg gcccggatca gcctcgccgc gcagtccggg ggcggggcgg gggcggctcc   5580
gctgcggaca cgccctcact ccccgccccg gccccgcccg cccccggaac ccccgcctgc   5640
ccctggccgc cctgggccac gccccgccgt ccgcgggtcc cgccgcccgc gccctccagg   5700
acccgcccgc ggccccaggg tccctccccg tagccgccgc cgccgtcgct cgctctcctc   5760
gctctttcct cccacttggc cgcttggcct gcctcgctcg cgcctgtttt ctcttttccg   5820
ccctctcccc caccccgcct ctccctctct ctgtgtctct cggtctctgc gcctctccgc   5880
ctctgtcccc accccaaact ccgcgcgtgt ggcgcttctc cgggttctgc ctctgcttct   5940
ccttctccct ccgactccgc ttcgctctcc agtccctggc agccccgccc ccggcccttt   6000
ctagtctcct tctctctcct gctccgtttt tccgtccctg acgctcgctc cctctctccg   6060
tggctccctc tgcctccccc tcggaccctc cgtccctctc tcggtccctc tgagctcccc   6120
tttccttctc cctctgcctt cccgaaccct gtgtctcccc tccacactca gcctccctcc   6180
accacctttc tcaggcactg tccaggcctt cgctcctcga gtggtaatac aatggccggt   6240
tcccatggac ctgcatcgtg gtgtaactat aacggtccta aggtagcgac cgcggagact   6300
aggtgtattt atctaagcga tcgcttaatt aaggccggcc gccgcaataa aatatcttta   6360
ttttcattac atctgtgtgt tggttttttg tgtgaatcca tagtactaac atacgctctc   6420
catcaaaaca aaacgaaaca aaacaaacta gcaaaatagg ctgtccccag tgcaagtcca   6480
ggtgccagaa catttctcta tccataatgc aggggtaccg ggtgatgacg gtgaaaacct   6540
ccaattgcgg agtactgtcc tccgagcgga gtactgtcct ccgagcggag tactgtcctc   6600
cgagcggagt actgtcctcc gagcggagta ctgtcctccg agcggagtac tgtcctccga   6660
gcggagagtc cccggggacc tagagggtat ataatgggtg ccttagctgg tgtgtgacct   6720
catcttcctg tacgcccctg caggggcgcg ccacgcgtcg aagaaggtga gtaatcttaa   6780
catgctcttt tttttttttt ttgctaatcc cttttgtgtg ctgatgttag gatgacattt   6840
acaacaaatg tttgttcctg acaggaaaaa ccttgctggg taccttcgtt gccggacact   6900
tcttgtcctc tactttggaa aaaaggaatt gagagccgct agcgccacca tggatgcaat   6960
gaagcggggg ctctgctgtg tgctgctgct gtgtggagca gtgttcgttt cgcccagcca   7020
ggaaatccat gcccgattca gaaggggcgc aagaagctac caagtgatct gccgggatga   7080
aaaaacgcag atgatatacc agcaacatca gtcatggctg cgccctgtgc tcagaagcaa   7140
ccgggtggag tattgctggt gcaacagtgg cagggcacag tgccacagcg tccctgtcaa   7200
aagttgcagc gagccaaggt gtttcaacgg gggcacctgt cagcaggccc tgtacttctc   7260
agatttcgtg tgccagtgcc ccgaaggatt tgctgggaag tgctgtgaaa tagataccag   7320
ggccacctgt tacgaggacc agggcatcag ctacaggggc acctggagca cagcggagag   7380
tggcgctgag tgtaccaact ggaacagcag cgcgttggcc cagaagccct acagcgggcg   7440
gaggccagat gccatcagac tcggcctggg gaaccacaac tactgccgga acccagatcg   7500
agactcaaag ccctggtgct acgtctttaa ggcggggaag tacagctcag agttctgctc   7560
```

```
caccccctgcc tgctctgagg gaaacagtga ctgctacttt gggaatgggt cagcctaccg   7620
tggcacgcac agcctcaccg agtcgggtgc ctcctgcctc ccgtggaaca gcatgatcct   7680
gataggcaat gtttacacag cacagaaccc cagtgcccag gcactgggcc tgggcaaaca   7740
taattactgc cggaatcctg atggggatgc caagccctgg tgccacgtcc tgaagaaccg   7800
caggctgacg tgggagtatt gcgatgtgcc cagctgctcc acctgtggcc tgagacagta   7860
cagccagcct cagtttcgca tcaaaggcgg cctgttcgcc gacatcgcct cccacccctg   7920
gcaggctgcc atctttgcca agcacaggag gtcgcccgga gagcggttcc tgtgcggggg   7980
catactcatc agctcctgct ggattctctc tgccgcccac tgcttccagg agaggtttcc   8040
gccccaccac ctgacggtga tcttgggcag aacataccgg gtggtccctg gcgaggagga   8100
gcagaaattt gaagtcgaaa aatacattgt ccataaggag ttcgatgatg acacttacga   8160
caatgacatt gcgctgctgc aactgaaatc ggattcgtcc cgctgtgccc aggagagcag   8220
cgtggtcaga accgtgtgcc ttccccccggc ggacctccag ctgccggact ggacggagtg   8280
tgagctgtcc ggctacggca agcatgaggc cctgtctcct ttctattcgg agcggctgaa   8340
ggaggctcat gtcagactgt acccatccag ccgctgcaca tcacaacatt tacttaacag   8400
aacagtcacc gacaacatgc tgtgtgctgg agacactcgg agcggcggcc cccaggcaaa   8460
cttgcacgac gcctgccagg gcgattcggg aggccccctg gtgtgtctga acgatggccg   8520
catgactttg gtgggcatca tcagctgggg cctgggctgt ggacagaagg atgtgcccgg   8580
cgtgtacacc aaggttacca actacctaga ctggattcgt gacaacatgc gaccgtgaat   8640
cgattgcgca aagctttcgc gataggcgag accaatgggt gtgtacgtag cggccgcgtc   8700
gacgatagct tgatgggtgg catccctgtg acccctcccc agtgcctctc ctggccctgg   8760
aagttgccac tccagtgccc accagccttg tcctaataaa attaagttgc atcattttgt   8820
ctgactaggt gtccttctat aatattatgg ggtggagggg ggtggtatgg agcaaggggc   8880
aagttgggaa gacaacctgt agggcctgcg gggtctattg ggaaccaagc tggagtgcag   8940
tggcacaatc ttggctcact gcaatctccg cctcctgggt tcaagcgatt ctcctgcctc   9000
agcctcccga gttgttggga ttccaggcat gcatgaccag gctcagctaa tttttgtttt   9060
tttggtagag acggggtttc accatattgg ccaggctggt ctccaactcc taatctcagg   9120
tgatctaccc accttggcct cccaaattgc tgggattaca ggcgtgaacc actgctccct   9180
tccctgtcct tctgatttta aaataactat accagcagga ggacgtccag acacagcata   9240
ggctacctgg ccatgcccaa ccggtgggac atttgagttg cttgcttggc actgtcctct   9300
catgcgttgg gtccactcag tagatgcctg ttgaattctg atttaaatcg gtccgcgtac   9360
ggcgtggtag gtccgaacga atccatggat taccctgtta tccctactca aggacatcat   9420
ccctttagtg agggttaatt cacgcagtgg gtacggaact aaaggcagca cacatcgtgt   9480
aatcatggtc atagctgttt cctgtgtgaa attgttatcc gctacgtctc tccccccgcag   9540
taagggctag attaactcgt ctcgtgaata tccggaactc cctttagtga gggttaattg   9600
cgttgcgctc actgcccgct ttccagtcgg gaaacctgtc gtgccagctt aatcatggtc   9660
atagctgttt cctgtgtgaa attgttatcc gctaccggaa acgcttcctt catgtgagca   9720
aaaggccagc aaaaggccag gaaccgtaaa aaggccgcgt tgctggcgtt tttccatagg   9780
ctccgccccc ctgacgagca tcacaaaaat cgacgctcaa gtcagaggtg gcgaaacccg   9840
acaggactat aaagatacca ggcgtttccc cctggaagct ccctcgtgcg ctctcctgtt   9900
```

-continued ccgaccctgc cgcttaccgg atacctgtcc gcctttctcc cttcgggaag cgtggcgctt 9960
tctcatagct cacgctgtag gtatctcagt tcggtgtagg tcgttcgctc caagctgggc 10020
tgtgtgcacg aaccccccgt tcagcccgac cgctgcgcct tatccggtaa ctatcgtctt 10080
gagtccaacc cggtaagaca cgacttatcg ccactggcag cagccactgg taacaggatt 10140
agcagagcga ggtatgtagg cggtgctaca gagttcttga agtggtggcc taactacggc 10200
tacactagaa gaacagtatt tggtatctgc gctctgctga agccagttac cttcggaaaa 10260
agagttggta gctcttgatc cggcaaacaa accaccgctg gtagcggtgg tttttttgtt 10320
tgcaagcagc agattacgcg cagaaaaaaa ggatctcaag aagatccttt gatcttttct 10380
acggggtctg acgctcagtg gaacgaaaac tcacgttaag ggattttggt catgatctat 10440
gtcgggtgcg gagaaagagg taatgaaatg gcatacgagt aaacttggtc tgacaccgct 10500
gcatgagatt atcaaaaagg atcttcacct agatcctttt aaattaaaaa tgaagtttta 10560
aatcaatcta aagtatatat gagtaaactt ggtctgacag ttaccaatgc ttaatcagtg 10620
aggcacctat ctcagcgatc tgtctatttc gttcatccat agttgcctga ctccccgtcg 10680
tgtagataac tacgatacgg gagggcttac catctggccc cagtgctgca atgataccgc 10740
gagacccacg ctcaccggct ccagatttat cagcaataaa ccagccagcc ggaagcgccg 10800
agcgcagaag tggtcctgca actttatccg cctccatcca gtctattaac tgttgccggg 10860
aagctagagt aagtagttcg ccagttaata gtttgcggag cgttgttgcc attgctacag 10920
gcatcgtggt gtcacgctcg tcgtttggta tggcttcatt cagctccggt tcccaacgat 10980
caaggcgagt tacatgatcc cccatgttgt gcaaaaaagc ggttagctcc ttcggtcctc 11040
cgatggttgt cagaagtaag ttggccgcag tgttatcact catggttatg gcagcactgc 11100
ataattctct tactgtcatg ccatccgtaa gatgcttttc tgtgactggt gagtattcaa 11160
ccaagtcatt ctgagaatag tgtatgcggc gaccgagttg ctcttgcccg gcgtcaatac 11220
gggataatac cgcgccacat agcagaactt taaaagtgct catcattggg aagcgttctt 11280
cggggcgaaa actctcaagg atcttaccgc tgttgagatc cagttcgatg taacccacac 11340
gagcacccaa ctgatcttca gcatctttta ctttcaccag cgtttctggg tgagcaaaaa 11400
caggaaggca aaatgccgca aaaaagggaa taagggcgac acggaaatgt tgaatactca 11460
tacgcttcct ttttcaatag tattgaagca tttatcaggg ttattgtctc gggagcgaat 11520
acatatttga atgtatttag aaaaa 11545

<210> SEQ ID NO 12
<211> LENGTH: 10207
<212> TYPE: DNA
<213> ORGANISM: Artificial Sequence
<220> FEATURE:
<223> OTHER INFORMATION: Synthetic NxcI cardomyocyte promoter hypoxia inducible gene switch expressing EPO

<400> SEQUENCE: 12
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gccctaggac gaaaggaggt cgtgaaatgg ataaaaaaat 180
acagcgtttt tcatgtacaa ctatactagt tgtagtgcct aaataatgct tttaaaactt 240
aaaaataatc aatgtcctca gcggggtgtc ggggatttag gtgacactat aggctgagcg 300
ccgcacaggc atctagaggc tatggcaggg cctgccgccc cgacgttggc tgcgagccct 360

-continued

```
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa cctttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca    2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
```

```
cggtgaacat ctgctcgaac tcgaagtcgg ccatgtccag ggcgccgtag ggggcgctgt   2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccccag tatgatgcct tctctaaatt taccagaaag   3060
aaaggacctg ggatgcttgt cctttaagtg tctctaaaca tggtttgcat agctggatct   3120
cagcttatct gtgcctttcg gctttcgctt ccatacatgg atctgttccc aacagtaact   3180
ccaagctgtc gaaaagaagc tatctggcag ctctctgctt catccaacac atggatgata   3240
aaaatacaca tatagcgatt cttccctcga gtaggcgaga ccaatgggtg cgccatgggc   3300
tcttccaaaa atttaggtga cactataggg caccgctcgc acctgcgcac aggcccgcgg   3360
ctacaaacta cgaacgatca ttctagatac cacatttgta gaggttttac ttgctttaaa   3420
aaacctccca catctccccc tgaacctgaa acataaaatg aatgcaaatg ttttattaac   3480
ttgtttattg cagcttataa tggttacaaa ttaagcaata gcatcacaaa tttcacaaat   3540
taagcatttt tttcactgca ttctagttgt ggtttgtcca aactcatcaa tgtatcttat   3600
catgtctaat cgattcacag gttggtgggg ctctccagga tggggggggg ctgggtgtgg   3660
ctcatgtcgg ccacgtccca aatctcctcc aggaaggggg gcagcttcct gttcttcagc   3720
ttcaggctga tacacatatt gctgttctgc attcccaggg tcctcagctc gctcaggatg   3780
ctcaggatct tgccgtagat cacgctgctc ctggcgctgc cgctcagctg gttcaggatg   3840
tagatcctca gggtgttcag gtagtacctc tggatctcct ccaccagctg gggctgctcc   3900
aggccgggcc tgtcgctgaa gatcaccacg gcggtcagca gggcgtagtg gatgttgtcc   3960
agggccatgc tgtacataca tctgcagaag tgcaggaggt cctcgatcac ctcggccatg   4020
ccagccttcc tgtagttgtc cctggtgtaa gcctggttgt tggcgaacag gatgctgtcg   4080
ctggcggcgt cgtacctcct ggccaccctc agcatcatca cctcgctgct gcaagccttc   4140
agcagggtga tctggtcggg ctggctgatc ttggcgaatc cgggcaggcc cttggcgaac   4200
tccacgatca gctgcacggt caggatggtc atctcggtga tctgcctgaa gggggtgtcg   4260
ctctcctcgt tctcgtcgtc ggcctgctgc caggtctggg tgatcctttt caggtcctcg   4320
tcgctgggct gctcgtagcc gtcctgatac cagatcagcc tggcgatcag gaactgctgg   4380
ttggcggtca gctgggggat gttcttctgc ctgttggtca ccagcagctt gtcgctcagg   4440
aacctgggca cgacctcgtg aatcctggcg gcctcggggg ggggggctc gcactgcatg   4500
atggggggca tgtggtcatc gacggtggtg gtgctcacgg gcagcttgtc cttctccttc   4560
tgggccttct tctccttcct tttcatggcg cactgggtct cgggcaccac gcactcgggc   4620
ctgatcccgg gaaactcggg gctcacggtc agctgcctct ggcccttgtt gctgctctcc   4680
tcgctgctgc tggtggcgct gatcctgtgc tgcctcaggg tcaggggcat gtcggtctcc   4740
acgctggcca gcctgtcggt cacggcgtcc ttgttcacgt tgtcctgcac gaacaggccg   4800
gtcagcaggg ccttgatgtc ttgcaggctg tccatcttca ggatcatgtc caggtcctcc   4860
ctggggaaga tcagcaggaa cagctgctcc agcctctcca gcctgctctc cacctcggtc   4920
aggtgggccc tggtcagggg gctcctcttg gtcttggggc tgtatctgca ctcccagttg   4980
ttcttcaggc acttggcgca cttgggcttc tccttgctgc acttcagctt cttcagcctg   5040
cagatgtcgc aagcctgctc gatgctgctc agcagcttca tggtggccaa ttgccccccc   5100
```

```
ccccccccgc atgcacagga agatgagctc acacaccagc taaggcaccc attatatacc   5160
ctctaggtct tcgcggacgt gcgggaaccc acgtgggggc tccgtcacgt actccgagtc   5220
ccgcacgcac tcagcgtcgc tctggggccc cacgtccggc cctgacgtgc ggcttcgttt   5280
gtcacgtcgc ggacgtgcgg gaacccacgt gggggctccg tcacgtactc cgagtcccgc   5340
acgcactcag cgtcgctctg gggccccacg tccggccctg acgtgcggct tcgtttgtca   5400
cgtcgcggac gtgcgggaac ccacgtgggg gctccgtcac gtactccgag tcccgcacgc   5460
actcagcgtc gctctggggc cccacgtccg gccctgacgt gcggcttcgt ttgtcacgtc   5520
gcggacgtgc gggaacccac gtgggggctc cgtcacgtac tccgagtccc gcacgcactc   5580
agcgtcgctc tggggcccca cgtccggccc tgacgtgcgg cttcgtttgt cacgtcgcgg   5640
acgtgcggga acccacgtgg gggctccgtc acgtactccg agtcccgcac gcactcagcg   5700
tcgctctggg gccccacgtc cggccctgac gtgcggcttc gtttgtcacg tcgcggacgt   5760
gcgggaaccc acgtgggggc tccgtcacgt actccgagtc ccgcacgcac tcagcgtcgc   5820
tctggggccc cacgtccggc cctgacgtgc ggcttcgttt gtcacgtcgc ggacgtgcgg   5880
gaacccacgt gggggctccg tcacgtactc cgagtcccgc acgcactcag cgtcgctctg   5940
gggccccacg tccggccctg acgtgcggct tcgtttgtca cgtcctcgag tggtaataca   6000
atggccggtt cccatggacc tgcatcgtgg tgtaactata acggtcctaa ggtagcgacc   6060
gcggagacta ggtgtattta tctaagcgat cgcttaatta aggccggccg ccgcaataaa   6120
atatctttat tttcattaca tctgtgtgtt ggttttttgt gtgaatccat agtactaaca   6180
tacgctctcc atcaaaacaa aacgaaacaa aacaaactag caaaataggc tgtccccagt   6240
gcaagtccag gtgccagaac atttctctat ccataatgca ggggtaccgg gtgatgacgg   6300
tgaaaacctc caattgcgga gtactgtcct ccgagcggag tactgtcctc cgagcggagt   6360
actgtcctcc gagcggagta ctgtcctccg agcggagtac tgtcctccga gcggagtact   6420
gtcctccgag cggagagtcc ccggggacct agagggtata taatgggtgc cttagctggt   6480
gtgtgacctc atcttcctgt acgcccctgc aggggcgcgc cacgcgtcga agaaggtgag   6540
taatcttaac atgctctttt tttttttttt tgctaatccc ttttgtgtgc tgatgttagg   6600
atgacattta caacaaatgt ttgttcctga caggaaaaac cttgctgggt accttcgttg   6660
ccggacactt cttgtcctct actttggaaa aaaggaattg agagccgcta gcgccaccat   6720
gggggtgcat gaatgtcctg cctggctgtg gcttctcctg tccctgctgt cgctccctct   6780
gggcctccca gtcctgggcg ctccaccacg cctcatctgt gacagccgag tcctggagag   6840
atacctgttg gaggccaagg aagccgagaa tatcacgacg ggctgtgctg aacactgctc   6900
cttgaatgag aatatcactg tcccagacac caaagttaat ttctatgcct ggaagcggat   6960
ggaggtcggg cagcaggccg tagaagtctg gcagggcctg gccctgctgt cggaagctgt   7020
cctgcggggc caggccctgt tggtcaacag cagccagccg tgggagcccc tgcaactgca   7080
tgtggataaa gccgtcagtg gccttcgcag cctcaccact ctgcttcggg ctctgcgagc   7140
ccagaaggaa gccatctccc ctccagatgc ggccagcgcc gctccactcc gaacaatcac   7200
tgctgacact ttccgcaaac tgttccgagt ctactccaat ttcctccggg gaaagctgaa   7260
gctgtacaca ggggaggctt gcaggacagg ggacagatga atcgattgcg caaagctttc   7320
gcgataggcg agaccaatgg gtgtgtacgt agcggccgcg tcgacgatag cttgatgggt   7380
ggcatccctg tgacccctcc ccagtgcctc tcctggccct ggaagttgcc actccagtgc   7440
ccaccagcct tgtcctaata aaattaagtt gcatcatttt gtctgactag gtgtccttct   7500
```

```
ataatattat ggggtggagg ggggtggtat ggagcaaggg gcaagttggg aagacaacct   7560
gtagggcctg cggggtctat tgggaaccaa gctggagtgc agtggcacaa tcttggctca   7620
ctgcaatctc cgcctcctgg gttcaagcga ttctcctgcc tcagcctccc gagttgttgg   7680
gattccaggc atgcatgacc aggctcagct aatttttgtt tttttggtag agacggggtt   7740
tcaccatatt ggccaggctg gtctccaact cctaatctca ggtgatctac ccaccttggc   7800
ctcccaaatt gctgggatta caggcgtgaa ccactgctcc cttccctgtc cttctgattt   7860
taaaataact ataccagcag gaggacgtcc agacacagca taggctacct ggccatgccc   7920
aaccggtggg acatttgagt tgcttgcttg gcactgtcct ctcatgcgtt gggtccactc   7980
agtagatgcc tgttgaattc tgatttaaat cggtccgcgt acggcgtggt aggtccgaac   8040
gaatccatgg attaccctgt tatccctact caaggacatc atccctttag tgagggttaa   8100
ttcacgcagt gggtacggaa ctaaaggcag cacacatcgt gtaatcatgg tcatagctgt   8160
ttcctgtgtg aaattgttat ccgctacgtc tctcccccgc agtaagggct agattaactc   8220
gtctcgtgaa tatccggaac tccctttagt gagggttaat tgcgttgcgc tcactgcccg   8280
ctttccagtc gggaaacctg tcgtgccagc ttaatcatgg tcatagctgt ttcctgtgtg   8340
aaattgttat ccgctaccgg aaacgcttcc ttcatgtgag caaaaggcca gcaaaaggcc   8400
aggaaccgta aaaaggccgc gttgctggcg tttttccata ggctccgccc ccctgacgag   8460
catcacaaaa atcgacgctc aagtcagagg tggcgaaacc cgacaggact ataaagatac   8520
caggcgtttc cccctggaag ctccctcgtg cgctctcctg ttccgaccct gccgcttacc   8580
ggatacctgt ccgcctttct cccttcggga agcgtggcgc tttctcatag ctcacgctgt   8640
aggtatctca gttcggtgta ggtcgttcgc tccaagctgg gctgtgtgca cgaacccccc   8700
gttcagcccg accgctgcgc cttatccggt aactatcgtc ttgagtccaa cccggtaaga   8760
cacgacttat cgccactggc agcagccact ggtaacagga ttagcagagc gaggtatgta   8820
ggcggtgcta cagagttctt gaagtggtgg cctaactacg gctacactag aagaacagta   8880
tttggtatct gcgctctgct gaagccagtt accttcggaa aaagagttgg tagctcttga   8940
tccggcaaac aaaccaccgc tggtagcggt ggtttttttg tttgcaagca gcagattacg   9000
cgcagaaaaa aaggatctca agaagatcct ttgatctttt ctacggggtc tgacgctcag   9060
tggaacgaaa actcacgtta agggattttg gtcatgatct atgtcgggtg cggagaaaga   9120
ggtaatgaaa tggcatacga gtaaacttgg tctgacaccg ctgcatgaga ttatcaaaaa   9180
ggatcttcac ctagatcctt ttaaattaaa aatgaagttt taaatcaatc taaagtatat   9240
atgagtaaac ttggtctgac agttaccaat gcttaatcag tgaggcacct atctcagcga   9300
tctgtctatt tcgttcatcc atagttgcct gactccccgt cgtgtagata actacgatac   9360
gggagggctt accatctggc cccagtgctg caatgatacc gcgagaccca cgctcaccgg   9420
ctccagattt atcagcaata aaccagccag ccggaagcgc cgagcgcaga agtggtcctg   9480
caactttatc cgcctccatc cagtctatta actgttgccg ggaagctaga gtaagtagtt   9540
cgccagttaa tagtttgcgg agcgttgttg ccattgctac aggcatcgtg gtgtcacgct   9600
cgtcgtttgg tatggcttca ttcagctccg gttcccaacg atcaaggcga gttacatgat   9660
cccccatgtt gtgcaaaaaa gcggttagct ccttcggtcc tccgatggtt gtcagaagta   9720
agttggccgc agtgttatca ctcatggtta tggcagcact gcataattct cttactgtca   9780
tgccatccgt aagatgcttt tctgtgactg gtgagtattc aaccaagtca ttctgagaat   9840
```

-continued agtgtatgcg gcgaccgagt tgctcttgcc cggcgtcaat acgggataat accgcgccac 9900
atagcagaac tttaaaagtg ctcatcattg ggaagcgttc ttcggggcga aaactctcaa 9960
ggatcttacc gctgttgaga tccagttcga tgtaacccac acgagcaccc aactgatctt 10020
cagcatcttt tactttcacc agcgtttctg ggtgagcaaa aacaggaagg caaaatgccg 10080
caaaaaaggg aataagggcg acacggaaat gttgaatact catacgcttc ctttttcaat 10140
agtattgaag catttatcag ggttattgtc tcgggagcga atacatattt gaatgtattt 10200
agaaaaa 10207

<210> SEQ ID NO 13
<211> LENGTH: 16979
<212> TYPE: DNA
<213> ORGANISM: Artificial Sequence
<220> FEATURE:
<223> OTHER INFORMATION: Synthetic ubiquitous+ hPlexin D1 + hypoxia
inducible gene switch construct expressing relaxin and HGF

<400> SEQUENCE: 13
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gcgggtgtcg gggatttagg tgacactata ggctgagcgc 180
cgcacaggca tctagaggct atggcagggc ctgccgcccc gacgttggct gcgagccctg 240
ggccttcacc cgaacttggg gggtggggtg gggaaaagga agaaacgcgg gcgtattggc 300
cccaatgggg tctcggtggg gtatcgacag agtgccagcc ctgggaccga accccgcgtt 360
tatgaacaaa cgacccaaca ccgtgcgttt tattctgtct ttttattgcc gtcatagcgc 420
gggttccttc cggtattgtc tccttccgtg tttcaatcga tttagaagaa ctcgtcaaga 480
aggcgataga aggcgatgcg ctgcgaatcg gggcggcga taccgtaaag gacgaggaag 540
cggtcagccc attcgccgcc aagttcttca gcaatatcac gggtagccaa cgctatgtcc 600
tgatagcggt cggccacacc cagccgtcca cagtcgatga atccagaaaa gcggccattt 660
tccaccatga tattcggcaa gcaggcatcg ccgtgggtca cgacgagatc ctcgccgtcg 720
ggcatcctcg ccttgagcct ggcgaacagt tcggctggcg cgagcccctg atgctcctcg 780
tccagatcat cctgatcgac aagaccggct tccatccgag tacgtgctcg ctcgatgcga 840
tgtttcgctt ggtggtcgaa tgggcatgta gccggatcaa gcgtatgcag ccgccgcatt 900
gcatcagcca tgatggatac tttctcggca ggagcaaggt gagatgacag gagatcctgc 960
cccggcactt cgcccaatag cagccagtcc cttcccgctt cagtgacaac gtcgagcacg 1020
gctgcgcaag gaacgcccgt cgtggccagc cacgatagcc gcgctgcctc gtcctggagt 1080
tcattcaggg caccggacag gtcggtcttg acaaaaagaa ccgggcgccc ctgcgctgac 1140
agccggaaca cggcggcatc agagcagccg attgtctgtt gtgcccagtc atagccgaat 1200
agcctctcca cccaagcggc cggagaacca gcgtgcaatc catcttgttc aatggccgat 1260
cccatggtgg ccaattgggt gtctgagcga tgtggctcgg ctggcgacgc aaaagaagat 1320
gcggctgact gtcgaacagg aggagcagag agcgaagcgg gaggctgcgg gctcaatttg 1380
catgcggaat agctctgagg ccgaggcagc ttcggcctct gcataaataa aaaaaattag 1440
tcagccatgg ggcggagaat gggcggaact gggcggagtt aggggcggga tgggcggagt 1500
taggggcggg actatggttg ctgactaatt gagatgcttg ctttgcatac ttctgcctgc 1560
tggggagcct ggggactttc cacacctggt tgctgactaa ttgagatgct tgctttgcat 1620

-continued

```
acttctgcct gctggggagc ctggggactt tccacaccct aacctcgagg ccatcgtggc   1680
acgccagggt tttcccagtc acgacgttgt aaaacgacgg ccagtgctct tctcccccgc   1740
gggaggtttt ataaatccga ctgtctagat tgttgttaaa tcacacaaaa aaccaacaca   1800
cagatgtaat gaaaataaag atattttatt atcgattcag ctgtcgctgg ggctctccag   1860
catctccatc aggaaggtgt cgatgggcac gtcgccgatc agcctgaaga agaacaggtg   1920
ctccaggcac ttcaggccga tgctcctcag gctgggcagc ctcagcagca gcttggcgaa   1980
tctgccgggc tcgtcggggt gggtggtcct ggtgtactcc tccagggcgg cgtacacctt   2040
ctccctcagc agctccacct cctgggcgct tttcaggccc ctcacctcgg ggttgaacag   2100
gatgatggcc ctcaggcagc ccagctcggt cttgtccatc ctcatgtccc tcatcttgct   2160
caccagctcg gtcagcaccc tgtcgaagat ggcgcccact ccggcgctgt gggcgctgtt   2220
cctatggacg tgcaggccgg tggccagcag gatgccgtcc ctcacgtcga tgctcctgtg   2280
gctgaagctg gcgatcagca gctcgttcca tccggccctc agcaggatca cctggtcgtc   2340
caggggcagg ctgctgaagt ggggaatcct cttggcccac tccaccaggg tgaacagctg   2400
cttgtcggcg gcctggcaga tgttggtcac ggggtcgttg gggctgctgc cgctgccgcc   2460
ggttccgccg gggccctcca cgccctggtc gcttttctgc tccacggcga gttcggcctc   2520
cagaatcctg tccacgggca tctccatatg gccgccgtac tcgtcgatgc ccagggcgtc   2580
ggtgaacatc tgctcgaact cgaagtcggc catgtccagg gcgccgtagg gggcgctgtc   2640
gtggggggtg aagccggggc cggggctgtc gccgtcgccc agcatgtcca ggtcgaagtc   2700
gtccagggcg tcggcgtggg ccatggccac gtcctcgccg tccaggtgca gctcgtcgcc   2760
caggctcacg tcggtggggg gggccacctt cctttcttc ttggggccca tggtggccaa   2820
ttgccccccc cccccccgc atgccgtcta acaaaaaagc caaaaacggc cagaatttag   2880
cggacaattt actagtctaa cactgaaaat tacatattga cccaaatgat tacatttcaa   2940
aaggtgccta aaaaacttca caaaacacac tcgccaaccc cgagcgcacg tacccagccc   3000
agcagcccgc tactcaccaa gtgacgatca cagcgatcca caaacaagaa ccgcgaccca   3060
aatcccggct gcgacggaac tagctgtgcc acacccggcg cgtccttata taatcatcgg   3120
cgttcaccgc cccacggaga tccctccgca gaatcgccga gaagggacta cttttcctcg   3180
cctgttccgc tctctggaaa gaaaaccagt gccctagagt cacccaagtc ccgtcctaaa   3240
atgtccttct gctgatactg gggttctaag gccgagtctt atgagcagcg ggccgctgtc   3300
ctgagcgtcc gggcggaagg atcaggacgc tcgctgcgcc cttcgtctga cgtggcagcg   3360
ctcgccgtga ggaggggggc gcccgcggga ggcgccaaaa cccggcgcgg aggccctcga   3420
gtaggcgaga ccaatgggtg cgccatgggc tcttccaaaa atttaggtga cactataggg   3480
caccgctcgc acctgcgcac aggcccgcgg ctacaaacta cgaacgatca ttctagatac   3540
cacatttgta gaggttttac ttgctttaaa aaacctccca catctccccc tgaacctgaa   3600
acataaaatg aatgcaaatg ttttattaac ttgtttattg cagcttataa tggttacaaa   3660
ttaagcaata gcatcacaaa tttcacaaat taagcatttt tttcactgca ttctagttgt   3720
ggtttgtcca aactcatcaa tgtatcttat catgtctaat cgattcacag gttggtgggg   3780
ctctccagga tgggggggg ctgggtgtgg ctcatgtcgg ccacgtccca aatctcctcc   3840
aggaaggggg gcagcttcct gttcttcagc ttcaggctga tacacatatt gctgttctgc   3900
attcccaggg tcctcagctc gctcaggatg ctcaggatct tgccgtagat cacgctgctc   3960
ctggcgctgc cgctcagctg gttcaggatg tagatcctca gggtgttcag gtagtacctc   4020
```

-continued

```
tggatctcct ccaccagctg gggctgctcc aggccgggcc tgtcgctgaa gatcaccacg   4080
gcggtcagca gggcgtagtg gatgttgtcc agggccatgc tgtacataca tctgcagaag   4140
tgcaggaggt cctcgatcac ctcggccatg ccagccttcc tgtagttgtc cctggtgtaa   4200
gcctggttgt tggcgaacag gatgctgtcg ctggcggcgt cgtacctcct ggccaccctc   4260
agcatcatca cctcgctgct gcaagccttc agcagggtga tctggtcggg ctggctgatc   4320
ttggcgaatc cgggcaggcc cttggcgaac tccacgatca gctgcacggt caggatggtc   4380
atctcggtga tctgcctgaa gggggtgtcg ctctcctcgt tctcgtcgtc ggcctgctgc   4440
caggtctggg tgatcctttt caggtcctcg tcgctgggct gctcgtagcc gtcctgatac   4500
cagatcagcc tggcgatcag gaactgctgg ttggcggtca gctgggggat gttcttctgc   4560
ctgttggtca ccagcagctt gtcgctcagg aacctgggca cgacctcgtg aatcctggcg   4620
gcctcggggg ggggggctc gcactgcatg atggggggca tgtggtcatc gacggtggtg   4680
gtgctcacgg gcagcttgtc cttctccttc tgggccttct tctccttcct tttcatggcg   4740
cactgggtct cgggcaccac gcactcgggc ctgatcccgg gaaactcggg gctcacggtc   4800
agctgcctct ggcccttgtt gctgctctcc tcgctgctgc tggtggcgct gatcctgtgc   4860
tgcctcaggg tcaggggcat gtcggtctcc acgctggcca gcctgtcggt cacggcgtcc   4920
ttgttcacgt tgtcctgcac gaacaggccg gtcagcaggg ccttgatgtc ttgcaggctg   4980
tccatcttca ggatcatgtc caggtcctcc ctggggaaga tcagcaggaa cagctgctcc   5040
agcctctcca gcctgctctc cacctcggtc aggtgggccc tggtcagggg gctcctcttg   5100
gtcttggggc tgtatctgca ctcccagttg ttcttcaggc acttggcgca cttgggcttc   5160
tccttgctgc acttcagctt cttcagcctg cagatgtcgc aagcctgctc gatgctgctc   5220
agcagcttca tggtggccaa ttgccccccc cccccccgc atgccccgga ggcggcggga   5280
ggcggggggc gggtccgggc cacgatgcgc ttcctgcccg cgccagccgc ccccgacccc   5340
ggcgtccggg cccggatcag cctcgccgcg cagtccgggg gcggggcggg ggcggctccg   5400
ctgcggacac gccctcactc cccgccccgg ccccgcccgc ccccggaacc cccgcctgcc   5460
cctggccgcc ctgggccacg ccccgccgtc cgcgggtccc gccgcccgcg ccctccagga   5520
cccgcccgcg gccccagggt ccctccccgt agccgccgcc gccgtcgctc gctctcctcg   5580
ctctttcctc ccacttggcc gcttggcctg cctcgctcgc gcctgttttc tcttttccgc   5640
cctctccccc accccgcctc tccctctctc tgtgtctctc ggtctctgcg cctctccgcc   5700
tctgtcccca ccccaaactc cgcgcgtgtg gcgcttctcc gggttctgcc tctgcttctc   5760
cttctccctc cgactccgct tcgctctcca gtccctggca gccccgcccc cggccctttc   5820
tagtctcctt ctctctcctg ctccgttttt ccgtccctga cgctcgctcc ctctctccgt   5880
ggctccctct gcctccccct cggaccctcc gtccctctct cggtccctct gagctcccct   5940
ttccttctcc ctctgccttc ccgaaccctg tgtctcccct ccacactcag cctccctcca   6000
ccacctttct caggcactgt ccaggccttc gctcctcgag tggtaataca atggccggtt   6060
cccatggacc tgcatcgtgg tgatctatgt cgggtgcgga gaaagaggta atgaaatggc   6120
agaaatggca ccacctaagg tagcgaccgc ggagactagg tgtatttatc taagcgatcg   6180
cttaattaag gccggccgcc gcaataaaat atctttattt tcattacatc tgtgtgttgg   6240
tttttttgtgt gaatccatag tactaacata cgctctccat caaaacaaaa cgaaacaaaa   6300
caaactagca aaataggctg tccccagtgc aagtccaggt gccagaacat ttctctatcc   6360
```

```
ataatgcagg ggtaccgggt gatgacggtg aaaacctcca attgcggagt actgtcctcc   6420
gagcggagta ctgtcctccg agcggagtac tgtcctccga gcggagtact gtcctccgag   6480
cggagtactg tcctccgagc ggagtactgt cctccgagcg gagagtcccc ggggacctag   6540
agggtatata atgggtgcct tagctggtgt gtgacctcat cttcctgtac gcccctgcag   6600
gggcgcgcca cgcgtcgaag aaggtgagta atcttaacat gctctttttt tttttttttg   6660
ctaatccctt ttgtgtgctg atgttaggat gacatttaca acaaatgttt gttcctgaca   6720
ggaaaaacct tgctgggtac cttcgttgcc ggacacttct tgtcctctac tttggaaaaa   6780
aggaattgag agccgctagc gccaccatgc ctcgcctgtt ttttttccac ctgttgggag   6840
tctgtttact actgaaccaa ttttccagag cagtcgcgga ctcatggatg gaggaagtta   6900
tcaagttatg cggcagagaa ttagttcgcg cgcagattgc catttgcggc atgagcacct   6960
ggagcaaaag gtctctgagc caggaagatg ctcctcagac acctagacca gtggcagaaa   7020
ttgtgccatc cttcatcaac aaagatacag aaaccataaa tatgatgtca gaatttgttg   7080
ctaatttgcc acaggagctg aagctgaccc tgtctgagat gcagccagca ttaccacagc   7140
tacaacagca cgtccctgtg ctgaaggatt ccagcctgct gtttgaagaa tttaagaaac   7200
ttattcgcaa tagacaaagt gaagccgcag acagcagtcc ttcagagctg aagtacctgg   7260
gcttggatac tcattctcga aaaaagagac aactctacag tgcattggct aacaagtgtt   7320
gccatgttgg ttgtaccaaa agaagccttg ctagattttg ctgaatcgat tgcgcaaagc   7380
tttcgcgata ggcgagacca atgggtgtgt acgtagcggc cgcgtcgacg atagcttgat   7440
gggtggcatc cctgtgaccc ctccccagtg cctctcctgg ccctggaagt tgccactcca   7500
gtgcccacca gccttgtcct aataaaatta agttgcatca ttttgtctga ctaggtgtcc   7560
ttctataata ttatggggtg gaggggggtg gtatggagca aggggcaagt tgggaagaca   7620
acctgtaggg cctgcggggt ctattgggaa ccaagctgga gtgcagtggc acaatcttgg   7680
ctcactgcaa tctccgcctc ctgggttcaa gcgattctcc tgcctcagcc tcccgagttg   7740
ttgggattcc aggcatgcat gaccaggctc agctaatttt tgtttttttg gtagagacgg   7800
ggtttcacca tattggccag gctggtctcc aactcctaat ctcaggtgat ctacccacct   7860
tggcctccca aattgctggg attacaggcg tgaaccactg ctcccttccc tgtccttctg   7920
atttaaaat aactatacca gcaggaggac gtccagacac agcataggct acctggccat   7980
gcccaaccgg tgggacattt gagttgcttg cttggcactg tcctctcatg cgttgggtcc   8040
actcagtaga tgcctgttga attctgattt aaatcggtcc gcgtacggcg tggtaggtcc   8100
gaacgaatcc atggattacc ctgttatgtg gtcctccagg gttgccgttc cttaactata   8160
acggtcctaa ggtagcgacc gcggagacta ggtgtattta tctaagcgat cgcttaatta   8220
aggccggccg ccgcaataaa atatctttat tttcattaca tctgtgtgtt ggtttttgt   8280
gtgaatccat agtactaaca tacgctctcc atcaaaacaa aacgaaacaa aacaaactag   8340
caaaataggc tgtccccagt gcaagtccag gtgccagaac atttctctat ccataatgca   8400
ggggtaccgg gtgatgacgg tgaaaacctc caattgtgct gtatataaaa ccagtggtta   8460
tatgtacagt actgctgtat ataaaaccag tggttatatg tacagtacgt cgactgctgt   8520
atataaaacc agtggttata tgtacagtac tgctgtatat aaaaccagtg gttatatgta   8580
cagtaccccg gggacctaga gggtatataa tgggtgcctt agctggtgtg tgacctcatc   8640
ttcctgtacg cccctgcagg ggcgcgccac gcgtcgaaga aggtgagtaa tcttaacatg   8700
ctcttttttt tttttttgc taatcccttt tgtgtgctga tgttaggatg acatttacaa   8760
```
caaatgtttg ttcctgacag gaaaaacctt gctgggtacc ttcgttgccg gacacttctt 8820
gtcctctact ttggaaaaaa ggaattgaga gccgctagcg ccaccatgtg ggtgaccaaa 8880
ctcctgccag ccctgctgct ccagcacgtc ctcctgcatc tcctcctgct ccccatcgcc 8940
atcccctatg cagagggaca aaggaaaaga agaaatacaa ttcatgagtt caaaaaatca 9000
gcaaagacta ccctaatcaa aatagatcca gcactgaaga taaaaaccaa aaaagtgaat 9060
accgccgacc aatgtgctaa tagatgtact aggaacaaag gacttccatt cacttgcaag 9120
gcttttgttt ttgataaagc aagaaaacaa tgcctctggt tccccttcaa tagcatgtca 9180
agtggagtga aaaaagaatt tggccatgaa tttgacctct atgaaaacaa agactacatt 9240
agaaactgca tcattggtaa aggacgcagc tacaagggaa cagtatctat cactaagagt 9300
ggcatcaaat gtcagccctg gagttccatg ataccacacg aacacagctt tttgccttcg 9360
agctatcggg gtaaagacct acaggaaaac tactgtcgaa atcccagagg cgaagaaggg 9420
ggaccctggt gtttcacaag caatccagag gtacgctacg aagtctgtga cattcctcag 9480
tgttcagaag ttgagtgcat gacctgtaat ggggagagtt atcgaggtct catggatcat 9540
acagaatcag gcaagatttg tcagcgctgg gatcatcaga caccacaccg gcacaaattc 9600
ttgcctgaaa gataccccga caagggcttt gatgataatt attgccgcaa tcccgatggc 9660
cagccgaggc cctggtgcta tactcttgac cctcacaccc gctgggagta ttgcgcaatc 9720
aagacatgcg ctgacaatac tatgaatgac actgatgttc ctttggaaac aactgagtgc 9780
atccaaggtc aaggagaagg ctacaggggc actgtcaata ccatttggaa tggcatcccc 9840
tgtcagcgtt gggattctca gtatcctcac gagcatgaca tgactcctga aaatttcaag 9900
tgcaaggacc tacgagaaaa ttactgccga aatccagatg ggtctgaatc accctggtgt 9960
tttaccactg atccaaacat ccgagttggc tactgctccc aaattccaaa ctgtgatatg 10020
tcacatggac aagattgtta tcgtgggaat ggcaaaaatt atatgggcaa cttatcccaa 10080
acaagaagcg gactaacctg ttcaatgtgg gacaagaaca tggaggactt acatcgtcat 10140
atcttctggg aaccagatgc aagtaagctg aatgagaatt actgccgaaa tccagatgat 10200
gatgctcatg gaccctggtg ctacacggga aatccactca ttccttggga ttattgccct 10260
atttctcgtt gtgaaggtga taccacacct acaatagtca atttagacca tcccgtaata 10320
tcttgtgcca aaacgaaaca gctgcgagtt gtaaatggga ttccaacacg aacaaacata 10380
ggatggatgg ttagtttgag atacagaaac aagcatatct gcggaggatc attgataaag 10440
gagagttggg ttcttactgc acgacagtgt ttccctagca gagacttgaa agattatgag 10500
gcttggcttg gcatccacga tgtccacggc agaggcgatg agaaatgcaa acaggttctc 10560
aatgtttccc agctggtata tggccctgaa ggaagcgacc tggtgctgat gaagctggcc 10620
agacccgctg tcctggatga ttttgttagt acgattgatt tacctaatta tggatgcaca 10680
attcctgaaa agaccagttg cagtgtttat ggctggggct acactggact gattaactat 10740
gatggcctat tacgagtggc acatctctat ataatgggaa atgagaaatg cagccagcat 10800
catcgaggga aggtgactct gaatgagtct gaaatatgtg ctggggctga aaagattgga 10860
tcaggaccat gtgaggggga ttatggtggc ccacttgttt gtgagcaaca taaaatgaga 10920
atggttcttg gtgtcattgt tcctggtcgt ggatgtgcca ttccaaatcg tcctggtatt 10980
tttgtccgag tagcctacta cgccaaatgg atacacaaaa ttattttaac atataaggtg 11040
ccccagtcat agatcgattg cgcaaagctt tcgcgatagg cgagaccaat gggtgtgtac 11100

-continued

```
gtagcggccg ctcgagaact tgtttattgc agcttataat ggttacaaat aaagcaatag  11160
catcacaaat ttcacaaata aagcattttt ttcactgcat tctagttgtg gtttgtccaa  11220
actcatcaat gtatcttatc atgtctcgta cggcgtggta ggtccgaacg aatccatgga  11280
ttaccctgtt atccctactc atcttcgtcg gacgcgccgt taatatttga tcagccattc  11340
tctgtatgag tactaacgaa cgtgacgcgg tgttactggt aactatgact ctcttaaggt  11400
agccaaatac atcatccctt tagtgagggt taattcacgc agtgccgcgg cgtgtagaaa  11460
atacctatca gctcgaggac gtgacaaacg aagccgcacg tcagggccgg acgtggggcc  11520
ccagagcgac gctgagtgcg tgcgggactc ggagtacgtg acggagcccc cacgtgggtt  11580
cccgcacgtc cgcgacgtga caaacgaagc cgcacgtcag ggccggacgt ggggccccag  11640
agcgacgctg agtgcgtgcg ggactcggag tacgtgacgg agcccccacg tgggttcccg  11700
cacgtccgcg acgtgacaaa cgaagccgca cgtcagggcc ggacgtgggg ccccagagcg  11760
acgctgagtg cgtgcgggac tcggagtacg tgacggagcc cccacgtggg ttcccgcacg  11820
tccgcgacgt gacaaacgaa gccgcacgtc agggccggac gtggggcccc agagcgacgc  11880
tgagtgcgtg cgggactcgg agtacgtgac ggagccccca cgtgggttcc cgcacgtccg  11940
cgacgtgaca aacgaagccg cacgtcaggg ccggacgtgg ggccccagag cgacgctgag  12000
tgcgtgcggg actcggagta cgtgacggag cccccacgtg ggttcccgca cgtccgcgac  12060
gtgacaaacg aagccgcacg tcagggccgg acgtggggcc ccagagcgac gctgagtgcg  12120
tgcgggactc ggagtacgtg acggagcccc cacgtgggtt cccgcacgtc cgcgacgtga  12180
caaacgaagc cgcacgtcag ggccggacgt ggggccccag agcgacgctg agtgcgtgcg  12240
ggactcggag tacgtgacgg agcccccacg tgggttcccg cacgtccgcg aagacctaga  12300
gggtatataa tgggtgcctt agctggtgtg tgagctcatc ttcctgtgca tgcggggggg  12360
gggggggca attggccacc atgaaagccc tcaccgctag acaacaggaa gtgtttgacc  12420
tcatcaggga ccatatctcc cagacaggaa tgccccctac cagggccgaa atcgctcaga  12480
ggctgggatt caggagccct aacgctgccg aagaacatct gaaagccctc gccaggaagg  12540
gagtgattga gattgtgtcc ggcgcttcca ggggcattag actcctgcaa gaggaggaag  12600
aaggactccc cctcgtggga agggtcgccg ctggcgaacc cctcctggct caacaacaca  12660
ttgagggaca ctatcaggtc gatcctagcc tctttaaacc caatgccgat ttcctcctga  12720
gggtgtccgg catgagcatg aaggatattg gaatcatgga cggagacctc ctggctgtgc  12780
ataagacaca ggatgtgagg aacggacagg tcgtggtcgc caggatcgac gacgaagtga  12840
cagtgaaaag actcaagaaa cagggaaaca aagtggaact gctccccgaa aactccgagt  12900
ttaagcctat cgtcgtggat ctgaggcagc aatcctttac cattgaggga ctggctgtgg  12960
gagtgattag aaatggcgat tggctcgaat ttcccgggat tagacctgag tgtgtggtcc  13020
ccgaaaccca atgcgctatg aaaagaaaag agaaaaaggc tcagaaagag aaagacaaac  13080
tgcctgtgtc caccacaacc gtcgatgatc acatgccccc tatcatgcag tgtgagcctc  13140
cccctcccga agccgctaga atccacgaag tcgtccccag gttcctctcc gataagctcc  13200
tggaaaccaa tagacaaaag aatatccctc aactcaccgc taaccaacag tttctgattg  13260
ccaggctgat ttggtatcag gatggctatg agcaaccctc cgacgaagac ctcaagagga  13320
tcacacagac atggcaacag gctgacgatg agaatgagga aagcgatacc cctttcaggc  13380
agattaccga aatgacaatc ctcaccgtcc agctcatcgt cgagtttgcc aaaggactcc  13440
ccggattcgc taagattagc caacccgatc agattaccct cctgaaagcc tgtagctccg  13500
```

```
aggtcatgat gctgagagtg gctagaaggt acgatgccgc ttccgatagc gtcctgtttg  13560
ccaataacca agcctatacc agggacaatt acaggaaggc tggcatggcc tatgtgattg  13620
aggatgtgct ccacttttgc agatgtatgt actccatggc tctcgataac attcactatg  13680
ccctcctgac agccgtcgtg attttctccg acaggcccgg actggaacag cctcaactcg  13740
tggaagaaat tcagaggtac tatctgaata ccctcagaat ttacattctg aatcagctct  13800
ccggcagcgc tagatccagc gtcatctatg gcaaaatcct ctccattctg tccgagctga  13860
gaacactggg aatgcaaaac tccaatatgt gcattagcct caagctcaag aatagaaaac  13920
tgcctccctt tctggaagaa atttgggatg tggctgacat gagccatacc caacccccctc  13980
ccattctgga aagccctacc aatctgtaaa tcgatagccg cctggctgag atggggtggg  14040
cagggcagag ctgatcaggg ccgagcagaa ccgcactctt cccaaataaa gcttcctcct  14100
tgaaacacaa atgtttctta cttacacccc atcctgattt cttttcttga gaccagagag  14160
tgggaaagct ctctcttgac ctgaggatgg atctgaaaat tatgagcccc ttgaggacag  14220
ggaatgttat tcatctttga attccgcagc atctagcacc aggtcttgta cagagcaggt  14280
gcccaataaa tggttgaatg aatatatgaa aagtagaggc agagggctgg gcacagtggc  14340
tcacgcctgt aatcctagca ctttgggagg ctgaggtggg tggatcactt gaggtcagga  14400
gttcgagacc agcttggcca acatggctaa acctcatctc tattaaaaat acaaaaatta  14460
gctgggctgg tgcctgtaat cccagctact caggaggctg aggcaggaga atcacttgaa  14520
cccaggagga ggagtttgca gtgagccgag atcgcaccat tgcactccag cctgggcgat  14580
aggagcaaaa ctccatctca aaaacaaaaa acaaaacaaa acaaaaagaa aaaagaaaag  14640
taggggcaga gatgtggggc aggagaggtg actcgggctc agctgcatgg tcctgctctg  14700
cttctttttt cttggagttt gtccgttgga tgacaatgat agtggtgaac aggtatggag  14760
ggcttactaa gtaccaggtg tctagacgag gacgctcggg cttggaccca tggcacatcg  14820
tgtaatcatg gtcatagctg tttcctgtgt gaaattgtta tccgctacgt ctctcccccg  14880
cagtaagggc tagattaact cgtctcgtga atatccggaa ctccctttag tgagggttaa  14940
ttgcgttgcg ctcactgccc gctttccagt cgggaaacct gtcgtgccag cttaatcatg  15000
gtcatagctg tttcctgtgt gaaattgtta tccgctaccg gaaacgcttc cttcatgtga  15060
gcaaaaggcc agcaaaaggc caggaaccgt aaaaaggccg cgttgctggc gtttttccat  15120
aggctccgcc cccctgacga gcatcacaaa aatcgacgct caagtcagag gtggcgaaac  15180
ccgacaggac tataaagata ccaggcgttt ccccctggaa gctccctcgt gcgctctcct  15240
gttccgaccc tgccgcttac cggatacctg tccgcctttc tcccttcggg aagcgtggcg  15300
ctttctcata gctcacgctg taggtatctc agttcggtgt aggtcgttcg ctccaagctg  15360
ggctgtgtgc acgaaccccc cgttcagccc gaccgctgcg ccttatccgg taactatcgt  15420
cttgagtcca acccggtaag acacgactta tcgccactgg cagcagccac tggtaacagg  15480
attagcagag cgaggtatgt aggcggtgct acagagttct tgaagtggtg gcctaactac  15540
ggctacacta gaagaacagt atttggtatc tgcgctctgc tgaagccagt taccttcgga  15600
aaaagagttg gtagctcttg atccggcaaa caaaccaccg ctggtagcgg tggttttttt  15660
gtttgcaagc agcagattac gcgcagaaaa aaaggatctc aagaagatcc tttgatcttt  15720
tctacggggt ctgacgctca gtggaacgaa aactcacgtt aagggatttt ggtcatgcct  15780
aggacgaaag gaggtcgtga aatggataaa aaaatacagc gtttttcatg tacaactata  15840
```

```
ctagttgtag tgcctaaata atgcttttaa aacttaaaaa tacgtttaaa ccctcagcga    15900
aatggcatac gagtaaactt ggtctgacac cgctgcatga gattatcaaa aaggatcttc    15960
acctagatcc ttttaaatta aaaatgaagt tttaaatcaa tctaaagtat atatgagtaa    16020
acttggtctg acagttacca atgcttaatc agtgaggcac ctatctcagc gatctgtcta    16080
tttcgttcat ccatagttgc ctgactcccc gtcgtgtaga taactacgat acgggagggc    16140
ttaccatctg gccccagtgc tgcaatgata ccgcgagacc cacgctcacc ggctccagat    16200
ttatcagcaa taaaccagcc agccggaagc gccgagcgca gaagtggtcc tgcaacttta    16260
tccgcctcca tccagtctat taactgttgc cgggaagcta gagtaagtag ttcgccagtt    16320
aatagtttgc ggagcgttgt tgccattgct acaggcatcg tggtgtcacg ctcgtcgttt    16380
ggtatggctt cattcagctc cggttcccaa cgatcaaggc gagttacatg atcccccatg    16440
ttgtgcaaaa aagcggttag ctccttcggt cctccgatgg ttgtcagaag taagttggcc    16500
gcagtgttat cactcatggt tatggcagca ctgcataatt ctcttactgt catgccatcc    16560
gtaagatgct tttctgtgac tggtgagtat tcaaccaagt cattctgaga atagtgtatg    16620
cggcgaccga gttgctcttg cccggcgtca atacgggata ataccgcgcc acatagcaga    16680
actttaaaag tgctcatcat tgggaagcgt tcttcggggc gaaaactctc aaggatctta    16740
ccgctgttga gatccagttc gatgtaaccc acacgagcac ccaactgatc ttcagcatct    16800
tttactttca ccagcgtttc tgggtgagca aaaacaggaa ggcaaaatgc cgcaaaaaag    16860
ggaataaggg cgacacggaa atgttgaata ctcatacgct ccttttttca atagtattga    16920
agcatttatc agggttattg tctcgggagc gaatacatat ttgaatgtat ttagaaaaa    16979
```

<210> SEQ ID NO 14
<211> LENGTH: 13188
<212> TYPE: DNA
<213> ORGANISM: Artificial Sequence
<220> FEATURE:
<223> OTHER INFORMATION: Synthetic cardiomycyte + hypoxia inducible +
      hPlexin DI inducible gene switch constant encoding IGF-1

<400> SEQUENCE: 14

```
taaacaaata ggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gccctaggac gaaaggaggc cgtgaaatgg ataaaaaaat     180
acagcgtttt tcatgtacaa ctatactagt tgtagtgcct aaataatgct tttaaaactt     240
aaaaataatc aatgtcctca gcggggtgtc ggggatttag gtgacactat aggctgagcg     300
ccgcacaggc atctagaggc tatggcaggg cctgccgccc cgacgttggc tgcgagccct     360
gggccttcac ccgaacttgg ggggtggggt gggaaaagg aagaaacgcg ggcgtattgg     420
ccccaatggg gtctcggtgg ggtatcgaca gagtgccagc cctgggaccg aaccccgcgt     480
ttatgaacaa acgacccaac accgtgcgtt ttattctgtc tttttattgc cgtcatagcg     540
cgggttcctt ccggtattgt ctccttccgt gtttcaatcg attcaaaaga actcgtccag     600
cagacggtaa aaagcaatgc gttgagaatc cggtgcagca atgccataca gcaccagaaa     660
gcgatcagcc cattcaccgc ccagttcttc agcaatgtca cggggttgcca gtgcgatgtc     720 ctgatagcga tcagccacgc ccaggcgacc gcagtcgata aagccggaga acggccgtt     780 ttccaccata atgtttggca gacaagcatc gccgtgggtc acaaccaggt cctcgccatc     840
tggcatacgt gctttcaggc gtgcgaacag ttctgccggt gccagaccct gatgttcctc     900
```

-continued

```
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggttgaaca    2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag gggcgctgt    2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccccag tatgatgcct tctctaaatt taccagaaag   3060
aaaggacctg ggatgcttgt cctttaagtg tctctaaaca tggtttgcat agctggatct   3120
cagcttatct gtgcctttcg gctttcgctt ccatacatgg atctgttccc aacagtaact   3180
ccaagctgtc gaaaagaagc tatctggcag ctctctgctt catccaacac atggatgata   3240
aaaatacaca tatagcgatt cttccctcga gtaggcgaga ccaatgggtg cgccatgggc   3300
```

-continued tcttccaaaa atttaggtga cactataggg caccgctcgc acctgcgcac aggcccgcgg 3360
ctacaaacta cgaacgatca ttctagatac cacatttgta gaggttttac ttgctttaaa 3420
aaacctccca catctccccc tgaacctgaa acataaaatg aatgcaaatg ttttattaac 3480
ttgtttattg cagcttataa tggttacaaa ttaagcaata gcatcacaaa tttcacaaat 3540
taagcatttt tttcactgca ttctagttgt ggtttgtcca aactcatcaa tgtatcttat 3600
catgtctaat cgattcacag gttggtgggg ctctccagga tggggggggg ctgggtgtgg 3660
ctcatgtcgg ccacgtccca aatctcctcc aggaaggggg gcagcttcct gttcttcagc 3720
ttcaggctga tacacatatt gctgttctgc attcccaggg tcctcagctc gctcaggatg 3780
ctcaggatct tgccgtagat cacgctgctc ctggcgctgc cgctcagctg gttcaggatg 3840
tagatcctca gggtgttcag gtagtacctc tggatctcct ccaccagctg ggctgctcc 3900
aggccgggcc tgtcgctgaa gatcaccacg gcggtcagca gggcgtagtg gatgttgtcc 3960
agggccatgc tgtacataca tctgcagaag tgcaggaggt cctcgatcac ctcggccatg 4020
ccagccttcc tgtagttgtc cctggtgtaa gcctggttgt tggcgaacag gatgctgtcg 4080
ctggcggcgt cgtacctcct ggccaccctc agcatcatca cctcgctgct gcaagccttc 4140
agcagggtga tctggtcggg ctggctgatc ttggcgaatc cgggcaggcc cttggcgaac 4200
tccacgatca gctgcacggt caggatggtc atctcggtga tctgcctgaa gggggtgtcg 4260
ctctcctcgt tctcgtcgtc ggcctgctgc caggtctggg tgatcctttt caggtcctcg 4320
tcgctgggct gctcgtagcc gtcctgatac cagatcagcc tggcgatcag gaactgctgg 4380
ttggcggtca gctgggggat gttcttctgc ctgttggtca ccagcagctt gtcgctcagg 4440
aacctgggca cgacctcgtg aatcctggcg gcctcggggg ggggggggctc gcactgcatg 4500
atggggggca tgtggtcatc gacggtggtg gtgctcacgg gcagcttgtc cttctccttc 4560
tgggccttct tctccttcct tttcatggcg cactgggtct cgggcaccac gcactcgggc 4620
ctgatcccgg gaaactcggg gctcacggtc agctgcctct ggcccttgtt gctgctctcc 4680
tcgctgctgc tggtggcgct gatcctgtgc tgcctcaggg tcaggggcat gtcggtctcc 4740
acgctggcca gcctgtcggt cacggcgtcc ttgttcacgt tgtcctgcac gaacaggccg 4800
gtcagcaggg ccttgatgtc ttgcaggctg tccatcttca ggatcatgtc caggtcctcc 4860
ctggggaaga tcagcaggaa cagctgctcc agcctctcca gcctgctctc cacctcggtc 4920
aggtgggccc tggtcagggg gctcctcttg gtcttggggc tgtatctgca ctcccagttg 4980
ttcttcaggc acttggcgca cttgggcttc tccttgctgc acttcagctt cttcagcctg 5040
cagatgtcgc aagcctgctc gatgctgctc agcagcttca tggtggccaa ttgccccccc 5100
cccccccgc atgcacagga agatgagctc acacaccagc taaggcaccc attatatacc 5160
ctctaggtct tcgcggacgt gcgggaaccc acgtgggggc tccgtcacgt actccgagtc 5220
ccgcacgcac tcagcgtcgc tctggggccc cacgtccggc cctgacgtgc ggcttcgttt 5280
gtcacgtcgc ggacgtgcgg gaacccacgt gggggctccg tcacgtactc cgagtcccgc 5340
acgcactcag cgtcgctctg gggccccacg tccggccctg acgtgcggct tcgtttgtca 5400
cgtcgcggac gtgcgggaac ccacgtgggg gctccgtcac gtactccgag tcccgcacgc 5460
actcagcgtc gctctggggc cccacgtccg gccctgacgt gcggcttcgt ttgtcacgtc 5520
gcggacgtgc gggaacccac gtgggggctc cgtcacgtac tccgagtccc gcacgcactc 5580
agcgtcgctc tggggcccca cgtccggccc tgacgtgcgg cttcgtttgt cacgtcgcgg 5640

-continued

```
acgtgcggga acccacgtgg gggctccgtc acgtactccg agtcccgcac gcactcagcg   5700
tcgctctggg gccccacgtc cggccctgac gtgcggcttc gtttgtcacg tcgcggacgt   5760
gcgggaaccc acgtgggggc tccgtcacgt actccgagtc ccgcacgcac tcagcgtcgc   5820
tctggggccc cacgtccggc cctgacgtgc ggcttcgttt gtcacgtcgc ggacgtgcgg   5880
gaacccacgt gggggctccg tcacgtactc cgagtcccgc acgcactcag cgtcgctctg   5940
gggccccacg tccggccctg acgtgcggct tcgtttgtca cgtcctcgag tggtaataca   6000
atggccggtt cccatggacc tgcatcgtgg tgtaactata acggtcctaa ggtagcgacc   6060
gcggagacta ggtgtattta tctaagcgat cgcttaatta aggccggccg ccgcaataaa   6120
atatctttat tttcattaca tctgtgtgtt ggttttttgt gtgaatccat agtactaaca   6180
tacgctctcc atcaaaacaa aacgaaacaa aacaaactag caaaataggc tgtccccagt   6240
gcaagtccag gtgccagaac atttctctat ccataatgca ggggtaccgg gtgatgacgg   6300
tgaaaacctc caattgcgga gtactgtcct ccgagcggag tactgtcctc cgagcggagt   6360
actgtcctcc gagcggagta ctgtcctccg agcggagtac tgtcctccga gcggagtact   6420
gtcctccgag cggagagtcc ccggggacct agagggtata taatgggtgc cttagctggt   6480
gtgtgacctc atcttcctgt acgcccctgc aggggcgcgc cacgcgtcga agaaggtgag   6540
taatcttaac atgctctttt tttttttttt tgctaatccc ttttgtgtgc tgatgttagg   6600
atgacattta caacaaatgt ttgttcctga caggaaaaac cttgctgggt accttcgttg   6660
ccggacactt cttgtcctct actttggaaa aaaggaattg agagccgcta gcgccaccat   6720
gggaaaaatc agcagcctgc ccacccaatt atttaagtgc tgcttttgtg atttcttgaa   6780
ggtgaagatg cacaccatgt cctcctcgca tctgttctac ctggcgctgt gcctgctgac   6840
cttcaccagc tctgccacgg ctggaccgga gaccctctgc ggggccgagc tggtggatgc   6900
cctgcaattc gtgtgtggag acaggggctt ctacttcaac aagcccacag ggtatggctc   6960
cagcagtcgg agagcccccc agacaggcat cgtggatgag tgctgcttca gaagctgtga   7020
tctaaggagg ctggagatgt attgcgcacc cctcaagcct gccaagtcag ctcgctctgt   7080
ccgtgcccag cgccacaccg acatgcccaa gacccagaag tatcagcccc catctaccaa   7140
caagaacacg aagtctcaga gaaggaaagg aagtacattt gaagaacgca agtagatcga   7200
ttgcgcaaag ctttcgcgat aggcgagacc aatgggtgtg tacgtagcgg ccgcgtcgac   7260
gatagcttga tgggtggcat ccctgtgacc cctccccagt gcctctcctg gccctggaag   7320
ttgccactcc agtgcccacc agccttgtcc taataaaatt aagttgcatc attttgtctg   7380
actaggtgtc cttctataat attatggggt ggaggggggt ggtatggagc aaggggcaag   7440
ttgggaagac aacctgtagg gcctgcgggg tctattggga accaagctgg agtgcagtgg   7500
cacaatcttg gctcactgca atctccgcct cctgggttca agcgattctc ctgcctcagc   7560
ctcccgagtt gttgggattc caggcatgca tgaccaggct cagctaattt ttgttttttt   7620
ggtagagacg gggtttcacc atattggcca ggctggtctc caactcctaa tctcaggtga   7680
tctacccacc ttggcctccc aaattgctgg gattacaggc gtgaaccact gctcccttcc   7740
ctgtccttct gattttaaaa taactatacc agcaggagga cgtccagaca cagcataggc   7800
tacctggcca tgcccaaccg gtgggacatt tgagttgctt gcttggcact gtcctctcat   7860
gcgttgggtc cactcagtag atgcctgttg aattctgatt taaatcggtc cgcgtacggc   7920
gtggtaggtc cgaacgaatc catggattac cctgttatcc ctactcaagg acatcatccc   7980
tttagtgagg gttaattcac gcagtgccgc ggcgtgtaga aaatacctat cagctcgagg   8040
```

-continued

```
agcgaaggcc tggacagtgc ctgagaaagg tggtggaggg aggctgagtg tggaggggag   8100
acacagggtt cgggaaggca gagggagaag gaaaggggag ctcagaggga ccgagagagg   8160
gacggagggt ccgaggggga ggcagaggga gccacggaga gagggagcga gcgtcaggga   8220
cggaaaaacg gagcaggaga gagaaggaga ctagaaaggg ccgggggcgg ggctgccagg   8280
gactggagag cgaagcggag tcggagggag aaggagaagc agaggcagaa cccggagaag   8340
cgccacacgc gcggagtttg gggtggggac agaggcggag aggcgcagag accgagagac   8400
acagagagag ggagaggcgg ggtgggggag agggcggaaa agagaaaaca ggcgcgagcg   8460
aggcaggcca agcggccaag tgggaggaaa gagcgaggag agcgagcgac ggcggcggcg   8520
gctacgggga gggaccctgg ggccgcgggc gggtcctgga gggcgcgggc ggcgggaccc   8580
gcggacggcg gggcgtggcc cagggcggcc aggggcaggc gggggttccg ggggcgggcg   8640
gggccggggc ggggagtgag ggcgtgtccg cagcggagcc gcccccgccc cgcccccgga   8700
ctgcgcggcg aggctgatcc gggcccggac gccggggtcg ggggcggctg gcgcgggcag   8760
gaagcgcatc gtggcccgga cccgcccccc gcctcccgcc gcctccgggg catgcggggg   8820
gggggggggg caattggcca ccatgaagct cctgtccagc attgagcaag cctgtgacat   8880
ttgcaggctg aaaaagctca agtgtagcaa agagaaaccc aaatgcgcta agtgtctgaa   8940
aaacaactgg gaatgcagat actcccccaa aaccaaaaga tccccccctca ccagggccca   9000
tctgacagag gtcgagtcca gactcgaaag gctggaacag ctctttctcc tgattttccc   9060
tagagaagac ctcgacatga tcctcaagat ggactccctg caagacatta aggctctgct   9120
caccggactg tttgtgcaag acaatgtgaa taaggatgcc gtcaccgata gactcgcctc   9180
cgtggaaacc gatatgcctc tgacactgag gcagcataga attagcgcta cctccagctc   9240
cgaggaaagc tccaacaaag gccaaagaca actgacagtg tcccccgagt tccccgggat   9300
tagacctgag tgtgtggtcc ccgaaaccca atgcgctatg aaaagaaaag agaaaaaggc   9360
tcagaaagag aaagacaaac tgcctgtgtc caccacaacc gtcgatgatc acatgccccc   9420
tatcatgcag tgtgagcctc cccctcccga agccgctaga atccacgaag tcgtccccag   9480
gttcctctcc gataagctcc tggaaaccaa tagacaaaag aatatccctc aactcaccgc   9540
taaccaacag tttctgattg ccaggctgat ttggtatcag gatggctatg agcaaccctc   9600
cgacgaagac ctcaagagga tcacacagac atggcaacag gctgacgatg agaatgagga   9660
aagcgatacc cctttcaggc agattaccga aatgacaatc ctcaccgtcc agctcatcgt   9720
cgagtttgcc aaaggactcc ccggattcgc taagattagc caacccgatc agattaccct   9780
cctgaaagcc tgtagctccg aggtcatgat gctgagagtg gctagaaggt acgatgccgc   9840
ttccgatagc gtcctgtttg ccaataacca agcctatacc agggacaatt acaggaaggc   9900
tggcatggcc tatgtgattg aggatgtgct ccacttttgc agatgtatgt actccatggc   9960
tctcgataac attcactatg ccctcctgac agccgtcgtg attttctccg acaggcccgg  10020
actggaacag cctcaactcg tggaagaaat tcagaggtac tatctgaata ccctcagaat  10080
ttacattctg aatcagctct ccggcagcgc tagatccagc gtcatctatg gcaaaatcct  10140
ctccattctg tccgagctga gaacactggg aatgcaaaac tccaatatgt gcattagcct  10200
caagctcaag aatagaaaac tgcctccctt tctggaagaa atttgggatg tggctgacat  10260
gagccatacc caaccccctc ccattctgga aagccctacc aatctgtaaa tcgatagccg  10320
cctggctgag atggggtggg cagggcagag ctgatcaggg ccgagcagaa ccgcactctt  10380
```

-continued

```
cccaaataaa gcttcctcct tgaaacacaa atgtttctta cttacacccc atcctgattt  10440
cttttcttga gaccagagag tgggaaagct ctctcttgac ctgaggatgg atctgaaaat  10500
tatgagcccc ttgaggacag ggaatgttat tcatctttga attccgcagc atctagcacc  10560
aggtcttgta cagagcaggt gcccaataaa tggttgaatg aatatatgaa aagtagaggc  10620
agagggctgg gcacagtggc tcacgcctgt aatcctagca ctttgggagg ctgaggtggg  10680
tggatcactt gaggtcagga gttcgagacc agcttggcca acatggctaa acctcatctc  10740
tattaaaaat acaaaaatta gctgggctgg tgcctgtaat cccagctact caggaggctg  10800
aggcaggaga atcacttgaa cccaggagga ggagtttgca gtgagccgag atcgcaccat  10860
tgcactccag cctgggcgat aggagcaaaa ctccatctca aaaacaaaaa acaaaacaaa  10920
acaaaaagaa aaaagaaaag taggggcaga gatgtggggc aggagaggtg actcgggctc  10980
agctgcatgg tcctgctctg cttctttttt cttggagttt gtccgttgga tgacaatgat  11040
agtggtgaac aggtatggag ggcttactaa gtaccaggtg tctagacgag gacgctcggg  11100
cttggaccca tggcacatcg tgtaatcatg gtcatagctg tttcctgtgt gaaattgtta  11160
tccgctacgt ctctcccccg cagtaagggc tagattaact cgtctcgtga atatccggaa  11220
ctccctttag tgagggttaa ttgcgttgcg ctcactgccc gctttccagt cgggaaacct  11280
gtcgtgccag cttaatcatg gtcatagctg tttcctgtgt gaaattgtta tccgctaccg  11340
gaaacgcttc cttcatgtga gcaaaaggcc agcaaaaggc caggaaccgt aaaaaggccg  11400
cgttgctggc gtttttccat aggctccgcc cccctgacga gcatcacaaa aatcgacgct  11460
caagtcagag gtggcgaaac ccgacaggac tataaagata ccaggcgttt ccccctggaa  11520
gctccctcgt gcgctctcct gttccgaccc tgccgcttac cggatacctg tccgcctttc  11580
tcccttcggg aagcgtggcg ctttctcata gctcacgctg taggtatctc agttcggtgt  11640
aggtcgttcg ctccaagctg ggctgtgtgc acgaaccccc cgttcagccc gaccgctgcg  11700
ccttatccgg taactatcgt cttgagtcca acccggtaag acacgactta tcgccactgg  11760
cagcagccac tggtaacagg attagcagag cgaggtatgt aggcggtgct acagagttct  11820
tgaagtggtg gcctaactac ggctacacta gaagaacagt atttggtatc tgcgctctgc  11880
tgaagccagt taccttcgga aaaagagttg gtagctcttg atccggcaaa caaaccaccg  11940
ctggtagcgg tggttttttt gtttgcaagc agcagattac gcgcagaaaa aaaggatctc  12000
aagaagatcc tttgatcttt tctacggggt ctgacgctca gtggaacgaa aactcacgtt  12060
aagggatttt ggtcatgatc tatgtcgggt gcggagaaag aggtaatgaa atggcatacg  12120
agtaaacttg gtctgacacc gctgcatgag attatcaaaa aggatcttca cctagatcct  12180
tttaaattaa aaatgaagtt ttaaatcaat ctaaagtata tatgagtaaa cttggtctga  12240
cagttaccaa tgcttaatca gtgaggcacc tatctcagcg atctgtctat ttcgttcatc  12300
catagttgcc tgactccccg tcgtgtagat aactacgata cgggagggct taccatctgg  12360
ccccagtgct gcaatgatac cgcgagaccc acgctcaccg gctccagatt tatcagcaat  12420
aaaccagcca gccggaagcg ccgagcgcag aagtggtcct gcaactttat ccgcctccat  12480
ccagtctatt aactgttgcc gggaagctag agtaagtagt tcgccagtta atagtttgcg  12540
gagcgttgtt gccattgcta caggcatcgt ggtgtcacgc tcgtcgtttg gtatggcttc  12600
attcagctcc ggttcccaac gatcaaggcg agttacatga tcccccatgt tgtgcaaaaa  12660
agcggttagc tccttcggtc ctccgatggt tgtcagaagt aagttggccg cagtgttatc  12720
actcatggtt atggcagcac tgcataattc tcttactgtc atgccatccg taagatgctt  12780
```

```
ttctgtgact ggtgagtatt caaccaagtc attctgagaa tagtgtatgc ggcgaccgag  12840
ttgctcttgc ccggcgtcaa tacgggataa taccgcgcca catagcagaa ctttaaaagt  12900
gctcatcatt gggaagcgtt cttcggggcg aaaactctca aggatcttac cgctgttgag  12960
atccagttcg atgtaaccca cacgagcacc caactgatct tcagcatctt ttactttcac  13020
cagcgtttct gggtgagcaa aaacaggaag gcaaaatgcc gcaaaaaagg gaataagggc  13080
gacacggaaa tgttgaatac tcatacgctt cctttttcaa tagtattgaa gcatttatca  13140
gggttattgt ctcgggagcg aatacatatt tgaatgtatt tagaaaaa              13188
```

<210> SEQ ID NO 15
<211> LENGTH: 13314
<212> TYPE: DNA
<213> ORGANISM: Artificial Sequence
<220> FEATURE:
<223> OTHER INFORMATION: Synthetic constitutive + TNF + inducible promoter gene switch encoding etanercept

<400> SEQUENCE: 15

```
taaacaaata ggggttccgc gcacatttcc ccgaaaagtg ccacctgacg tactgaggac     60
gccagggttt tcccagtcac gacgttgtaa aacgacggcc agtagcagac aagcccgtca    120
gggcgcgtca gcgggtgttg gccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
```

-continued gtcagccatg gggcggagaa tgggcggaac tgggcggagt taggggcggg atgggcggag 1680
ttaggggcgg gactatggtt gctgactaat tgagatgctt gctttgcata cttctgcctg 1740
ctggggagcc tggggacttt ccacacctgg ttgctgacta attgagatgc ttgctttgca 1800
tacttctgcc tgctggggag cctggggact ttccacaccc taacctcgag gccatcgtgg 1860
cacgccaggg ttttcccagt cacgacgttg taaaacgacg gccagtgctc ttctcccccg 1920
cgggaggttt tataaatccg actgtctaga ttgttgttaa atcacacaaa aaaccaacac 1980
acagatgtaa tgaaaataaa gatattttat tatcgattca gctgtcgctg gggctctcca 2040
gcatctccat caggaaggtg tcgatgggca cgtcgccgat cagcctgaag aagaacaggt 2100
gctccaggca cttcaggccg atgctcctca ggctgggcag cctcagcagc agcttggcga 2160
atctgccggg ctcgtcgggg tgggtggtcc tggtgtactc ctccagggcg gcgtacacct 2220
tctccctcag cagctccacc tcctgggcgc ttttcaggcc cctcacctcg ggttgaaca 2280
ggatgatggc cctcaggcag cccagctcgg tcttgtccat cctcatgtcc ctcatcttgc 2340
tcaccagctc ggtcagcacc ctgtcgaaga tggcgcccac tccggcgctg tgggcgctgt 2400
tcctatggac gtgcaggccg gtggccagca ggatgccgtc cctcacgtcg atgctcctgt 2460
ggctgaagct ggcgatcagc agctcgttcc atccggccct cagcaggatc acctggtcgt 2520
ccaggggcag gctgctgaag tggggaatcc tcttggccca ctccaccagg gtgaacagct 2580
gcttgtcggc ggcctggcag atgttggtca cggggtcgtt ggggctgctg ccgctgccgc 2640
cggttccgcc ggggccctcc acgccctggt cgcttttctg ctccacggcg agttcggcct 2700
ccagaatcct gtccacgggc atctccatat ggccgccgta ctcgtcgatg cccagggcgt 2760
cggtgaacat ctgctcgaac tcgaagtcgg ccatgtccag ggcgccgtag gggcgctgt 2820
cgtgggggt gaagccgggg ccggggctgt cgccgtcgcc cagcatgtcc aggtcgaagt 2880
cgtccagggc gtcggcgtgg gccatggcca cgtcctcgcc gtccaggtgc agctcgtcgc 2940
ccaggctcac gtcggtgggg ggggccacct tccttttctt cttggggccc atggtggcca 3000
attgcccccc cccccccccg catgccgtct aacaaaaaag ccaaaaacgg ccagaattta 3060
gcggacaatt tactagtcta acactgaaaa ttacatattg acccaaatga ttacatttca 3120
aaaggtgcct aaaaaacttc acaaaacaca ctcgccaacc ccgagcgcac gtacccagcc 3180
cagcagcccg ctactcacca agtgacgatc acagcgatcc acaaacaaga accgcgaccc 3240
aaatcccggc tgcgacggaa ctagctgtgc cacacccggc gcgtccttat ataatcatcg 3300
gcgttcaccg ccccacggag atccctccgc agaatcgccg agaagggact acttttcctc 3360
gcctgttccg ctctctggaa agaaaaccag tgccctagag tcacccaagt cccgtcctaa 3420
aatgtccttc tgctgatact ggggttctaa ggccgagtct tatgagcagc gggccgctgt 3480
cctgagcgtc cgggcggaag gatcaggacg ctcgctgcgc ccttcgtctg acgtggcagc 3540
gctcgccgtg aggaggggg cgcccgcggg aggcgccaaa acccggcgcg gaggccctcg 3600
agtaggcgag accaatgggt gcgccatggg ctcttccaaa aatttaggtg acactatagg 3660
gcaccgctcg cacctgcgca caggcccgcg gctacaaact acgaacgatc attctagata 3720
ccacatttgt agaggtttta cttgctttaa aaaacctccc acatctcccc ctgaacctga 3780
aacataaaat gaatgcaaat gttttattaa cttgtttatt gcagcttata atggttacaa 3840
attaagcaat agcatcacaa atttcacaaa ttaagcattt ttttcactgc attctagttg 3900
tggtttgtcc aaactcatca atgtatctta tcatgtctaa tcgattcaca ggttggtggg 3960

-continued

```
gctctccagg atgggggggg gctgggtgtg gctcatgtcg gccacgtccc aaatctcctc   4020
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
cctggcgctg ccgctcagct ggttcaggat gtagatcctc agggtgttca ggtagtacct   4200
ctggatctcc tccaccagct ggggctgctc caggccgggc ctgtcgctga agatcaccac   4260
ggcggtcagc agggcgtagt ggatgttgtc cagggccatg ctgtacatac atctgcagaa   4320
gtgcaggagg tcctcgatca cctcggccat gccagccttc ctgtagttgt ccctggtgta   4380
agcctggttg ttggcgaaca ggatgctgtc gctggcggcg tcgtacctcc tggccaccct   4440
cagcatcatc acctcgctgc tgcaagcctt cagcagggtg atctggtcgg gctggctgat   4500
cttggcgaat ccgggcaggc ccttggcgaa ctccacgatc agctgcacgg tcaggatggt   4560
catctcggtg atctgcctga agggggtgtc gctctcctcg ttctcgtcgt cggcctgctg   4620
ccaggtctgg gtgatccttt tcaggtcctc gtcgctgggc tgctcgtagc cgtcctgata   4680
ccagatcagc ctggcgatca ggaactgctg gttggcggtc agctgggggga tgttcttctg   4740
cctgttggtc accagcagct tgtcgctcag gaacctgggc acgacctcgt gaatcctggc   4800
ggcctcgggg gggggggcct cgcactgcat gatgggggggc atgtggtcat cgacggtggt   4860
ggtgctcacg ggcagcttgt ccttctcctt ctgggccttc ttctccttcc ttttcatggc   4920
gcactgggtc tcgggcacca cgcactcggg cctgatcccg ggaaactcgg ggctcacggt   4980
cagctgcctc tggcccttgt tgctgctctc ctcgctgctg ctggtggcgc tgatcctgtg   5040
ctgcctcagg gtcaggggca tgtcggtctc cacgctggcc agcctgtcgg tcacggcgtc   5100
cttgttcacg ttgtcctgca cgaacaggcc ggtcagcagg gccttgatgt cttgcaggct   5160
gtccatcttc aggatcatgt ccaggtcctc cctggggaag atcagcagga acagctgctc   5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc cccccccccg catgcctgtc tgacgggcaa   5460
tgctcctctg agagttgtta cagttcagac atggtaatga ctggttttat acagctttgc   5520
ccctcccaca tggcattttt ttttctccct ctgtcttttg atctgtgtcc tttgagtgat   5580
tcaacatttt actcaggaag acatcattag aatagaaata cttgtttgta aaggcatggt   5640
ttaagaaatt ttgggggagg atgaggtcac tctgaaactt aagaatttgt caatatcctc   5700
gagtggtaat acaatggccg gttcccatgg acctgcatcg tggtgtaact ataacggtcc   5760
taaggtagcg accgcggaga ctaggtgtat ttatctaagc gatcgcttaa ttaaggccgg   5820
ccgccgcaat aaaatatctt tattttcatt acatctgtgt gttggttttt tgtgtgaatc   5880
catagtacta acatacgctc tccatcaaaa caaaacgaaa caaaacaaac tagcaaaata   5940
ggctgtcccc agtgcaagtc caggtgccag aacatttctc tatccataat gcaggggtac   6000
cgggtgatga cggtgaaaac ctccaattgc ggagtactgt cctccgagcg gagtactgtc   6060
ctccgagcgg agtactgtcc tccgagcgga gtactgtcct ccgagcggag tactgtcctc   6120
cgagcggagt actgtcctcc gagcggagag tccccgggga cctagagggt atataatggg   6180
tgccttagct ggtgtgtgac ctcatcttcc tgtacgcccc tgcaggggcg cgccacgcgt   6240
cgaagaaggt gagtaatctt aacatgctct tttttttttt ttttgctaat ccctttttgtg   6300
tgctgatgtt aggatgacat ttacaacaaa tgtttgttcc tgacaggaaa aaccttgctg   6360
```
ggtaccttcg ttgccggaca cttcttgtcc tctactttgg aaaaaaggaa ttgagagccg 6420
ctagcgccac catgctgccc gcccaggtcg ccttcacccc ctacgccccc gagcccggca 6480
gcacctgtag actgagagag tattacgacc agaccgccca gatgtgctgc tccaagtgca 6540
gccccggcca gcacgccaag gtgttctgca ccaagaccag cgacaccgtc tgcgacagct 6600
gcgaggacag cacctacacc cagctgtgga actgggtgcc cgagtgcctg agctgcggca 6660
gcagatgtag cagcgaccag gtggagaccc aggcttgcac cagagagcag aacagaatct 6720
gcacctgtag acccggctgg tactgcgccc tgagcaagca ggagggctgc cgcctgtgcg 6780 ccccctgag aaagtgcaga cccggcttcg gcgtggccag acccggcacc gagaccagcg 6840
acgttgtgtg caagccctgt gcccccggca ccttcagcaa caccaccagc agcaccgaca 6900
tctgccgccc ccaccagatt tgcaacgtgg tggccatccc cggcaacgcc agcatggacg 6960
ccgtgtgtac cagcaccagc cccacccgca gcatggcccc cggcgctgtc cacctccccc 7020
agcccgtgag caccagaagc cagcacaccc agcccacccc cgagcccagc accgccccca 7080
gcaccagctt cctgctgcct atgggaccca gcccccccgc cgagggcagc accggcgacg 7140
agcccaagag ctgcgacaag acccacacct gtccccctg ccccgccccc gagctgctgg 7200
gcggccccag cgtgttcctg ttccccccca agcccaagga caccctgatg atctccagaa 7260
cccccgaggt gacatgcgtg gtggtggacg tgagccacga ggacccccag gtgaagttca 7320
actggtacgt ggacggcgtg caagtgcata acgccaagac caagcccaga gagcagcagt 7380
acaacagcac ctacagagtg gtgagcgtgc tgaccgtgct gcaccagaac tggctggacg 7440
gcaaggagta caagtgcaag gtgtccaaca aggccctgcc cgcccccatc gagaaaacca 7500
tcagcaaggc caagggccag cccagagagc cccaggtgta caccctgccc cccagcagag 7560
aggagatgac caagaaccag gtgtccctga cctgtctggt gaagggcttc taccccagcg 7620
acatcgccgt ggagtgggag agcaacggcc agcccgagaa caactacaag accacccccc 7680
ccgtgctgga cagcgacggc agcttcttcc tgtacagcaa gctgaccgtg gacaagagca 7740
gatggcagca gggcaacgtg ttcagctgct ccgtgatgca cgaggccctg cacaaccact 7800
acacccagaa gtccctgagc ctgagccccg gcaagtgaat cgattgcgca aagctttcgc 7860
gataggcgag accaatgggt gtgtacgtag cggccgcgtc gacgatagct tgatgggtgg 7920
catccctgtg acccctcccc agtgcctctc ctggccctgg aagttgccac tccagtgccc 7980
accagccttg tcctaataaa attaagttgc atcattttgt ctgactaggt gtccttctat 8040
aatattatgg ggtggagggg ggtggtatgg agcaaggggc aagttgggaa gacaacctgt 8100
agggcctgcg gggtctattg ggaaccaagc tggagtgcag tggcacaatc ttggctcact 8160
gcaatctccg cctcctgggt tcaagcgatt ctcctgcctc agcctcccga gttgttggga 8220
ttccaggcat gcatgaccag gctcagctaa tttttgtttt tttggtagag acggggtttc 8280
accatattgg ccaggctggt ctccaactcc taatctcagg tgatctaccc accttggcct 8340
cccaaattgc tgggattaca ggcgtgaacc actgctccct tccctgtcct tctgatttta 8400
aaataactat accagcagga ggacgtccag acacagcata ggctacctgg ccatgcccaa 8460
ccggtgggac atttgagttg cttgcttggc actgtcctct catgcgttgg gtccactcag 8520
tagatgcctg ttgaattctg atttaaatcg gtccgcgtac ggcgtggtag gtccgaacga 8580
atccatggat taccctgtta tccctactca aggacatcat ccctttagtg agggttaatt 8640
cacgcagtgc cgcggcgtgt agaaaatacc tatcagctcg agcacggggc tcccactctc 8700

-continued

```
aactccgcag cctcagcccc ctcaatgctg aggagcagag ctggtctcct gccctgacag   8760
ctgccaggca catcttgttc cctcaggttg cacaactggg ataaatgacc cgggatgaag   8820
aaaccactgg catccaggaa cttgtcttag accgttttgt aggggaaatg acctgcaggg   8880
actttcccca gggaccacat ccagcttttc ttcgctccca agaaaccagc agggagcatg   8940
cggggggggg ggggggcaat tggccaccat gaagctcctg tccagcattg agcaagcctg   9000
tgacatttgc aggctgaaaa agctcaagtg tagcaaagag aaacccaaat gcgctaagtg   9060
tctgaaaaac aactgggaat gcagatactc ccccaaaacc aaaagatccc ccctcaccag   9120
ggcccatctg acagaggtcg agtccagact cgaaaggctg gaacagctct ttctcctgat   9180
tttccctaga gaagacctcg acatgatcct caagatggac tccctgcaag acattaaggc   9240
tctgctcacc ggactgtttg tgcaagacaa tgtgaataag gatgccgtca ccgatagact   9300
cgcctccgtg gaaaccgata tgcctctgac actgaggcag catagaatta gcgctacctc   9360
cagctccgag gaaagctcca acaaaggcca aagacaactg acagtgtccc ccgagttccc   9420
cgggattaga cctgagtgtg tggtccccga aacccaatgc gctatgaaaa gaaaagagaa   9480
aaaggctcag aaagagaaag acaaactgcc tgtgtccacc acaaccgtcg atgatcacat   9540
gcccccctatc atgcagtgtg agcctccccc tcccgaagcc gctagaatcc acgaagtcgt   9600
ccccaggttc ctctccgata agctcctgga aaccaataga caaaagaata tccctcaact   9660
caccgctaac caacagtttc tgattgccag gctgatttgg tatcaggatg gctatgagca   9720
accctccgac gaagacctca agaggatcac acagacatgg caacaggctg acgatgagaa   9780
tgaggaaagc gataccccctt tcaggcagat taccgaaatg acaatcctca ccgtccagct   9840
catcgtcgag tttgccaaag gactccccgg attcgctaag attagccaac ccgatcagat   9900
taccctcctg aaagcctgta gctccgaggt catgatgctg agagtggcta gaaggtacga   9960
tgccgcttcc gatagcgtcc tgtttgccaa taaccaagcc tataccaggg acaattacag  10020
gaaggctggc atggcctatg tgattgagga tgtgctccac ttttgcagat gtatgtactc  10080
catggctctc gataacattc actatgccct cctgacagcc gtcgtgattt tctccgacag  10140
gcccggactg gaacagcctc aactcgtgga agaaattcag aggtactatc tgaataccct  10200
cagaatttac attctgaatc agctctccgg cagcgctaga tccagcgtca tctatggcaa  10260
aatcctctcc attctgtccg agctgagaac actgggaatg caaaactcca atatgtgcat  10320
tagcctcaag ctcaagaata gaaaactgcc tcccctttctg gaagaaattt gggatgtggc  10380
tgacatgagc catacccaac cccctcccat tctggaaagc cctaccaatc tgtaaatcga  10440
tagccgcctg gctgagatgg ggtgggcagg gcagagctga tcagggccga gcagaaccgc  10500
actcttccca aataaagctt cctccttgaa acacaaatgt ttcttactta caccccatcc  10560
tgatttcttt tcttgagacc agagagtggg aaagctctct cttgacctga ggatggatct  10620
gaaaattatg agccccttga ggacagggaa tgttattcat ctttgaattc cgcagcatct  10680
agcaccaggt cttgtacaga gcaggtgccc aataaatggt tgaatgaata tatgaaaagt  10740
agaggcagag ggctgggcac agtggctcac gcctgtaatc ctagcacttt gggaggctga  10800
ggtgggtgga tcacttgagg tcaggagttc gagaccagct tggccaacat ggctaaacct  10860
catctctatt aaaaatacaa aaattagctg ggctggtgcc tgtaatccca gctactcagg  10920
aggctgaggc aggagaatca cttgaaccca ggaggaggag tttgcagtga gccgagatcg  10980
caccattgca ctccagcctg ggcgatagga gcaaaactcc atctcaaaaa caaaaaaacaa  11040
aacaaaacaa aaagaaaaaa gaaaagtagg ggcagagatg tggggcagga gaggtgactc  11100
```
gggctcagct gcatggtcct gctctgcttc ttttttcttg gagtttgtcc gttggatgac 11160
aatgatagtg gtgaacaggt atggagggct tactaagtac caggtgtcta gacgaggacg 11220
ctcgggcttg gacccatggc acatcgtgta atcatggtca tagctgtttc ctgtgtgaaa 11280
ttgttatccg ctacgtctct cccccgcagt aagggctaga ttaactcgtc tcgtgaatat 11340
ccggaactcc ctttagtgag ggttaattgc gttgcgctca ctgcccgctt tccagtcggg 11400
aaacctgtcg tgccagctta atcatggtca tagctgtttc ctgtgtgaaa ttgttatccg 11460
ctaccggaaa cgcttccttc atgtgagcaa aaggccagca aaaggccagg aaccgtaaaa 11520
aggccgcgtt gctggcgttt ttccataggc tccgcccccc tgacgagcat cacaaaaatc 11580
gacgctcaag tcagaggtgg cgaaacccga caggactata aagataccag gcgtttcccc 11640
ctggaagctc cctcgtgcgc tctcctgttc cgaccctgcc gcttaccgga tacctgtccg 11700
cctttctccc ttcgggaagc gtggcgcttt ctcatagctc acgctgtagg tatctcagtt 11760
cggtgtaggt cgttcgctcc aagctgggct gtgtgcacga accccccgtt cagcccgacc 11820
gctgcgcctt atccggtaac tatcgtcttg agtccaaccc ggtaagacac gacttatcgc 11880
cactggcagc agccactggt aacaggatta gcagagcgag gtatgtaggc ggtgctacag 11940
agttcttgaa gtggtggcct aactacggct acactagaag aacagtattt ggtatctgcg 12000
ctctgctgaa gccagttacc ttcggaaaaa gagttggtag ctcttgatcc ggcaaacaaa 12060
ccaccgctgg tagcggtggt ttttttgttt gcaagcagca gattacgcgc agaaaaaaag 12120
gatctcaaga agatcctttg atcttttcta cggggtctga cgctcagtgg aacgaaaact 12180
cacgttaagg gattttggtc atgatctatg tcgggtgcgg agaaagaggt aatgaaatgg 12240
catacgagta aacttggtct gacaccgctg catgagatta tcaaaaagga tcttcaccta 12300
gatcctttta aattaaaaat gaagttttaa atcaatctaa agtatatatg agtaaacttg 12360
gtctgacagt taccaatgct taatcagtga ggcacctatc tcagcgatct gtctatttcg 12420
ttcatccata gttgcctgac tccccgtcgt gtagataact acgatacggg agggcttacc 12480
atctggcccc agtgctgcaa tgataccgcg agacccacgc tcaccggctc cagatttatc 12540
agcaataaac cagccagccg gaagcgccga gcgcagaagt ggtcctgcaa ctttatccgc 12600
ctccatccag tctattaact gttgccggga agctagagta agtagttcgc cagttaatag 12660
tttgcggagc gttgttgcca ttgctacagg catcgtggtg tcacgctcgt cgtttggtat 12720
ggcttcattc agctccggtt cccaacgatc aaggcgagtt acatgatccc ccatgttgtg 12780
caaaaaagcg gttagctcct tcggtcctcc gatggttgtc agaagtaagt tggccgcagt 12840
gttatcactc atggttatgg cagcactgca taattctctt actgtcatgc catccgtaag 12900
atgcttttct gtgactggtg agtattcaac caagtcattc tgagaatagt gtatgcggcg 12960
accgagttgc tcttgcccgg cgtcaatacg ggataatacc gcgccacata gcagaacttt 13020
aaaagtgctc atcattggga agcgttcttc ggggcgaaaa ctctcaagga tcttaccgct 13080
gttgagatcc agttcgatgt aacccacacg agcacccaac tgatcttcag catcttttac 13140
tttcaccagc gtttctgggt gagcaaaaac aggaaggcaa aatgccgcaa aaaagggaat 13200
aagggcgaca cggaaatgtt gaatactcat acgcttcctt tttcaatagt attgaagcat 13260
ttatcagggt tattgtctcg ggagcgaata catatttgaa tgtatttaga aaaa 13314

<210> SEQ ID NO 16
<211> LENGTH: 11013
<212> TYPE: DNA

<213> ORGANISM: Artificial Sequence
<220> FEATURE:
<223> OTHER INFORMATION: Synthetic TNF inducible promoter gene switch
construct expressing etanercept

<400> SEQUENCE: 16
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gcgggtgtcg gggatttagg tgacactata ggctgagcgc 180
cgcacaggca tctagaggct atggcagggc ctgccgcccc gacgttggct gcgagccctg 240
ggccttcacc cgaacttggg gggtggggtg gggaaaagga agaaacgcgg gcgtattggc 300
cccaatgggg tctcggtggg gtatcgacag agtgccagcc ctgggaccga accccgcgtt 360
tatgaacaaa cgacccaaca ccgtgcgttt tattctgtct ttttattgcc gtcatagcgc 420
gggttccttc cggtattgtc tccttccgtg tttcaatcga ttcaaaagaa ctcgtccagc 480
agacggtaaa aagcaatgcg ttgagaatcc ggtgcagcaa tgccatacag caccagaaag 540
cgatcagccc attcaccgcc cagttcttca gcaatgtcac gggttgccag tgcgatgtcc 600
tgatagcgat cagccacgcc caggcgaccg cagtcgataa agccggagaa acggccgttt 660
tccaccataa tgtttggcag acaagcatcg ccgtgggtca caaccaggtc ctcgccatct 720
ggcatacgtg ctttcaggcg tgcgaacagt tctgccggtg ccagaccctg atgttcctcg 780
tccaggtcat cctgatcaac caggccagct tccatgcgag tgcgtgcgcg ctcgatacgg 840
tgtttagctt ggtgatcgaa tgggcaagta gctgggtcca gggtatgcag acggcgcata 900
gcatcagcca tgatggaaac cttttctgcc ggtgccagat gagaggacag cagatcctgg 960
cctggaacct cgcccagcag cagccagtcg cggccagcct cggtcacaac atccagcaca 1020
gctgcgcatg gaacgccggt agtagccagc caggacagac gagctgcttc atcttgcagt 1080
tcgttcagtg cgccggacag atcggtctta acaaacagca ccggacggcc ttgagcggac 1140
agacggaaca cagctgcgtc ggagcaaccg atagtctgtt gagcccagtc atagccaaac 1200
agacgttcca cccaagcagc cggagaacca gcgtgcagac cgtcttgttc aatcatggtg 1260
gcaattgggt gtctgagcga tgtggctcgg ctggcgacgc aaaagaagat gcggctgact 1320
gtcgaacagg aggagcagag agcgaagcgg gaggctgcgg gctcaatttg catgctttag 1380
ttcctcacct tgtcgtatta tactatgccg atatactatg ccgatgatta attgtcaacg 1440
tatacggaat agctctgagg ccgaggcagc ttcggcctct gcataaataa aaaaaattag 1500
tcagccatgg ggcggagaat gggcggaact gggcggagtt aggggcggga tgggcggagt 1560
taggggcggg actatggttg ctgactaatt gagatgcttg ctttgcatac ttctgcctgc 1620
tggggagcct ggggactttc cacacctggt tgctgactaa ttgagatgct tgctttgcat 1680
acttctgcct gctggggagc ctggggactt tccacaccct aacctcgagg ccatcgtggc 1740
acgccagggt tttcccagtc acgacgttgt aaaacgacgg ccagtgctct tctcccccgc 1800
gggaggtttt ataaatccga ctgtctagat accacatttg tagaggtttt acttgcttta 1860
aaaaacctcc cacatctccc cctgaacctg aaacataaaa tgaatgcaaa tgttttatta 1920
acttgtttat tgcagcttat aatggttaca aattaagcaa tagcatcaca aatttcacaa 1980
attaagcatt tttttcactg cattctagtt gtggtttgtc caaactcatc aatgtatctt 2040
atcatgtcta atcgattcac aggttggtgg ggctctccag gatgggggg ggctgggtgt 2100 ggctcatgtc ggccacgtcc caaatctcct ccaggaaggg gggcagcttc ctgttcttca 2160

-continued

```
gcttcaggct gatacacata ttgctgttct gcattcccag ggtcctcagc tcgctcagga   2220
tgctcaggat cttgccgtag atcacgctgc tcctggcgct gccgctcagc tggttcagga   2280
tgtagatcct cagggtgttc aggtagtacc tctggatctc ctccaccagc tggggctgct   2340
ccaggccggg cctgtcgctg aagatcacca cggcggtcag cagggcgtag tggatgttgt   2400
ccagggccat gctgtacata catctgcaga agtgcaggag gtcctcgatc acctcggcca   2460
tgccagcctt cctgtagttg tccctggtgt aagcctggtt gttggcgaac aggatgctgt   2520
cgctggcggc gtcgtacctc ctggccaccc tcagcatcat cacctcgctg ctgcaagcct   2580
tcagcagggt gatctggtcg ggctggctga tcttggcgaa tccgggcagg cccttggcga   2640
actccacgat cagctgcacg gtcaggatgg tcatctcggt gatctgcctg aagggggtgt   2700
cgctctcctc gttctcgtcg tcggcctgct gccaggtctg ggtgatcctt ttcaggtcct   2760
cgtcgctggg ctgctcgtag ccgtcctgat accagatcag cctggcgatc aggaactgct   2820
ggttggcggt cagctggggg atgttcttct gcctgttggt caccagcagc ttgtcgctca   2880
ggaacctggg cacgacctcg tgaatcctgg cggcctcggg gggggggggc tcgcactgca   2940
tgatgggggg catgtggtca tcgacggtgg tggtgctcac gggcagcttg tccttctcct   3000
tctgggcctt cttctccttc cttttcatgg cgcactgggt ctcgggcacc acgcactcgg   3060
gcctgatccc gggaaactcg gggctcacgg tcagctgcct ctggcccttg ttgctgctct   3120
cctcgctgct gctggtggcg ctgatcctgt gctgcctcag ggtcaggggc atgtcggtct   3180
ccacgctggc cagcctgtcg gtcacggcgt ccttgttcac gttgtcctgc acgaacaggc   3240
cggtcagcag ggccttgatg tcttgcaggc tgtccatctt caggatcatg tccaggtcct   3300
ccctggggaa gatcagcagg aacagctgct ccagcctctc cagcctgctc tccacctcgg   3360
tcaggtgggc cctggtcagg gggctcctct tggtcttggg gctgtatctg cactcccagt   3420
tgttcttcag gcacttggcg cacttgggct tctccttgct gcacttcagc ttcttcagcc   3480
tgcagatgtc gcaagcctgc tcgatgctgc tcagcagctt catggtggca gatctggtcg   3540
cgggaggctg ctggttttcc actacccgaa aaaaatccag cgtctaagca gctgcaagga   3600
gagcctttca gagaagcggg tcctggcagc ggcggggaag tgtccccaaa tgggcagaat   3660
agcctccccg cgtcgggaga gtcgcgtcct tgctcgggtg ttgtaagttc cagtgcaaag   3720
tgcccgcccg ctgctatggg caaagtttcg tggatgcggc tagggttgcg caccgctggc   3780
tgggggatca gcgggagggc tgggccagag gcgaagcccc ctattcgctc cggatctccc   3840
ttcccaggac gcccgcagcg cagctctgct cgccgggctc ctccacccta gcccgccgcc   3900
cgctcgctcc ctctgcctct cgctggaatt actacagcga gttgccggct cagctgtcgc   3960
tggggctctc cagcatctcc atcaggaagg tgtcgatggg cacgtcgccg atcagcctga   4020
agaagaacag gtgctccagg cacttcaggc cgatgctcct caggctgggc agcctcagca   4080
gcagcttggc gaatctgccg ggctcgtcgg ggtgggtggt cctggtgtac tcctccaggg   4140
cggcgtacac cttctccctc agcagctcca cctcctgggc gcttttcagg cccctcacct   4200
cggggttgaa caggatgatg gccctcaggc agcccagctc ggtcttgtcc atcctcatgt   4260
ccctcatctt gctcaccagc tcggtcagca ccctgtcgaa gatggcgccc actccggcgc   4320
tgtgggcgct gttcctatgg acgtgcaggc cggtggccag caggatgccg tccctcacgt   4380
cgatgctcct gtggctgaag ctggcgatca gcagctcgtt ccatccggcc ctcagcagga   4440
tcacctggtc gtccaggggc aggctgctga agtggggaat cctcttggcc cactccacca   4500
gggtgaacag ctgcttgtcg gcggcctggc agatgttggt cacggggtcg ttggggctgc   4560
```

```
tgccgctgcc gccggttccg ccggggccct ccacgccctg gtcgcttttc tgctccacgg   4620
cgagttcggc ctccagaatc ctgtccacgg gcatctccat atggccgccg tactcgtcga   4680
tgcccagggc gtcggtgaac atctgctcga actcgaagtc ggccatgtcc agggcgccgt   4740
agggggcgct gtcgtggggg gtgaagccgg ggccggggct gtcgccgtcg cccagcatgt   4800
ccaggtcgaa gtcgtccagg gcgtcggcgt gggccatggc cacgtcctcg ccgtccaggt   4860
gcagctcgtc gcccaggctc acgtcggtgg ggggggccac cttccttttc ttcttggggc   4920
ccatggtggc caattgcccc cccccccccc cgcatgcagc tcctgaagcc agtgaggccc   4980
gatgcagata ccgcggagtg aaatagaaag tctgtgcttt ataaagggtc ttgttgcaga   5040
ggcggaggga aatcccttca aggggaaacc cagggcagag ccagggaaaa aagtttaaca   5100
gacacccagc caagttccac tattaacccc ttcagttgct ctcactgctg aagctcctct   5160
ctctgtcctg gcaaaagaag acacttccaa gactataaaa tacaggcttt tcctcatctt   5220
cgactccaaa aggctatctt tactggaaag ataaaggaca atgctgattg cagaatgaag   5280
ctttctgaat ccaatgtggg ttaagggggt ggggagagaa aaaatggaga cagagtagta   5340
aattctactc tggtttttga actggataaa taacgactat gccatgtgaa ttgattttct   5400
ccatcaagga aatatgtttg caattctaaa agagattaat ttttttctct tacaagagaa   5460
aggaaaaagt tatttctttt gatgagtcat tttttaaaaa agggacacca taacttctta   5520
gttttatatt tattcataaa aatagttctt ttagcaacaa acatcaactt tttgaaacta   5580
ttttcttgag tagaaagtaa aggactgtaa ctgaaattgc tgccaaaaca agggaaacaa   5640
tttttttttg ttttagaaaa gttaccaata atttggttaa attgctggat aattggaatt   5700
tttttgcata cttaaatgca agtgtatgga atccatctga agtggcaaat ctcttggctc   5760
gagtaggcga gaccaatggg tgcgccatgg gctcttccaa aaatttaggt gacactatag   5820
ggcaccgctc gcacctgcgc acaggcataa gccaaatgga actacgagac ctgcatcgtg   5880
gtgtaactat aacggtccta aggtagcgac cgcggagact aggtgtattt atctaagcga   5940
tcgcttaatt aaggccggcc gccgcaataa aatatcttta ttttcattac atctgtgtgt   6000
tggttttttg tgtgaatcca tagtactaac atacgctctc catcaaaaca aaacgaaaca   6060
aaacaaacta gcaaaatagg ctgtccccag tgcaagtcca ggtgccagaa catttctcta   6120
tccataatgc aggggtaccg ggtgatgacg gtgaaaacct ccaattgcgg agtactgtcc   6180
tccgagcgga gtactgtcct ccgagcggag tactgtcctc cgagcggagt actgtcctcc   6240
gagcggagta ctgtcctccg agcggagtac tgtcctccga gcggagagtc cccggggacc   6300
tagagggtat ataatgggtg ccttagctgg tgtgtgacct catcttcctg tacgcccctg   6360
caggggcgcg ccacgcgtcg aagaaggtga gtaatcttaa catgctcttt tttttttttt   6420
ttgctaatcc cttttgtgtg ctgatgttag gatgacattt acaacaaatg tttgttcctg   6480
acaggaaaaa ccttgctggg taccttcgtt gccggacact tcttgtcctc tactttggaa   6540
aaaaggaatt gagagccgct agcgccacca tgctgcccgc ccaggtcgcc ttcacccccct   6600
acgcccccga gcccggcagc acctgtagac tgagagagta ttacgaccag accgcccaga   6660
tgtgctgctc caagtgcagc cccggccagc acgccaaggt gttctgcacc aagaccagcg   6720
acaccgtctg cgacagctgc gaggacagca cctacaccca gctgtggaac tgggtgcccg   6780
agtgcctgag ctgcggcagc agatgtagca gcgaccaggt ggagacccag gcttgcacca   6840
gagagcagaa cagaatctgc acctgtagac ccggctggta ctgcgccctg agcaagcagg   6900
```

-continued

```
agggctgccg cctgtgcgcc cccctgagaa agtgcagacc cggcttcggc gtggccagac   6960
ccggcaccga gaccagcgac gttgtgtgca agccctgtgc ccccggcacc ttcagcaaca   7020
ccaccagcag caccgacatc tgccgccccc accagatttg caacgtggtg gccatccccg   7080
gcaacgccag catggacgcc gtgtgtacca gcaccagccc cacccgcagc atggcccccg   7140
gcgctgtcca cctcccccag cccgtgagca ccagaagcca gcacacccag cccacccccg   7200
agcccagcac cgcccccagc accagcttcc tgctgcctat gggacccagc ccccccgccg   7260
agggcagcac cggcgacgag cccaagagct gcgacaagac ccacacctgt ccccccctgcc   7320
ccgcccccga gctgctgggc ggccccagcg tgttcctgtt ccccccccaag cccaaggaca   7380
ccctgatgat ctccagaacc cccgaggtga catgcgtggt ggtggacgtg agccacgagg   7440
acccccaggt gaagttcaac tggtacgtgg acggcgtgca agtgcataac gccaagacca   7500
agcccagaga gcagcagtac aacagcacct acagagtggt gagcgtgctg accgtgctgc   7560
accagaactg gctggacggc aaggagtaca agtgcaaggt gtccaacaag gccctgcccg   7620
cccccatcga gaaaaccatc agcaaggcca agggccagcc cagagagccc caggtgtaca   7680
ccctgccccc cagcagagag gagatgacca agaaccaggt gtccctgacc tgtctggtga   7740
agggcttcta ccccagcgac atcgccgtgg agtgggagag caacggccag cccgagaaca   7800
actacaagac caccccccc gtgctggaca gcgacggcag cttcttcctg tacagcaagc   7860
tgaccgtgga caagagcaga tggcagcagg gcaacgtgtt cagctgctcc gtgatgcacg   7920
aggccctgca caaccactac acccagaagt ccctgagcct gagccccggc aagtgaatcg   7980
attgcgcaaa gctttcgcga taggcgagac caatgggtgt gtacgtagcg gccgcgtcga   8040
cgatagcttg atgggtggca tccctgtgac ccctccccag tgcctctcct ggccctggaa   8100
gttgccactc cagtgcccac cagccttgtc ctaataaaat taagttgcat cattttgtct   8160
gactaggtgt ccttctataa tattatgggg tggagggggg tggtatggag caaggggcaa   8220
gttgggaaga caacctgtag ggcctgcggg gtctattggg aaccaagctg gagtgcagtg   8280
gcacaatctt ggctcactgc aatctccgcc tcctgggttc aagcgattct cctgcctcag   8340
cctcccgagt tgttgggatt ccaggcatgc atgaccaggc tcagctaatt tttgtttttt   8400
tggtagagac ggggtttcac catattggcc aggctggtct ccaactccta atctcaggtg   8460
atctacccac cttggcctcc caaattgctg ggattacagg cgtgaaccac tgctcccttc   8520
cctgtccttc tgattttaaa ataactatac cagcaggagg acgtccagac acagcatagg   8580
ctacctggcc atgcccaacc ggtgggacat ttgagttgct tgcttggcac tgtcctctca   8640
tgcgttgggt ccactcagta gatgcctgtt gaattctgat ttaaatcggt ccgcgtacgg   8700
cgtggtaggt ccgaacgaat ccatggatta ccctgttatc cctactcaag gacatcatcc   8760
ctttagtgag ggttaattca cgcagtgggt acggaactaa aggcagcaca catcgtgtaa   8820
tcatggtcat agctgtttcc tgtgtgaaat tgttatccgc tacgtctctc cccgcagta    8880
agggctagat taactcgtct cgtgaatatc cggaactccc tttagtgagg gttaattgcg   8940
ttgcgctcac tgcccgcttt ccagtcggga aacctgtcgt gccagcttaa tcatggtcat   9000
agctgtttcc tgtgtgaaat tgttatccgc taccggaaac gcttccttca tgtgagcaaa   9060
aggccagcaa aaggccagga accgtaaaaa ggccgcgttg ctggcgtttt tccataggct   9120
ccgcccccct gacgagcatc acaaaaatcg acgctcaagt cagaggtggc gaaacccgac   9180
aggactataa agataccagg cgtttccccc tggaagctcc ctcgtgcgct ctcctgttcc   9240
gaccctgccg cttaccggat acctgtccgc ctttctccct tcgggaagcg tggcgctttc   9300
```
tcatagctca cgctgtaggt atctcagttc ggtgtaggtc gttcgctcca agctgggctg 9360
tgtgcacgaa ccccccgttc agcccgaccg ctgcgcctta tccggtaact atcgtcttga 9420
gtccaacccg gtaagacacg acttatcgcc actggcagca gccactggta acaggattag 9480
cagagcgagg tatgtaggcg gtgctacaga gttcttgaag tggtggccta actacggcta 9540
cactagaaga acagtatttg gtatctgcgc tctgctgaag ccagttacct tcggaaaaag 9600
agttggtagc tcttgatccg gcaaacaaac caccgctggt agcggtggtt tttttgtttg 9660
caagcagcag attacgcgca gaaaaaaagg atctcaagaa gatcctttga tcttttctac 9720
ggggtctgac gctcagtgga acgaaaactc acgttaaggg attttggtca tgcctaggac 9780
gaaaggaggt cgtgaaatgg ataaaaaaat acagcgtttt tcatgtacaa ctatactagt 9840
tgtagtgcct aaataatgct tttaaaactt aaaaataatc tatgtcgggt gcggagaaag 9900
aggtaatgaa atggcaaatc aatgtcctca gcgaaatggc atacgagtaa acttggtctg 9960
acaccgctgc atgagattat caaaaaggat cttcacctag atccttttaa attaaaaatg 10020
aagttttaaa tcaatctaaa gtatatatga gtaaacttgg tctgacagtt accaatgctt 10080
aatcagtgag gcacctatct cagcgatctg tctatttcgt tcatccatag ttgcctgact 10140
ccccgtcgtg tagataacta cgatacggga gggcttacca tctggcccca gtgctgcaat 10200
gataccgcga gacccacgct caccggctcc agatttatca gcaataaacc agccagccgg 10260
aagcgccgag cgcagaagtg gtcctgcaac tttatccgcc tccatccagt ctattaactg 10320
ttgccgggaa gctagagtaa gtagttcgcc agttaatagt ttgcggagcg ttgttgccat 10380
tgctacaggc atcgtggtgt cacgctcgtc gtttggtatg gcttcattca gctccggttc 10440
ccaacgatca aggcgagtta catgatcccc catgttgtgc aaaaaagcgg ttagctcctt 10500
cggtcctccg atggttgtca gaagtaagtt ggccgcagtg ttatcactca tggttatggc 10560
agcactgcat aattctctta ctgtcatgcc atccgtaaga tgcttttctg tgactggtga 10620
gtattcaacc aagtcattct gagaatagtg tatgcggcga ccgagttgct cttgcccggc 10680
gtcaatacgg gataataccg cgccacatag cagaacttta aaagtgctca tcattgggaa 10740
gcgttcttcg gggcgaaaac tctcaaggat cttaccgctg ttgagatcca gttcgatgta 10800
acccacacga gcacccaact gatcttcagc atcttttact ttcaccagcg tttctgggtg 10860
agcaaaaaca ggaaggcaaa atgccgcaaa aaagggaata agggcgacac ggaaatgttg 10920
aatactcata cgcttccttt ttcaatagta ttgaagcatt tatcagggtt attgtctcgg 10980
gagcgaatac atatttgaat gtatttagaa aaa 11013

<210> SEQ ID NO 17
<211> LENGTH: 15706
<212> TYPE: DNA
<213> ORGANISM: Artificial Sequence
<220> FEATURE:
<223> OTHER INFORMATION: Synthetic dual promoter inflammation + hypoxia inducible gene switch construct encoding etanercept and EPO

<400> SEQUENCE: 17
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gcgggtgtcg gggatttagg tgacactata ggctgagcgc 180
cgcacaggca tctagaggct atggcagggc ctgccgcccc gacgttggct gcgagccctg 240
ggccttcacc cgaacttggg gggtggggtg gggaaaagga agaaacgcgg gcgtattggc 300

```
cccaatgggg tctcggtggg gtatcgacag agtgccagcc ctgggaccga accccgcgtt    360
tatgaacaaa cgacccaaca ccgtgcgttt tattctgtct ttttattgcc gtcatagcgc    420
gggttccttc cggtattgtc tccttccgtg tttcaatcga tttagaagaa ctcgtcaaga    480
aggcgataga aggcgatgcg ctgcgaatcg ggggcggcga taccgtaaag gacgaggaag    540
cggtcagccc attcgccgcc aagttcttca gcaatatcac gggtagccaa cgctatgtcc    600
tgatagcggt cggccacacc cagccgtcca cagtcgatga atccagaaaa gcggccattt    660
tccaccatga tattcggcaa gcaggcatcg ccgtgggtca cgacgagatc ctcgccgtcg    720
ggcatcctcg ccttgagcct ggcgaacagt tcggctggcg cgagcccctg atgctcctcg    780
tccagatcat cctgatcgac aagaccggct tccatccgag tacgtgctcg ctcgatgcga    840
tgtttcgctt ggtggtcgaa tgggcatgta gccggatcaa gcgtatgcag ccgccgcatt    900
gcatcagcca tgatggatac tttctcggca ggagcaaggt gagatgacag gagatcctgc    960
cccggcactt cgcccaatag cagccagtcc cttcccgctt cagtgacaac gtcgagcacg   1020
gctgcgcaag gaacgcccgt cgtggccagc cacgatagcc gcgctgcctc gtcctggagt   1080
tcattcaggg caccggacag gtcggtcttg acaaaaagaa ccgggcgccc ctgcgctgac   1140
agccggaaca cggcggcatc agagcagccg attgtctgtt gtgcccagtc atagccgaat   1200
agcctctcca cccaagcggc cggagaacca gcgtgcaatc catcttgttc aatggccgat   1260
cccatggtgg ccaattgggt gtctgagcga tgtggctcgg ctggcgacgc aaaagaagat   1320
gcggctgact gtcgaacagg aggagcagag agcgaagcgg gaggctgcgg gctcaatttg   1380
catgcggaat agctctgagg ccgaggcagc ttcggcctct gcataaataa aaaaaattag   1440
tcagccatgg ggcggagaat gggcggaact gggcggagtt aggggcggga tgggcggagt   1500
taggggcggg actatggttg ctgactaatt gagatgcttg ctttgcatac ttctgcctgc   1560
tggggagcct ggggactttc cacacctggt tgctgactaa ttgagatgct tgctttgcat   1620
acttctgcct gctggggagc ctggggactt tccacaccct aacctcgagg ccatcgtggc   1680
acgccagggt tttcccagtc acgacgttgt aaaacgacgg ccagtgctct tctcccccgc   1740
gggaggtttt ataaatccga ctgtctagat tgttgttaaa tcacacaaaa aaccaacaca   1800
cagatgtaat gaaaataaag atattttatt atcgattcag ctgtcgctgg ggctctccag   1860
catctccatc aggaaggtgt cgatgggcac gtcgccgatc agcctgaaga agaacaggtg   1920
ctccaggcac ttcaggccga tgctcctcag gctgggcagc ctcagcagca gcttggcgaa   1980
tctgccgggc tcgtcggggt gggtggtcct ggtgtactcc tccagggcgg cgtacacctt   2040
ctccctcagc agctccacct cctgggcgct tttcaggccc ctcacctcgg ggttgaacag   2100
gatgatggcc ctcaggcagc ccagctcggt cttgtccatc ctcatgtccc tcatcttgct   2160
caccagctcg gtcagcaccc tgtcgaagat ggcgcccact ccggcgctgt gggcgctgtt   2220
cctatggacg tgcaggccgg tggccagcag gatgccgtcc ctcacgtcga tgctcctgtg   2280
gctgaagctg gcgatcagca gctcgttcca tccggccctc agcaggatca cctggtcgtc   2340
caggggcagg ctgctgaagt ggggaatcct cttggcccac tccaccaggg tgaacagctg   2400
cttgtcggcg gcctggcaga tgttggtcac ggggtcgttg ggctgctgc cgctgccgcc   2460
ggttccgccg gggccctcca cgccctggtc gcttttctgc tccacggcga gttcggcctc   2520
cagaatcctg tccacgggca tctccatatg gccgccgtac tcgtcgatgc ccagggcgtc   2580
ggtgaacatc tgctcgaact cgaagtcggc catgtccagg gcgccgtagg gggcgctgtc   2640
```

-continued

```
gtggggggtg aagccggggc cggggctgtc gccgtcgccc agcatgtcca ggtcgaagtc   2700
gtccagggcg tcggcgtggg ccatggccac gtcctcgccg tccaggtgca gctcgtcgcc   2760
caggctcacg tcggtggggg gggccacctt ccttttcttc ttggggccca tggtggccaa   2820
ttgccccccc cccccccgc atgccgtcta acaaaaaagc caaaaacggc cagaatttag   2880
cggacaattt actagtctaa cactgaaaat tacatattga cccaaatgat tacatttcaa   2940
aaggtgccta aaaaacttca caaaacacac tcgccaaccc cgagcgcacg tacccagccc   3000
agcagcccgc tactcaccaa gtgacgatca cagcgatcca caaacaagaa ccgcgaccca   3060
aatcccggct gcgacggaac tagctgtgcc acacccggcg cgtccttata taatcatcgg   3120
cgttcaccgc cccacggaga tccctccgca gaatcgccga gaagggacta cttttcctcg   3180
cctgttccgc tctctggaaa gaaaaccagt gccctagagt cacccaagtc ccgtcctaaa   3240
atgtccttct gctgatactg gggttctaag gccgagtctt atgagcagcg ggccgctgtc   3300
ctgagcgtcc gggcggaagg atcaggacgc tcgctgcgcc cttcgtctga cgtggcagcg   3360
ctcgccgtga ggaggggggc gcccgcggga ggcgccaaaa cccggcgcgg aggccctcga   3420
gtaggcgaga ccaatgggtg cgccatgggc tcttccaaaa atttaggtga cactataggg   3480
caccgctcgc acctgcgcac aggcccgcgg ctacaaacta cgaacgatca ttctagatac   3540
cacatttgta gaggttttac ttgctttaaa aaacctccca catctccccc tgaacctgaa   3600
acataaaatg aatgcaaatg ttttattaac ttgtttattg cagcttataa tggttacaaa   3660
ttaagcaata gcatcacaaa tttcacaaat taagcatttt tttcactgca ttctagttgt   3720
ggtttgtcca aactcatcaa tgtatcttat catgtctaat cgattcacag gttggtgggg   3780
ctctccagga tggggggggg ctgggtgtgg ctcatgtcgg ccacgtccca aatctcctcc   3840
aggaaggggg gcagcttcct gttcttcagc ttcaggctga tacacatatt gctgttctgc   3900
attcccaggg tcctcagctc gctcaggatg ctcaggatct tgccgtagat cacgctgctc   3960
ctggcgctgc cgctcagctg gttcaggatg tagatcctca gggtgttcag gtagtacctc   4020
tggatctcct ccaccagctg ggctgctcc aggccgggcc tgtcgctgaa gatcaccacg   4080
gcggtcagca gggcgtagtg gatgttgtcc agggccatgc tgtacataca tctgcagaag   4140
tgcaggaggt cctcgatcac ctcggccatg ccagccttcc tgtagttgtc cctggtgtaa   4200
gcctggttgt tggcgaacag gatgctgtcg ctggcggcgt cgtacctcct ggccacccct   4260
agcatcatca cctcgctgct gcaagccttc agcagggtga tctggtcggg ctggctgatc   4320
ttggcgaatc cgggcaggcc cttggcgaac tccacgatca gctgcacggt caggatggtc   4380
atctcggtga tctgcctgaa gggggtgtcg ctctcctcgt tctcgtcgtc ggcctgctgc   4440
caggtctggg tgatcctttt caggtcctcg tcgctgggct gctcgtagcc gtcctgatac   4500
cagatcagcc tggcgatcag gaactgctgg ttggcggtca gctgggggat gttcttctgc   4560
ctgttggtca ccagcagctt gtcgctcagg aacctgggca cgacctcgtg aatcctggcg   4620
gcctcggggg gggggggctc gcactgcatg atggggggca tgtggtcatc gacggtggtg   4680
gtgctcacgg gcagcttgtc cttctccttc tgggccttct tctccttcct tttcatggcg   4740
cactgggtct cgggcaccac gcactcgggc ctgatcccgg gaaactcggg gctcacggtc   4800
agctgcctct ggcccttgtt gctgctctcc tcgctgctgc tggtggcgct gatcctgtgc   4860
tgcctcaggg tcaggggcat gtcggtctcc acgctggcca gcctgtcggt cacggcgtcc   4920
ttgttcacgt tgtcctgcac gaacaggccg gtcagcaggg ccttgatgtc ttgcaggctg   4980
tccatcttca ggatcatgtc caggtcctcc ctggggaaga tcagcaggaa cagctgctcc   5040
```

```
agcctctcca gcctgctctc cacctcggtc aggtgggccc tggtcagggg gctcctcttg   5100
gtcttggggc tgtatctgca ctcccagttg ttcttcaggc acttggcgca cttgggcttc   5160
tccttgctgc acttcagctt cttcagcctg cagatgtcgc aagcctgctc gatgctgctc   5220
agcagcttca tggtggccaa ttgccccccc cccccccgc atgctccctg ctggtttctt   5280
gggagcgaag aaaagctgga tgtggtccct ggggaaagtc cctgcaggtc atttccccta   5340
caaaacggtc taagacaagt tcctggatgc cagtggtttc ttcatcccgg gtcatttatc   5400
ccagttgtgc aacctgaggg aacaagatgt gcctggcagc tgtcagggca ggagaccagc   5460
tctgctcctc agcattgagg gggctgaggc tgcggagttg agagtgggag ccccgtgctc   5520
gagtggtaat acaatggccg gttcccatgg acctgcatcg tggtgatcta tgtcgggtgc   5580
ggagaaagag gtaatgaaat ggcagaaatg gcaccaccta aggtagcgac cgcggagact   5640
aggtgtattt atctaagcga tcgcttaatt aaggccggcc gccgcaataa aatatcttta   5700
ttttcattac atctgtgtgt tggttttttg tgtgaatcca tagtactaac atacgctctc   5760
catcaaaaca aaacgaaaca aaacaaacta gcaaaatagg ctgtccccag tgcaagtcca   5820
ggtgccagaa catttctcta tccataatgc aggggtaccg ggtgatgacg gtgaaaacct   5880
ccaattgcgg agtactgtcc tccgagcgga gtactgtcct ccgagcggag tactgtcctc   5940
cgagcggagt actgtcctcc gagcggagta ctgtcctccg agcggagtac tgtcctccga   6000
gcggagagtc cccggggacc tagagggtat ataatgggtg ccttagctgg tgtgtgacct   6060
catcttcctg tacgcccctg caggggcgcg ccacgcgtcg aagaaggtga gtaatcttaa   6120
catgctcttt tttttttttt ttgctaatcc cttttgtgtg ctgatgttag gatgacattt   6180
acaacaaatg tttgttcctg acaggaaaaa ccttgctggg taccttcgtt gccggacact   6240
tcttgtcctc tactttggaa aaaaggaatt gagagccgct agcgccacca tgctgcccgc   6300
ccaggtcgcc ttcacccccct acgcccccga gcccggcagc acctgtagac tgagagagta   6360
ttacgaccag accgcccaga tgtgctgctc caagtgcagc cccggccagc acgccaaggt   6420
gttctgcacc aagaccagcg acaccgtctg cgacagctgc gaggacagca cctacaccca   6480
gctgtggaac tgggtgcccg agtgcctgag ctgcggcagc agatgtagca gcgaccaggt   6540
ggagacccag gcttgcacca gagagcagaa cagaatctgc acctgtagac ccggctggta   6600
ctgcgccctg agcaagcagg agggctgccg cctgtgcgcc cccctgagaa agtgcagacc   6660
cggcttcggc gtggccagac ccggcaccga gaccagcgac gttgtgtgca agccctgtgc   6720
ccccggcacc ttcagcaaca ccaccagcag caccgacatc tgccgccccc accagatttg   6780
caacgtggtg gccatccccg gcaacgccag catggacgcc gtgtgtacca gcaccagccc   6840
cacccgcagc atggcccccg gcgctgtcca cctcccccag cccgtgagca ccagaagcca   6900
gcacacccag cccacccccg agcccagcac cgcccccagc accagcttcc tgctgcctat   6960
gggacccagc ccccccgccg agggcagcac cggcgacgag cccaagagct gcgacaagac   7020
ccacacctgt ccccctgcc ccgcccccga gctgctgggc ggccccagcg tgttcctgtt   7080
cccccccaag cccaaggaca ccctgatgat ctccagaacc cccgaggtga catgcgtggt   7140
ggtggacgtg agccacgagg acccccaggt gaagttcaac tggtacgtgg acggcgtgca   7200
agtgcataac gccaagacca agcccagaga gcagcagtac aacagcacct acagagtggt   7260
gagcgtgctg accgtgctgc accagaactg gctggacggc aaggagtaca agtgcaaggt   7320
gtccaacaag gccctgcccg cccccatcga gaaaaccatc agcaaggcca agggccagcc   7380
```

-continued

```
cagagagccc caggtgtaca ccctgccccc cagcagagag gagatgacca agaaccaggt   7440
gtccctgacc tgtctggtga agggcttcta ccccagcgac atcgccgtgg agtgggagag   7500
caacggccag cccgagaaca actacaagac cacccccccc gtgctggaca gcgacggcag   7560
cttcttcctg tacagcaagc tgaccgtgga caagagcaga tggcagcagg gcaacgtgtt   7620
cagctgctcc gtgatgcacg aggccctgca caaccactac acccagaagt ccctgagcct   7680
gagccccggc aagtgaatcg attgcgcaaa gctttcgcga taggcgagac caatgggtgt   7740
gtacgtagcg gccgcgtcga cgatagcttg atgggtggca tccctgtgac ccctccccag   7800
tgcctctcct ggccctggaa gttgccactc cagtgcccac cagccttgtc ctaataaaat   7860
taagttgcat cattttgtct gactaggtgt ccttctataa tattatgggg tggagggggg   7920
tggtatggag caaggggcaa gttgggaaga caacctgtag ggcctgcggg gtctattggg   7980
aaccaagctg gagtgcagtg gcacaatctt ggctcactgc aatctccgcc tcctgggttc   8040
aagcgattct cctgcctcag cctcccgagt tgttgggatt ccaggcatgc atgaccaggc   8100
tcagctaatt tttgtttttt tggtagagac ggggtttcac catattggcc aggctggtct   8160
ccaactccta atctcaggtg atctacccac cttggcctcc caaattgctg ggattacagg   8220
cgtgaaccac tgctcccttc cctgtccttc tgattttaaa ataactatac cagcaggagg   8280
acgtccagac acagcatagg ctacctggcc atgcccaacc ggtgggacat ttgagttgct   8340
tgcttggcac tgtcctctca tgcgttgggt ccactcagta gatgcctgtt gaattctgat   8400
ttaaatcggt ccgcgtacgg cgtggtaggt ccgaacgaat ccatggatta ccctgttatg   8460
tggtcctcca gggttgccgt tccttaacta taacggtcct aaggtagcga ccgcggagac   8520
taggtgtatt tatctaagcg atcgcttaat taaggccggc cgccgcaata aaatatcttt   8580
attttcatta catctgtgtg ttggtttttt gtgtgaatcc atagtactaa catacgctct   8640
ccatcaaaac aaaacgaaac aaaacaaact agcaaaatag gctgtcccca gtgcaagtcc   8700
aggtgccaga acatttctct atccataatg caggggtacc gggtgatgac ggtgaaaacc   8760
tccaattgtg ctgtatataa aaccagtggt tatatgtaca gtactgctgt atataaaacc   8820
agtggttata tgtacagtac gtcgactgct gtatataaaa ccagtggtta tatgtacagt   8880
actgctgtat ataaaaccag tggttatatg tacagtaccc cggggaccta gagggtatat   8940
aatgggtgcc ttagctggtg tgtgacctca tcttcctgta cgcccctgca ggggcgcgcc   9000
acgcgtcgaa gaaggtgagt aatcttaaca tgctcttttt tttttttttt gctaatccct   9060
tttgtgtgct gatgttagga tgacatttac aacaaatgtt tgttcctgac aggaaaaacc   9120
ttgctgggta ccttcgttgc cggacacttc ttgtcctcta ctttggaaaa aaggaattga   9180
gagccgctag cgccaccatg ggcgtccacg aatgccctgc ctggctgtgg ctgctcctgt   9240
ccctgctgtc tctcccctc ggcctccccg tcctgggagc ccctcccagg ctgatttgcg   9300
atagcagggt gctggagaga tacctgttgg aagccaagga agccgagaat atcacaaccg   9360
gatgcgccga gcactgctcc ctgaatgaga atatcacagt gcctgacaca aaggtcaact   9420
tttacgcttg gaaaagaatg gaggtcggcc aacaggctgt ggaagtgtgg cagggactgg   9480
ctctgctgtc cgaagccgtc ctgaggggcc aagccctcct ggtcaactcc agccaaccct   9540
gggagcctct gcaactgcat gtggataagg ctgtgtccgg cctcagatcc ctgacaaccc   9600
tcctgagagc cctgggcgct cagaaagagg ctatctcccc ccctgacgct gcctccgccg   9660
ctcccctcag aacaatcaca gccgatacct ttagaaaact gtttagagtc tactccaact   9720
ttctgagggg caaactgaaa ctgtataccg gagaggcttg caggaccgga gacaggtaaa   9780
```

-continued tcgattgcgc aaagctttcg cgataggcga gaccaatggg tgtgtacgta gcggccgctc 9840
gagaacttgt ttattgcagc ttataatggt tacaaataaa gcaatagcat cacaaatttc 9900
acaaataaag catttttttc actgcattct agttgtggtt tgtccaaact catcaatgta 9960
tcttatcatg tctcgtacgg cgtggtaggt ccgaacgaat ccatggatta ccctgttatc 10020
cctactcatc ttcgtcggac gcgccgttaa tatttgatca gccattctct gtatgagtac 10080
taacgaacgt gacgcggtgt tactggtaac tatgactctc ttaaggtagc caaatacatc 10140
atccctttag tgagggttaa ttcacgcagt gccgcggcgt gtagaaaata cctatcagct 10200
cgaggacgtg acaaacgaag ccgcacgtca gggccggacg tggggcccca gagcgacgct 10260
gagtgcgtgc gggactcgga gtacgtgacg gagcccccac gtgggttccc gcacgtccgc 10320
gacgtgacaa acgaagccgc acgtcagggc cggacgtggg gccccagagc gacgctgagt 10380
gcgtgcggga ctcggagtac gtgacggagc ccccacgtgg gttcccgcac gtccgcgacg 10440
tgacaaacga agccgcacgt cagggccgga cgtggggccc cagagcgacg ctgagtgcgt 10500
gcgggactcg gagtacgtga cggagccccc acgtgggttc ccgcacgtcc gcgacgtgac 10560
aaacgaagcc gcacgtcagg gccggacgtg gggccccaga gcgacgctga gtgcgtgcgg 10620
gactcggagt acgtgacgga gcccccacgt gggttcccgc acgtccgcga cgtgacaaac 10680
gaagccgcac gtcagggccg gacgtggggc cccagagcga cgctgagtgc gtgcgggact 10740
cggagtacgt gacggagccc ccacgtgggt tcccgcacgt ccgcgacgtg acaaacgaag 10800
ccgcacgtca gggccggacg tggggcccca gagcgacgct gagtgcgtgc gggactcgga 10860
gtacgtgacg gagcccccac gtgggttccc gcacgtccgc gacgtgacaa acgaagccgc 10920
acgtcagggc cggacgtggg gccccagagc gacgctgagt gcgtgcggga ctcggagtac 10980
gtgacggagc ccccacgtgg gttcccgcac gtccgcgaag acctagaggg tatataatgg 11040
gtgccttagc tggtgtgtga gctcatcttc ctgtgcatgc gggggggggg gggggcaatt 11100
ggccaccatg aaagccctca ccgctagaca acaggaagtg tttgacctca tcagggacca 11160
tatctcccag acaggaatgc cccctaccag ggccgaaatc gctcagaggc tgggattcag 11220
gagccctaac gctgccgaag aacatctgaa agccctcgcc aggaagggag tgattgagat 11280
tgtgtccggc gcttccaggg gcattagact cctgcaagag gaggaagaag gactccccct 11340
cgtgggaagg gtcgccgctg gcgaacccct cctggctcaa caacacattg agggacacta 11400
tcaggtcgat cctagcctct ttaaacccaa tgccgatttc ctcctgaggg tgtccggcat 11460
gagcatgaag gatattggaa tcatggacgg agacctcctg gctgtgcata agacacagga 11520
tgtgaggaac ggacaggtcg tggtcgccag gatcgacgac gaagtgacag tgaaaagact 11580
caagaaacag ggaaacaaag tggaactgct ccccgaaaac tccgagttta agcctatcgt 11640
cgtggatctg aggcagcaat cctttaccat tgagggactg gctgtgggag tgattagaaa 11700
tggcgattgg ctcgaatttc ccgggattag acctgagtgt gtggtccccg aaacccaatg 11760
cgctatgaaa agaaaagaga aaaaggctca gaaagagaaa gacaaactgc ctgtgtccac 11820
cacaaccgtc gatgatcaca tgccccctat catgcagtgt gagcctcccc ctcccgaagc 11880
cgctagaatc cacgaagtcg tccccaggtt cctctccgat aagctcctgg aaaccaatag 11940
acaaaagaat atccctcaac tcaccgctaa ccaacagttt ctgattgcca ggctgatttg 12000
gtatcaggat ggctatgagc aaccctccga cgaagacctc aagaggatca cacagacatg 12060
gcaacaggct gacgatgaga atgaggaaag cgatacccct ttcaggcaga ttaccgaaat 12120

-continued

```
gacaatcctc accgtccagc tcatcgtcga gtttgccaaa ggactccccg gattcgctaa  12180
gattagccaa cccgatcaga ttaccctcct gaaagcctgt agctccgagg tcatgatgct  12240
gagagtggct agaaggtacg atgccgcttc cgatagcgtc ctgtttgcca ataaccaagc  12300
ctataccagg gacaattaca ggaaggctgg catggcctat gtgattgagg atgtgctcca  12360
cttttgcaga tgtatgtact ccatggctct cgataacatt cactatgccc tcctgacagc  12420
cgtcgtgatt ttctccgaca ggcccggact ggaacagcct caactcgtgg aagaaattca  12480
gaggtactat ctgaataccc tcagaattta cattctgaat cagctctccg gcagcgctag  12540
atccagcgtc atctatggca aaatcctctc cattctgtcc gagctgagaa cactgggaat  12600
gcaaaactcc aatatgtgca ttagcctcaa gctcaagaat agaaaactgc ctccctttct  12660
ggaagaaatt tgggatgtgg ctgacatgag ccatacccaa ccccctccca ttctggaaag  12720
ccctaccaat ctgtaaatcg atagccgcct ggctgagatg gggtgggcag ggcagagctg  12780
atcagggccg agcagaaccg cactcttccc aaataaagct tcctccttga aacacaaatg  12840
tttcttactt acaccccatc ctgatttctt ttcttgagac cagagagtgg gaaagctctc  12900
tcttgacctg aggatggatc tgaaaattat gagccccttg aggacaggga atgttattca  12960
tctttgaatt ccgcagcatc tagcaccagg tcttgtacag agcaggtgcc caataaatgg  13020
ttgaatgaat atatgaaaag tagaggcaga gggctgggca cagtggctca cgcctgtaat  13080
cctagcactt tgggaggctg aggtgggtgg atcacttgag gtcaggagtt cgagaccagc  13140
ttggccaaca tggctaaacc tcatctctat taaaaataca aaaattagct gggctggtgc  13200
ctgtaatccc agctactcag gaggctgagg caggagaatc acttgaaccc aggaggagga  13260
gtttgcagtg agccgagatc gcaccattgc actccagcct gggcgatagg agcaaaactc  13320
catctcaaaa acaaaaaaca aaacaaaaca aaaagaaaaa agaaaagtag gggcagagat  13380
gtggggcagg agaggtgact cggctcagc tgcatggtcc tgctctgctt ctttttctt  13440 ggagtttgtc cgttggatga caatgatagt ggtgaacagg tatggagggc ttactaagta  13500
ccaggtgtct agacgaggac gctcgggctt ggacccatgg cacatcgtgt aatcatggtc  13560
atagctgttt cctgtgtgaa attgttatcc gctacgtctc tcccccgcag taagggctag  13620
attaactcgt ctcgtgaata tccggaactc cctttagtga gggttaattg cgttgcgctc  13680
actgcccgct ttccagtcgg gaaacctgtc gtgccagctt aatcatggtc atagctgttt  13740
cctgtgtgaa attgttatcc gctaccggaa acgcttcctt catgtgagca aaaggccagc  13800
aaaaggccag gaaccgtaaa aaggccgcgt tgctggcgtt tttccatagg ctccgccccc  13860
ctgacgagca tcacaaaaat cgacgctcaa gtcagaggtg gcgaaacccg acaggactat  13920
aaagatacca ggcgtttccc cctggaagct ccctcgtgcg ctctcctgtt ccgaccctgc  13980
cgcttaccgg atacctgtcc gcctttctcc cttcgggaag cgtggcgctt tctcatagct  14040
cacgctgtag gtatctcagt tcggtgtagg tcgttcgctc caagctgggc tgtgtgcacg  14100
aaccccccgt tcagcccgac cgctgcgcct tatccggtaa ctatcgtctt gagtccaacc  14160
cggtaagaca cgacttatcg ccactggcag cagccactgg taacaggatt agcagagcga  14220
ggtatgtagg cggtgctaca gagttcttga agtggtggcc taactacggc tacactagaa  14280
gaacagtatt tggtatctgc gctctgctga agccagttac cttcggaaaa agagttggta  14340
gctcttgatc cggcaaacaa accaccgctg gtagcggtgg tttttttgtt tgcaagcagc  14400
agattacgcg cagaaaaaaa ggatctcaag aagatccttt gatcttttct acggggtctg  14460
acgctcagtg gaacgaaaac tcacgttaag ggattttggt catgcctagg acgaaaggag  14520
```
gtcgtgaaat ggataaaaaa atacagcgtt tttcatgtac aactatacta gttgtagtgc 14580
ctaaataatg cttttaaaac ttaaaaatac gtttaaaccc tcagcgaaat ggcatacgag 14640
taaacttggt ctgacaccgc tgcatgagat tatcaaaaag gatcttcacc tagatccttt 14700
taaattaaaa atgaagtttt aaatcaatct aaagtatata tgagtaaact tggtctgaca 14760
gttaccaatg cttaatcagt gaggcaccta tctcagcgat ctgtctattt cgttcatcca 14820
tagttgcctg actccccgtc gtgtagataa ctacgatacg ggagggctta ccatctggcc 14880
ccagtgctgc aatgataccg cgagacccac gctcaccggc tccagattta tcagcaataa 14940
accagccagc cggaagcgcc gagcgcagaa gtggtcctgc aactttatcc gcctccatcc 15000
agtctattaa ctgttgccgg gaagctagag taagtagttc gccagttaat agtttgcgga 15060
gcgttgttgc cattgctaca ggcatcgtgg tgtcacgctc gtcgtttggt atggcttcat 15120
tcagctccgg ttcccaacga tcaaggcgag ttacatgatc ccccatgttg tgcaaaaaag 15180
cggttagctc cttcggtcct ccgatggttg tcagaagtaa gttggccgca gtgttatcac 15240
tcatggttat ggcagcactg cataattctc ttactgtcat gccatccgta agatgctttt 15300
ctgtgactgg tgagtattca accaagtcat tctgagaata gtgtatgcgg cgaccgagtt 15360
gctcttgccc ggcgtcaata cgggataata ccgcgccaca tagcagaact ttaaaagtgc 15420
tcatcattgg aaagcgttct tcggggcgaa aactctcaag gatcttaccg ctgttgagat 15480
ccagttcgat gtaacccaca cgagcaccca actgatcttc agcatctttt actttcacca 15540
gcgtttctgg gtgagcaaaa acaggaaggc aaaatgccgc aaaaaaggga ataagggcga 15600
cacggaaatg ttgaatactc atacgcttcc tttttcaata gtattgaagc atttatcagg 15660
gttattgtct cgggagcgaa tacatatttg aatgtattta gaaaaa 15706

<210> SEQ ID NO 18
<211> LENGTH: 17505
<212> TYPE: DNA
<213> ORGANISM: Artificial Sequence
<220> FEATURE:
<223> OTHER INFORMATION: Synthetic dual promoter gene switch construct encoding human Factor VIII:C

<400> SEQUENCE: 18
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gccctaggac gaaaggaggt cgtgaaatgg ataaaaaaat 180
acagcgtttt tcatgtacaa ctatactagt tgtagtgcct aaataatgct tttaaaactt 240
aaaaataatc aatgtcctca gcggggtgtc ggggatttag gtgacactat aggctgagcg 300
ccgcacaggc atctagaggc tatggcaggg cctgccgccc cgacgttggc tgcgagccct 360
gggccttcac ccgaacttgg ggggtggggt ggggaaaagg aagaaacgcg ggcgtattgg 420
ccccaatggg gtctcggtgg ggtatcgaca gagtgccagc cctgggaccg aaccccgcgt 480
ttatgaacaa acgacccaac accgtgcgtt ttattctgtc tttttattgc cgtcatagcg 540
cgggttcctt ccggtattgt ctccttccgt gtttcaatcg attcaaaaga actcgtccag 600
cagacggtaa aaagcaatgc gttgagaatc cggtgcagca atgccataca gcaccagaaa 660
gcgatcagcc cattcaccgc ccagttcttc agcaatgtca cgggttgcca gtgcgatgtc 720
ctgatagcga tcagccacgc ccaggcgacc gcagtcgata aagccggaga aacggccgtt 780
ttccaccata atgtttggca gacaagcatc gccgtgggtc acaaccaggt cctcgccatc 840

```
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctccccg    1920
cgggaggttt tataaatccg actgtctaga ttgttgttaa atcacacaaa aaaccaacac   1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg ggcttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag gggcgctgt    2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc cccccccccg catgccgtct aacaaaaaag ccaaaaacgg ccagaattta   3060
gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
```

-continued

```
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
gcctgttccg ctctctggaa agaaaaccag tgccctagag tcacccaagt cccgtcctaa   3420
aatgtccttc tgctgatact ggggttctaa ggccgagtct tatgagcagc gggccgctgt   3480
cctgagcgtc cgggcggaag gatcaggacg ctcgctgcgc ccttcgtctg acgtggcagc   3540
gctcgccgtg aggagggggg cgcccgcggg aggcgccaaa acccggcgcg gaggccctcg   3600
agtaggcgag accaatgggt gcgccatggg ctcttccaaa aatttaggtg acactatagg   3660
gcaccgctcg cacctgcgca caggcccgcg gctacaaact acgaacgatc attctagata   3720
ccacatttgt agaggtttta cttgctttaa aaaacctccc acatctcccc ctgaacctga   3780
aacataaaat gaatgcaaat gttttattaa cttgtttatt gcagcttata atggttacaa   3840
attaagcaat agcatcacaa atttcacaaa ttaagcattt ttttcactgc attctagttg   3900
tggtttgtcc aaactcatca atgtatctta tcatgtctaa tcgattcaca ggttggtggg   3960
gctctccagg atgggggggg gctgggtgtg gctcatgtcg gccacgtccc aaatctcctc   4020
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
cctggcgctg ccgctcagct ggttcaggat gtagatcctc agggtgttca ggtagtacct   4200
ctggatctcc tccaccagct ggggctgctc caggccgggc ctgtcgctga agatcaccac   4260
ggcggtcagc agggcgtagt ggatgttgtc cagggccatg ctgtacatac atctgcagaa   4320
gtgcaggagg tcctcgatca cctcggccat gccagccttc ctgtagttgt ccctggtgta   4380
agcctggttg ttggcgaaca ggatgctgtc gctggcggcg tcgtacctcc tggccaccct   4440
cagcatcatc acctcgctgc tgcaagcctt cagcagggtg atctggtcgg gctggctgat   4500
cttggcgaat ccgggcaggc ccttggcgaa ctccacgatc agctgcacgg tcaggatggt   4560
catctcggtg atctgcctga agggggtgtc gctctcctcg ttctcgtcgt cggcctgctg   4620
ccaggtctgg gtgatccttt tcaggtcctc gtcgctgggc tgctcgtagc cgtcctgata   4680
ccagatcagc ctggcgatca ggaactgctg gttggcggtc agctggggga tgttcttctg   4740
cctgttggtc accagcagct tgtcgctcag gaacctgggc acgacctcgt gaatcctggc   4800
ggcctcgggg gggggggct cgcactgcat gatgggggc atgtggtcat cgacggtggt   4860
ggtgctcacg ggcagcttgt ccttctcctt ctgggccttc ttctccttcc ttttcatggc   4920
gcactgggtc tcgggcacca cgcactcggg cctgatcccg ggaaactcgg ggctcacggt   4980
cagctgcctc tggcccttgt tgctgctctc ctcgctgctg ctggtggcgc tgatcctgtg   5040
ctgcctcagg gtcaggggca tgtcggtctc cacgctggcc agcctgtcgg tcacggcgtc   5100
cttgttcacg ttgtcctgca cgaacaggcc ggtcagcagg gccttgatgt cttgcaggct   5160
gtccatcttc aggatcatgt ccaggtcctc cctggggaag atcagcagga acagctgctc   5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc ccccccccg catgccacta agatctgcat   5460
tttgacctag tttaaaagta aaacataagc gtgtcacctc aggatcattg tatttcttgc   5520
ttttacacct aatattcttc aaaattagca actattcctt caaaatgcct taaatacgtt   5580
```

```
aatattccgc aagcctcccc tcaattttac aaggctaagt cacttaatac gaaattcgtc   5640
attcaaggtt tcaacgtcaa cagcggaaaa tccagagcgc tctcttacca agcgtccaca   5700
gctttcccca ctaactgttc cggatattca aactcccccg accgaactcc aatctgcctc   5760
aaacctaagc acggtgttag gcaaactgaa aacaaaacca aacccacaag actcgcgaaa   5820
taaaaatccc attgaaacac aagaaggggc acctttctca cactgggatt ccaaagtaaa   5880
ggcttccaga aaccacacaa actacctctt ttccgccttc cccgcgaagt aaactcgaca   5940
gaatcgccga tcggttaggc gtccgttagt ttccgtcaac ccgcgcgcgc caaccgccct   6000
cgccccccctc aggtcaacaa ggcccactgt cccggaaagg cccagcgccg cgtcacctcg   6060
ccctcccctc ccccacgccc tcccctcagc ggcccaccca accccaagaa gcctccacct   6120
tgacctcacc cattccccccc tctcacaccc ccccaaggtc gttacggctg cgggccagta   6180
cctgttagcg gataccagga tcctgccaat caccaaccac gtccacccac agggacacaa   6240
acaagctcac ccaacaaagc caaccgcccc taaatgctcc gggctggcgg aggcaaattt   6300
atgcaacgag tgttgcgtca cttatcaccc ctcacgtaga cgccgtctcc gtgcgccgct   6360
gaaagtagtt cgccgcgccc aacctcccga gaggcagttt aggcttttca actgagcccc   6420
aaattcctca tagccgtaag aaaggctcct aaaaaaattat ttcccttctc ctctatgcgc   6480
ttctcttcct tctttaggaa aatataagaa aattatcagg cggatgaatt tgagttgaag   6540
aaaccttcct cgaaagctct ggaaacttcc ttgcagcgcc ggcactgatt ggttaggcct   6600
gcgaaggcga ggtcggcgct gattggtggg ggacgcggtg gctctgttgt tgctgggctc   6660
cacctggggt ggcttagcgc cgaggttgct aagtaactga gcgcgcgtcg ccgcacaggt   6720
ctttcctttt ttttcttgag acggatttcg ctcttgtttc ccaggctgga gtgcaatggc   6780
gcgatctcgg ctcatcgcaa cctccgcctc ccgggttcaa gcgattctcc tgcctcagcc   6840
tcccaagtag ctgggattac agctcgagtg gtaatacaat ggccggttcc catggacctg   6900
catcgtggtg taactataac ggtcctaagg tagcgaccgc ggagactagg tgtatttatc   6960
taagcgatcg cttaattaag gccggccgcc gcaataaaat atctttattt tcattacatc   7020
tgtgtgttgg tttttttgtgt gaatccatag tactaacata cgctctccat caaaacaaaa   7080
cgaaacaaaa caaactagca aaataggctg tccccagtgc aagtccaggt gccagaacat   7140
ttctctatcc ataatgcagg ggtaccgggt gatgacggtg aaaacctcca attgcggagt   7200
actgtcctcc gagcggagta ctgtcctccg agcggagtac tgtcctccga gcggagtact   7260
gtcctccgag cggagtactg tcctccgagc ggagtactgt cctccgagcg gagagtcccc   7320
ggggacctag agggtatata atgggtgcct tagctggtgt gtgacctcat cttcctgtac   7380
gcccctgcag ggcgcgccca cgcgtcgaag aaggtgagta atcttaacat gctctttttt   7440
tttttttttg ctaatccctt ttgtgtgctg atgttaggat gacatttaca acaaatgttt   7500
gttcctgaca ggaaaaacct tgctgggtac cttcgttgcc ggacacttct tgtcctctac   7560
tttggaaaaa aggaattgag agccgctagc gccaccatgg ctaccaggag atattacctc   7620
ggcgctgtgg aactgtcctg ggattacatg cagtccgacc tcggcgaact gcctgtggat   7680
gccaggttcc ctcccagggt gcctaagtcc ttccctttca atacctccgt ggtctacaaa   7740
aagacactgt ttgtggaatt tacagaccat ctgtttaaca ttgccaaacc caggcccccct   7800
tggatgggcc tcctgggacc cacaatccaa gccgaagtgt atgacacagt ggtcatcaca   7860
ctgaaaaaca tggcctccca ccccgttagc ctgcacgctg tcggcgtcag ctattggaaa   7920
```

-continued

```
gcctccgagg gagccgaata cgatgaccaa acctcccaga gggagaaaga ggatgacaaa   7980
gtgtttcccg gaggctccca cacatacgtc tggcaagtgc tcaaggaaaa cggacctatg   8040
gcctccgacc ctctgtgtct gacatactcc tacctgagcc atgtggatct ggtcaaggat   8100
ctgaatagcg gactgattgg cgctctgctc gtgtgtagag aaggctccct ggctaaggaa   8160
aagacacaga cactgcataa gtttatcctc ctgtttgccg tttttgatga gggaaagtcc   8220
tggcatagcg aaaccaaaaa ctccctgatg caggatagag atgccgccag tgctagagct   8280
tggcctaaga tgcacaccgt caatggctat gtgaatagat ccctgcctgg cctcatcgga   8340
tgccatagaa aaagcgtcta ctggcacgtc atcggaatgg gaaccacacc cgaagtgcat   8400
agcattttcc ttgaaggaca cacattcctc gtgaggaacc atagacaagc ctccctggaa   8460
atctccccca ttacctttct gacagcccaa accctcctga tggacctcgg ccaattcctc   8520
ctgttttgcc atatctccag ccatcagcat gacggaatgg aagcctatgt gaaagtggat   8580
agctgtcccg aggagcccca gctcagaatg aagaataacg aagaagccga ggactacgat   8640
gacgatctga cagactccga gatggatgtc gtgaggttcg atgacgataa ctcccccctcc  8700
ttcattcaga ttagatccgt ggctaagaaa caccctaaga catgggtcca ctatatcgct   8760
gccgaggaag aagattggga ctatgcccct ctggtcctgg ctcccgatga caggagctat   8820
aagtcccagt atctgaataa cggaccccag agaatcggca ggaagtataa gaaagtgagg   8880
ttcatggcct ataccgatga gacattcaaa accagggagg ctatccaaca cgaaagcgga   8940
atcctcggcc ctctgctcta cggagaggtc ggcgataccc tcctgattat ctttaagaat   9000
caggccagta ggccctataa catttaccct cacggaatca cagatgtgag acctctgtat   9060
agcaggagac tccccaaagg cgtcaagcat ctgaaagact ttcccattct gcctggcgaa   9120
atctttaagt ataagtggac cgtcaccgtc gaggatggcc ctaccaaaag cgatcccagg   9180
tgcctcacca ggtactatag ctccttcgtc aacatggaga gggacctcgc ctccggcctc   9240
atcggacccc tcctgatttg ctataaggaa agcgtcgatc aaagaggaaa ccaaatcatg   9300
agcgataaga ggaacgtcat cttgttctcc gtgtttgacg aaaacaggag ctggtacttg   9360
accgaaaaca ttcagaggtt cctccccaat cccgctggcg tccagcttga ggaccctgag   9420
tttcaagcct ccaacattat gcacagcatt aacggatacg ttttcgatag cctccagctg   9480
tccgtctgcc tccacgaggt cgcttactgg tacattctgt ccatcggagc ccaaaccgat   9540
ttcctgagcg tctttttag cggatacaca ttcaaacaca aaatggtcta cgaggataca    9600
ctgacactgt ttccctttag cggagagaca gtgtttatga gcatggagaa ccctggcctc   9660
tggattctgg gatgccataa ctccgacttt agaaatagag gaatgacagc cctcctgaaa   9720
gtgtccagct gtgacaaaaa cacaggcgat tactatgagg atagctatga ggacatttcc   9780
gcctatctgc tgtcaaaaaa caatgccatt gagcctagat ccttctccca gaatagcagg   9840
caccctagca caagacaaaa gcaattcaat gccacaacca ttcccgaaaa cgacatcgaa   9900
aagacagacc cttggtttgc ccatagaaca cccatgccca aaatccaaaa cgtcagctcc   9960
agcgatctgc tcatgctcct gaggcagtcc ccccacaccc acggcctgag cctgtccgat  10020
ctgcaagagg ctaagtatga gacattctcc gacgatccct cccccggagc cattgactcc  10080
aacaatagcc tgagcgaaat gacacacttt agaccccagc tgcaccatag cggagacatg  10140
gtgtttaccc ctgagtccgg cctccagctc agactcaacg aaaagctcgg cacaaccgct  10200
gccacagagc tgaagaaact ggatttcaaa gtgtccagca caagcaataa cctcatctcc  10260
accattccct ccgacaatct ggctgccgga accgataaca caagctccct gggacccccct  10320
```

```
tccatgcccg tccactatga ctcccagctc gacacaaccc tttttggaaa gaaaagctcc  10380
cccctcaccg aaagcggagg ccctctgtcc ctgtccgagg aaaacaatga cagcaagctg  10440
ctggagagcg gactgatgaa ctcccaggaa agctcctggg gaaagaatgt gtccagcaca  10500
gagtccggca ggctgtttaa gggaaagaga gcccacggcc ctgccctcct gacaaaggat  10560
aacgctctgt ttaaggtcag cattagcctc ctgaaaacca ataagacaag caataactcc  10620
gccacaaaca gaaagaccca cattgacgga ccctccctgc tcatcgaaaa ctccccctcc  10680
gtgtggcaga atatcctcga atccgacaca gagtttaaga aagtgacacc cctcatccat  10740
gacaggatgc tcatggataa gaatgccaca gccctcagac tcaaccacat gagcaacaaa  10800
accacaagca gcaagaacat ggagatggtc cagcaaaaga aagagggacc cattcccccct  10860
gacgctcaga atcccgatat gtccttcttt aagatgctgt ttctgcctga gtccgccagg  10920
tggattcaga ggacccacgg caaaaactcc ctgaatagcg gacagggacc ctcccccaaa  10980
cagctcgtgt ccctgggacc cgaaaagtcc gtggaaggcc aaaactttct gtccgagaaa  11040
aacaaagtgg tcgtgggaaa gggagagttt accaaggacg ttggcctgaa ggaaatggtg  11100
tttcctagct ccagaaatct gtttctgaca aacctcgaca atctgcatga gaataacaca  11160
cacaatcagg aaaagaaaat ccaagaggaa atcgaaaaga aagagacact gattcaggaa  11220
aacgtcgtgc tcccccaaat ccataccgtc accggaacca aaaactttat gaaaaacctt  11280
ttcctcctgt ccaccaggca gaatgtggaa ggctcctacg atggcgctta cgctcccgtc  11340
ctgcaagact ttagatccct gaatgactcc accaatagaa caaagaaaca cacagcccat  11400
ttctccaaga aaggcgagga ggaaaacctg gaaggactgg gaaaccaaac caaacagatt  11460
gtggaaaagt atgcctgtac cacaagaatt agccctaaca caagccaaca gaatttcgtc  11520
acccaaagat ccaagagagc cctgaagcaa ttcaggctgc ctctggaaga aacagagctg  11580
gagaaaagaa ttatcgtgga tgatacctcc acccaatggt ccaagaatat gaaacacctc  11640
acccctagca cactgacaca gattgactat aacgaaaagg aaaagggagc cattacccaa  11700
agccctctgt ccgactgtct gacaagatcc cactccatcc ctcaggctaa caggagccct  11760
ctgcctatcg ctaaggtcag ctccttccct agcattagac ctatctatct gacaagagtc  11820
ctgtttcagg ataactccag ccatctgcct gccgcctctt atagaaaaaa ggatagcgga  11880
gtgcaagagt ccagccattt cctccaggga gccaaaaaga ataacctgag cctcgccatt  11940
ctgacactgg aaatgacagg cgatcagagg gaggtcggct ccctgggaac ctccgccaca  12000
aactccgtga catacaaaaa ggtcgagaat accgtcctgc ctaagcctga cctccccaaa  12060
acctccggca aagtggaact gctccccaaa gtgcatatct atcagaaaga cctctttcct  12120
accgaaacct ccaacggaag ccccggccac ctggatctgg tcgagggaag cctcctgcaa  12180
ggcacagagg gagccattaa gtggaacgaa gccaatagac ctggcaaagt gcctttcctc  12240
agagtcgcca cagagtccag cgctaagaca cccagcaagc tgctggaccc cctcgcctgg  12300
gacaatcact atggcacaca gattcccaaa gaggaatgga aagccaaga gaaaagccct  12360
gagaaaaccg ctttcaaaaa gaaagacaca atcctgagcc tcaacgcttg cgaaagcaat  12420
cacgctatcg ctgccattaa cgaaggccaa aacaaacccg aaatcgaagt gacatgggcc  12480
aagcagggca ggaccgaaag actctgctcc cagaatcccc ctgtgctcaa gaggcaccaa  12540
agagaaatca caagaacaac cctccagtcc gaccaagagg aaatcgacta cgatgacaca  12600
atctccgtgg aaatgaaaaa ggaggacttt gacatttacg atgaggatga gaatcagtcc  12660
```
cccaggagct ttcagaaaaa gacaagacat tactttatcg ctgccgtcga gaggctgtgg 12720
gactatggca tgagcagcag ccctcacgtc ctgaggaaca gagcccagag cggaagcgtc 12780
ccccaattca aaaaggtcgt gtttcaggag ttcacagacg gcagcttcac ccaacccctc 12840
tacaggggcg aactgaatga gcatctggga ctgctcggcc cttacattag agccgaggtg 12900
gaggataaca ttatggtcac ctttagaaat caggccagca ggccctatag cttttactcc 12960
agcctcatct cctacgagga agatcagagg cagggagccg aacccaggaa gaatttcgtc 13020
aagcctaacg aaaccaaaac ctatttctgg aaggtccagc atcacatggc ccctaccaaa 13080
gacgaatttg attgcaaagc ctgggcctat ttctccgacg ttgacctgga gaaagacgtg 13140
cattccggcc tcatcggacc cctcctggtc tgccatacca ataccctcaa ccctgcccac 13200
ggcagacagg tgaccgtcca ggagtttgct ctgtttttca caatctttga cgaaaccaaa 13260
agctggtact ttaccgaaaa catggagagg aactgtagag ccccctgtaa cattcagatg 13320
gaggacccca cattcaaaga gaattacagg ttccatgcca ttaacggata cattatggat 13380
accctccccg gactggtcat ggctcaggat cagaggatca ggtggtatct gctgtctatg 13440
ggctccaacg aaaacattca ctccatccat ttctccggcc atgtgtttac cgtcagaaaa 13500
aaggaggagt ataagatggc cctctacaat ctgtatcccg gagtgtttga gacagtggaa 13560
atgctcccct ccaaggctgg catttggagg gtggaatgcc tcatcggaga gcatctgcac 13620
gccggaatgt ccaccctgtt tctcgtgtat agcaataagt gtcagacacc cctcggcatg 13680
gcctccggcc atatcaggga ctttcagatt accgccagcg gacagtatgg ccaatgggct 13740
cccaaactgg ctagactcca ctatagcgga agcattaacg cttggtccac caaagagcct 13800
ttctcctgga ttaaggtgga cctcctggct cccatgatta tccacggaat caaaacccaa 13860
ggcgctagac aaaagtttag ctccctgtat atctcccagt ttatcattat gtatagcctc 13920
gacggaaaga aatggcaaac ctatagagga aactccaccg gaaccctcat ggtgttcttt 13980
ggcaatgtgg atagctccgg cattaagcat aacattttca atcccccctat cattgccagg 14040
tacattagac tccaccctac ccattactcc atcaggagca cactgaggat ggaactgatg 14100
ggctgtgacc tcaactcctg ctccatgccc ctcggcatgg aaagcaaagc cattagcgat 14160
gcccaaatca cagcctccag ctatttcaca aatatgttcg ctacctggag ccctagcaaa 14220
gccaggctgc atctgcaagg caggagcaat gcctggagac ctcaggtcaa caatcccaaa 14280
gagtggctgc aagtggattt ccaaaagaca atgaaagtga caggcgtcac cacacaggga 14340
gtgaaaagcc tcctgacaag catgtacgtc aaggagttcc tcatctccag ctcccaggat 14400
ggccatcagt ggaccctgtt ctttcagaat ggcaaagtga aagtgtttca gggaaaccaa 14460
gactccttca cacccgtcgt gaatagcctc gaccctcccc tcctgacaag atacctgaga 14520
atccaccccc aaagctgggt gcatcagatt gccctcagaa tggaggtcct gggatgcgaa 14580
gcccaagacc tctactaaat cgattgcgca aagctttcgc gataggcgag accaatgggt 14640
gtgtacgtag cggccgcgtc gacgatagct tgatgggtgg catccctgtg acccctcccc 14700
agtgcctctc ctggccctgg aagttgccac tccagtgccc accagccttg tcctaataaa 14760
attaagttgc atcattttgt ctgactaggt gtccttctat aatattatgg ggtggagggg 14820
ggtggtatgg agcaaggggc aagttgggaa gacaacctgt agggcctgcg ggtctattg 14880
ggaaccaagc tggagtgcag tggcacaatc ttggctcact gcaatctccg cctcctgggt 14940
tcaagcgatt ctcctgcctc agcctcccga gttgttggga ttccaggcat gcatgaccag 15000
gctcagctaa tttttgtttt tttggtagag acggggtttc accatattgg ccaggctggt 15060
ctccaactcc taatctcagg tgatctaccc accttggcct cccaaattgc tgggattaca 15120
ggcgtgaacc actgctccct tccctgtcct tctgatttta aaataactat accagcagga 15180
ggacgtccag acacagcata ggctacctgg ccatgcccaa ccggtgggac atttgagttg 15240
cttgcttggc actgtcctct catgcgttgg gtccactcag tagatgcctg ttgaattctg 15300
atttaaatcg gtccgcgtac ggcgtggtag gtccgaacga atccatggat taccctgtta 15360
tccctactca aggacatcat ccctttagtg agggttaatt cacgcagtgg gtacggaact 15420
aaaggcagca cacatcgtgt aatcatggtc atagctgttt cctgtgtgaa attgttatcc 15480
gctacgtctc tcccccgcag taagggctag attaactcgt ctcgtgaata tccggaactc 15540
cctttagtga gggttaattg cgttgcgctc actgcccgct ttccagtcgg gaaacctgtc 15600
gtgccagctt aatcatggtc atagctgttt cctgtgtgaa attgttatcc gctaccggaa 15660
acgcttcctt catgtgagca aaaggccagc aaaaggccag gaaccgtaaa aaggccgcgt 15720
tgctggcgtt tttccatagg ctccgccccc ctgacgagca tcacaaaaat cgacgctcaa 15780
gtcagaggtg gcgaaacccg acaggactat aaagatacca ggcgtttccc cctggaagct 15840
ccctcgtgcg ctctcctgtt ccgaccctgc cgcttaccgg atacctgtcc gcctttctcc 15900
cttcgggaag cgtggcgctt tctcatagct cacgctgtag gtatctcagt tcggtgtagg 15960
tcgttcgctc caagctgggc tgtgtgcacg aaccccccgt tcagcccgac cgctgcgcct 16020
tatccggtaa ctatcgtctt gagtccaacc cggtaagaca cgacttatcg ccactggcag 16080
cagccactgg taacaggatt agcagagcga ggtatgtagg cggtgctaca gagttcttga 16140
agtggtggcc taactacggc tacactagaa gaacagtatt tggtatctgc gctctgctga 16200
agccagttac cttcggaaaa agagttggta gctcttgatc cggcaaacaa accaccgctg 16260
gtagcggtgg tttttttgtt tgcaagcagc agattacgcg cagaaaaaaa ggatctcaag 16320
aagatccttt gatcttttct acggggtctg acgctcagtg gaacgaaaac tcacgttaag 16380
ggattttggt catgatctat gtcgggtgcg gagaaagagg taatgaaatg gcatacgagt 16440
aaacttggtc tgacaccgct gcatgagatt atcaaaaagg atcttcacct agatcctttt 16500
aaattaaaaa tgaagtttta aatcaatcta aagtatatat gagtaaactt ggtctgacag 16560
ttaccaatgc ttaatcagtg aggcacctat ctcagcgatc tgtctatttc gttcatccat 16620
agttgcctga ctccccgtcg tgtagataac tacgatacgg gagggcttac catctggccc 16680
cagtgctgca atgataccgc gagacccacg ctcaccggct ccagatttat cagcaataaa 16740
ccagccagcc ggaagcgccg agcgcagaag tggtcctgca actttatccg cctccatcca 16800
gtctattaac tgttgccggg aagctagagt aagtagttcg ccagttaata gtttgcggag 16860
cgttgttgcc attgctacag gcatcgtggt gtcacgctcg tcgtttggta tggcttcatt 16920
cagctccggt tcccaacgat caaggcgagt tacatgatcc cccatgttgt gcaaaaaagc 16980
ggttagctcc ttcggtcctc cgatggttgt cagaagtaag ttggccgcag tgttatcact 17040
catggttatg gcagcactgc ataattctct tactgtcatg ccatccgtaa gatgcttttc 17100
tgtgactggt gagtattcaa ccaagtcatt ctgagaatag tgtatgcggc gaccgagttg 17160
ctcttgcccg gcgtcaatac gggataatac cgcgccacat agcagaactt taaaagtgct 17220
catcattggg aagcgttctt cggggcgaaa actctcaagg atcttaccgc tgttgagatc 17280
cagttcgatg taacccacac gagcacccaa ctgatcttca gcatctttta ctttcaccag 17340
cgtttctggg tgagcaaaaa caggaaggca aaatgccgca aaaaagggaa taagggcgac 17400
acggaaatgt tgaatactca tacgcttcct ttttcaatag tattgaagca tttatcaggg 17460
ttattgtctc gggagcgaat acatatttga atgtatttag aaaaa 17505

<210> SEQ ID NO 19
<211> LENGTH: 16379
<212> TYPE: DNA
<213> ORGANISM: Artificial Sequence
<220> FEATURE:
<223> OTHER INFORMATION: Synthetic single promoter gene switch construct encoding human factor VIII:C

<400> SEQUENCE: 19
taaacaaata ggggttccgc gcacatttcc ccgaaaagtg ccacctgacg tactgaggac 60
gccagggttt tcccagtcac gacgttgtaa aacgacggcc agtagcagac aagcccgtca 120
gggcgcgtca gcgggtgttg gcgggtgtcg gggatttagg tgacactata ggctgagcgc 180
cgcacaggca tctagaggct atggcagggc ctgccgcccc gacgttggct gcgagccctg 240
ggccttcacc cgaacttggg gggtggggtg gggaaaagga agaaacgcgg gcgtattggc 300
cccaatgggg tctcggtggg gtatcgacag agtgccagcc ctgggaccga accccgcgtt 360
tatgaacaaa cgacccaaca ccgtgcgttt tattctgtct ttttattgcc gtcatagcgc 420
gggttccttc cggtattgtc tccttccgtg tttcaatcga ttcaaaagaa ctcgtccagc 480
agacggtaaa aagcaatgcg ttgagaatcc ggtgcagcaa tgccatacag caccagaaag 540
cgatcagccc attcaccgcc cagttcttca gcaatgtcac gggttgccag tgcgatgtcc 600
tgatagcgat cagccacgcc caggcgaccg cagtcgataa agccggagaa acggccgttt 660
tccaccataa tgtttggcag acaagcatcg ccgtgggtca caaccaggtc ctcgccatct 720
ggcatacgtg ctttcaggcg tgcgaacagt tctgccggtg ccagaccctg atgttcctcg 780
tccaggtcat cctgatcaac caggccagct tccatgcgag tgcgtgcgcg ctcgatacgg 840
tgtttagctt ggtgatcgaa tgggcaagta gctgggtcca gggtatgcag acggcgcata 900
gcatcagcca tgatggaaac cttttctgcc ggtgccagat gagaggacag cagatcctgg 960
cctggaacct cgcccagcag cagccagtcg cggccagcct cggtcacaac atccagcaca 1020
gctgcgcatg gaacgccggt agtagccagc caggacagac gagctgcttc atcttgcagt 1080
tcgttcagtg cgccggacag atcggtctta acaaacagca ccggacggcc ttgagcggac 1140
agacggaaca cagctgcgtc ggagcaaccg atagtctgtt gagcccagtc atagccaaac 1200
agacgttcca cccaagcagc cggagaacca gcgtgcagac cgtcttgttc aatcatggtg 1260
gcaattgggt gtctgagcga tgtggctcgg ctggcgacgc aaaagaagat gcggctgact 1320
gtcgaacagg aggagcagag agcgaagcgg gaggctgcgg gctcaatttg catgctttag 1380
ttcctcacct tgtcgtatta tactatgccg atatactatg ccgatgatta attgtcaacg 1440
tatacggaat agctctgagg ccgaggcagc ttcggcctct gcataaataa aaaaaattag 1500
tcagccatgg ggcggagaat gggcggaact gggcggagtt aggggcggga tgggcggagt 1560
taggggcggg actatggttg ctgactaatt gagatgcttg ctttgcatac ttctgcctgc 1620
tggggagcct ggggactttc cacacctggt tgctgactaa ttgagatgct tgctttgcat 1680
acttctgcct gctggggagc ctggggactt tccacaccct aacctcgagg ccatcgtggc 1740
acgccagggt tttcccagtc acgacgttgt aaaacgacgg ccagtgctct tctcccccgc 1800
gggaggtttt ataaatccga ctgtctagat accacatttg tagaggtttt acttgcttta 1860
aaaaacctcc cacatctccc cctgaacctg aaacataaaa tgaatgcaaa tgttttatta 1920
acttgtttat tgcagcttat aatggttaca aattaagcaa tagcatcaca aatttcacaa 1980
attaagcatt tttttcactg cattctagtt gtggtttgtc caaactcatc aatgtatctt 2040
atcatgtcta atcgattcac aggttggtgg ggctctccag gatggggggg ggctgggtgt 2100
ggctcatgtc ggccacgtcc caaatctcct ccaggaaggg gggcagcttc ctgttcttca 2160
gcttcaggct gatacacata ttgctgttct gcattcccag ggtcctcagc tcgctcagga 2220
tgctcaggat cttgccgtag atcacgctgc tcctggcgct gccgctcagc tggttcagga 2280
tgtagatcct cagggtgttc aggtagtacc tctggatctc ctccaccagc tggggctgct 2340
ccaggccggg cctgtcgctg aagatcacca cggcggtcag cagggcgtag tggatgttgt 2400
ccagggccat gctgtacata catctgcaga agtgcaggag gtcctcgatc acctcggcca 2460
tgccagcctt cctgtagttg tccctggtgt aagcctggtt gttggcgaac aggatgctgt 2520
cgctggcggc gtcgtacctc ctggccaccc tcagcatcat cacctcgctg ctgcaagcct 2580
tcagcagggt gatctggtcg ggctggctga tcttggcgaa tccgggcagg cccttggcga 2640
actccacgat cagctgcacg gtcaggatgg tcatctcggt gatctgcctg aagggggtgt 2700
cgctctcctc gttctcgtcg tcggcctgct gccaggtctg ggtgatcctt ttcaggtcct 2760
cgtcgctggg ctgctcgtag ccgtcctgat accagatcag cctggcgatc aggaactgct 2820
ggttggcggt cagctggggg atgttcttct gcctgttggt caccagcagc ttgtcgctca 2880
ggaacctggg cacgacctcg tgaatcctgg cggcctcggg gggggggggc tcgcactgca 2940
tgatgggggg catgtggtca tcgacggtgg tggtgctcac gggcagcttg tccttctcct 3000
tctgggcctt cttctccttc cttttcatgg cgcactgggt ctcgggcacc acgcactcgg 3060
gcctgatccc gggaaactcg gggctcacgg tcagctgcct ctggcccttg ttgctgctct 3120
cctcgctgct gctggtggcg ctgatcctgt gctgcctcag ggtcaggggc atgtcggtct 3180
ccacgctggc cagcctgtcg gtcacggcgt ccttgttcac gttgtcctgc acgaacaggc 3240
cggtcagcag ggccttgatg tcttgcaggc tgtccatctt caggatcatg tccaggtcct 3300
ccctggggaa gatcagcagg aacagctgct ccagcctctc cagcctgctc tccacctcgg 3360
tcaggtgggc cctggtcagg gggctcctct tggtcttggg gctgtatctg cactcccagt 3420
tgttcttcag gcacttggcg cacttgggct tctccttgct gcacttcagc ttcttcagcc 3480
tgcagatgtc gcaagcctgc tcgatgctgc tcagcagctt catggtggca gatctggtcg 3540
cgggaggctg ctggttttcc actacccgaa aaaaatccag cgtctaagca gctgcaagga 3600
gagcctttca gagaagcggg tcctggcagc ggcggggaag tgtccccaaa tgggcagaat 3660
agcctccccg cgtcgggaga gtcgcgtcct tgctcgggtg ttgtaagttc cagtgcaaag 3720
tgcccgcccg ctgctatggg caaagtttcg tggatgcggc tagggttgcg caccgctggc 3780
tgggggatca gcgggagggc tgggccagag gcgaagcccc ctattcgctc cggatctccc 3840
ttcccaggac gcccgcagcg cagctctgct cgccgggctc ctccacccta gcccgccgcc 3900
cgctcgctcc ctctgcctct cgctggaatt actacagcga gttgccggct cagctgtcgc 3960
tggggctctc cagcatctcc atcaggaagg tgtcgatggg cacgtcgccg atcagcctga 4020
agaagaacag gtgctccagg cacttcaggc cgatgctcct caggctgggc agcctcagca 4080
gcagcttggc gaatctgccg ggctcgtcgg ggtgggtggt cctggtgtac tcctccaggg 4140
cggcgtacac cttctccctc agcagctcca cctcctgggc gcttttcagg cccctcacct 4200
cggggttgaa caggatgatg gccctcaggc agcccagctc ggtcttgtcc atcctcatgt 4260
ccctcatctt gctcaccagc tcggtcagca ccctgtcgaa gatggcgccc actccggcgc 4320

-continued

```
tgtgggcgct gttcctatgg acgtgcaggc cggtggccag caggatgccg tccctcacgt   4380
cgatgctcct gtggctgaag ctggcgatca gcagctcgtt ccatccggcc ctcagcagga   4440
tcacctggtc gtccaggggc aggctgctga agtggggaat cctcttggcc cactccacca   4500
gggtgaacag ctgcttgtcg gcggcctggc agatgttggt cacggggtcg ttggggctgc   4560
tgccgctgcc gccggttccg ccggggccct ccacgccctg gtcgcttttc tgctccacgg   4620
cgagttcggc ctccagaatc ctgtccacgg gcatctccat atggccgccg tactcgtcga   4680
tgcccagggc gtcggtgaac atctgctcga actcgaagtc ggccatgtcc agggcgccgt   4740
agggggcgct gtcgtggggg gtgaagccgg ggccggggct gtcgccgtcg cccagcatgt   4800
ccaggtcgaa gtcgtccagg gcgtcggcgt gggccatggc cacgtcctcg ccgtccaggt   4860
gcagctcgtc gcccaggctc acgtcggtgg ggggggccac cttccttttc ttcttggggc   4920
ccatggtggc caattgcccc cccccccccc cgcatgccgt ctaacaaaaa agccaaaaac   4980
ggccagaatt tagcggacaa tttactagtc taacactgaa aattacatat tgacccaaat   5040
gattacattt caaaaggtgc ctaaaaaact tcacaaaaca cactcgccaa ccccgagcgc   5100
acgtacccag cccagcagcc cgctactcac caagtgacga tcacagcgat ccacaaacaa   5160
gaaccgcgac ccaaatcccg gctgcgacgg aactagctgt gccacacccg gcgcgtcctt   5220
atataatcat cggcgttcac cgccccacgg agatccctcc gcagaatcgc cgagaaggga   5280
ctacttttcc tcgcctgttc cgctctctgg aaagaaaacc agtgccctag agtcacccaa   5340
gtcccgtcct aaaatgtcct tctgctgata ctggggttct aaggccgagt cttatgagca   5400
gcgggccgct gtcctgagcg tccgggcgga aggatcagga cgctcgctgc gcccttcgtc   5460
tgacgtggca gcgctcgccg tgaggagggg ggcgcccgcg ggaggcgcca aaacccggcg   5520
cggaggccct cgagtaggcg agaccaatgg gtgcgccatg ggctcttcca aaaatttagg   5580
tgacactata gggcaccgct cgcacctgcg cacaggcata agccaaatgg aactacgaga   5640
cctgcatcgt ggtgtaacta taacggtcct aaggtagcga ccgcggagac taggtgtatt   5700
tatctaagcg atcgcttaat taaggccggc cgccgcaata aaatatcttt attttcatta   5760
catctgtgtg ttggtttttt gtgtgaatcc atagtactaa catacgctct ccatcaaaac   5820
aaaacgaaac aaaacaaact agcaaaatag gctgtcccca gtgcaagtcc aggtgccaga   5880
acatttctct atccataatg caggggtacc gggtgatgac ggtgaaaacc tccaattgcg   5940
gagtactgtc ctccgagcgg agtactgtcc tccgagcgga gtactgtcct ccgagcggag   6000
tactgtcctc cgagcggagt actgtcctcc gagcggagta ctgtcctccg agcggagagt   6060
ccccggggac ctagagggta tataatgggt gccttagctg gtgtgtgacc tcatcttcct   6120
gtacgcccct gcaggggcgc gccacgcgtc gaagaaggtg agtaatctta acatgctctt   6180
tttttttttt tttgctaatc ccttttgtgt gctgatgtta ggatgacatt tacaacaaat   6240
gtttgttcct gacaggaaaa accttgctgg gtaccttcgt tgccggacac ttcttgtcct   6300
ctactttgga aaaaaggaat tgagagccgc tagcgccacc atggctacca ggagatatta   6360
cctcggcgct gtggaactgt cctgggatta catgcagtcc gacctcggcg aactgcctgt   6420
ggatgccagg ttccctccca gggtgcctaa gtccttccct ttcaatacct ccgtggtcta   6480
caaaaagaca ctgtttgtgg aatttacaga ccatctgttt aacattgcca aacccaggcc   6540
cccttggatg ggcctcctgg gacccacaat ccaagccgaa gtgtatgaca cagtggtcat   6600
cacactgaaa aacatggcct cccaccccgt tagcctgcac gctgtcggcg tcagctattg   6660
```

-continued

```
gaaagcctcc gagggagccg aatacgatga ccaaacctcc cagagggaga aagaggatga   6720
caaagtgttt cccggaggct cccacacata cgtctggcaa gtgctcaagg aaaacggacc   6780
tatggcctcc gaccctctgt gtctgacata ctcctacctg agccatgtgg atctggtcaa   6840
ggatctgaat agcggactga ttggcgctct gctcgtgtgt agagaaggct ccctggctaa   6900
ggaaaagaca cagacactgc ataagtttat cctcctgttt gccgtttttg atgagggaaa   6960
gtcctggcat agcgaaacca aaaactccct gatgcaggat agagatgccg ccagtgctag   7020
agcttggcct aagatgcaca ccgtcaatgg ctatgtgaat agatccctgc ctggcctcat   7080
cggatgccat agaaaaagcg tctactggca cgtcatcgga atgggaacca cacccgaagt   7140
gcatagcatt ttccttgaag gacacacatt cctcgtgagg aaccatagac aagcctccct   7200
ggaaatctcc cccattacct ttctgacagc ccaaaccctc ctgatggacc tcggccaatt   7260
cctcctgttt tgccatatct ccagccatca gcatgacgga atggaagcct atgtgaaagt   7320
ggatagctgt cccgaggagc cccagctcag aatgaagaat aacgaagaag ccgaggacta   7380
cgatgacgat ctgacagact ccgagatgga tgtcgtgagg ttcgatgacg ataactcccc   7440
ctccttcatt cagattagat ccgtggctaa gaaacaccct aagacatggg tccactatat   7500
cgctgccgag gaagaagatt gggactatgc ccctctggtc ctggctcccg atgacaggag   7560
ctataagtcc cagtatctga ataacggacc ccagagaatc ggcaggaagt ataagaaagt   7620
gaggttcatg gcctataccg atgagacatt caaaaccagg gaggctatcc aacacgaaag   7680
cggaatcctc ggccctctgc tctacggaga ggtcggcgat accctcctga ttatctttaa   7740
gaatcaggcc agtaggccct ataacattta ccctcacgga atcacagatg tgagacctct   7800
gtatagcagg agactcccca aaggcgtcaa gcatctgaaa gactttccca ttctgcctgg   7860
cgaaatcttt aagtataagt ggaccgtcac cgtcgaggat ggccctacca aaagcgatcc   7920
caggtgcctc accaggtact atagctcctt cgtcaacatg gagagggacc tcgcctccgg   7980
cctcatcgga cccctcctga tttgctataa ggaaagcgtc gatcaaagag gaaaccaaat   8040
catgagcgat aagaggaacg tcatcttgtt ctccgtgttt gacgaaaaca ggagctggta   8100
cttgaccgaa aacattcaga ggttcctccc caatcccgct ggcgtccagc ttgaggaccc   8160
tgagtttcaa gcctccaaca ttatgcacag cattaacgga tacgttttcg atagcctcca   8220
gctgtccgtc tgcctccacg aggtcgctta ctggtacatt ctgtccatcg gagcccaaac   8280
cgatttcctg agcgtctttt ttagcggata cacattcaaa cacaaaatgg tctacgagga   8340
tacactgaca ctgtttccct ttagcggaga gacagtgttt atgagcatgg agaaccctgg   8400
cctctggatt ctgggatgcc ataactccga ctttagaaat agaggaatga cagccctcct   8460
gaaagtgtcc agctgtgaca aaaacacagg cgattactat gaggatagct atgaggacat   8520
ttccgcctat ctgctgtcaa aaaacaatgc cattgagcct agatccttct cccagaatag   8580
caggcaccct agcacaagac aaaagcaatt caatgccaca accattcccg aaaacgacat   8640
cgaaaagaca gacccttggt ttgcccatag aacacccatg cccaaaatcc aaaacgtcag   8700
ctccagcgat ctgctcatgc tcctgaggca gtcccccaca ccccacggcc tgagcctgtc   8760
cgatctgcaa gaggctaagt atgagacatt ctccgacgat ccctccccgg gagccattga   8820
ctccaacaat agcctgagcg aaatgacaca ctttagaccc cagctgcacc atagcggaga   8880
catggtgttt acccctgagt ccggcctcca gctcagactc aacgaaaagc tcggcacaac   8940
cgctgccaca gagctgaaga aactggattt caaagtgtcc agcacaagca ataacctcat   9000
ctccaccatt ccctccgaca atctggctgc cggaaccgat aacacaagct ccctgggacc   9060
```

```
ccccttccatg cccgtccact atgactccca gctcgacaca acccttttttg gaaagaaaag   9120
ctccccccctc accgaaagcg gaggccctct gtccctgtcc gaggaaaaca atgacagcaa   9180
gctgctggag agcggactga tgaactccca ggaaagctcc tggggaaaga atgtgtccag   9240
cacagagtcc ggcaggctgt ttaagggaaa gagagcccac ggccctgccc tcctgacaaa   9300
ggataacgct ctgtttaagg tcagcattag cctcctgaaa accaataaga caagcaataa   9360
ctccgccaca aacagaaaga cccacattga cggaccctcc ctgctcatcg aaaactcccc   9420
ctccgtgtgg cagaatatcc tcgaatccga cacagagttt aagaaagtga cacccctcat   9480
ccatgacagg atgctcatgg ataagaatgc cacagccctc agactcaacc acatgagcaa   9540
caaaaccaca agcagcaaga acatggagat ggtccagcaa aagaaagagg gacccattcc   9600
ccctgacgct cagaatcccg atatgtcctt ctttaagatg ctgtttctgc ctgagtccgc   9660
caggtggatt cagaggaccc acggcaaaaa ctccctgaat agcggacagg gaccctcccc   9720
caaacagctc gtgtccctgg gacccgaaaa gtccgtggaa ggccaaaact ttctgtccga   9780
gaaaaacaaa gtggtcgtgg gaaagggaga gtttaccaag gacgttggcc tgaaggaaat   9840
ggtgtttcct agctccagaa atctgtttct gacaaacctc gacaatctgc atgagaataa   9900
cacacacaat caggaaaaga aaatccaaga ggaaatcgaa aagaaagaga cactgattca   9960
ggaaaacgtc gtgctccccc aaatccatac cgtcaccgga accaaaaact ttatgaaaaa  10020
ccttttcctc ctgtccacca ggcagaatgt ggaaggctcc tacgatggcg cttacgctcc  10080
cgtcctgcaa gactttagat ccctgaatga ctccaccaat agaacaaaga aacacacagc  10140
ccatttctcc aagaaaggcg aggaggaaaa cctggaagga ctgggaaacc aaaccaaaca  10200
gattgtggaa aagtatgcct gtaccacaag aattagccct aacacaagcc aacagaattt  10260
cgtcacccaa agatccaaga gagccctgaa gcaattcagg ctgcctctgg aagaaacaga  10320
gctggagaaa agaattatcg tggatgatac ctccacccaa tggtccaaga atatgaaaca  10380
cctcacccct agcacactga cacagattga ctataacgaa aaggaaaagg gagccattac  10440
ccaaagccct ctgtccgact gtctgacaag atcccactcc atccctcagg ctaacaggag  10500
ccctctgcct atcgctaagg tcagctcctt ccctagcatt agacctatct atctgacaag  10560
agtcctgttt caggataact ccagccatct gcctgccgcc tcttatagaa aaaaggatag  10620
cggagtgcaa gagtccagcc atttcctcca gggagccaaa aagaataacc tgagcctcgc  10680
cattctgaca ctggaaatga caggcgatca gagggaggtc ggctccctgg gaacctccgc  10740
cacaaactcc gtgacataca aaaaggtcga gaataccgtc ctgcctaagc ctgacctccc  10800
caaaacctcc ggcaaagtgg aactgctccc caaagtgcat atctatcaga aagacctctt  10860
tcctaccgaa acctccaacg gaagccccgg ccacctggat ctggtcgagg gaagcctcct  10920
gcaaggcaca gagggagcca ttaagtggaa cgaagccaat agacctggca aagtgccttt  10980
cctcagagtc gccacagagt ccagcgctaa gacacccagc aagctgctgg accccctcgc  11040
ctgggacaat cactatggca cacagattcc caaagaggaa tggaaaagcc aagagaaaag  11100
ccctgagaaa accgctttca aaaagaaaga cacaatcctg agcctcaacg cttgcgaaag  11160
caatcacgct atcgctgcca ttaacgaagg ccaaaacaaa cccgaaatcg aagtgacatg  11220
ggccaagcag ggcaggaccg aaagactctg ctcccagaat ccccctgtgc tcaagaggca  11280
ccaaagagaa atcacaagaa caaccctcca gtccgaccaa gaggaaatcg actacgatga  11340
cacaatctcc gtggaaatga aaaaggagga ctttgacatt tacgatgagg atgagaatca  11400
```

-continued

```
gtcccccagg agctttcaga aaaagacaag acattacttt atcgctgccg tcgagaggct  11460
gtgggactat ggcatgagca gcagccctca cgtcctgagg aacagagccc agagcggaag  11520
cgtcccccaa ttcaaaaagg tcgtgtttca ggagttcaca gacggcagct tcacccaacc  11580
cctctacagg ggcgaactga atgagcatct gggactgctc ggcccttaca ttagagccga  11640
ggtggaggat aacattatgg tcacctttag aaatcaggcc agcaggccct atagctttta  11700
ctccagcctc atctcctacg aggaagatca gaggcaggga gccgaaccca ggaagaattt  11760
cgtcaagcct aacgaaacca aaacctattt ctggaaggtc cagcatcaca tggcccctac  11820
caaagacgaa tttgattgca aagcctgggc ctatttctcc gacgttgacc tggagaaaga  11880
cgtgcattcc ggcctcatcg gacccctcct ggtctgccat accaataccc tcaaccctgc  11940
ccacggcaga caggtgaccg tccaggagtt tgctctgttt ttcacaatct ttgacgaaac  12000
caaaagctgg tactttaccg aaaacatgga gaggaactgt agagcccccct gtaacattca  12060
gatggaggac cccacattca aagagaatta caggttccat gccattaacg gatacattat  12120
ggataccctc cccggactgg tcatggctca ggatcagagg atcaggtggt atctgctgtc  12180
tatgggctcc aacgaaaaca ttcactccat ccatttctcc ggccatgtgt ttaccgtcag  12240
aaaaaaggag gagtataaga tggccctcta caatctgtat cccggagtgt ttgagacagt  12300
ggaaatgctc ccctccaagg ctggcatttg gagggtggaa tgcctcatcg gagagcatct  12360
gcacgccgga atgtccaccc tgtttctcgt gtatagcaat aagtgtcaga cacccctcgg  12420
catggcctcc ggccatatca gggactttca gattaccgcc agcggacagt atggccaatg  12480
ggctcccaaa ctggctagac tccactatag cggaagcatt aacgcttggt ccaccaaaga  12540
gcctttctcc tggattaagg tggacctcct ggctcccatg attatccacg gaatcaaaac  12600
ccaaggcgct agacaaaagt ttagctccct gtatatctcc cagtttatca ttatgtatag  12660
cctcgacgga aagaaatggc aaacctatag aggaaactcc accggaaccc tcatggtgtt  12720
ctttggcaat gtggatagct ccggcattaa gcataacatt ttcaatcccc ctatcattgc  12780
caggtacatt agactccacc ctacccatta ctccatcagg agcacactga ggatggaact  12840
gatgggctgt gacctcaact cctgctccat gcccctcggc atggaaagca aagccattag  12900
cgatgcccaa atcacagcct ccagctattt cacaaatatg ttcgctacct ggagccctag  12960
caaagccagg ctgcatctgc aaggcaggag caatgcctgg agacctcagg tcaacaatcc  13020
caaagagtgg ctgcaagtgg atttccaaaa gacaatgaaa gtgacaggcg tcaccacaca  13080
gggagtgaaa agcctcctga caagcatgta cgtcaaggag ttcctcatct ccagctccca  13140
ggatggccat cagtggaccc tgttctttca gaatggcaaa gtgaaagtgt ttcagggaaa  13200
ccaagactcc ttcacacccg tcgtgaatag cctcgaccct cccctcctga caagatacct  13260
gagaatccac ccccaaagct gggtgcatca gattgccctc agaatggagg tcctgggatg  13320
cgaagcccaa gacctctact aaatcgattg cgcaaagctt tcgcgatagg cgagaccaat  13380
gggtgtgtac gtagcggccg cgtcgacgat agcttgatgg gtggcatccc tgtgacccct  13440
ccccagtgcc tctcctggcc ctggaagttg ccactccagt gcccaccagc cttgtcctaa  13500
taaaattaag ttgcatcatt ttgtctgact aggtgtcctt ctataatatt atggggtgga  13560
ggggggtggt atggagcaag gggcaagttg ggaagacaac ctgtagggcc tgcggggtct  13620
attgggaacc aagctggagt gcagtggcac aatcttggct cactgcaatc tccgcctcct  13680
gggttcaagc gattctcctg cctcagcctc ccgagttgtt gggattccag gcatgcatga  13740
ccaggctcag ctaatttttg tttttttggt agagacgggg tttcaccata ttggccaggc  13800
```
tggtctccaa ctcctaatct caggtgatct acccaccttg gcctcccaaa ttgctgggat 13860
tacaggcgtg aaccactgct cccttccctg tccttctgat tttaaaataa ctataccagc 13920
aggaggacgt ccagacacag cataggctac ctggccatgc ccaaccggtg ggacatttga 13980
gttgcttgct tggcactgtc ctctcatgcg ttgggtccac tcagtagatg cctgttgaat 14040
tctgatttaa atcggtccgc gtacggcgtg gtaggtccga acgaatccat ggattaccct 14100
gttatcccta ctcaaggaca tcatcccttt agtgagggtt aattcacgca gtgggtacgg 14160
aactaaaggc agcacacatc gtgtaatcat ggtcatagct gtttcctgtg tgaaattgtt 14220
atccgctacg tctctccccc gcagtaaggg ctagattaac tcgtctcgtg aatatccgga 14280
actcccttta gtgagggtta attgcgttgc gctcactgcc cgctttccag tcgggaaacc 14340
tgtcgtgcca gcttaatcat ggtcatagct gtttcctgtg tgaaattgtt atccgctacc 14400
ggaaacgctt ccttcatgtg agcaaaaggc cagcaaaagg ccaggaaccg taaaaaggcc 14460
gcgttgctgg cgtttttcca taggctccgc ccccctgacg agcatcacaa aaatcgacgc 14520
tcaagtcaga ggtggcgaaa cccgacagga ctataaagat accaggcgtt tccccctgga 14580
agctccctcg tgcgctctcc tgttccgacc ctgccgctta ccggatacct gtccgccttt 14640
ctcccttcgg gaagcgtggc gctttctcat agctcacgct gtaggtatct cagttcggtg 14700
taggtcgttc gctccaagct gggctgtgtg cacgaacccc ccgttcagcc cgaccgctgc 14760
gccttatccg gtaactatcg tcttgagtcc aacccggtaa gacacgactt atcgccactg 14820
gcagcagcca ctggtaacag gattagcaga gcgaggtatg taggcggtgc tacagagttc 14880
ttgaagtggt ggcctaacta cggctacact agaagaacag tatttggtat ctgcgctctg 14940
ctgaagccag ttaccttcgg aaaaagagtt ggtagctctt gatccggcaa acaaaccacc 15000
gctggtagcg gtggtttttt tgtttgcaag cagcagatta cgcgcagaaa aaaaggatct 15060
caagaagatc ctttgatctt ttctacgggg tctgacgctc agtggaacga aaactcacgt 15120
taagggattt tggtcatgcc taggacgaaa ggaggtcgtg aaatggataa aaaaatacag 15180
cgtttttcat gtacaactat actagttgta gtgcctaaat aatgctttta aaacttaaaa 15240
ataatctatg tcgggtgcgg agaaagaggt aatgaaatgg caaatcaatg tcctcagcga 15300
aatggcatac gagtaaactt ggtctgacac cgctgcatga gattatcaaa aaggatcttc 15360
acctagatcc ttttaaatta aaaatgaagt tttaaatcaa tctaaagtat atatgagtaa 15420
acttggtctg acagttacca atgcttaatc agtgaggcac ctatctcagc gatctgtcta 15480
tttcgttcat ccatagttgc ctgactcccc gtcgtgtaga taactacgat acgggagggc 15540
ttaccatctg gccccagtgc tgcaatgata ccgcgagacc cacgctcacc ggctccagat 15600
ttatcagcaa taaaccagcc agccggaagc gccgagcgca gaagtggtcc tgcaacttta 15660
tccgcctcca tccagtctat taactgttgc cgggaagcta gagtaagtag ttcgccagtt 15720
aatagtttgc ggagcgttgt tgccattgct acaggcatcg tggtgtcacg ctcgtcgttt 15780
ggtatggctt cattcagctc cggttcccaa cgatcaaggc gagttacatg atcccccatg 15840
ttgtgcaaaa aagcggttag ctccttcggt cctccgatgg ttgtcagaag taagttggcc 15900
gcagtgttat cactcatggt tatggcagca ctgcataatt ctcttactgt catgccatcc 15960
gtaagatgct tttctgtgac tggtgagtat tcaaccaagt cattctgaga atagtgtatg 16020
cggcgaccga gttgctcttg cccggcgtca atacgggata ataccgcgcc acatagcaga 16080
actttaaaag tgctcatcat tggaagcgt tcttcggggc gaaaactctc aaggatctta 16140
ccgctgttga gatccagttc gatgtaaccc acacgagcac ccaactgatc ttcagcatct 16200
tttactttca ccagcgtttc tgggtgagca aaaacaggaa ggcaaaatgc cgcaaaaaag 16260
ggaataaggg cgacacggaa atgttgaata ctcatacgct tcctttttca atagtattga 16320
agcatttatc agggttattg tctcgggagc gaatacatat ttgaatgtat ttagaaaaa 16379

<210> SEQ ID NO 20
<211> LENGTH: 158
<212> TYPE: PRT
<213> ORGANISM: Homo sapiens
<220> FEATURE:
<223> OTHER INFORMATION: Human Insulin like growth factor (IGF-1)

<400> SEQUENCE: 20

Met Gly Lys Ile Ser Ser Leu Pro Thr Gln Leu Phe Lys Cys Cys Phe
1 5 10 15

Cys Asp Phe Leu Lys Val Lys Met His Thr Met Ser Ser Ser His Leu
20 25 30

Phe Tyr Leu Ala Leu Cys Leu Leu Thr Phe Thr Ser Ser Ala Thr Ala
35 40 45

Gly Pro Glu Thr Leu Cys Gly Ala Glu Leu Val Asp Ala Leu Gln Phe
50 55 60

Val Cys Gly Asp Arg Gly Phe Tyr Phe Asn Lys Pro Thr Gly Tyr Gly
65 70 75 80

Ser Ser Ser Arg Arg Ala Pro Gln Thr Gly Ile Val Asp Glu Cys Cys
85 90 95

Phe Arg Ser Cys Asp Leu Arg Arg Leu Glu Met Tyr Cys Ala Pro Leu
100 105 110

Lys Pro Ala Lys Ser Ala Arg Ser Val Arg Ala Gln Arg His Thr Asp
115 120 125

Met Pro Lys Thr Gln Lys Tyr Gln Pro Pro Ser Thr Asn Lys Asn Thr
130 135 140

Lys Ser Gln Arg Arg Lys Gly Ser Thr Phe Glu Glu Arg Lys
145 150 155

<210> SEQ ID NO 21
<211> LENGTH: 288
<212> TYPE: PRT
<213> ORGANISM: Homo sapiens
<220> FEATURE:
<223> OTHER INFORMATION: Human basic fibroblast growth factor (bFGF)

<400> SEQUENCE: 21

Met Val Gly Val Gly Gly Gly Asp Val Glu Asp Val Thr Pro Arg Pro
1 5 10 15

Gly Gly Cys Gln Ile Ser Gly Arg Gly Ala Arg Gly Cys Asn Gly Ile
20 25 30

Pro Gly Ala Ala Ala Trp Glu Ala Ala Leu Pro Arg Arg Arg Pro Arg
35 40 45

Arg His Pro Ser Val Asn Pro Arg Ser Arg Ala Ala Gly Ser Pro Arg
50 55 60

Thr Arg Gly Arg Arg Thr Glu Glu Arg Pro Ser Gly Ser Arg Leu Gly
65 70 75 80

Asp Arg Gly Arg Gly Arg Ala Leu Pro Gly Gly Arg Leu Gly Gly Arg
85 90 95

Gly Arg Gly Arg Ala Pro Glu Arg Val Gly Gly Arg Gly Arg Gly Arg
100 105 110

```
Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 22
<211> LENGTH: 193
<212> TYPE: PRT
<213> ORGANISM: Homo sapiens
<220> FEATURE:
<223> OTHER INFORMATION: Human erythropoietin

<400> SEQUENCE: 22

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Gln Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190
```

Arg

<210> SEQ ID NO 23
<211> LENGTH: 134
<212> TYPE: PRT
<213> ORGANISM: Homo sapiens
<220> FEATURE:
<223> OTHER INFORMATION: Human BNP

<400> SEQUENCE: 23

```
Met Asp Pro Gln Thr Ala Pro Ser Arg Ala Leu Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
        35                  40                  45

His Leu Gln Gly Lys Leu Ser Glu Leu Gln Val Glu Gln Thr Ser Leu
    50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
            100                 105                 110

Phe Gly Arg Lys Met Asp Arg Ile Ser Ser Ser Ser Gly Leu Gly Cys
        115                 120                 125

Lys Val Leu Arg Arg His
    130
```

<210> SEQ ID NO 24
<211> LENGTH: 562
<212> TYPE: PRT
<213> ORGANISM: Homo sapiens
<220> FEATURE:
<223> OTHER INFORMATION: Human tPA

<400> SEQUENCE: 24

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160
```

```
Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Asn Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285

Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
            340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
            420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
            500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro
```

<210> SEQ ID NO 25

<211> LENGTH: 185
<212> TYPE: PRT
<213> ORGANISM: Homo sapiens
<220> FEATURE:
<223> OTHER INFORMATION: Human relaxin

<400> SEQUENCE: 25

```
Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
    50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
    130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185
```

<210> SEQ ID NO 26
<211> LENGTH: 728
<212> TYPE: PRT
<213> ORGANISM: Homo sapiens
<220> FEATURE:
<223> OTHER INFORMATION: Human hepatocyte growth factor (HGF)

<400> SEQUENCE: 26

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
```

```
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560
```

-continued

```
Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

THERAPEUTIC GENE-SWITCH CONSTRUCTS AND BIOREACTORS FOR THE EXPRESSION OF BIOTHERAPEUTIC MOLECULES, AND USES THEREOF

CROSS-REFERENCE TO RELATED APPLICATIONS

The present application claims the benefit of the filing date of U.S. Provisional Application No. 61/047,899, files Apr. 25, 2008 and U.S. Provisional Application No. 60/975,986, filed Sep. 28, 2007, both of which are incorporated herein by reference in their entireties.

REFERENCE TO SEQUENCE LISTING SUBMITTED ELECTRONICALLY VIA EFS-WEB

The content of the electronically submitted sequence listing (Name: Sequence Listing.ST25.txt; Size: 243,000 bytes; and Date of Creation: Sep. 29, 2008) filed herewith with the application is incorporated herein by reference in its entirety:

BACKGROUND OF THE INVENTION

Field of the Invention

The present invention relates to methods and compositions for treating, ameliorating, or preventing a disease, disorder, or condition in a subject by introducing into the subject a therapeutic gene switch construct that controls expression of one or more therapeutic products. In a further embodiment, the present invention relates to methods and compositions for treating, ameliorating, or preventing a disease, disorder, or condition in a subject by introducing into the subject a "bioreactor," a therapeutic implant composed of a cell or cells that secrete a therapeutic protein. A bioreactor may be immuno-isolated by encapsulation or non-immunoisolated. In particular embodiments, the bioreactor comprises a therapeutic gene switch construct.

Background of the Invention

The concept of treating or preventing a disease in a subject through introduction of a polynucleotide encoding a therapeutic molecule, e.g., a therapeutic polypeptide or therapeutic polynucleotide into cells of the subject, or introducing into the subject modified cells engineered to secrete the therapeutic molecule has been in existence for many years. Several difficulties in the practical aspects of the concept have hindered progress towards successful therapies. Direct introduction of genetic material into a subject to be treated presents difficulties such as: safety of delivery, obtaining sufficient expression levels of the therapeutic product for a sufficient period of time, limiting expression of the therapeutic product to desired cells, and maintaining the ability to modulate or pulse the expression of the therapeutic product, including the ability to turn off expression of the therapeutic product if it is no longer needed. Cell based therapies are subject to rejection via the subject's immune response, therefore immuno-isolation strategies such as cell encapsulation methods have been developed to increase the longevity of implanted cells and allow use of xenogeneic cells, i.e., cells from a different species. Current encapsulated and non-encapsulated cell therapies are engineered to secrete the therapeutic protein constitutively. Once implanted, protein secretion can not be regulated. To improve the safety and clinical application of direct or cell-mediated bioreactor therapeutic protein delivery it would be advantageous to be able to turn off the protein production or regulate the rate at which protein production occurs.

Thus, there is a need in the art for new therapeutic methods and compositions that provide these desired characteristics.

SUMMARY OF THE INVENTION

The present invention relates to methods and compositions for treating, ameliorating, or preventing a disease, disorder, or condition in a subject.

In one embodiment, the present invention provides a method for treating, ameliorating, or preventing a disease, disorder, or condition in a subject, comprising:

(a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is constitutively active and (2) a second polynucleotide encoding a therapeutic polypeptide or therapeutic polynucleotide in operable association with a factor-regulated promoter which is activated by said ligand-dependent transcription factor, where the first and second polynucleotides are introduced so as to permit their expression in the presence of ligand; and (b) administering ligand to the subject to induce expression of the therapeutic polypeptide or therapeutic polynucleotide.

A further embodiment of the invention provides a method for expressing a therapeutic polypeptide or therapeutic polynucleotide in a subject, comprising:

(a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is activated under conditions associated with the disease, disorder, or condition to be treated, and (2) a second polynucleotide encoding a therapeutic polypeptide or therapeutic polynucleotide in operable association with a factor-regulated promoter which is activated by said ligand-dependent transcription factor, where the first and second polynucleotides are introduced so as to permit their expression in the subject under conditions associated with the disease, disorder, or condition; and (b) administering ligand to the subject to induce expression of the therapeutic polypeptide or therapeutic polynucleotide.

A further embodiment of the invention provides a method for expressing a therapeutic polypeptide or therapeutic polynucleotide in a subject, comprising:

(a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is activated under conditions associated with a disease, disorder, or condition treatable by the therapeutic polypeptide or therapeutic polynucleotide, and (2) a second polynucleotide encoding the therapeutic polypeptide or therapeutic polynucleotide in operable association with a factor-regulated promoter which is activated by the ligand-dependent transcription factor, wherein said the and second polynucleotides are introduced so as to permit expression of the first polynucleotide under conditions associated with the disease, disorder, or condition; and (b) administering ligand to the subject to induce expression of the therapeutic polypeptide or therapeutic polynucleotide.

In the methods described above, in one embodiment, the first polynucleotide encoding the therapeutic gene switch and the second polynucleotide encoding the therapeutic polypeptide or polynucleotide linked to a factor-regulated promoter are part of one larger polynucleotide, e.g., a vector. In another embodiment, the first polynucleotide encoding the therapeutic gene switch and the second polynucleotide encoding the therapeutic polypeptide or polynucleotide linked to a factor-regulated promoter are separate polynucleotides which may be administered as a nucleic acid composition.

The invention further relates to therapeutic gene switch constructs that are useful in the disclosed methods.

The invention additionally relates to vectors comprising the therapeutic gene switch constructs of the invention.

The invention further provides a method for expressing a therapeutic polypeptide or therapeutic polynucleotide in one or more modified cells, comprising:

(a) introducing into a cell (1) a first polynucleotide encoding a gene switch, where the gene switch comprises at least one transcription factor sequence encoding a ligand-dependent transcription factor through operable association with a therapeutic switch promoter which is activated under conditions associated with a disease, disorder, or condition, and (2) a second polynucleotide encoding a therapeutic polypeptide or therapeutic polynucleotide through operable association with a factor-regulated promoter which is activated by the ligand-dependent transcription factor, thereby producing a modified cell; and (b) administering ligand to the modified cell to induce expression of said therapeutic polypeptide or therapeutic polynucleotide.

The invention further relates to modified cells comprising the therapeutic gene switch constructs of the invention.

The invention also relates to bioreactor devices comprising modified cells of the invention either non-encapsulated, or encapsulated in such a way to shield the cells from the subject's immune system. Such bioreactors may take the form, for example, of coated cells, micro-encapsulated cells, or macro-encapsulated cells.

The invention also relates to kits for carrying out the methods of the invention, comprising, e.g., gene switch constructs, vectors, ligands, etc.

DETAILED DESCRIPTION OF THE INVENTION

Figure 1:
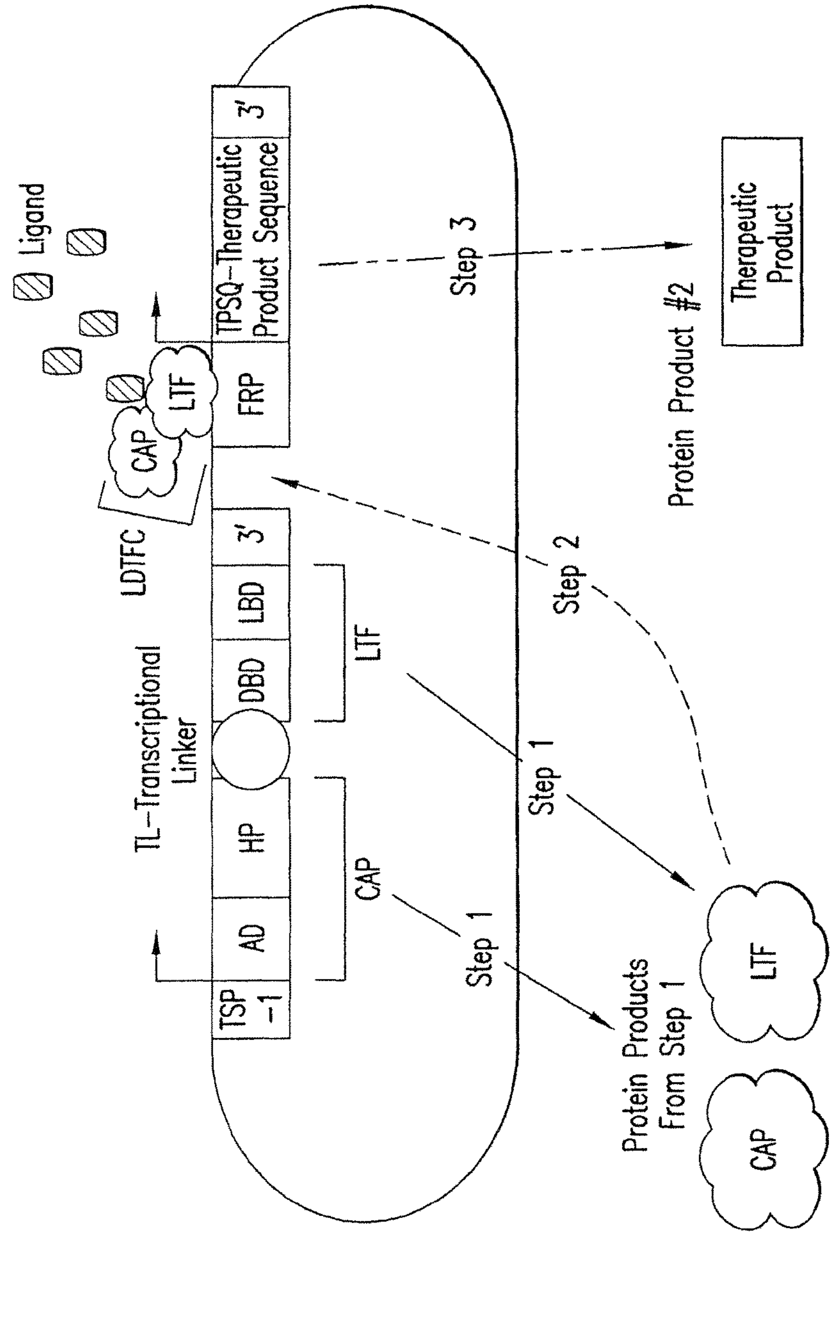
FIG. 1 shows an embodiment of the therapeutic gene switch of the invention in which two transcription factor sequences encoding two separate portions of a ligand-dependent transcription factor complex are under the control of a single promoter. "AD" represents a transactivation domain; "HP" represents a heterodimerization partner domain. The AD and HP domains are expressed as a fusion protein termed a "coactivation protein" or "CAP." "DBD" represents a DNA binding domain; "LBD" represents a ligand binding domain. The DBD and LBD domains are expressed as a fusion protein termed a "ligand-dependent transcription factor," or "LTF." "Transcriptional Linker" represents an IRES (Internal ribosomal entry site) or means of generating two separate protein products from a single open reading frame. "Therapeutic Product Sequence" represents a polynucleotide encoding a therapeutic polypeptide or therapeutic polynucleotide; "Therapeutic Product" represents a therapeutic polypeptide or therapeutic polynucleotide; and "TSP-1," represents either a constitutive therapeutic switch promoter, or a therapeutic switch promoter activated under conditions associated with a disease, disorder, or condition. CAP and LTF combine to form a ligand-dependent transcription factor complex (LDTFC) which in combination with ligand activates a factor-regulated promoter (FRP).

The invention relates to methods and compositions for using a gene switch to express a therapeutic polypeptide or therapeutic polynucleotide in a cell. The methods and compositions may be used in vitro, ex vivo or in vivo. The invention further relates to methods and compositions for using a gene switch controlling expression of a therapeutic polypeptide or therapeutic polynucleotide for the treatment, amelioration, or prevention of diseases, disorders, or conditions in a subject. The methods of the invention can be carried out either ex vivo (by introducing the gene switch into isolated cells of a subject or non-autologous cells, and introducing the modified cells to the subject or into a different subject) or in vivo (by introducing the gene switch directly into cells of the subject). The methods of the invention involve the use of a gene switch in which expression of a ligand-dependent transcription factor is under the control of one or more therapeutic switch promoters. The methods also include, without limitation, applications of the gene switch technology in direct introduction into the subject to be treated, non-encapsulated and encapsulated cell therapies. The methods and compositions described herein provide a highly specific and tightly regulated therapeutic technique in which the level and timing of expression of a therapeutic product is controlled by administration of ligand to cells comprising the gene switch.

The following definitions are provided and should be helpful in understanding the scope and practice of the present invention.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the invention comprises one or more nucleic acids as described herein.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning : A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the present invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. A preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}P$-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (←→) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→→) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the present invention is the UltraVector™ Production System (Intrexon Corp., Blacksburg, Va.) as described in WO 2007/038276, incorporated herein by reference. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYCl, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $1P_L$, $1P_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad. Sci. USA.* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

"Therapeutic switch promoter" ("TSP") refers to a promoter that controls expression of a gene switch component. Gene switches and their various components are described in detail elsewhere herein. In certain embodiments a TSP is constitutive, i.e., continuously active. A consitutive TSP may be either constitutive-ubiquitous (i.e., generally functions, without the need for additional factors or regulators, in any tissue or cell) or constitutive-tissue or cell specific (i.e., generally functions, without the need for additional factors or regulators, in a specific tissue type or cell type). In certain embodiments a TSP of the invention is activated under conditions associated with a disease, disorder, or condition. In certain embodiments of the invention where two or more TSPs are involved the promoters may be a combination of constitutive and activatable promoters. As used herein, a "promoter activated under conditions associated with a disease, disorder, or condition" includes, without limitation, disease-specific promoters, promoters responsive to particular physiological, developmental, differentiation, or pathological conditions, promoters responsive to specific biological molecules, and promoters specific for a particular tissue or cell type associated with the disease, disorder, or condition, e.g. tumor tissue or malignant cells. TSPs can comprise the sequence of naturally occurring promoters, modified sequences derived from naturally occurring promoters, or synthetic sequences (e.g., insertion of a response element into a minimal promoter sequence to alter the responsiveness of the promoter).

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" ("RE") refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 1) (see Cherbas et. al., *Genes Dev.* 5:120 (1991)); AGGTCAN$_{(n)}$AGGTCA, where N$_{(n)}$ can be one or more spacer nucleotides (SEQ ID NO: 2) (see D'Avino et al., *Mol. Cell. Endocrinol.* 113:1 (1995)); and GGGTTGAATGAATTT (SEQ ID NO: 3) (see Antoniewski et al., *Mol. Cell Biol.* 14:4465 (1994)).

"Factor-regulated promoter" ("FRP") refers to a promoter comprising at least one response element that is recognized by the DNA binding domain of a ligand-dependent transcription factor encoded by a gene switch of the invention.

The terms "operably linked," "operably associated," "through operable association," and the like refer to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain.

As used herein, the terms "biorcactor" or "biorcactor device" includes a cell or cells intended to secrete a therapeutic protein or therapeutic polynucleotide. In certain non-limiting embodiments, the bioreactor comprises modified cells as described elsewhere herein. In certain, but not all embodiments, bioreactor cells may be "immunoisolated." Bioreactor cells are considered "immunoisolated" from a subject when the cells are treated such that the cells, upon introduction or implantation into the subject, are protected from the subject's immune system. For example, immunoisolated bioreactor cells may be contained within a barrier system which allows dissemination of said therapeutic protein or therapeutic polynucleotide, but which prevents direct contact of bioreactor cells with cells of the subject's immune system. Immunoisolated cells may be, for example, coated or encapsulated. Immunoisolation methods include but are not limited to conformal coating of cells, microencapsulation where cells are suspended in a biocompatible material and separated into spherical masses, or macroencapsulation, where the cells are enclosed in devices composed of natural or synthetic polymers that are used to enclose cells.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a modified cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

A "3' reg" as defined herein, is an expression modulating element situated 3' to a coding region of a gene or transcript. Such elements include, without limitation: primary transcript-encoded Splicing elements, UTR from processed transcript, a polyadenylation signal or a DNA-encoded Transcription termination domain.

Termination control regions, i.e., terminator or polyadenylation nucleotide sequences, may also be derived from various genes native to the preferred hosts. Optionally, a termination site may be unnecessary, however, it is most preferred if included. In a one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., *DNA* 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in PCR Technology: *Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., *Cell* 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the present invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS.* 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." The present invention is useful to search for orthogonal ligands and orthogonal receptor-based gene expression systems such as those described in US 2002/0110861 A1, which is incorporated herein by reference in its entirety.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The terms "therapeutic product" and "therapeutic molecule" as used herein refer to a therapeutic polypeptide ("TP", encoded by a "therapeutic proteins sequence" ("TPSQ")) or therapeutic polynucleotide which imparts a beneficial function to the subject to be treated. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. Non-limiting examples of therapeutic products are disclosed elsewhere herein. The therapeutic product may comprise a naturally occurring sequence, a synthetic sequence or a combination of natural and synthetic sequences.

The term "ligand-dependent transcription factor complex" or "LDTFC" refers to a transcription factor comprising one or more protein subunits, which complex can regulate gene expression driven by a "factor-regulated promoter" as defined herein. A model LDTFC is an "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor ("RXR") protein or a chimera of USP and RXR. The terms "LDTFC" and "EcR complex" also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. As used herein, the term "ligand," as applied to LDTFC-based gene switches e.g., EcD complex based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the LDTFC, e.g., EcR complex, may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "subject" means an intact insect, plant or animal. It is also anticipated that the ligands will work equally well when the subject is a fungus or yeast. When the subject is an intact animal, preferably the animal is a vertebrate, most preferably a mammal.

EcR ligands, when used with a LDTFC, e.g., an EcR complex, which in turn is bound to the response element linked to an exogenous gene (e.g., a reporter gene), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of a LDTFC, e.g., an EcR complex, to a specific control, or regulatory, DNA element. The EcR protein, like other members of the nuclear receptor family, possesses at least three domains, an AD, a DBD, and a LBD. This receptor, like a subset of the nuclear receptor family, also possesses less well-defined regions responsible for heterodimerization properties (referred to herein as a "heterodimerization partner" or "HP"). Binding of the ligand to the ligand binding domain of a LTF, e.g., an EcR protein, after heterodimerization with a CAP including, e.g., an AD and/or an HP, e.g., a USP or RXR protein, enables the DNA binding domains of the heterodimeric proteins to bind to the response element in an activated form, thus resulting in expression or suppression of the exogenous gene. This mechanism does not exclude the potential for ligand binding to individual subunits, e.g., LTF or CAP, e.g., an EcR or USP, and the resulting formation of active homodimer complexes (e.g. EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729 (1985)) to accommodate chimeric LDTFCs, e.g., EcR complexes. Another advantage of chimeric systems is that they allow choice of a promoter used to drive the exogenous gene according to a desired end result.

Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Numerous genomic and cDNA nucleic acid sequences coding for a variety of polypeptides, such as transcription factors and reporter genes, are well known in the art. Those skilled in the art have access to nucleic acid sequence information for virtually all known genes and can either obtain the nucleic acid molecule directly from a public depository, the institution that published the sequence, or employ routine methods to prepare the molecule.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

One embodiment of the invention comprises methods for treating, ameliorating, or preventing a disease, disorder, or condition in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex; and (b) administering ligand to said subject to induce expression of said therapeutic polypeptide or therapeutic polynucleotide;

wherein said therapeutic polypeptide or therapeutic polynucleotide is expressed at a level sufficient to treat, ameliorate, or prevent said disease, disorder, or condition.

One embodiment of the invention comprises methods for treating, ameliorating, or preventing a disease, disorder, or condition in a subject, comprising:

(a) introducing into a subject (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, and (2) a second polynucleotide encoding a therapeutic polypeptide or therapeutic polynucleotide operably associated with a factor-regulated promoter which is activated by said ligand-dependent transcription factor complex, wherein said first and second polynucleotides are introduced so as to permit expression of said ligand-dependent transcription factor complex; and (b) administering ligand to said subject to induce expression of said therapeutic polypeptide or therapeutic polynucleotide.

One embodiment of the invention comprises methods for expressing a therapeutic polypeptide or therapeutic polynucleotide in a subject, comprising:

(a) introducing into a subject (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, and (2) a second polynucleotide encoding said therapeutic polypeptide or therapeutic polynucleotide operably associated with a factor-regulated promoter which is activated by said ligand-dependent transcription factor complex, wherein said first and second polynucleotides are introduced so as to permit expression of said ligand-dependent transcription factor complex; and (b) administering ligand to said subject to induce expression of said therapeutic polypeptide or therapeutic polynucleotide.

In certain embodiments, the therapeutic switch promoter described in the methods is constitutive. In certain embodiments, the therapeutic switch promoter is activated under conditions associated with a disease, disorder, or condition, e.g., the promoter is activated in response to a disease, in response to a particular physiological, developmental, differentiation, or pathological condition, and/or in response to one or more specific biological molecules; and/or the promoter is activated in particular tissue or cell types. In certain embodiments, the disease, disorder, or condition is responsive to the therapeutic polypeptide or polynucleotide. For example in certain non-limiting embodiments the therapeutic polynucleotide or polypeptide is useful to treat, prevent, ameliorate, reduce symptoms, prevent progression, or cure the disease, disorder or condition, but need not accomplish any one or all of these things. In certain embodiments, the first and second polynucleotides are introduced so as to permit expression of the ligand-dependent transcription factor complex under consitions associated with a disease, disorder or condition. In one embodiment, the therapeutic methods are carried out such that the therapeutic polypeptide or therapeutic polynucleotide is expressed and disseminated through the subject at a level sufficient to treat, ameliorate, or prevent said disease, disorder, or condition. As used herein, "disseminated" means that the polypeptide is expressed and released from the modified cell sufficiently to have an effect or activity in the subject. Dissemination may be systemic, local or anything in between. For example, the therapeutic polypeptide or therapeutic polynucleotide might be systemically disseminated through the bloodstream or lymph system. Alternatively, the therapeutic polypeptide or therapeutic polynucleotide might be disseminated locally in a tissue or organ to be treated.

In one embodiment, the therapeutic methods are carried out by administering compositions of the invention, such as the first and second polynucleotides described above, directly to the subject to be treated, such that the polynucleotides are taken up, in vivo, by cells of the subject to be treated, and one or more therapeutic polypeptides or polynucleotides will be expressed by those cells under appropriate conditions, as described in detail elsewhere herein. Polynucleotides may be directly delivered to a subject to be treated by a variety of methods including, without limitation, viral vectors, e.g., retroviral vectors, adeno-associated virus vectors, pox virus vectors, e.g., vaccinia virus vectors, baculovirus vectors, herpes virus vectors, e.g., herpes simplex vectors or Epstein-Barr virus vectors, adenovirus vectors, geminivirus vectors, or caulimovirus vectors; non-viral vectors such as plasmids, which may be delivered, for example complexed with liposomes, electrically charged lipids (cytofectins), biopolymers or as DNA-protein complexes.

In another embodiment, the therapeutic methods are carried out by introducing the compositions of the invention, such as the first and second polynucleotides described above, into the subject to be treated contained in one or more modified cells. Following administration of the modified cells the one or more therapeutic polypeptides or polynucleotides are expressed by the modified cells under appropriate conditions, as described in detail elsewhere herein. The term "modified cell" refers to a cell or cells into which at least a first and second polynucleotide as described above have been inserted. As such, "a modified cell" refers to the cell harboring the first and second polynucleotides, which may or may not be a cell from, or related to, the subject to be treated. Such cells are included in the definition of "bioreactors" or "bioreactor devices" as described herein. As defined herein, however, a "bioreactor" or "bioreactor device" need not be not a modified cell, rather, a bioreactor or bioreactor device as defined herein is any cell or cells intended to secrete a therapeutic protein or therapeutic polynucleotide, whether or not the cell(s) are "modified cells."

In one embodiment, the therapeutic methods are carried out by introducing the compositions of the invention, such as the first and second polynucleotides described above, into cells that have been isolated from said subject, i.e., autologous cells, to produce modified cells, and the modified cells are re-introduced into said subject.

Alternatively, modified cells may be prepared by introducing the compositions of the invention, such as the first and second polynucleotides described above, into cells which are not isolated from the subject, i.e., they are non-autologous relative to the subject, to produce modified non-autologous (MNA) cells. Such MNA cells may be allogeneic relative to the subject to be treated, i.e., they are derived from a genetically non-identical member of the same species as the subject. For example, in treating a human subject, the cells would be human cells, but not directly derived from the subject to be treated. Alternatively, MNA cells may be xenogeneic relative to the subject to be treated. i.e., they are derived from a different species than the subject to be treated. For example, in treating a human subject the cells might be mouse cells, monkey cells, or pig cells.

MNA cells suitable for use in the present invention may be generated from any number of cells types, including, but not limited to immortalized cells, primary cells, and cells capable of terminal differentiation. Non-limiting examples of cells suitable for generating MNA modified cells for the present invention include C2C12 mouse myoblast cells, HEK293 human embryonic kidney cells, ARPE-19 cells, hMSC cells, pancreatic islet cells, MDCK cell, BHK cell, hybridoma cell CHO cell, an astrocyte derived cell, an oligodendrocyte derived cell, a myoblast derived cell, a parathyroid derived cell. In a specific embodiment where pancreatic islet cells are used to generate modified cells to treat a human subject, the pancreatic islet cells may be xenogeneic, e.g., porcine islet cells, or allogeneic, e.g., human islet cells derived from cadavers.

In one embodiment, the therapeutic methods are carried out in vivo.

In one embodiment, the polynucleotide encoding the gene switch and the polynucleotide encoding the therapeutic polypeptide or therapeutic polynucleotide linked to a promoter are part of one larger polynucleotide, e.g., a vector. In another embodiment, the polynucleotide encoding the gene switch and the polynucleotide encoding the therapeutic polypeptide or therapeutic polynucleotide linked to a promoter are separate polynucleotides, which may be combined to form a "nucleic acid composition.".

In certain embodiments, a bioreactor of the invention comprises modified or non-modified cells surrounded by a barrier (e.g., encapsulated) prior to being introduced into the subject. Such a bioreactor may be used with any subject instead of having to modify autologous cells from each individual. Cellular encapsulation methods have been used to immunoisolate cells while allowing, either selectively or unselectively, the release of desired biological materials. It may be desirable to provide encapsulation compositions and methods for making them, which are capable of providing improved structural characteristics and/or immune protection. Such compositions and methods may find use, where encapsulated cells can withstand mechanical, chemical or immune destruction within the subject to be treated, and would additionally provide for free permeability to nutrients, ions, oxygen, and other materials needed to both maintain the tissue and support normal metabolic functions, but impermeable to bacteria, lymphocytes, and large proteins of the type responsible for immunochemical reactions. Barriers suitable for use in the present invention allow dissemination of a therapeutic protein or therapeutic polynucleotide expressed by modified or non-modified cells contained within the barrier, but prevent direct contact of the cells with cells of the subject's immune system. The barrier may also function to prevent non-autologous or autologous modified or non-modified cells from escaping from the site of introduction, e.g., rogue cells that might cause harm to the subject if allowed to circulate. In one embodiment the barrier is a selectively permeable barrier, e.g., a barrier that is permeable to small molecules such as hormones and small peptides but impermeable to larger polypeptides such as antibodies. For example, the barrier may be impermeable to molecules with a molecular weight greater than about 100,000, about 50,000, about 25,000, about 10,000, about 5,000 or about 1,000 daltons.

Any number of barrier systems are suitable for use in the present invention. In one embodiment, for example, the barrier comprises a conformal coating which encases one or more cells. Typically a conformal coating is made of a polymer material, e.g., polyethylene glycol or hydroxyethyl methacrylate-methyl methacrylate (HEMA-MMA). Conformal coatings typically enclose a small number of modified cells, e.g., 1-10 cells, 1-20 cells, 1-30 cells 1-50 cells 1-70 cells or 1-90 cells. See, e.g., Shoichet M S, Winn S R., *Adv Drug Delivery Rev.* 42:81-102 (2000), which is incorporated herein by reference in its entirety.

In other embodiments, a barrier system suitable for use in the present invention comprises a bioreactor, which comprises encapsulated cells. Two non-limiting encapsulation methods, microencapsulation and macroencapsulation, are known in the art. Typically, in microencapsulation, the cells are suspended in a biologically compatible encapsulation material which is then shaped into bead-like structures, whereas in macroencapsulation the device is generally manufactured prior to the addition of cells and can be composed of one or more synthetic membranes. As compared to conformal coatings, barrier systems comprising encapsulated cells tend to be more uniform in size, and tend to have uniform pore size allowing better control of protein dissemination. For encapsulation, living cells and other sensitive materials may be treated under sufficiently mild conditions allowing the cells or biomaterial to remain substantially unaffected by the encapsulation process, yet permitting the foiuiation of a capsule of sufficient strength to exist over long periods of time.

Living cell(s) can be encapsulated and the resulting encapsulated cell(s) maintain long term in vivo activity by encapsulating the cells within a biocompatible semi-permeable membrane. One way to increase biocompatibility is to add an outer surface of biocompatible negatively-charged material. The term "biocompatible" as used herein refers collectively to both the intact capsule and its contents. Specifically, it refers to the capability of the implanted intact encapsulated cell to avoid detrimental effects of the body's various protective systems, such as immune system or foreign body fibrotic response, and remain functional for a significant period of time.

Biorcactors comprising encapsulated cells which are suitable for use in the present invention are especially useful for the administration of cells to an animal, wherein the immune response of the animal towards the cell is to be minimized. Cells which produce antibodies, enzymes, and other bioactive materials can also be administered. The small size of the resulting encapsulated cells within the subject of the invention facilitate administration of the microcapsules by injection, implantation or transplantation into a subject.

Living cells can be encapsulated in a variety of gels, e.g., alginate, to form implantable bead-like structures, e.g., microbeads or microspheres to physically isolate the cells once implanted into a subject to be treated. To prevent entry of smaller molecular weight substances such as antibodies and complement (with a molecular weight of about 150 kDa) into these bead-like structures, they can be coated with a material such as poly-L-lysine, chitosan, or PAN-PVC, which provides an outer shell with a controlled pore size or they can be treated by e.g., cross-linking, to control their internal porosity. Additional examples of useful materials include conventional biocompatible materials made up of natural or synthetic polymers or co-polymers, such as poly-L-lysine-alginate, collagen, gelatin, laminin, methyl methacrylate, hydroxyethyl methacrylate, MATRIGEL, VIRTOGEN, polyvinylalcohol, agarose, polyethylene glycol, hydrogels, polylactic acid, polyglycolic acid, poly(lactide-co-glycolide), polyhydroxybutyrate-polyhydroxyvalerate, copolymer, poly(lactide-co-caprolactone), polyesteramides, polyorthoesters, poly 13-hydroxybutyric acid, polyanhydrides, polyethylene terephthalate, polyetrafluoroethylene, pllyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, and poly(acrylonitrile/covinyl chloride).

One form of encapsulation is microencapsulation, which involves suspension of the cells in a liquid or gelatinous encapsulation material, which is then formed into a supporting particulate matrix, e.g., a hydrogel matrix to form a bead-like structure, which serves as a core of an implantable device. The core maintains a proper cell distribution, provides strength, and enhances cell viability, longevity, and function. The core can also contribute to immunoisolation. It also protects the internal cells contained in the bead-like structures from direct cell-cell interactions that can elicit an undesirable immune response in the subject to be treated.

A barrier system may contain multiple layers, e.g., where each layer serves a different purpose (e.g., support, control of permeability). Barriers may comprise contrast agents or other properties that render the barrier imageable (e.g., by x-ray, sonography, etc.) to ensure proper positioning of the implanted cells. Examples of barrier systems useful for cell implantation are described in U.S. Pat. No. 7,226,978, U.S. Pat. No. RE39,542 (agarose), U.S. Pat. Nos. 6,960,351, 6,916,640, 6,911,227 (polyethylene glycol), U.S. Pat. Nos. 6,818,018, 6,808,705, 6,783,964, 6,762,959, 6,727,322, 6,610,668 (poly--14-N-acetylglucosamine (p-GlcNAc) polysaccharide), U.S. Pat. No. 6,558,665, U.S. Pat. No.

RE38,027, U.S. Pat Nos. 6,495,161, 6,368,612, 6,365,385, 6,337,008, 6,306,454 (polyalkylene), U.S. Pat. Nos. 6,303, 355, 6,287,558 (gel super matrix), U.S. Pat. Nos. 6,281,015, 6,264,941, 6,258,870, 6,180,007, 6,126,936 (polyamine acid), U.S. Pat. Nos. 6,123,700, 6,083,523, 6,020,200, 5,916,790, 5,912,005, 5,908,623, 5,902,745, 5,858,746, 5,846,530 (polysaccaharides), U.S. Pat. Nos. 5,843,743, 5,837,747, 5,837,234, 5,834,274, 5,834,001, 5,801,033, 5,800,829, 5,800,828, 5,798,113, 5,788,988, 5,786,216, 5,773,286, 5,759,578, 5,700,848, 5,656,481, 5,653,975, 5,648,099, 5,550,178, 5,550,050, 4,806,355, 4,689,293, 4,680,174, 4,673,566, 4,409,331, 4,352,883, and U.S. Patent Application Publications 2006/0263405 (alginate/polymer) and 2004/0005302 (alignate-poly-L-lysine), each incorporated herein by references in its entirety.

In certain embodiments, a barrier system suitable for use in the present invention comprises microencapsulated cells. Microencapsulation generates approximately spherical and relatively uniform bead-like structures comprising encapsulated cells, where the bead-like structures are about 100-700 μm in diameter, e.g., about 100, 200, 300, 400, 500, 600 or 700 μm in diameter. Microencapsulated cells of the invention may be produced using a variety of encapsulation materials as described above. In one embodiment, the encapsulation material comprises a hydrogel. In another embodiment the encapsulation material comprises a polymer. Suitable polymers include, without limitation, cellulose, e.g., cellulose sulfate, and alginate. For example, one microcapsule of the invention comprises polyanionic alginate and a poly-cationic polymer to interact and form a physical permselective membrane barrier. An alternative method of microencapsulation comprises the formation of poly (L-lactide) acid (PLLA) or a poly-L-omithinc (PLO) alginate microspheres. See, e.g., Darrabic, M. D. et al. *Biomaterials* 26:6846-6852 (2005) and Blasi, P. et al. *Int J. Pharm.* 324:27-36 (2006). Alginate based microencapsulation materials may further contain ultra high viscosity (UHV) polymers, which may also be biodegradable. See, e.g., Zimmermann, U. et al. *Ann NY Acad Sci.* 944:199-215 (2001).

Bioreactors of the present invention comprising microencapsulated cells typically comprise at least one up to about 1000 cells per "bead," e.g., modified or non-modified cells intended to secrete a desired therapeutic polypeptide or polynucleotide as described herein. For example, a bioreactor of the invention which comprises microencapsulated cells may result in at least 50, at least 100, at least 200, at least 400, at least 500, at least 800 to about 1000 or more cells per "bead."

In certain embodiments, a bioreactor suitable for use in the present invention comprises cells enclosed in a macroencapsulation device. As compared to bioreactors comprising microencapsulated cells, bioreactors comprising macroencapsulation devices are typically larger and often nonspherical encapsulated cell entities, and may be composed of one or more synthetic membranes, e.g., one, two, three, four, 8, 10, or more membranes, which may be the same composition of different compositions. As denoted by the name, macrocapsulated cell devices are of a size such that individual entities may be easily manipulated. For example, a typical macroencapsulation device may be an oblong shape, about 3 mm, 4 mm, 5 mm, 6 mm, 7 mm, 8 mm, 9 mm, 10 mm or more long and about 1 mm, 2 mm, 3 mm, 4 mm, or 5 mm or more in diameter. An exemplary but non-limiting macroencapsulation device of the invention is about 6 mm long and about 1 mm in diameter.

In certain embodiments a macroencapsulation device suitable for use in the present invention comprises two or more synthetic membranes, where the synthetic membranes have different pore sizes so as to regulate transit of therapeutic molecules through the device and their dissemination into the environment. In certain embodiments, a macroencapsulation device of the invention comprises a semi-permeable polymer outer membrane and an internal scaffold to support the cells. In non-limiting examples, the outer membrane comprises pores of about 15 nm to allow exchange of nutrients of therapeutic molecules. The internal scaffold may comprise any number of materials. In one non-limiting example the scaffold comprises poly (ethylene terephthalate) yarn (available from Neurotech (www.neurotechusa.com)).

In another non-limiting example, a macroencapsulaton device suitable for use in the invention comprises a polymeric membrane bilayer, where the bilayer comprises an outer layer of 5 μm poly(tetrafluoroethylene) (PTFE) membrane laminated onto an inner tighter pore 0.45 uM PTFE immunobarrier layer (available from Theracyte (www.theracyte.com)). Such a macroencapsulation device may further comprise a non-woven poly mesh layer exterior to said polymeric membrane bilayer. In yet another non-limiting example, a macroencapsulation device suitable for use in the invention is composed of polyethersulfone (PES) hollow fibers. See, e.g., Li, Y., et al. *J. Membrane Sci.* 245:53-60 (2004).

Macroencapsulation devices suitable for use in the present invention may optionally have additional structures to allow convenient implantation into and retrieval from a subject to be treated. For example, a macroencapsulation device may comprise, without limitation, a suture clip, a loading port, a tether, or other structure for ease of use.

The interior space of macroencapsulation devices of the invention is typically suitable to comprise at least one up to about $10^5$ cells, e.g., modified or non-modified cells intended to secrete a desired therapeutic polypeptide or polynucleotide. For example, a macroencapsulation device of the invention may comprise at least 500, at least 1,000, at least 2,000, at least 4,000, at least 5,000, at least 8,000 to about 10,000 or more cells.

Some bioreactor devices, e.g., encapsulated or coated modified or non-modified cells of the present invention intended to secrete a desired therapeutic polypeptide or polynucleotide, may further comprise protective cells, e.g., within the barrier or capsule, where the protective cells are capable of providing protection to the modified or non-modified cells intended to secrete a desired therapeutic polypeptide or polynucleotide. Non-limiting examples of such protective cells include modified or non-modified sertoli cells and erythrocytes. Additionally, some bioreactor devices, e.g., encapsulated or coated modified or non-modified cells of the present invention intended to secrete a desired therapeutic polypeptide or polynucleotide, may further comprise an outer coating capable of creating a more compatible or protective micro-environment. Exemplary, non-limiting micro-environments which may be created include an anti-inflammatory micro-environment and a pro-angiogenic micro-environment.

In still other embodiments, bioreactor devices of the present invention may include modified cells with a "safety-shutoff" mechanism. For example, modified cells contained in a bioreactor device may comprise a regulated suicide gene which encodes a lethal polypeptide where the gene, upon activation, would induce destruction of the modified cell itself. For example, a modified cell might be programmed to die if it escapes from a barrier system, or if it undergoes oncogenic conversion. Non-limiting examples of lethal polypeptides suitable for use in the present invention are described in more detail below.

The subject on which the therapeutic methods are carried out may be any subject for which treatment or prevention is desired. For example, the subject may be one that is exhibiting one or more symptoms of a disease, disorder, or condition. The subject may also be one that is predisposed to a disease, disorder, or condition, e.g., due to genetics, family history, or environmental exposure. The subject may be a member of the general public, e.g., as part of a preventative immunization against a disease, disorder, or condition in a population.

The disease, disorder, or condition to be treated or prevented by the methods of the invention may be any disease, disorder, or condition for which one or more therapeutic switch promoters is available. Examples of diseases or disorders which may be treated or prevented by the methods of the invention include, without limitation, hyperproliferative diseases, disorders, or conditions (e.g., cancer), cardiovascular diseases, disorders, or conditions, neural diseases, disorders, or conditions, autoimmune diseases, disorders, or conditions, bone diseases, disorders, or conditions, gastrointestinal diseases, disorders, or conditions, blood diseases, disorders, or conditions, metabolic diseases, disorders, or conditions, inflammatory diseases, disorders, or conditions, and infectious diseases, disorders, or conditions.

The therapeutic switch promoters of the invention may be any promoter that is useful for treating, ameliorating, or preventing a specific disease, disorder, or condition. Examples include, without limitation, promoters of genes that exhibit increased expression only during a specific disease, disorder, or condition and promoters of genes that exhibit increased expression under specific cell conditions (e.g., proliferation, apoptosis, change in pH, oxidation state, oxygen level). In some embodiments where the gene switch comprises more than one transcription factor sequence, the specificity of the therapeutic methods can be increased by combining a disease- or condition-specific promoter with a tissue- or cell type-specific promoter to limit the tissues in which the therapeutic product is expressed. Thus, tissue- or cell type-specific promoters are encompassed within the definition of therapeutic switch promoter.

As an example of disease-specific promoters, useful promoters for treating cancer include the promoters of oncogenes. Examples of classes of oncogenes include, but are not limited to, growth factors, growth factor receptors, protein kinases, programmed cell death regulators and transcription factors. Specific examples of oncogenes include, but are not limited to, sis, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as therapeutic switch promoters in the present invention are disclosed in the references listed in Tables 1 and 2, along with the disease/disorder (Table 1) or tissue specificity (Table 2) associated with each promoter. The promoter sequences disclosed in these references are herein incorporated by reference in their entirety.

TABLE 1

| Promoter Sequence | Disease/Disorder | Patent/Published Application No. |
|---|---|---|
| Her-2/neu (ERBB2/c-erbB-2) | cancer | 5,518,885 |
| osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| insulin | pancreatic cancer | 6,716,824 |
| PEG-3 | cancer | 6,737,523 |
| telomerase reverse transcriptase | cancer | 6,777,203 |
| melanoma differentiation associated gene-7 | cancer | 6,841,362 |
| prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| $PCA3_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid transporter-2 | nervous system ischemia | 2004/0171108 |

TABLE 1-continued

| Promoter Sequence | Disease/Disorder | Patent/Published Application No. |
|---|---|---|
| MDTS9 | renal failure | 2006/0014931 |
| LIM, pyrroline 5-carboxylate reductase, SIM2 | prostate disorders | 2006/0134688 |
| Bax | apoptosis | 5,744,310 |
| fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/ Published Application No. |
|---|---|---|
| troponin T | skeletal muscle | 5,266,488 |
| myoD | muscle | 5,352,595 |
| actin | muscle | 5,374,544 |
| smooth muscle 22α | arterial smooth muscle | 5,837,534 |
| utrophin | muscle | 5,972,609 |
| myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| $CRF_{2\alpha}$ receptor | brain | 7,071,323 |
| nerve growth factor | neurons | 2003/159159 |

TABLE 2-continued

| Promoter Sequence | Tissue Specificity | Patent/ Published Application No. |
|---|---|---|
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| megsin | renal cells | 6,790,617 |
| prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |

Other genes that exhibit changes in expression levels during specific diseases or disorders and therefore may provide promoters that are useful in the present invention include, without limitation, the genes (along with the associated disease/disorder) listed in Table 3.

TABLE 3

| Gene | Disease/Disorder | Patent/Published Application No. |
|---|---|---|
| MLH1, MSH2, MSH6, PMS1, APC | Colorectal cancer | 7,148,016 |
| LEF-1 | Colon cancer | 2002/0169300 |
| $F_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM-1 | Prostate cancer | 2002/0042062 |
| PCADM-1 | Prostate cancer | 2003/0100033 |
| $PCA3_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the patent 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/0115094 |
| SEQ ID NO: 1 of the patent U.S. application publication 2005/0037372, incorporated by reference herein | Hepatocellular carcinoma | 2005/0037372 |

TABLE 3-continued

| Gene | Disease/Disorder | Patent/Published Application No. |
|---|---|---|
| $ATB_0$ | Hepatocellular carcinoma | 2006/0280725 |
| SEQ ID NOS: 1, 3 of the U.S. patent application publication 2007/0042420, incorporated by reference herein | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application publication 2002/0198362, incorporated by reference herein | Hematological cancers | 2002/0198362 |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, incorporated by reference herein | Ovarian cancer | 2007/0054268 |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/$hTAF_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S. patent application publication 2003/0044813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |

TABLE 3-continued

| Gene | Disease/Disorder | Patent/Published Application No. |
|---|---|---|
| Cables | Cancer | 2003/0109443 |
| Pp 32r1 | Cancer | 2003/0129631 |
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1,3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| JAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HLJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2002/0064786 |
| GCA-associated genes | Giant cell arteritis | 6,743,903 |
| PRV-1 | Polycythemia vera | 6,686,153 |
| SEQ ID NOS: 2, 4 of the U.S. Pat. No. 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEG1 | Pathological angiogenesis | 2002/0111325 |
| PRO256 | Cardiovascular disorders | 2002/0123091 |
| AOP2 | Atherosclerosis | 2002/0142417 |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |

TABLE 3-continued

| Gene | Disease/Disorder | Patent/Published Application No. |
|---|---|---|
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. Pat. No. 5,763,591, incorporated by reference herein | Insulin-dependent diabetes mellitus | 5,763,591 |
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, incorporated by reference herein | Diabetes, hyperlipidemia | 2004/0053397 |
| Neuronatin | Metabolic disorders | 2004/0259777 |
| Ncb5or | Diabetes | 2005/0031605 |
| 7B2 | Endocrine disorders | 2005/0086709 |
| PTHrP, PEX | Metabolic bone diseases | 2005/0113303 |
| KChIP1 | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Body weight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |

TABLE 3-continued

| Gene | Disease/Disorder | Patent/Published Application No. |
|---|---|---|
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders, wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Corneodesmosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi syndrome | 2002/0115144 |
| SEQ ID NOS: 1-16 of the U.S. patent application publication 2002/0127555, incorporated by reference herein | Endometriosis | 2002/0127555 |
| FGF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |
| CXCL1O | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease, disorder, or condition is identified, the promoter of the gene may be used in the gene switch of the invention. The sequence of many genes, including the promoter region, is known in the art and available in public databases, e.g., GenBank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it is a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J. Physiol. Lung Cell. Mol. Physiol.* 287: L52 (2004), which is incorporated by reference) by progressively deleting the 5'-flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene.

Another example of a protocol for acquiring and validating gene promoters includes the following steps: (1) acquire diseased and non-diseased cell/tissue samples of similar/same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

Gene Switch Systems

The gene switch may be any gene switch that regulates gene expression by addition or removal of a specific ligand. In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysonc receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.). In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (sec U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

Ecdysonc receptor (878aa) from *Drosophila* mclanogaster (Fruit fly)
(SEQ ID NO: 5)

```
  1 mkrrwsnngg fmrlpeesss evtsssnglv lpsgvnmsps sldshdycdq dlwlcgnesg
 61 sfggsnghgl sqqqqsvitl amhgcsstlp aqttiiping nangnggstn gqyvpgatnl
121 galangmlng gfngmqqqiq nghglinstt pstpttplhl qqnlggaggg giggmgilhh
181 angtpnglig vvgggggvgl gvggggvggl gmqhtprsds vnsissgrdd lspssslngy
241 sanescdakk skkgpaprvq eelclvcgdr asgyhynalt cegckgffrr svtksavycc
301 kfgracemdm ymrrkcqecr lkkclavgmr pecvvpenqc amkrrekkaq kekdkmttsp
361 ssqhggngsl asgggqdfvk keildlmtce ppghatipll pdeilakcqa rnipsltynq
421 laviykliwy qdgyeqpsee dlrrimsqpd enesqtdvsf rhiteitilt vglivefakg
481 lpaftkipqe dqitllkacs sevmmlrmar rydhssdsif fannrsytrd sykmagmadn
541 iedllhfcrq mfsmkvdnve yalltaivif sdrpglekaq lveaiqsyyi dtlriyilnr
601 hcgdsmslvf yakllsilte lrtlgnqnae mcfslklknr klpkfleeiw dvhaippsvq
661 shlgitqeen erleraermr asvggaitag idcdsastsa aaaaaqhqpq pqpqpqpssl
721 tqndsqhqtq pqlqpqlppq lqggqlqpqlq pqlqtqlqpq iqpqpqllpv sapvpasvta
781 pgslsaysts seymggsaai gpitpattss itaavtasst tsavpmgngv gvgvgvggnv
841 smyanaqtam almgvalhsh qeqliggvav ksehstta
```

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises a AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

Figure 2:
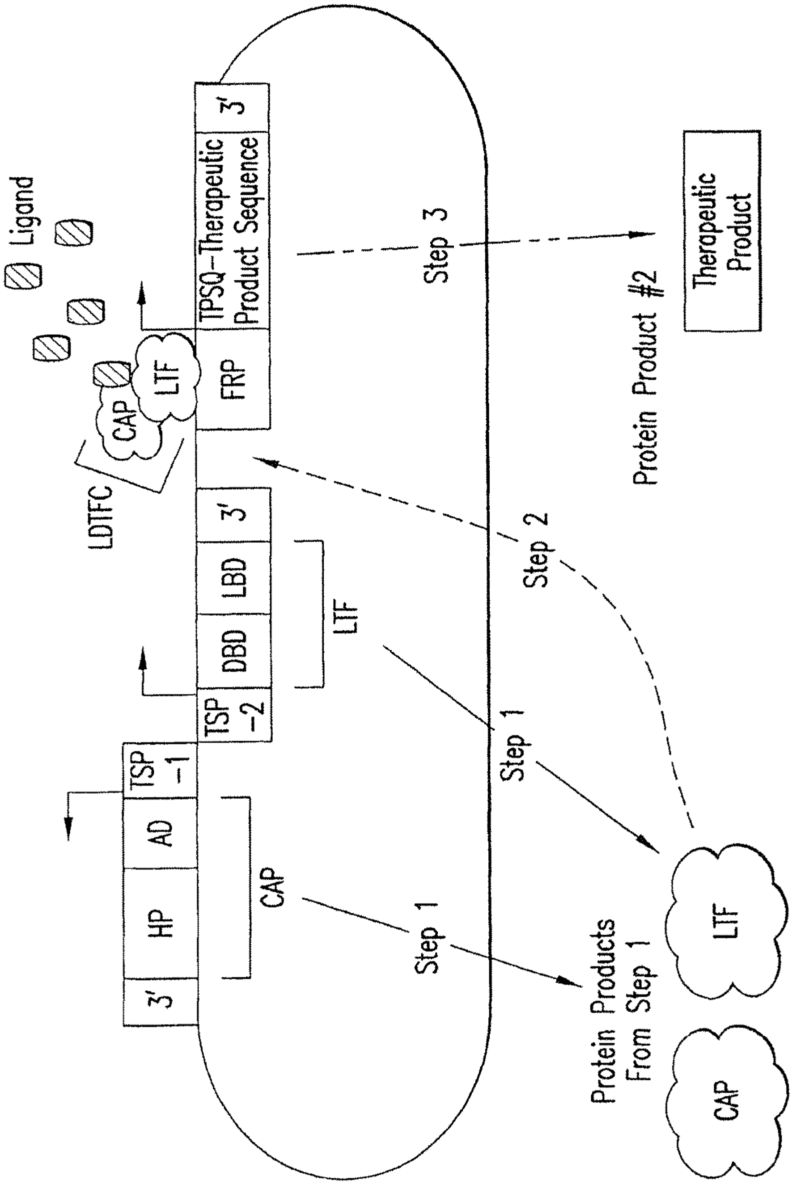
FIG. 2 shows an embodiment of the therapeutic gene switch of the invention in which two transcription factor sequences (CAP and LTF) encoding two separate portions of a ligand-dependent transcription factor complex are under the control of different promoters. The terms AD, HP, CAP, DBD, LBD, LTF, "Therapeutic Product Sequence," "Therapeutic Product," TSP, LDTFC, and FRP are defined in the legend to FIG. 1. "TSP-1" and "TSP-2" represent two different therapeutic switch promoters, each of which is, independently, either a constitutive promoter or a promoter activated under conditions associated with a disease, disorder, or condition. In one embodiment TSP-1 is a constitutive promoter and TSP-2 is a promoter activated under conditions associated with a disease, disorder, or condition. CAP and LTF combine to form a LDTFC which in combination with ligand activates a FRP.

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2). FIG. 2 also demonstrates the ability to modify the therapeutic gene switch to treat any disease, disorder, or condition simply by inserting the appropriate TSPs.

In a further embodiment, both the first and the second transcription factor sequence, e.g., a CAP or a LTF, are under the control of a single therapeutic switch promoter (e.g. TSP-1 in FIG. 1). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex will be synthesized upon activation of TSP-1. TSP-1 can be a constitutive promoter or only activated under conditions associated with the disease, disorder, or condition.

Figure 4:
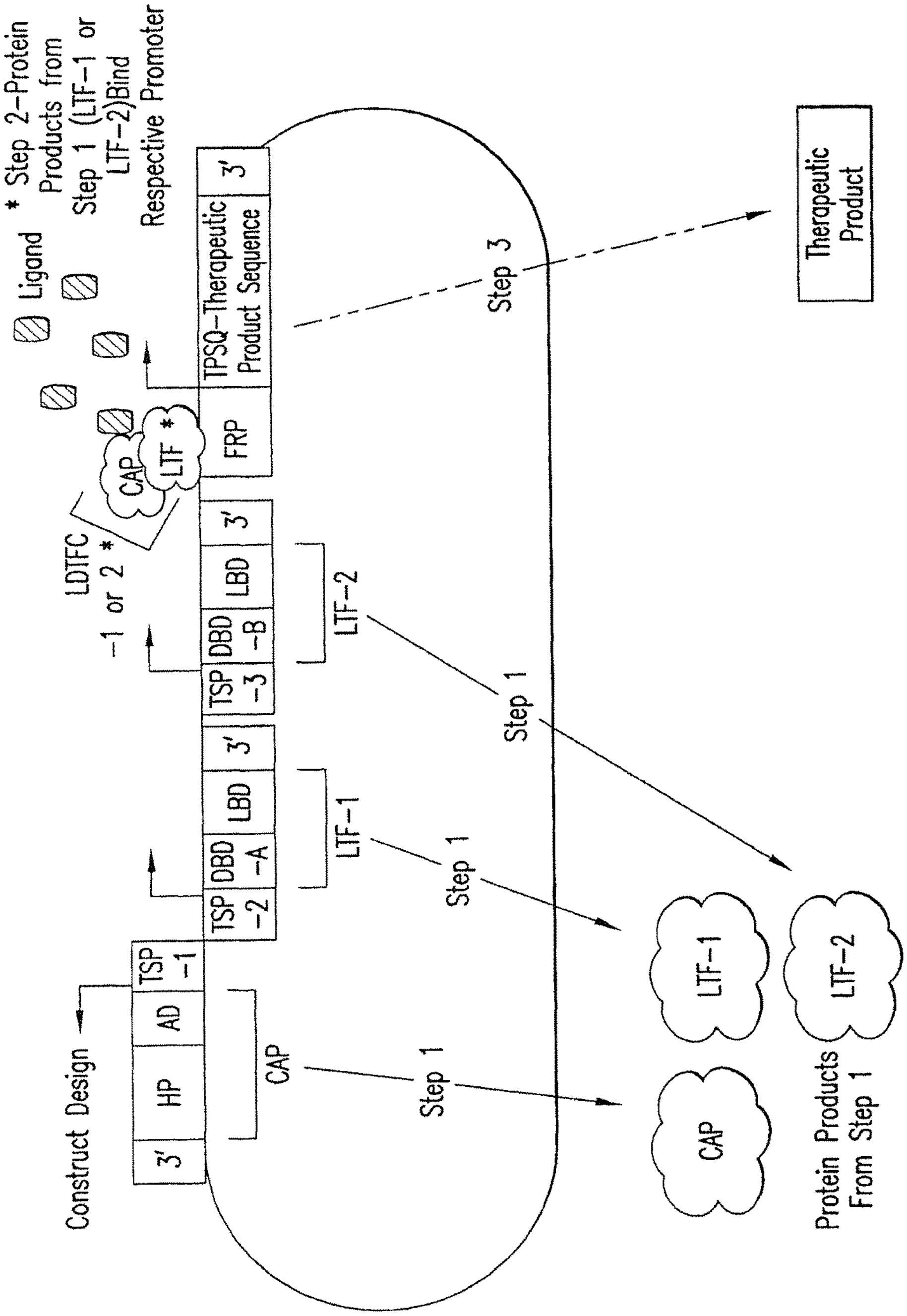
FIG. 4 shows an embodiment of the therapeutic gene switch of the invention in which three transcription factor sequences encoding CAP and two separate LTF portions of a ligand-dependent transcription factor complex are under the control of different promoters. The terms AD, HP, CAP, DBD, LBD, LTF, "Therapeutic Product Sequence," "Therapeutic Product," TSP, LDTFC, and FRP are defined in the legend to FIG. 1. TSP-1, TSP-2, and TSP-3 represent three different therapeutic switch promoters, each of which is, independently, either a constitutive promoter or a promoter activated under conditions associated with a disease, disorder, or condition. In one embodiment, TSP-1 is a constitutive promoter and TSP-2 and TSP-3 are different promoters, each of which is independently activated under conditions associated with a disease, disorder, or condition. Either LTF-1 or LTF-2 may combine with CAP to form LDTFC-1 or LDTFC-2. Either LDTFC-1 or LDTFC-2, in combination with ligand, activates FRP.

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4) and the other transcription factor sequence, e.g., CAP, is under the control of a constitutive therapeutic switch promoter (e.g., TSP-1 in FIG. 4). In this embodiment, one portion of the ligand-dependent transcription factor complex will be constitutively present while the second portion will only be synthesized under conditions associated with the disease, disorder, or condition.

Figure 3:
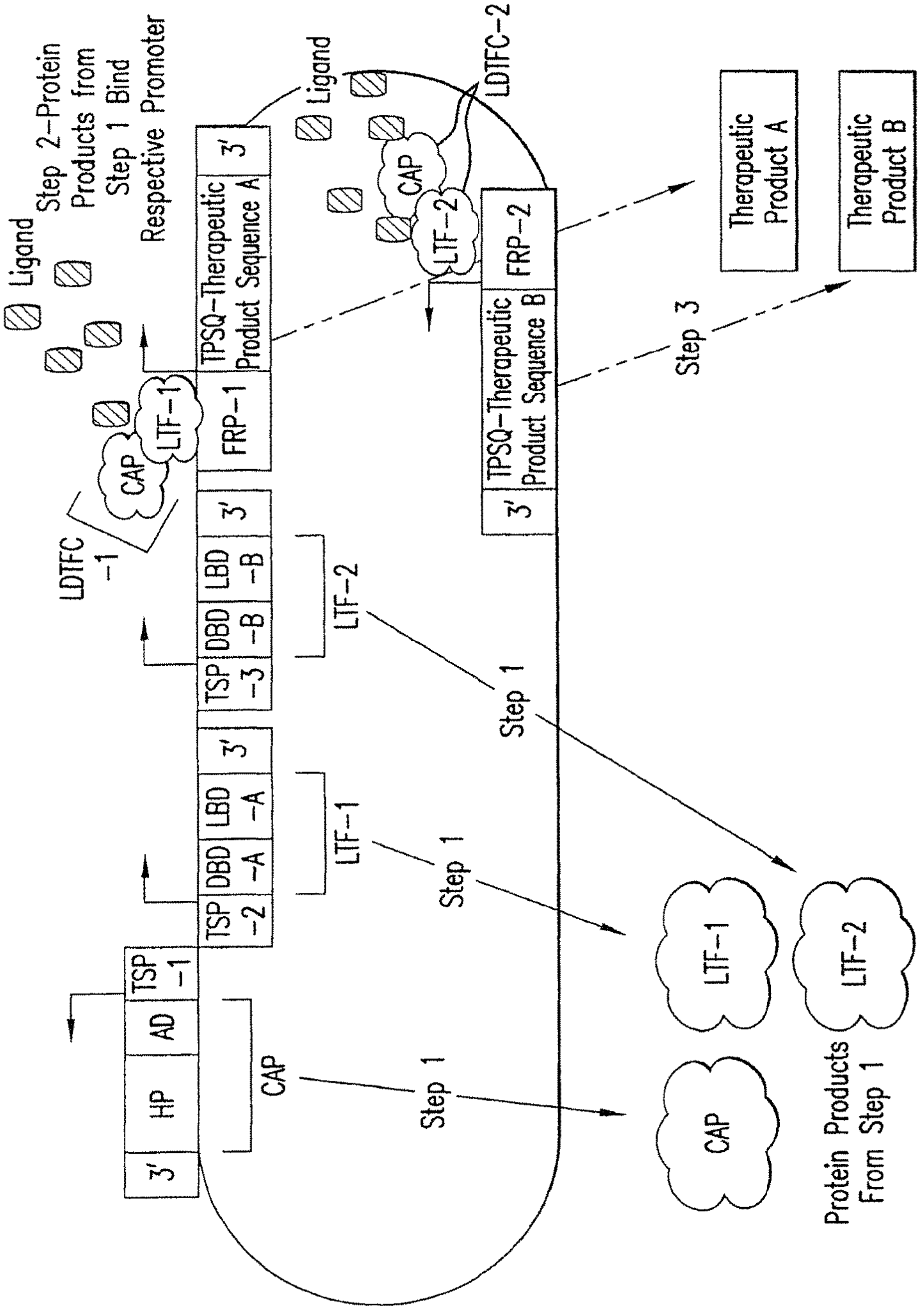
FIG. 3 shows an embodiment of the therapeutic gene switch of the invention in which three transcription factor sequences (CAP, LTF-1, and LTF-2), which may combine to form two separate LDTFCs under the control of different promoters. The terms AD, HP, CAP, DBD, LBD, LTF, "Therapeutic Product Sequence," "Therapeutic Product," TSP, LDTFC, and FRP are defined in the legend to FIG. 1. DBD-A represents a first DNA binding domain which is fused with an LBD to form LTF-1, DBD-B represents a second DNA binding domain which is fused with an LBD to form LTF-2. "Therapeutic Product A" represents a first therapeutic polypeptide or therapeutic polynucleotide; "Therapeutic Product B" represents a second therapeutic polypeptide or therapeutic polynucleotide; and TSP-1, TSP-2, and TSP-3 represent three different therapeutic switch promoters, each of which is, independently, either a constitutive promoter or a promoter activated under conditions associated with a disease, disorder, or condition. In one embodiment, TSP-1 is a constitutive therapeutic switch promoter and TSP-2, and TSP-3 are different therapeutic switch promoters, each of which is independently activated under conditions associated with a disease, disorder, or condition. CAP and LTF-1 combine to form LDTFC-1 which in combination with ligand activates FRP-1. CAP and LTF-2 combine to form LDTFC-2 which in combination with ligand activates FRP-2.

In another embodiment, one transcription factor sequence, e.g., CAP, is under the control of a first TSP (e.g., TSP-1 in FIG. 3) and two or more different second transcription factor sequences, e.g., LTF-1 and LTF-2 are under the control of different TSPs (e.g., TSP-2 and TSP-3 in FIG. 3). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising a AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from the group consisting of a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In a preferred embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from the group consisting of a vertebrate RXR, an invertebrate RXR, and a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA,* 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises (a) a first polynucleotide encoding a first chimeric protein which binds to rapamycin or an analog thereof and which comprises at least one FK506-binding protein (FKBP) domain and at least one protein domain heterologous thereto, wherein the FKBP domain comprises a peptide sequence selected from:
 (1) a naturally occurring FKBP
 (2) a variant of a naturally occurring FKBP in which up to 10 amino acid residues have been deleted, inserted, or replaced with substitute amino acids, and
 (3) an FKBP encoded by a DNA sequence which selectively hybridizes to a DNA sequence encoding an FKBP of (1) or (2);
(b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:
 (4) a naturally occurring FRB domain,
 (5) a variant of a naturally occuring FRB domain in which up to 10 amino acid residues have been deleted, inserted, or replaced with substitute amino acids, and
 (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Procaryotic Repressor/Operator Based Gene Switch System

In one embodiment, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a therapeutic protein or therapeutic polypeptide, wherein said second polynucleotide is operably linked to a minimal promoter and at least one tet operator sequence. The first polynucleotide coding for a transactivator fusion protein may comprise therapeutic switch promoter as described elsewhere herein. The expression of the lethal protein is up-regulated in the absence of tetracycline. (see, e.g., Gossen et al. (1992) *Proc. Natl. Acad. Sci.* 89: 5547-5551; Gossen et al. (1993) *TIBS* 18: 471-475; Furth et al. (1994) *Proc. Natl. Acad. Sci.* 91: 9302-9306; and Shockett et al. (1995) *Proc. Natl. Acad. Sci.* 92: 6522-6526). The TetO expression system is disclosed in U.S. Pat. No. 5,464,758 B1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a therapeutic protein or therapeutic polypeptide, wherein said second polynucleotide is operably linked to a therapeutic switch promoter. In the Lac system, a lac operon is inactivated in the absence of lactose, or synthetic analogs such as isopropyl-b-D-thiogalactoside.

Additional gene switch systems include those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more therapeutic polypeptides or therapeutic polynucleotides, upon binding to one or more ligands. Within the scope of the present invention are any numbers of and/or combinations of gene switch systems.

In one embodiment, the present invention provides a nucleic acid composition comprising:

(c) a first gene switch system which comprises:
- i. a first gene expression cassette comprising a polynucleotide encoding a first hybrid polypeptide which comprises:
  1. a transactivation domain, which activates a factor-regulated promoter operably associated with a polynucleotide encoding a therapeutic polypeptide or therapeutic polynucleotide; and
  2. a heterodimer partner domain,
- ii. a second gene expression cassette comprising a polynucleotide encoding a second hybrid polypeptide which comprises:
  1. a DNA-binding domain, which recognizes a factor-regulated promoter operably associated with a polynucleotide encoding a therapeutic polypeptide or therapeutic polynucleotide; and
  2. a ligand binding domain; and
- iii. a third gene expression cassette comprising a polynucleotide encoding a therapeutic polypeptide or therapeutic polynucleotide comprising:
  1. a factor-regulated promoter, which is activated by the transactivation domain of the second hybrid polypeptide; and,
  2. a polynucleotide encoding a therapeutic polypeptide or therapeutic polynucleotide, and b. a second gene expression system which comprises:
- i. a first gene expression cassette comprising a polynucleotide encoding a first hybrid polypeptide which comprises:
  1. a transactivation domain, which activates a factor-regulated promoter operably associated with a polynucleotide encoding a therapeutic polypeptide or therapeutic polynucleotide; and
  2. a heterodimer partner domain,
- ii. a second gene expression cassette comprising a polynucleotide encoding a second hybrid polypeptide which comprises:
  1. a DNA-binding domain, which recognizes a factor-regulated promoter operably associated with a polynucleotide encoding a therapeutic polypeptide or therapeutic polynucleotide; and
  2. a ligand binding domain; and
- iii. a third gene expression cassette comprising a polynucleotide encoding a therapeutic polypeptide or therapeutic polynucleotide comprising:
  1. a factor-regulated promoter, which is activated by the transactivation domain of the second hybrid polypeptide; and,
  2. a polynucleotide encoding a therapeutic polypeptide or therapeutic polynucleotide.

The multiple inducible gene expression systems provide for expression of a given therapeutic polynucleotide or therapeutic polypeptide under conditions associated with different diseases, disorders or conditions, or expression of multiple therapeutic polypeptides or therapeutic polynucleotides either under the same conditions associated with the same disease disorder or condition, or under different conditions associated with different diseases, disorders, or conditions.

In certain embodiments, the combination of two or more gene switch systems may be (1) a dual-switch ccdysonc receptor based gene expression system and (2) a single-switch ecdysone receptor based gene switch. In other embodiments, the combination may be (1) an single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention.

Ligands

The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057

B1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I Formula I

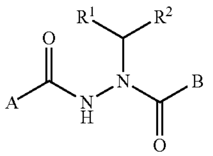

wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula IT Formula II

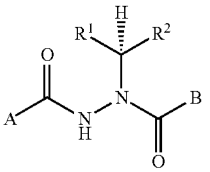

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof In certain embodiments, the ligand may be enantiomerically enriched compounds of Formula III Formula III

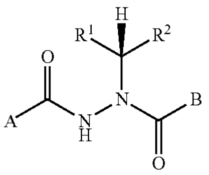

wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, a ligand may be (R)-3,5-dimethyl-benzoic acid N-(1-tert-butyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persul fates, 3-phenylpropionates, phosphates, pi crates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmaceutical composition are in the form of solutions, suspensions, tablets, capsules, ointments, elixirs, or injectable compositions.

Pharmaceutical Compositions

Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fattty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinatc (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

Possible pharmaceutical preparations which can be used rectally include, for example, suppositories, which consist of a combination of one or more of the ligands with a suppository base. Suitable suppository bases are, for example, natural or synthetic triglycerides, or paraffin hydrocarbons. In addition, it is also possible to use gelatin rectal capsules which consist of a combination of the ligand with a base. Possible base materials include, for example, liquid triglycerides, polyethylene glycols, or paraffin hydrocarbons.

Suitable formulations for parenteral administration include aqueous solutions of the ligand in water-soluble form, for example, water-soluble salts and alkaline solutions. In addition, suspensions of the ligand as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions may be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which ligand, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the ligand in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the ligand in a suitable high molecular weight alcohol such as propylene glycol or polyethylene glycol.

Examples of antioxidants which may be added to the pharmaceutical compositions include BHA and BHT.

In one embodiment, the pharmaceutical composition comprises 30 mg ligand per mL LABRASOL in a solid gelatin capsule. In another embodiment, the capsule contains 1, 2, 3, 4, 5, 6, 7, 8, 9, 10, 15, 20, 25, 30, 35, 40, 45, 50, 55, 60, 65, 70, 75, 80, 85, 90, 95 or 100 mg ligand.

Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression. In one embodiment, 0.1 to 7.5 mg/kg is administered to the subject. In another embodiment, 0.1 to 3 mg/kg is administered to the subject. In another embodiment, 0.1 to 3 mg/kg is administered.

Suitable routes of administering the pharmaceutical compositions include oral, rectal, topical (including dermal, buccal and sublingual), vaginal, parenteral (including subcutaneous, intramuscular, intravenous, intradermal, intrathecal, intra-tumoral and epidural) and by naso-gastric tube. It will be understood by those skilled in the art that the route of administration will depend upon the condition being treated and may vary with factors such as the condition of the recipient. The pharmaceutical compositions may be administered one or more times daily.

Therapeutic Molecules

The therapeutic molecule, e.g., the polynucleotide encoding a therapeutic polypeptide or therapeutic polynucleotide may be any sequence that encodes a polypeptide or polynucleotide that is useful for the treatment, amelioration, or prevention of a disease, disorder, or condition. Therapeutic polypeptides may be any polypeptide known to be effective for treating, ameliorating, or preventing a disease, disorder, or condition. Examples of classes of therapeutic polypeptides that may be used in the invention include, without limitation, cytokines, chemokines, hormones, antibodies, engineered immunoglobulin-like molecules, single chain antibodies, fusion proteins, enzymes, immune co-stimulatory molecules, immunomodulatory molecules, transdominant negative mutants of target proteins, toxins, conditional toxins, antigens, tumor suppressor proteins, growth factors, membrane proteins, vasoactive proteins and peptides, antiviral proteins or variants thereof. Therapeutic polynucleotides include, without limitation, antisense sequences, small interfering RNAs, ribozymes, and RNA external guide sequences. Therapeutic polynucleotides may be targeted to any transcript associated with a particular disease, disorder, or condition and for which it is desired to decrease or eliminate expression. Numerous genes exhibiting elevated expression during a disease, disorder, or condition are known in the art, including the genes listed in Tables 1-3 above.

The polynucleotide encoding a therapeutic polypeptide or therapeutic polynucleotide is operably linked to or operably associated with a factor-regulated promoter comprising at least one response element that is recognized by the DBD of the ligand-dependent transcription factor complex encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

Specific therapeutic polypeptides which may be expressed using a therapeutic gene-switch include, but are not limited to antibodies, including monoclonal antibodies, minimal antibodies, fusion proteins, endogenous protein mimetics, enzymes, hormones, cytokines, chemokines, growth factors, and fragments, variants or derivatives of any such polypeptides. Non-limiting representative therapeutic molecules are described below. All references to these molecules, including patent publications, scientific literature, and polynucleotide and polypeptide sequence accession numbers, are hereby incorporated by reference in their entireties.

Monoclonal Antibodies

Therapeutic gene-switch constructs of the present invention may be used to express therapeutic monoclonal antibodies, or fragments, variants or analogs thereof (collectively "monoclonal antibodies"). Such monoclonal antibodies are useful for treatment of diseases and disorders including, without limitation, cancer, autoimmune diseases (e.g., MS, Crohn's disease, rheumatoid arthritis), cancer, infectious diseases, inflammatory diseases, allergies, heart disases, and transplantation rejection. Antibodies for use in the present invention include any known therapeutic monoclonal antibodies including, but not limited to those listed below, monoclonal antibodies which bind to the same epitope or target as any known monoclonal antibodies. Monoclonal antibody constructs suitable for expression via therapeutic gene switch constructs include multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), and fragments comprising either a VL or VH domain. ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains.

In certain embodiments, the present invention includes therapeutic gene switch constructs which encode monoclonal antibodies against antigens including, but not limited to CTLA4, CD25, HER-2/neu (ErbB2), CD20, TNFα, EGFR, and VEGF.

Anti-CTLA4 antibodies employable in the present invention, and methods of producing them, are described in the International Application No. PCT/US99/30895, published on Jun. 29, 2000 as WO 00/37504 (e.g., ticilimumab, also known as 11.2.1 and CP-675,206), European Patent Appl. No. EP 1262193 A1, published Apr. 12, 2002, U.S. patent application Ser. No. 09/472,087, now issued as U.S. Pat. No. 6,682,736, U.S. patent application Ser. No. 09/948,939, now published as U.S. Pat. App. Pub. No. 2002/0086014 (e.g., ipilimumab, also known as 10D1 and MDX-010, Medarex, Princeton, N.J.), Anti-CD25 antibodies employable in the present invention include, without limitation, Daclizumab. See, e.g., U.S. Pat. No. 5,530,101. Daclizumab (brand name: Zenapax®, marketed by Roche) is a humanized IgG1 monoclonal antibody directed against CD25 (IL-2 receptor). Functioning as an IL-2 receptor antagonist, it binds with high affinity to the Tac subunit of the high-affinity IL-2 receptor complex. Daclizumab is indicated for the prophylaxis of acute organ rejection in renal transplant patients when used in combination with cyclosporine and corticosteroids.

Anti-HER-2/neu (ErbB2) antibodies employable in the invention include, without limitation, Trastuzumab. See, e.g., U.S. Pat. No. 5,677,171. Trastuzumab (brand name: Herceptin®, marketed by Genentech) is a humanized, monoclonal antibody targeted against the extracellular domain of the c-erbB2/HER2/neu protein, a transmembrane receptor protein (structurally related to the Epidermal Growth Factor receptor) which is overexpressed in certain types of breast cancer. As a mediator of antibody-dependent cellular cytotoxicity, trastuzumab is preferentially toxic to HER2-expressing cancer cells.

Anti-CD20 antibodies employable in the invention include, without limitation rituximab (see, e.g., U.S. Pat. No. 5,736,137). Rituximab (brand name: Rituxan®, marketed by Biogen Idec and Genentech) is a chimeric (murine/human) monoclonal IgG1κ antibody. Rituximab was initially designed and licensed for treatment of non-Hodgkin's lymphoma, and more recently has been licensed for treatment of anti-TNF refractory rheumatoid arthritis.

Anti-TNFα antibodies employable in the invention include, without limitation, Adalimumab (see, e.g., U.S. Pat. No. 7,223,394), and Infliximab (see, e.g., U.S. Pat. No. 7,138,118). Adalimumab, (brand name: Humira®, marketed by Abbott) is a recombinant human IgG1κ monoclonal antibody which binds specifically to TNFα, thereby blocking interaction of TNFα with the p55 and p75 surface TNF receptors. Adalimumab is licensed for use in rheumatoid arthritis, and juvenile idiopathic arthritis. Additional indications for adalimumab include Crohn's disease, plaque psoriasis, psoriatic arthritis, and ankylosing spondylitis. Infliximab (brand name: Remicade, marketed by Centocor) is a recombinant chimeric IgG1κ monoclonal antibody which binds specifically to TNFα, thereby blocking interaction of TNFα with the p55 and p75 surface TNF receptors. Infliximab is licensed for use in Crohn's disease. Additional indications include rheumatoid arthritis, psoriatic arthritis, severe chronic plaque psoriasis, and ankylosing spondylitis.

Anti EGFR (Epidermal Growth Factor Receptor) antibodies employable in the invention include, without limitation, Cetuximab (see, e.g., U.S. Pat. No. 6,217,866). Cetuximab (brand name: Erbitux®, marketed by Imclone and Bristol-Meyers Squibb (North America) and by Merck KGaA (other areas) wis a chimeric monoclonal antibody which binds specifically to EGFR. Cetuximab is indicated for metastatic colorectal cancer; and head and neck cancer.

Anti-VEGF antibodies employable in the invention include, without limitation, Bevacizumab (see, e.g., U.S. Pat. No. 6,383,486). Bevacizumab (brand name: Avastin®, marketed by Genentech) is a human monoclonal antibody that inhibits the function of vascular endothelial growth factor (VEGF), thus inhibiting tumor neoangiogenesis. Bevacizumab is indicated for treatment in combination with other anti-cancer chemotherapeutics for the first- and second-line treatment of patients with metastatic colorectal cancer and first-line treatment of patients with recurrent or metastatic non-squamous non-small cell lung cancer (NSCLC).

Fusion Proteins

Therapeutic gene-switch constructs of the present invention may be used to express therapeutic fusion proteins, such as a chimeric TNFα binding protein 2. Tumor necrosis factor binding protein 2 (Enbrel) is produced from the membrane form by proteolytic processing. Enbrel is a recombinant fusion protein consisting of two soluble TNF receptors joined by the Fc fragment of a human IgG1 molecule. It binds to TNF-alpha and blocks TNF-alpha interaction with its receptor. Enbrel is used to treat moderate to severe rheumatoid arthritis. The amino acid sequence coding for Enbrel is available from public database as accession number P20333.

The polynucleotide sequences of Enbrel are available from public databases as accession numbers DD292498 and DD 292499, sequences of which are incorporated by reference herein.

Enzymes

Therapeutic gene-switch constructs of the present invention may be used to express therapeutic enzymes, including tissue plasminogen activator. Plasminogen activator, tissue type isoform 3 preproprotein (tPA) is a secreted scrine protease which converts the proenzyme plasminogen to plasmin, a fibrinolytic enzyme. This enzyme plays a role in cell migration and tissue remodeling. The amino acid sequences coding for tPA are available from public databases as accession numbers NP_127509 and NP_000921 (both human), sequences of which are incorporated by reference herein.

The polynucleotide sequences coding for tPA are available from public databases as accession numbers NM _033011 and NM _000930 (both human), sequences of which are incorporated by reference herein.

Endogenous Protein Mimetics

Therapeutic gene-switch constructs of the present invention may be used to express therapeutic mimetics of endogenous proteins, such as the following.

Alphanate (Coagulation factor III), along with calcium and phospholipid, acts as a cofactor for factor IXa when it converts factor X to the activated form of factor Xa. Alphanate is purified Factor VIII (also know as Antihemophilic factor) and von Willebrand factor. Alphanate is approved for the prevention and control of bleeding in patients with Factor VIII deficiency due to hemophilia A or acquired Factor VIII deficiency. The amino acid sequences coding for factor VIII are available from public databases as accession numbers AAA52485 (human); and AAA37385 (mouse), sequences of which are incorporated by reference herein.

The polynucleotide sequences coding for factor VIII are available from public databases as accession numbers M14113 (human); and L05573 (mouse), sequences of which are incorporated by reference herein.

Aralast (Alpha-1 proteinase inhibitor) amino acid sequences are available from public databases as accession numbers AAB59375 (human alpha 1-antitrypsin); AAC28869 (mouse alpha-1 protease inhibitor); and AAA40788 (rat alpha-1-antitrypsin), sequences of which are incorporated by reference herein.

The polynucleotide sequences coding for alpha-1 proteinase inhibitor are available from public databases as accession numbers K01396 (human); M75721 (mouse); and M32247 (rat), sequences of which are incorporated by reference herein.

Nesiritide (Natrecor®) is a recombinant form of human B-type natriuretic peptide (hBNP) that has been approved for the intravenous treatment of patients with acute decompensated congestive heart failure (CHF) who have dyspnea at rest or with minimal activity. The amino acid sequence coding for Brain natriurctic peptide is available from public database as accession number NP_002512, sequence of which is incorporated by reference herein.

The polynucleotide sequence coding for brain natriuretic peptide is available from public database as accession number NM _002521, sequence of which is incorporated by reference herein.

The amino acid sequence coding for human insulin is available from public database as accession number AAH05255, sequence of which is incorporated by reference herein.

The polynucleotide sequence coding for human insulin is available from public database as accession number BC005255, sequence of which is incorporated by reference herein.

Granulocyte/macrophage colony-stimulating factor (GM-CSF) is a cytokine that functions as a white blood cell growth factor, stimulates stems cells to produce granulocytes (neutrophils, eosinophils, and basophils) and monocytes. The amino acid sequences coding for granulocyte/macrophage colony-stimulating factor (GM-CSF) are available from public databases as accession numbers AAA52122 (human); NP_034099 (mouse); NP_001032749 (rat Csf2ra); and NP_598239 (Csf2rb), sequences of which are incorporated by reference herein.

The polynucleotide sequences coding for GM-CSF are available from public databases as accession numbers M11734 (human); NM _009969 (mouse); NM _001037660 (rat Csf2ra); and NM _133555 (rat Csf2rb), sequences of which are incorporated by reference herein.

The amino acid sequences coding for erythropoietin are available from public databases as accession numbers AAH93628 (human); AAI19266 (mouse); and BAA01593 (rat), sequences of which are incorporated by reference herein.

The polynucleotide sequences coding for erythropoietin are available from public databases as accession numbers BC093628 (human); BC119265 (mouse); and D10763 (rat), sequences of which are incorporated by reference herein.

The amino acid sequences coding for growth hormone are available from public databases as accession numbers AAA98618 (human); NP_032143 (mouse); and NP_001030020 (rat), sequences of which are incorporated by reference herein.

The polynucleotide sequences coding for growth hormone are available from public databases as accession numbers M13438 (human); NM_008117 (mouse); and NM_001034848 (rat), sequences of which are incorporated by reference herein.

Recombinant Protein

Therapeutic gene-switch constructs of the present invention may be used to express therapeutic recombinant proteins, such as the botulinum toxin. The botulinum toxin inhibits neurotransmitter acetylcholine release at nerve terminals, and is available under the name BOTOX for the treatment of strabismus and blepharospasm associated with dystonia and cervical dystonia. BOTOX is also used for the treatment of hemifacial spasm and a number of other neurological disorders characterized by abnormal muscle contraction. The amino acid sequence coding for botulinum neurotoxin type A precursor (BoNT/A) (Bontoxilysin-A) (BOTOX) are available from public databases as accession numbers P10845.

Treatment of Cardiovascular Diseases

The present invention is further directed to a method of treating, ameliorating, or preventing cardiovascular disease, comprising administering to a subject in need of such treatment a therapeutic gene product which ameliorates, prevents, or treats cardiovascular related diseases under control of the switch proteins referenced earlier. Such treatment may be delivered directly to the subject to be treated, or via a bioreactor containing encapsulated or non-encapsulated non-modified or genetically modified cells which secrete one or more therapeutic proteins or therapeutic polypeptides as described elsewhere herein. According to this embodiment, the cell will express one or more therapeutic gene products effective in treating cardiovascular disease when transplanted into a subject, e.g., into an infarct zone of a cardiovascular disease patient. Examples of such therapeutic gene products are described in more detail below. In certain embodiments, a genetically modified cell of the present invention expresses the one or more therapeutic gene products constitutively, i.e., one or more heterologous therapeutic gene products are expressed in the cell continuously. Alternatively, expression of one, two, three, or more heterologous therapeutic gene products expressed by the cell is controlled by a therapeutic gene switch. In certain aspects, bioreactors for treatment, amelioration, or prevention of cardiovascular disease comprise encapsulated cells, e.g., the cells are encapsulated in an alginate-based formulation. Examples and methods of cell encapsulation, to provide, e.g., a physical or immunological barrier from the subject being treated, are described in detail elsewhere herein.

The invention further provides a nucleic acid composition comprising one or more polynucleotides which express therapeutic gene products, e.g., therapeutic polypeptides and/or therapeutic polynucleotides, useful for the treatment, amelioration, or prevention of cardiovascular disease through operable association with a promoter. In certain embodiments a promoter controlling expression of a therapeutic gene product is activated by a ligand-dependent transcription factor complex, where at least a portion of the transcription factor is expressed via operable linkage to one or more therapeutic switch promotcsr, where the activity of the therapeutic switch promoters is constitutive and/or is modulated under conditions associated with a tissue type or associated with a disease, disorder, or condition. In embodiments relating to the treatment, amelioration, or prevention of cardiovascular disease, a therapeutic switch promoter could be, for example, a heart-specific promoter, or a promoter which is activated during conditions such as congestive heart failure, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, and cardiogenic shock. Exemplary promoters are presented in Tables 1-3. Additional promoters are described elsewhere herein, for example in Examples 1-8. Additional promoters can al so be easily identified via methods described herein.

Examples of therapeutic switch promoters useful for regulated gene switch expression in cardiac cells or under conditions related to cardiac diseases, disorders, or conditions include, without limitation: the S100A6 promoter, which is tissue-specific for cardiac myocytes (Tsoporis et al., *J. Biol. Chem.* (2008) (Epub ahead of print; PMID: 18753141)); Atrial Naturetic Factor (ANF) promoter, Alpha-myosin heavy chain promoter, c-fos promoter, BNP promoter, or alpha actins promoter, all of which are tissue-specific for cardiomyocytes (Nelson et al., *J. Mol. Cell. Cardiol.* 39(3):479 (2005)); Erythropoietin promoter, which is activated in myocardium under ischemic conditions (Su et al., *Proc. Natl. Acad. Sci. U.S.A* 99(14):9480 (2002)); AlphaB-Crystallin (CRYAB) promoter including, for example, a BRG1-response element, which is tissue-specific for vertebrate eye lens (Duncan B. and Zhao K. DNA Cell. Biol. 26(10):745 (2007)); AlphaB-Crystallin (CRYAB) promoter with cis-acting regulatory elements, e.g., alpha BE-1, alpha BE-2, alpha BE-3, and MRF, which is tissue-specific for skeletal muscle (Gopal-Srivastava et al., *J. Mol. Cell Biol.* 15(12):7081 (1995)); NCX1 promoter, which is tissue-specific for cardiomyocytes (Xu et al., *J. Biol. Chem.* 281(45):34430 (2006)); Beta myosin heavy chain promoter, which is tissue-specific for cardiomyocytes (Nelson et al., *J. Mol. Cell Cardiol.* 39(3):479 (2005), Ross et al., *Development.* 122(6):1799 (1996), and Lee et al., *Mol. Cell. Biol.* 14(2):1220 (1994)), Myosin light chain-2 ventricular promoter including an HF-1a/HF-1b/MEF-2 combinatorial element (Ross et al., *Development.* 122(6):1799 (1996)) or an HF-1a/HF-1b element and an HF-3 regulatory element, (Lee et al., *Mol. Cell. Biol.* 14(2):1220 (1994)), which is tissue-specific for cardiac ventricles; Myosin light chain promoters, e.g., MLC1F and MLC3F, which are differentially activated during skeletal muscle development (Kelly et al., *J. Cell. Biol.* 129(2):383 (1995)); Myosin light chain 2v (MLC-2v) promoter, which is tissue-specific for cardiac muscles (Su et al., *Proc. Natl. Acad. Sci. USA.* 101(46): 16280 (2004)); and Cardiac troponin I (TnIc) promoter, which is tissue-specific and developmental stage-specific in cardiac muscles (Bhaysar et al., *J. Mol. Cell Cardiol.* 32(1): 95 (2000)).

The invention further provides one or more vectors comprising the aforementioned nucleic acid composition, and one or more genetically modified cells comprising such vectors. Such cells may be allogeneic, autologous, or xenogeneic relative to the subject to be treated. The invention further provides one or more encapsulation methodologies for the treatment, amelioration, or prevention of cardiovascular disease, comprising the aforementioned modified cells, where the cells have been treated in such a way as to be protected from a subject's immune system upon introduction into the subject. Such treatments include, without limitation, provision of a conformal coating, microencapsulation, or macroencapsulation.

Cardiovascular diseases include, but are not limited to congestive heart failure, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, and cardiogenic shock. Causes of such events include, without limitation, thrombosis, embolism, atherosclerosis, and stenosis. Populations predisposed include, without limitation, smokers, persons with diabetes, hypertension, or dyslipidemia.

Suitable therapeutic molecules for the treatment, amelioration, or prevention of cardiovascular disease include, without limitation, pro-angiogenic factors, cardioprotective factors, and cardioregenerative factors.

The therapeutic molecules useful for the present invention to prevent, treat, or ameliorate cardiovascular diseases include, without limitation, the atrial natriuretic factor (ANF), carperitide, brain Natriuretic factor (BNP), nesiritide, relaxin, vascular endothelial growth factor (VEGF165), hepatocyte growth factor (HGF), Angiopoietin-1 (Ang-1), basic fibroblast growth factor (bFGF), fibroblast growth factor 4 (FGF-4), insulin-like growth factor 1 (IGF-1), hypoxia-inducible factor1-alpha (HIF1-alpha), erythropoietin, tissue plasminogen activator (tPA), growth hormone, Stromal-Derivcd Factor-1 (SDF-1), sarco-endoplasmic reticulum Ca2+-ATPase (SERCA2a), adenylycyclase type VI (AC6), S100A1, parvalbumin, phosphatase inhibitor 2, and phosphatase inhibitor 1. These molecules are known to exert the effects on cardiac tissues through various mechanisms, e.g., hemodynamics, angiogenesis, cardiac regeneration, anti-fibrosis, and/or cardiac repair. These therapeutic molecules may provide multiple therapeutic actions and may be used in combination with each other or other molecules that are known in public.

In one embodiment, pro-angiogenic gene therapy clinical trials for the treatment, amelioration, or prevention of cardiovascular disease are currently being performed using therapeutic proteins useful for promoting neo-vascularization. These include, without limitation, pro-angiogenic factors such as VEGF, HGF, bFGF, Ang-1, FGF-4, TGF-1, and HIF1-alpha as well as fragments, variants and derivatives thereof. Identification of suitable molecules for promoting neo-vascularization are well within the capabilities of a person of ordinary skill in the art Such pro-angiogenic factors stimulate neo-angiogenesis to supply oxygen and nutrients within the infarct zone. This will limit infarct zone expansion and sustain any cardiac progenitors that migrate into the infarct.

Indeed, pro-angionic factor VEGF165 is known to induce neovascularization (Benest et al., *Microcirculation.* 13(6): 423 (2006); Riley et al., *Bioinaterials.* 27(35):5935 (2006); Shyu et al., *Life Sci.* 73(5):563 (2003); Arsic et al., *Mol Ther.* 7(4):450 (2003); Ye et al., *J. Heart Lung Transplant.* 24(9): 1393 (2005); Lubiatowski et al., *Plast. Reconstr. Surg.* 110(1):149 (2002) (Erratum in: *Plast. Reconstr. Surg.* 111 (3):1380 (2003)); Kim et al., *Ann. Thorac. Surg.* 83(2):640 (2007) (Comment in: *Ann. Thorac. Surg.* 83(2):646 (2007)); Thurston G., *J. Anat.* 200(6):575 (2002); Ryu et al., *Mol. Ther.* 13(4):705 (2006); Chae et al., *Arterioscler. Thromb. Vasc. Biol.* 20(12):2573 (2000); and Chen et al., *Acta. Pharmacol. Sin.* 28(4):493 (2007)). The shortcomings of early clinical trials in therapeutic neovascularization have been partly attributed to the single administration of high doses of growth factor. See Zacchigna et al., *Hum. Gene Ther.* 18(6):515 (2007) and Yla-Herttuala et al., *J Am Coll Cardiol.* 49(10):1015 (2007) (Comment in: *J Am Coll Cardiol.* 50(2):186 (2007)). Since then, preclinical data on VEGF expression and release has suggested that prolonged exposure results in the formation of stable vessels, whereas short-term delivery merely produces leaky vessels that regress easily. High local concentrations caused, for example, by VEGF-A-producing myoblasts results in leaky and abnormal vessels, whereas moderate amounts of the growth factor initiated the growth of healthy vessels. See Arsic et al., *Mol Ther.* 7(4):450 (2003); Benest et al., *Microcirculation.* 13(6):423 (2006); Yamauchi et al., *J Gene Med.* 5(11):994 (2003); Jiang et al., *Acta Cardiol.* 61(2):145 (2006); Ozawa et al., *J Clin Invest.* 113(4):516 (2004). Additionally, the combination of VEGF (initiation of angiogenesis) and Ang-1 (maturation of vessels) has been shown to result in more stable vascular growth. See Thurston G., *J Anat.* 200(6):575 (2002); Jiang et al., *Acta Cardiol.* 61(2): 145 (2006); Benest et al., *Microcirculation.* 13(6):423 (2006); Zhou et al., *Gene Ther.* 12(3):196 (2005) (Erratum in: *Gene Ther.* 12(6):552 (2005); Liu et al., *Scand Cardiovasc J.* 41(2):95 (2007); Shyu et al., *Life Sci.* 73(5):563 (2003); Yamauchi et al., *J Gene Med.* 5(11):994 (2003); Arsic et al., *Mol Ther.* 7(4):450 (2003); Ye et al., *J Heart Lung Transplant.* 24(9):1393 (2005); Ye et al., *Eur J Heart Fail.* 9(1):15 (2007); Lubiatowski et al., *Plast Reconstr Surg.* 110(1):149 (2002) (Erratum in: *Plast Reconstr Surg.* 111(3):1380 (2003)); Ryu et al., *Mol Ther.* 13(4):705 (2006); Chen et al., *Eur J Pharmacol.* 568(1-3):222 (2007); Chae et al., *Arterioscler Thromb Vase Biol.* 20(12):2573 (2000); and Chen et al., *Acta Pharmacol Sin.* 28(4):493 (2007).

Therefore, pro-angiogenic factor VEGF165 is known to prevent, treat or ameliorate various cardiovascular disease (Yamauchi et al., *J Gene Med.* 5(11):994 (2003) and Xu et al., *Cytotherapy.* 6(3):204 (2004) (Comment in: *Cytotherapy.* 7(1):74 (2005))) including, without limitation, myocardial infarction (Zhou et al., *Gene Ther.* 12(3):196 (2005) (Erratum in: *Gene Ther.* 12(6):552 (2005); Ye et al., *Circulation.* 116(11 Suppl):I113 (2007); Liu et al., *Scand Cardiovasc J.* 41(2):95 (2007); Ye et al., *Eur. J. Heart Fail.* 7(6):945 (2005); Zhang et al., *Cell Transplant.* 14(10):787 (2005); Bonaros et al., *Interact. Cardiovasc. Thorac. Surg.* 7(2):249 (2008); Shyu et al., *J. Biomed. Sci.* 13(1):47 (2006); Ventura et al., *J Biol Chem.* 282(19):14243 (2007); Sugimoto et al., *Jpn. J. Thorac. Cardiovasc. Surg.* 51(5):192 (2003); You et al., *Ann. Thorac. Surg.* 83(3):1110 (2007) (Comment in: *Ann Thorac Surg.* 83(3):1119 (2007)); Rong et al., *Chin. Med. J.* (*Engl*). 121(4):347 (2008); Yang et al., *Cardiology.* 107(1):17 (2007); Wang et al., *J. Mol. Cell Cardiol.* 40(5):736 (2006); Chen et al., *Eur J Clin Invest.* 35(11):677 (2005); Suzuki et al., *Circulation.* 104(12 Suppl 1):I207 (2001); Ye et al., *Ann. Acad. Med. Singapore.* 32(5 Suppl):S21 (2003); and Haider et al., *J Mol Med.* 82(8):539 (2004) (Comment in: *J Mol Med.* 82(8):485 (2004))) or ischemia or reperfusion injury (Becker et al., *Int J Cardiol.* 113(3):348 (2006); Gao et al., *Can. J. Cardiol.* 23(11):891 (2007); Ye et al. *Eur J Heart Fail.* 9(1):15 (2007); Chen et al., *Eur. J. Pharmacol.* 568(1-3):222 (2007); and Jiang et al., *Acta Cardiol.* 61(2):145 (2006)).

Furthermore, another pro-angiogenic factor HGF (human nucleotide sequence accession No.: M29145, human amino acid sequence accession No.: NP_000592.3), which provides multipotent actions, are useful for the present invention. HGF, mediated by c-Met receptor, provides a pro-angiogenic effect through mitogenic activity on endothelial cells, a cardioprotective anti-apoptotic effect on cardiomyocytes, an anti-fibrotic effect through suppression of TGF-beta1 signaling, and is a type I collagen regenerative factor through mobilization of CD117(+)/c-Met(+) stem cells into ischemic myocardium. See Li et al., *Chin Med J* (*Engl*) 121(4):336 (2008); Guo et al., *Arch. Med. Res.* 39(2):179 (2008); Ventura et al., *J. Biol. Chem.* 282(19):14243 (2007); Yang et al., *Gene Ther.* 13(22):1564 (2006); Tambara et al., *Circulation.* 112(9 Suppl):I129 (2005); Zhang et al., *Tissue Eng. Part A.* 14(6):1025 (2008); and Sakaguchi et al., *Ann. Thorac. Surg.* 79(5):1627 (2005).

Similarly, bFGF (amino acid sequence accession no. NP_001997) has been shown to have the added effect of cardioprotection by promoting angiogenesis, neovascularization, and tissue regeneration. (Doi et al., *Heart Vessels.* 22(2):104 (2007); Fujita et al., *J. Surg. Res.* 126(1):27 (2005); Fujita et al., *Wound Repair Regen.* 15(1):58 (2007); Hosaka et al., *Circulation.* 110(21):3322 (2004); Iwakura et al., *Heart Vessels.* 18(2):93 (2003); Lai et al., *Tissue Eng.* 12(9):2499 (2006); Nakajima et al., *J. Artif. Organs.* 7(2):58 (2004); Perets et al., *J. Biomed. Mater. Res. A.* 65(4):489 (2003); Pike et al., *Biomaterials.* 27(30):5242 (2006); Sakakibara et al., *J Thorac Cardiovasc Surg.* 124(1):50 (2002); Sakakibara et al., *Eur J Cardiothorac Surg.* 24(1): 105 (2003); Shao et al., *Circ J.* 70(4):471 (2006); Tabata Y. and Ikada Y., *Biomaterials.* 20(22):2169 (1999); Yamamoto et al., *Artif. Organs.* 27(2):181 (2003); Yamamoto et al., *Jpn. Circ. J.* 65(5):439 (2001); Yang et al., *Ophthalmic Res.* 32(1):19 (2000); and Zhu et al., *Chin. Med. Sci. J.* 15(4):210 (2000)) In certain embodiments, bFGF may be used to prevent, treat, or ameliorate osteoarthritis. See Inoue et al., *Arthritis Rheum.* 54(1):264 (2006);

IGF-1 (human amino acid sequence accession No.: NP_001104753.1) is also known to exert multipotent function of protecting cardiomyocytes from apoptosis and enhancing neovascularization (Su et al., *Am J Physiol Heart Circ Physiol.* 284(4):H1429 (2003); Chao et al., *J. Gene Med.* (4):277 (2003); Rabinovsky E. D. and Draghia-Akli R., *Mol Ther.* 9(1):46 (2004); and Barton et al., *Circulation.* 112(9 Suppl):I46 (2005)) and may be used in the present invention.

In addition, FGF-4 may be used as a therapeutic molecule to prevent, treat, or ameliorate chronic ischemic heart disease by inducing myocardial angio-/arteriogenesis. (Kapur N. K. and Rade J. J., *Trends Cardiovasc. Med.* 18(4):133 (2008); Henry et al., *J. Am. Coll. Cardiol.* 50(11):1038 (2007); Crines et al., *Am. J. Cardiol.* 92(9B):24N (2003); (no author listed) BioDrugs. 16(1):75 (2002)).

Furthermore, HIF1-alpha gene therapy, e.g., HIF1-alpha (aa 1-390)/VP16 (aa 413-490), is known to treat, prevent, or ameliorate ischemic disease by enhancing BNP gene expression (Rajagopalan et al., *Circulation.* 115(10):1234 (2007) (*Comment in: Circulation.* 115(10):1180 (2007)); Wilhide M. E. and Jones W. K., *Mol Pharmacol.* 69(6):1773 (2006) (*Comment on: Mol Pharmacol.* 69(6):1953 (2006)); Luo et al., *Mol Pharmacol.* 69(6):1953 (2006) (Comment in: *Mol. Pharmacol.* 69(6):1773 (2006)) or improve angiogenesis in myocardial infarction (Shyu et al., *Cardiovasc Res.* 54(3): 576 (2002); Vincent et al., *Circulation.* 102(18):2255 (2000)).

In certain embodiments, cardioprotective factors for the treatment, amelioration, or prevention of cardiovascular diseases are provided, either alone, or in combination with angiogenic factors and/or cardioregenerative factors. Cardioprotective molecules provide anti-fibrotic, anti-apoptotic signal to resident cardiomyocytes, limiting infact zone size and supplying survival signals to migrating stem cells. In certain embodiments, the cardioprotective factor is erythropoietin alfa (EPO) (human amino acid accession no. CAA26095.1), e.g., human erythropoietin alfa or EPOGEN®, manufactured by Amgen. Erythropoietin has been shown to have cardioprotective, angiogenic and neuroprotective effects (Ben-Dor et al., *Cardiovasc Drugs Ther.* 21(5):339 (2007); Lin et al., *Circ J.* 71(1):132 (2007); Prunier et al., *Am J Physiol Heart Circ Physiol.* 292(1):H522 (2007)).

Other cardioprotective hormones demonstrated to be protective against experimental myocardial ischemia-reperfusion injury include, without limitation, adrenomedullin, bradykinin, relaxin, ANF, also known as atrial natriuretic peptide (ANP, human nucleotide sequence accession No.: NM_006172, human amino acid sequence accession No.: NP_006163), BNP, also known as B-type natriuretic peptide or GC-B (human amino acid sequence accession No.: NP_002512.1; human nucleotide sequence accession No.: M25296), C-type natriuretic peptide (CNP), carperitide, tissue plasminogen activator (tPA) and urocortins. Many have also been shown to reduce fibrosis or mediate hemodynamics. Nesiritide (brand name Natrecor®, marketed by Scios), a recombinant form of human B-type natriuretic peptide, ANF, and Carperitide are used in the treatment, amelioration, or prevention of acute decompensated heart failure, and may also be used in the present invention (Burnett J. C. Jr., *J. Cardiol.* 48(5):235 (2006)).

Relaxin (human amino acid accession no. NP_604390.1), known for its effects on the female reproductive system, is also a potent vasodilator of the systemic and coronary circulation by a mechanism of action involving nitric oxide, and influences cardiac beating rate. Relaxin is also known as a cardiovascular drug that may prevent, treat, or ameliorate ischemic heart disease (acute and chronic myocardial infarction), cardiac fibrosis, and obliterative peripheral arterial disease and restore cardiac function in cell transplantation. (Nistri et al., *Pharmacol. Res.* 57(1):43 (2008); Samuel et al., *Adv. Exp. Med. Biol.* 612:88 (2007); Du X J., *J. Cell Mol. Med.* 11(5):1101 (2007); Formigli et al., *J. Cell Mol. Med.* 11(5):1087 (2007); Bathgate et al., *Mol. Cell Endocrinol.* 280(1-2):30 (2008); Nistri et al., *Cardiovasc. Hematol. Agents Med. Chem.* 5(2):101 (2007); Moore et al., *Endocrinology.* 148(4):1582 (2007); Lekgabe et al., *Endocrinology.* 147(12):5575 (2006); Samuel et al., *Pharmacol. Ther.* 112 (2):529 (2006); Zhang et al., *Peptides.* 26(9):1632 (2005); Perna et al., *Ann. N.Y. Acad. Sci.* 1041:431 (2005); Perna et al., *FASEB J.* 19(11):1525 (2005); Samuel et al., *Endocrinology.* 145(9):4125 (2004); Masini et al., *Br J Pharmacol.* 137(3):337 (2002); Ndisang et al., *Inflamm. Res.* 50 Suppl. 2:S122-3 (2001); Dschietzig et al., *FASEB. J.* 15(12):2187 (2001); Bani et al., *Am J Pathol.* 152(5):1367 (1998); and Masini et al., *Inflamm. Res.* 45 Suppl 1:S27 (1996))

In certain embodiments, therapeutic proteins of the invention useful for the treatment, amelioration, or prevention of cardiovascular diseases have multiple therapeutic benefits. For example, in the early phase after myocardial infarction, elevated (SDF-1, human nucleotide sequence accession No.: U16752, human amino acid sequence accession No.: NP_954637) levels have been reported in the infarct zone. This provides the required stimulus for mobilization of stem cells from BM niches to the damaged site as part of a natural repair process. SDF-1 recruits bone marrow haematopoietic stem cells (primarily $CD31^+$, $C\text{-}kit^+$ and $CD34^+$ cells) to the infarcted heart resulting in both neoangiogenic and cardioprotective activities. Furthermore, SDF-1 activates the cell-survival factor protein kinase B (PKB/Akt) via the G protein-coupled receptor CXCR4 regenerative factors. See also U.S. Patent Appl. Publ. No. 20060111290 A1; Elmadbouh et al., *J Mol Cell Cardiol.* 42(4):792 (2007); Bonaros et al., *Interact Cardiovasc Thorac Surg.* 7(2):249 (2008); Zhang et al., *J Mol Cell Cardiol.* 44(2):281 (2008); Ma et al., *Basic Res Cardiol.* 100(3):217 (2005); and Zhang et al., *Tissue Eng.* 13(8):2063 (2007).

In addition, tPA (human amino acid accession no. 28274638), e.g., human tissue Plasminogen Activator or Retavase®, manufactured by PDL BioPharma, Inc. is known to prevent, treat, or ameliorate post cardiac transplant complications by inhibiting graft atherosclerosis (Scholl et al., *J Heart Lung Transplant.* 20(3):322 (2001); Dunn et al., *Circulation.* 93(7):1439 (1996) (Comment in: *Circulation.* 93(7):1319 (1996)); and Gong et al., *Gene Ther.* 14(21): 1537 (2007)). Furthermore, the growth hormone is also known to prevent, treat, or ameliorate cardiovascular disease and may be used in the present invention (Isgaard J. and Bergh C. H., *BioDrugs.* 12(4):245 (1999); Fazio et al., *J. Clin. Endocrinol. Metab.* 92(11):4218 (2007); Climent et al., *Curr Med Chem.* 14(13):1399 (2007); Perez-Berbel et al., *Int J Cardiol.* 124(3):393 (2008) (*Comment on: Int J Cardiol.* 110(3):313 (2006)); and Le Corvoisier et al., *J Clin Endocrinol Metab.* 92(1):180 (2007)) by promoting angiogenesis and attenuate apoptosis (Rong et al., *Chin Med J (Eng).* 121(4):347 (2008)).

In other embodiments, the therapeutic molecules that restore cardiac function are included in the present invention. Cardiac repair molecules include, but are not limited to, SERCA2a, AC6, S100A1, parvalbumin, phosphatase inhibitor 2 and phosphatase inhibitor 1. For example, SERCA2a is known to improve cardiac contractility in vivo and in vitro and cardiac function in heart failure (Asahi et al., *Proc Natl Acad Sci USA.* 101(25):9199 (2004); Cavagna et al., *J Physiol.* 528 *Pt* 1:53 (2000); Chaudhri et al., *Mol Cell Biochem.* 251(1-2):103 (2003); Davia et al., *J Mol Cell Cardiol.* 33(5):1005 (2001); del Monte et al., *Circulation.* 100(23):2308 (1999) (Comment in: *Circulation.* 100(23): 2303 (1999); del Monte et al., *Circulation.* 104(12):1424 (2001); Hajjar et al., *Circ Res.* 81(2):145 (1997) (Comment in: *Circ Res.* 88(4):373 (2001) and Circulation. 101(7):790 (2000)); Kawase et al., *J Am Coll Cardiol.* 51(11):1112 (2008); Maier et al., *Cardiovasc Res.* 67(4):636 (2005) (Comment in: *Cardiovasc Res.* 67(4):581 (2005); Meyer M. and Dillmann W. H., *Cardiovasc Res.* 37(2):360 (1998); Miyamoto et al., *Proc Natl Acad Sci USA.* 97(2):793 (2000); Muller et al., *Cardiovasc Res.* 59(2):380 (2003); Sakata et al., *J Mol Cell Cardiol.* 42(4):852 (2007); Sakata et al., *Am J Physiol Heart Circ Physiol.* 292(2):H1204 (2007); Schmidt et al., *Circulation.* 101(7):790 (2000) (Comment in: *Circulation.* 101(7):738 (2000), *Circ Res.* 81(2):145 (1997), *Circ Res.* 83(9):889 (1998), and Circulation. 95(2):423 (1997)) Suarez et al., *Am J Physiol Heart Circ Physiol.* 287(5):H2164 (2004); Terracciano et al., *Cell Calcium.* 31(6):299 (2002); Trost et al., *Diabetes.* 51(4):1166 (2002); and Vetter et al., *FASEB J.* 16(12):1657 (2002))

Furthermore, AC6 is known to restore affinity of SERCA2a to calcium and maximum velocity of cardiac calcium uptake by sarcoplasmic reticulum in cardiomyopathy (Gao et al., *Proc Natl Acad Sci USA.* 95(3):1038 (1998); Roth et al., *Circulation.* 99(24):3099 (1999); Lai et al., *Circulation.* 102(19):2396 (2000); Roth et al., *Circulation.* 105(16):1989 (2002) (Comment in: *Circulation.* 105(16): 1876 (2002)); Gao et al., *Cardiovasc Res.* 56(2):197 (2002) (Comment in: *Cardiovasc Res.* 56(2):181 (2002)); Roth et al., *Basic Res Cardiol.* 98(6):380 (2003); Roth et al., *Am J Physiol Heart Circ Physiol.* 287(1):H172 (2004); Gao et al., *J Biol Chem.* 279(37):38797 (2004); Tang et al., *Am J Physiol Heart Circ Physiol.* 287(5):H1906 (2004); Lai et al., *Circulation.* 110(3):330 (2004) (Comment in: *Circulation.* 110(3):242 (2004); Roth et al., *Hum Gene Ther.* 15(10):989

(2004); Timofeyev et al., 0.1 *Mol Cell* Cardiol. 41(1):170 (2006) (Comment in: *J Mol Cell Cardiol.* 41(3):424 (2006); Takahashi et al., *Circulation.* 114(5):388 (2006) (Erratum in: *Circulation.* 114(11):e497 (2006); Comment in: *Circulation.* 114(5):365 (2006); Sastry et al., *J Am Coll Cardiol.* 48(3): 559 (2006); Rebolledo et al., *Hum Gene Ther.* 17(10):1043 (2006); Hammond H. K., *Ann NY Acad Sci.* 1080:426 (2006); Phan et al., *Trends Cardiovasc Med.* 17(7):215 (2007); Tang et al., *Circulation.* 117(1):61 (2008); and Lai et al., *J Am Coll Cardiol.* 51(15):1490 (2008)).

In certain embodiments, the Ca2+-binding protein S100A1 may restore cardiac function and therefore be used in the present invention. S100A1 is known to increase myocardial contraction in vivo and reduce propensity toward heart failure after myocardial infarction. (Most et al., *J Clin Invest.* 114(11):1550 (2004); Most et al., *Circulation.* 114(12):1258 (2006); Pleger et al., *Mol Ther.* 12(6):1120 (2005); Pleger et al., *Eur J Med Res.* 11(10):418 (2006); Remppis et al., *J Gene Med.* 6(4):387 (2004); Most et al., *Am J Physiol Regul Integr Comp Physiol.* 293(2):R568 (2007); Remppis et al., *Basic Res Cardiol.* 97 Suppl 1:156 (2002); Pleger et al., *Circulation.* 115(19):2506 (2007); and Most et al., *J Biol Chem.* 278(36):33809 (2003)). Other non-limiting examples of the therapeutic molecules that improve or restore cardiac function are: paralbumin (Hirsch et al., *Am J Physiol Heart Circ Physiol.* 286(6):H2314 (2004); Michele et al., *Mol Ther.* 10(2):399 (2004); and Sakata et al., *J Mol Cell Cardiol.* 42(4):852 (2007)), phosphatase inhibitor 2 (Yamada et al., *FASEB J.* 20(8):1197 (2006); Gupta et al., *Mol Cell Biochem.* 269(1-2):49 (2005); and Kirchhefer et al., *Cardiovasc Res.* 68(1):98 (2005)) and phosphatase inhibitor 1 (Gupta et al., *Mol Cell Biochem.* 269(1-2):49 (2005) and Gupta et al., *Am J Physiol Heart Circ Physiol.* 285(6):H2373 (2003))

Additional therapeutic molecules that may be useful for the present invention to prevent, treat, or ameliorate a disease or disorder include, but are not limited to, monoclonal antibodies (e.g., HERCEPTIN®-HC, HERCEPTIN®-LC, TICILIMUMAB®-HC, TICIUMUMAB®-LC, ZENAPAX®-HC, ZENAPAX®-LC, HUMIRA®-HC, HUMNZA®-LC, RITUXAN®-HC, RITUXAN®-LC, IPTUMUMABE-HC, IPILIMUMAB®-LC, AVASTINE-HC, AVASTIN®-LC, ERBITUX®-HC, and ERBITUX®-LC), recombinant enzymes (e.g., RETAVASE®, ACTRAPID®-A chain, ACTRAPID®-B chain, NEULASTA®, pre-pro insulin, EPOGEN®, and NORDITROPIN®), fusion protein (e.g., ENBREL®), or any purified proteins (e.g., ALPHANATE® and ARALAST®). In addition, identification of suitable therapeutic molecules for preventing, treating, or ameliorating a particular disease or disorder is well within the capabilities of a person of ordinary in the art.

Vectors and Host Cells

To introduce the polynucleotides into the cells, a vector can be used. The vector may be, for example, a plasmid vector or a single- or double-stranded RNA or DNA viral vector. Such vectors may be introduced into cells by well-known techniques for introducing DNA and RNA into cells. Viral vectors may be replication competent or replication defective. In the latter case, viral propagation generally will occur only in complementing viral competent cells.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the present invention, the vectors that are introduced into the cells further comprise a "selectable marker gene" which, when expressed, indicates that the therapeutic gene switch construct of the present invention has been integrated into the genome of the modified cell. In this manner, the selector gene can be a positive marker for the genome integration. While not critical to the methods of the present invention, the presence of a selectable marker gene allows the practitioner to select for a population of live cells where the vector construct has been integrated into the genome of the cells. Thus, certain embodiments of the present invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyltransferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.,* 103:9958 (2006), which is incorporated by reference herein. Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Particular vectors for use with the present invention are expression vectors that code for polypeptides or polynucleotides. Generally, such vectors comprise cis-acting control regions effective for expression in a modified cell, operatively linked to the polynucleotide to be expressed. Appropriate trans-acting factors are supplied by the modified cell, supplied by a complementing vector or supplied by the vector itself upon introduction into the cell.

A great variety of expression vectors can be used to express polypeptides or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or polypeptides in a cell may be used for expression in this regard.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* 290:304 (1981)); and the vaccinia virus promoter. All of the above listed references are incorporated by reference herein. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCMVDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231, all of which are incorporated by reference. An example of such vectors is the UltraVector™ Production System (Intrexon Corp., Blacksburg, Va.), as described in WO 2007/038276, incorporated herein by reference. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MIV, Ase I, Flp I, Pme I, Sda I, Sgf I, Srf I, and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-SceI has an 18 bp restriction site (5'TAGGGATAACAGGGTAAT3' (SEQ ID NO:4)), predicted to occur only once in every $7\times10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites were included in appropriate locations in a cloning vector plasmid.

Selection of appropriate vectors and promoters for expression in a host cell is a well-known procedure, and the requisite techniques for vector construction and introduction into the host cell, as well as its expression in the host cell are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y., which are hereby incorporated by reference. These stable transfection methods result in random insertion of the vector into the genome of the cell. Further, the copy number and orientation of the vectors are also, generally speaking, random.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001), which is hereby incorporated by reference. Other examples of recombinases and their respective sites that may be used for recombinase-site specific gene insertion include, but are not limited to, serine recombinases such as R4 and TP901-1 and recombinases described in WO 2006/083253, incorporated herein by reference.

In order to stably integrate the one or more gene expression systems in the genome of a modified cell, any known methods of integration may be used for the purpose of this invention. In one embodiment, locus-specific insertion may be carried out by recombinase-site specific gene insertion.

Briefly, bacterial recombinase enzymes, such as, but not limited to, PhiC31 integrase may act on "pseudo" recombination sites within the human genome. See US publication No. 2004/0003420 A1; Groth et al., *Proc. Natl. Acad. Science,* 97, 5995-6000 (2000). These pseudo recombination sites may be targets for locus-specific insertion using the recombinases. Recombinase-site specific gene insertion is described in Thyagarajan, B. et al., *Mol. Cell Biol.* 21(12): 3926-34 (2001).

In certain embodiments, the first inducible gene expression system further comprises an integrase, which will stably integrate the first gene switch system into pseudosites within the genome of the targeted cells. A second gene switch system may also comprise an integrase, which will integrate the second gene switch system into the pseudosites within the genome of the targeted cells. The first gene switch system may further comprise an integrase acceptor site, which may allow integration of the second inducible gene switch system in the pre-positioned acceptor site within the genome of the targeted cells.

The following polypeptide sequence was reported as a polypeptide sequence encoding the Streptoinyces phase PhiC31 integrase polypeptide sequence and has the accession number NP_047974 in Genbank.

```
Streptomyces phage phiC31 integrase (605 aa)
                                                       (SEQ ID NO: 6)
  1    mdtyagaydr qsrerenssa aspatqrsan edkaadlgre verdggrfrf vghfseapgt 61    safgtaerpe ferilnecra grlnmiivyd vsrfsrlkvm daipivsell algvtivstq 121    egvfrqgnvm dlihlimrld ashkesslks akildtknlq relggyvggk apygfelvse 181    tkeitrngrm vnvvinklah sttpltgpfe fepdvirwww reikthkhlp fkpgsqaaih 241    pgsitglckr mdadavptrg etigkktass awdpatvmri lrdpriagfa aeviykkkpd 301    gtpttkiegy riqrdpitlr pveldcgpii epaewyelqa wldgrgrgkg lsrgqailsa 361    mdklycecga vmtskrgees ikdsyrcrrr kvvdpsapgq hegtcnvsma aldkfvaeri 421    fnkirhaegd eetlallwea arrfgkltea peksgeranl vaeradalna leelyedraa 481    gaydgpvgrk hfrkqqaalt lrqqgaeerl aeleaaeapk lpldqwfped adadptgpks 541    wwgrasvddk rvfvglfvdk ivvtksttgr gqgtpiekra sitwakpptd ddeddaqdgt 601    edvaa
```

Other examples of recombinases and their respective sites that may be used for recombinase-site specific gene insertion include, but are not limited to, serine recombinases such as R4 and TP901-1. Site-specific recombinases (SSRs), such as the bacteriophage P1-derived Cre recombinase recognize specific DNA sequences ("recognition sites," "recognition sequences," or "integrase acceptor site") and catalyze recombination between two recognition sites. Cre recombinase, for example, recognizes the 34 base pair (bp) loxP motif (Austin et al., *Cell* 25,729-736 (1981)). If the two sites are located on the same DNA molecule in the same orientation, the intervening DNA sequence is excised by the recombinase from the parental molecule as a closed circle, leaving one recognition site on each of the reaction products. If the two sites are in inverted orientation, the recognition-site flanked region is inverted through recombinase mediated recombination. Alternatively, if the two recognition sites are located on different molecules, recombinase-mediated recombination will lead to integration of a circular molecule or translocation between two linear molecules.

In addition to Crc, a few recombinases have been shown to exhibit some activity in mammalian cells. The best characterized examples are the yeast derived FLP and Kw recombinases, which exhibit optimal activity at 30° C. and are unstable at 37° C. (Buchholz et al., *Nature Biotech.,* 16,657-662 (1998); Ringrose et al., *Eur. J. Biochem.,* 248, 903-912). Other recombinases that show some activity in mammalian cells include a mutant integrase of phage lambda, the integrases of phage HK022, mutant gamma delta-resolvase and beta-recombinase (Lorbach et al., *J. Mol. Biol.,* 296, 1175-81 (2000); Kolot et al., *Moi. Biol. Rep.* 26,207-213 (1999); Schwikardi et al., *FEBS Lett.,* 471,147-150 (2000); Diaz et al., *J. Biol. Chem.,* 274, 6634-6640 (1999)). Moreover, an improved version of the phiC31 integrase has been developed. This modified C31-Int (C31-Int (CNLS)) carries a C-terminal nuclear localization signal (NLS) and displays a recombination efficiency in mammalian cells that is significantly enhanced over the wild type form and is comparable to that of Cre recombinase (EP 1205490; US Publication No. 2004/0003420 A1). This makes the C31-Int a valuable tool for mammalian genome modification.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the present invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements, or even all elements present on the vector.

In a further embodiment, the vector may comprise a chemo-resistance gene, e.g., the multidrug resistance gene mdr 1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease, disorder, or condition. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the therapeutic polypeptide or therapeutic polynucleotide into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor complex to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor complex is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polyp eptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g., intraperitoneally, intrathecally, intraventricularly, direct injection into the tissue or organ where the cells were reintroduced). The optimal timing of ligand administration can be determined for each type of cell and disease, disorder, or condition using only routine techniques.

In a different embodiment, the ex vivo therapeutic methods may be carried out using non-autologous cells, e.g., cells that are allogeneic or xenogeneic to the subject, instead of autologous cells from the subject. The polynucleotides may be introduced into the non-autologous cells ex vivo to produce modified cells and the modified cells may then be introduced into the subject. The non-autologous cells may be any cells that are viable after transplantation into a subject, including, without limitation, stem cells (such as embryonic stem cells or hematopoietic stem cells) and fibroblasts.

The in vivo therapeutic methods of the invention involve direct in vivo introduction of the polynucleotides into the cells of the subject. The polynucleotides may be introduced into the subject systemically or locally (e.g., at the site of the disease, disorder, or condition). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathccally, intraventricularly, direct injection into the tissue or organ where the disease, disorder, or condition is occurring). The optimal timing of ligand administration can be determined for each type of cell and disease, disorder, or condition using only routine techniques.

In one embodiment, the ligand may be administered to the subject continuously or intermittently, and the pattern of ligand administration may be altered as necessary depending on the status of the disease, disorder, or condition. The level of expression of the therapeutic polypeptide or therapeutic polynucleotide can be modulated both by the schedule of ligand administration and the amount of ligand that is administered, permitting careful control of the therapeutic treatment.

The therapeutic methods of the invention may also be coupled with diagnostic technologies in order to improve treatment outcomes in various approaches tht are known in the art as pharmacodiagnostics or theranostics. For example, administration of the ligand may be coordinated with monitoring of the status or progression of the disease, disorder, or condition. In one embodiment, the polynucleotides of the invention are introduced into a cell together with one or more polynucleotides designed to diagnose or monitor a disease, disorder, or condition. In another embodiment, the diagnostic polynucleotides are present on the same vector comprising the polynucleotides of the invention. In this embodiment, the therapeutic treatment and the diagnostic test for monitoring effectiveness of the treatment are administered together in one unit, ensuring that all cells that receive the treatment also receive the diagnostic test. In one embodiment, the diagnostic polynucleotides comprise a diagnostic switch promoter (i.e., a promoter whose activity is modulated during a disease, disorder, or condition) operably linked to a reporter gene, and monitoring of the status of the disease, disorder, or condition involves detecting the level of expression of the reporter gene.

In another theranostic embodiment of the invention, the level of expression of a therapeutic polypeptide or therapeutic polynucleotide is monitored through detecting the level of expression of a reporter gene, wherein the level of expression of the reporter directly correlates with the level of expression of the therapeutic polypeptide or therapeutic polynucleotide. For example, the level of expression of a therapeutic protein such as interleukin-12 may be monitored non-invasively in various tissues through a bioneutral reporter such as the human type 2 somatostatin receptor, which may be imaged with a radiolabeled somatostatin analog (see, e.g., Zinn et al., *J. Nucl. Med* 41:887-895 (2000)). The reporter may be linked to the same promoter as the therapeutic polypeptide or polynucleotide, or may be placed under a different promoter that is modulated by the therapeutic polypeptide or polynucleotide.

An additional embodiment of the invention relates to methods for expressing a therapeutic polypeptide or therapeutic polynucleotide in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex, to produce modified cells; and (b) administering ligand to said subject to induce expression of said therapeutic polypeptide or therapeutic polynucleotide.

In one embodiment, the methods for expressing a therapeutic polypeptide or therapeutic polynucleotide in a subject may be carried out using laboratory animals (e.g., mice, rats, cats, dogs, monkeys) or farm animals (e.g., pigs, sheep, cows). For example, methods of expressing therapeutic products in animals may be carried out for research purposes or for the large scale production of therapeutic polypeptides or therapeutic polynucleotides.

A further embodiment of the invention relates to methods for expressing a therapeutic polypeptide or therapeutic polynucleotide in a cell, comprising:

(a) introducing into said cell (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex, to produce a modified cell; and (b) administering ligand to said modified cell to induce expression of said therapeutic polypeptide or therapeutic polynucleotide.

Another embodiment of the invention is a method for expressing a therapeutic polypeptide or therapeutic polynucleotide in one or more modified cells, comprising:

(a) introducing into a cell (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, wherein said therapeutic switch promoter is activated under conditions associated with a disease, disorder, or condition, and (2) a second polynucleotide encoding a therapeutic polypeptide or therapeutic polynucleotide operably associated with a factor-regulated promoter which is activated by said ligand-dependent transcription factor complex, thereby producing a modified cell; and (b) administering ligand to said modified cell to induce expression of said therapeutic polypeptide or therapeutic polynucleotide.

In one embodiment, the methods for expressing a therapeutic polypeptide or therapeutic polynucleotide in a cell may be carried out in vitro, e.g., in cells in culture. For example, in vitro methods of therapeutic product expression may be carried out for research use or for the large scale production of therapeutic polypeptides or therapeutic polynucleotides.

In any embodiments described herein, the polynucleotides or vector comprising the polynucleotides may comprise a sequence encoding a lethal polypeptide that can be turned on to express a product that will kill a cell containing the polynucleotides or vector. Lethal polypeptide expression can be used to eliminate the modified cells from a subject, either because treatment is no longer needed or because of a problem with the modified cells (e.g., hyperproliferation or toxicity). A lethal polypeptide, as used herein, is a polypeptide that, when expressed, is lethal to the cell that expresses the polypeptide, either because the polypeptide itself is lethal or the polypeptide produces a compound that is lethal. As used herein, a lethal polypeptide includes polypeptides that induce cell death in any fashion, including but not limited to, necrosis, apoptosis and cytotoxicity. Examples of lethal polypeptides include, but are not limited to, apoptosis inducing tumor suppressor genes such as, but not limited to, p53, Rb and BRCA-1, toxins such as diphtheria toxin (DTA), shigella neurotoxin, botulism toxin, tetanus toxin, cholera toxin, CSE-V2 and other variants of scorpion protein toxins to name a few, suicide genes such as cytosine deaminase and thymidine kinase, and cytotoxic genes, e.g., tumor necrosis factor, interferon-alpha. The present invention is not limited by the identity of the lethal polypeptide, provided that the polypeptide is capable of being lethal to the cell in which it is expressed. If the modified cells are short-lived cells (e.g., cells with a limited lifespan (e.g., about 10 days or less, such as dendritic cells), it may not be necessary to include a lethal polypeptide in the polynucleotides or vector as the cells will be naturally removed over a short period of time.

For each of the methods described above, in one embodiment, the polynucleotide encoding the gene switch and the polynucleotide encoding the therapeutic polyp eptide or therapeutic polynucleotide linked to a promoter are part of one larger polynucleotide, e.g., a vector. In another embodiment, the polynucleotide encoding the gene switch and the polynucleotide encoding the therapeutic polypeptide or therapeutic polynucleotide linked to a promoter are separate polynucleotides, which may be combined to form a "nucleic acid composition."

In one aspect, the invention relates to polynucleotides that may be used in the methods of the invention. In one embodiment, the polynucleotide encodes a gene switch, the gene switch comprising at least one transcription factor sequence, wherein said at least one transcription factor sequence encodes a ligand-dependent transcription factor complex, operably linked to a therapeutic switch promoter, wherein the activity of the promoter is modulated during said disease, disorder, or condition. In another embodiment, the polynucleotide further encodes a therapeutic polypeptide or therapeutic polynucleotide linked to a factor-regulated promoter which is activated by said ligand-dependent transcription factor complex. In one embodiment, the gene switch is an EcR-based gene switch. In another embodiment, the gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor complex. In one embodiment, the first therapeutic switch promoter and the second therapeutic switch promoter arc different. In another embodiment, the first therapeutic switch promoter and the second therapeutic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

Another aspect of the invention relates to vectors comprising any of the polynucleotides described above. In one embodiment, the vector is a plasmid vector or a viral vector.

In another aspect, the invention provides kits that may be used in conjunction with methods of the invention. Kits according to this aspect of the invention may comprise one or more containers, which may contain one or more components selected from the group consisting of one or more nucleic acid molecules, restriction enzymes and one or more cells comprising such nucleic acid molecules. Kits of the invention may further comprise one or more containers containing supporting cells suitable for supporting the cells of the invention in culture, one or more containers containing cell culture media suitable for culturing cells of the invention, one or more containers containing antibiotics suitable for use in culturing cells of the invention, one or more containers containing buffers, one or more containers containing transfection reagents, one or more containers containing substrates for enzymatic reactions, and/or one or more ligands for gene switch activation.

Kits of the invention may contain a wide variety of nucleic acid molecules that can be used with the invention. Examples of nucleic acid molecules that can be supplied in kits of the invention include those that contain promoters, sequences encoding gene switches, enhancers, repressors, selection markers, transcription signals, translation signals, primer hybridization sites (e.g., for sequencing or PCR), recombination sites, restriction sites and polylinkers, sites that suppress the termination of translation in the presence of a suppressor tRNA, suppressor tRNA coding sequences, sequences that encode domains and/or regions, origins of replication, telomeres, centromeres, and the like. In one embodiment, kits may comprise a polynucleotide comprising a gene switch without any therapeutic switch promoters, the polynucleotide being suitable for insertion of any therapeutic switch promoters of interest. Nucleic acid molecules of the invention may comprise any one or more of these features in addition to polynucleotides as described above.

Kits of the invention may comprise containers containing one or more recombination proteins. Suitable recombination proteins include, but are not limited to, Cre, Int, IHF, Xis, Flp, Fis, Hin, Gin, Cin, Tn3 resolvase, ΦC31, TndX, XerC, and XerD. Other suitable recombination sites and proteins are those associated with the GATEWAY™ Cloning Technology available from Invitrogen Corp., Carlsbad, Calif., and described in the product literature of the GATEWAY™ Cloning Technology (version E, Sep. 22, 2003), the entire disclosures of which are incorporated herein by reference.

Kits of the invention can also be supplied with primers. These primers will generally be designed to anneal to molecules having specific nucleotide sequences. For example, these primers can be designed for use in PCR to amplify a particular nucleic acid molecule. Sequencing primers may also be supplied with the kit.

One or more buffers (e.g., one, two, three, four, five, eight, ten, fifteen) may be supplied in kits of the invention. These buffers may be supplied at working concentrations or may be supplied in concentrated form and then diluted to the working concentrations. These buffers will often contain salt, metal ions, co-factors, metal ion chelating agents, etc. for the enhancement of activities or the stabilization of either the buffer itself or molecules in the buffer. Further, these buffers may be supplied in dried or aqueous forms. When buffers are supplied in a dried form, they will generally be dissolved in water prior to use.

Kits of the invention may contain virtually any combination of the components set out above or described elsewhere herein. As one skilled in the art would recognize, the components supplied with kits of the invention will vary with the intended use for the kits. Thus, kits may be designed to perform various functions set out in this application and the components of such kits will vary accordingly.

EXAMPLES

The examples which follow further illustrate the invention, but should not be construed to limit the scope of the invention in any way. The practice of the present invention, including the following examples will employ, unless otherwise indicated, conventional techniques of cell biology, cell culture, molecular biology, transgenic biology, microbiology, and recombinant DNA, which are within the skill of the art. Such techniques are explained fully in the literature. See, for example, Molecular Cloning: A Laboratory Manual (3-Volume Set), J. Sambrook, D. W. Russell, Cold Spring Harbor Laboratory Press (2001); Genes VIII, B. Lewin, Prentice Hall (2003); PCR Primer, C. W. Dieffenbach and G. S. Dvckslcr, CSHL Press (2003); DNA Cloning, D. N. Glover ed., Volumes I and II (1985); Oligonucleotide Synthesis: Methods and Applications (Methods in Molecular Biology), P. Herdewijn (Ed.), Humana Press (2004); Culture of Animal Cells: A Manual of Basic Technique, 4th edition, R. I. Freshney, Wiley-Liss (2000); Oligonucleotide Synthesis, M. J. Gait (Ed.), (1984); Mullis et. al U.S. Pat. No. 4,683,195; Nucleic Acid Hybridization, B. D. Hames & S. J. Higgins eds. (1984); Nucleic Acid Hybridization, M. L. M. Anderson, Springer (1999); Animal Cell Culture and Technology, 2nd edition, M. Butler, BIOS Scientific Publishers (2004); Immobilized Cells and Enzymes: A Practical Approach (Practical Approach Series), J. Woodward, IRL Press (1992); Transcription And Translation, B. D. Hames & S. J. Higgins (Eds.) (1984); Culture Of Animal Cells, R. I. Freshney, Alan R. Liss, Inc., (1987); A Practical Guide To Molecular Cloning, 3rd edition, B. Perbal, John Wiley & Sons Inc. (1988); Gene Transfer Vectors For Mammalian Cells, J. H. Miller and M. P. Calos eds., Cold Spring Harbor Laboratory (1987); Methods In Enzymology, Vols. 154 and 155, Wu et. al (Eds.); Immunochemical Methods In Cell And Molecular Biology, Mayer and Walker, (Eds.), Academic Press, London (1987); and in Ausubel et. al, Current Protocols in Molecular Biology, John Wiley and Sons, Baltimore, Md. (1989).

Example 1

Figure 5:
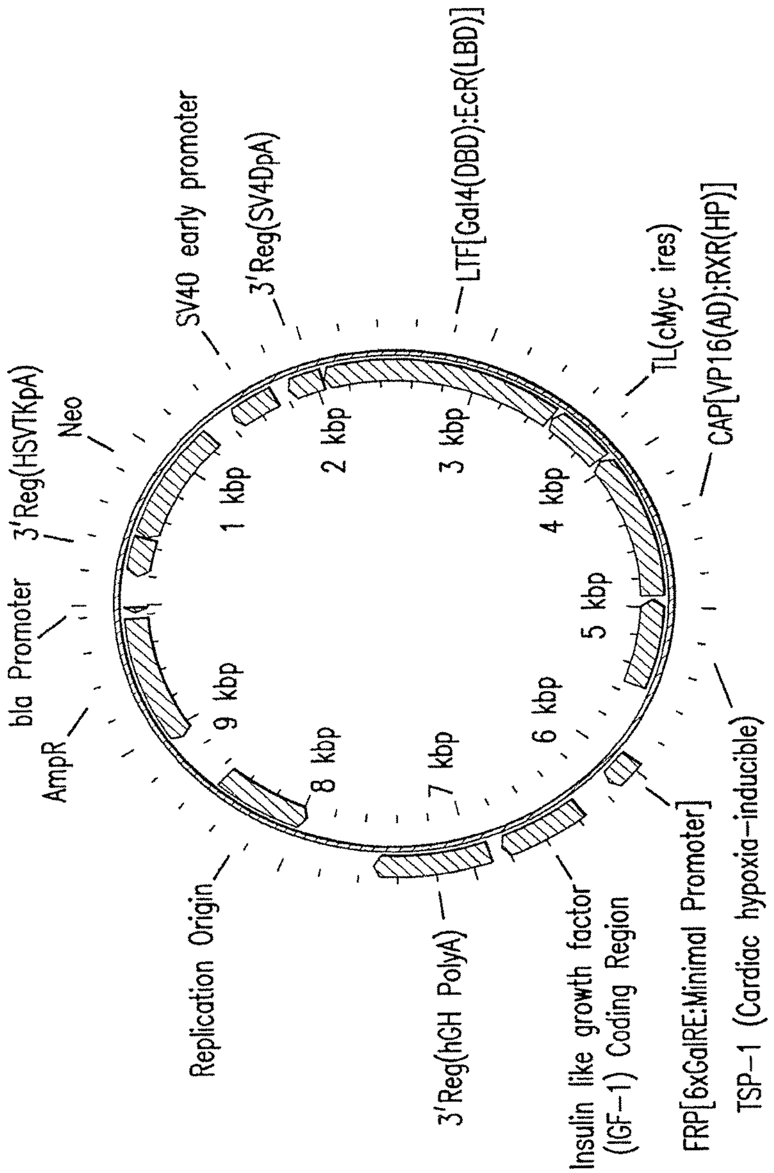
FIG. 5 is a diagram of a vector constructed under the scheme shown in FIG. 1, and engineered to express insulin growth factor-1 (IGF-1) under hypoxic conditions such as cardiac ischemia.

This example describes a gene therapy vector useful for the treatment of ischemic heart disease through the promotion of angiogenesis. Insulin like growth factor 1 is a hormone that may be useful in the treatment of ischemic heart disease. (IGF-1, GenBank Accession No.: NP_001104753.1, SEQ ID NO:20). Use of IGF-1 in preclinical models is associated with improved cardiac function, anti-apoptosis, neo-vascularization and cardiac muscle regeneration (reviewed in Santini, M. P., et al. *Novartis Found Symp.* 274:228-38 (2006); discussion 239-43, 272-6; and Saetrum Opgaard, O., and Wang, P. H. *Growth Horm IGF Res.* 15:89-94 (2005)). For this purpose, an example of inducible IGF-1 expression, in response to ischemia and/or inflammation is given. An inducible expression system for the expression if IGF-1 upon administration of ligand, under hypoxic conditions which occur in ischemic tissue is shown in FIG. 5.

```
SEQ ID NO: 20:
MGKISSLPTQLFKCCFCDFLKVKMHTMSSSHLFYLALCLLTFTSSATAG

PETLCGAELVDALQFVCGDRGFYFNKPTGYGSSSRRAPQTGIVDECCFR

SCDLRRLEMYCAPLKPAKSARSVRAQRHTDMPKTQKYQPPSTNKNTKSQ

RRKGSTFEERK
```

The complete nucleotide sequence of the construct shown in FIG. 5 is presented as SEQ ID NO:7. The nucleotide coordinates for salient elements of the construct are shown in Table 4.

TABLE 4

| Label | Direction | Length | Start | End |
|---|---|---|---|---|
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[Gal4(DBD):EcR(LBD)] | reverse | 1467 | 2057 | 3523 |
| TL (cMyc ires) | reverse | 408 | 3536 | 3943 |
| CAP[VP16(AD):RXR(HP)] | reverse | 975 | 3950 | 4924 |
| TSP-1 (Cardiac hypoxia-inducible) | reverse | 578 | 4958 | 5535 |
| FRP[6xGalRE:Minimal Promoter] | forward | 189 | 5946 | 6134 |
| Insulin like growth factor (IGF-1) Coding Region | forward | 477 | 6348 | 6824 |
| 3'Reg(hGH PolyA) | forward | 627 | 6897 | 7523 |
| Replication Origin | reverse | 589 | 7957 | 8545 |
| AmpR | reverse | 858 | 8920 | 9777 |
| bla Promoter | reverse | 39 | 9811 | 9849 |

The vector shown in FIG. 5 is modeled according to the gene switch system shown in FIG. 1. Under this system, both the CAP subunit, and the LTF subunit of the ligand-dependent transcription factor complex (LDTFC) are expressed through operable association with a single therapeutic switch promoter (TSP-1) via use of an internal ribosome entry site (IRES). The promoter utilized in this system is a UV-conformed synthetic hypoxia-inducible promoter.

The coding region for the therapeutic product, IGF-1, is operably associated with a factor-regulated promoter (FRP) which is activated upon contact with the LDTFC in the presence of ligand.

The construct shown in FIG. 5 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the transcription factor may be expressed under the appropriate physiological conditions. The LTF encoded by the vector will be expressed under hypoxic conditions associated with, e.g., cardiac ischemia. Ligand will be administered to the subject to be treated which will combine with the expressed LDTFC to drive expression of IGF-1 under control of the factor-regulated promoter. IGF-1 expression in turn promotes targeted angiogenesis in the ischemic tissue.

Example 2

This example describes a bioreactor/cell therapy vector useful for the treatment of ischemic cardiovascular disease through the promotion of angiogenesis and cardioprotection. The vector, shown in FIG. 6, will confer expression of human basic fibroblast growth factor (bFGF, GenBank Accession No.: NP_001997, SEQ ID NO:21) upon administration of ligand, under hypoxic conditions which occur in ischemic tissue.

```
SEQ ID NO: 21:
MVGVGGGDVEDVTPRPGGCQISGRGARGCNGIPGAAAWEAALPRRRPRRH

PSVNPRSRAAGSPRTRGRRTEERPSGSRLGDRGRGRALPGGRLGGRGRGR

APERVGGRGRGRGTAAPRAAPAARGSRPGPAGTMAAGSITTLPALPEDGG

SGAFPPGHFKDPKRLYCKNGGFFLRIHPDGRVDGVREKSDPHIKLQLQAE

ERGVVSIKGVCANRYLAMKEDGRLLASKCVTDECFFFERLESNNYNTYRS

RKYTSWYVALKRTGQYKLGSKTGPGQKAILFLPMSAKS
```

Figure 6:
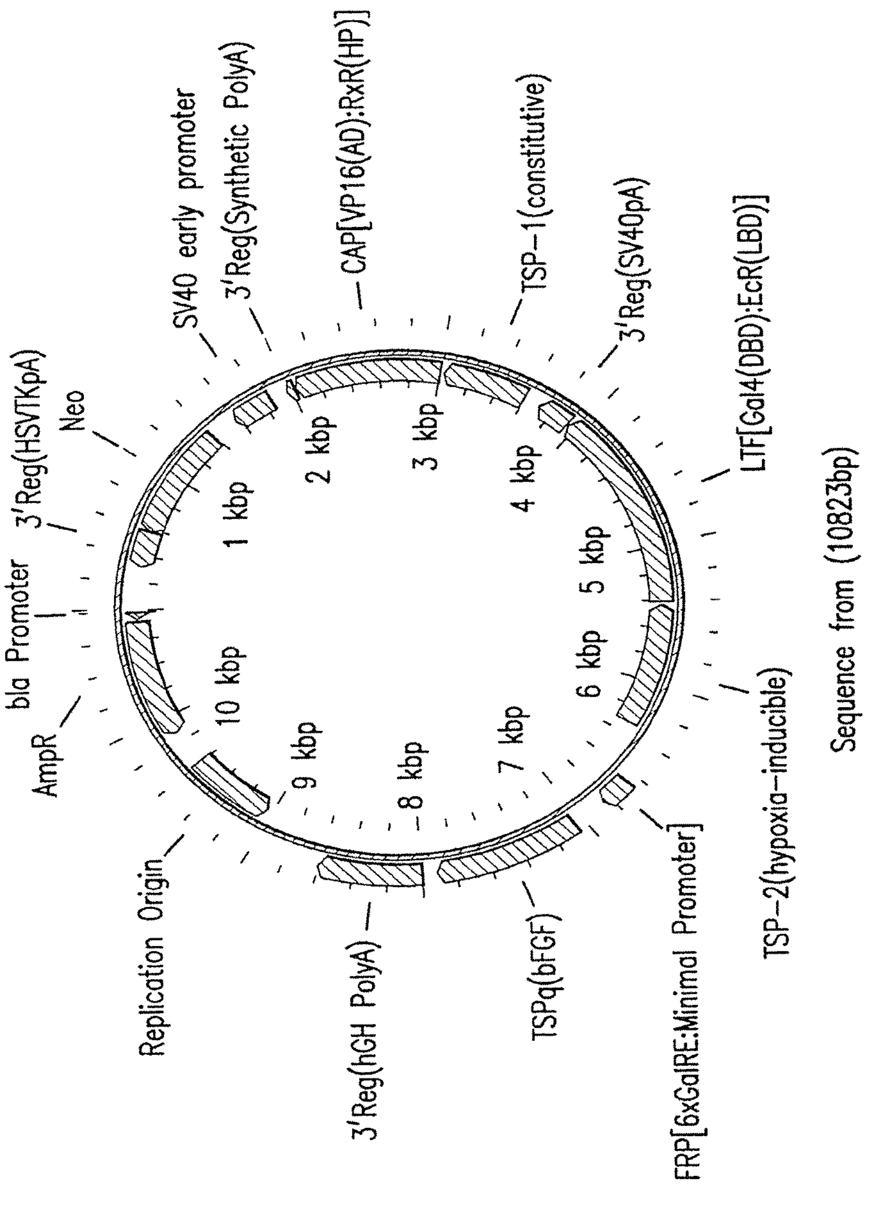
FIG. 6 is a diagram of a vector constructed under the scheme shown in FIG. 2, and engineered to express basic fibroblast growth factor (bFGF) under hypoxic conditions such as cardiac ischemia.

The complete nucleotide sequence of the construct shown in FIG. 6 is presented as SEQ ID NO:8. The nucleotide coordinates for salient elements of the construct are shown in Table 5.

TABLE 5

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1 (constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP-2(hypoxia-inducible) | reverse | 870 | 5446 | 6315 |
| FRP[6x GalRE:Minimal Promoter] | forward | 189 | 6648 | 6836 |
| TSPq(bFGF) | forward | 867 | 7050 | 7916 |
| 3'Reg(hGH PolyA) | forward | 627 | 7989 | 8615 |
| Replication Origin | reverse | 589 | 9049 | 9637 |
| AmpR | reverse | 858 | 9882 | 10739 |
| bla Promoter | reverse | 39 | 10773 | 10811 |

The vector shown in FIG. 6 is modeled according to the gene switch system shown in FIG. 2. Under this system, the CAP subunit of the LDTFC is expressed through operable association with a first, constitutive therapeutic switch promoter, TSP-1, and the LTF subunit of the LDTFC is expressed through operable association with a second, inducible therapeutic switch promoter (TSP-2). The promoter used in this construct is the hypoxia-inducible control promoter-1.

The coding region for the therapeutic product, bFGF, is operably associated with a FRP which is activated upon contact with the LDTFC in the presence of ligand.

The construct shown in FIG. 6 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed under hypoxic conditions associated with, e.g., cardiac ischemia. Ligand will be administered to the subject to be treated which will combine with the expressed LDTFC to drive expression of bFGF under control of the FRP. bFGF expression in turn promotes targeted angiogenesis and/or cardioprotection in the ischemic tissue.

Example 3

This example describes a bioreactor/cell therapy vector useful for the treatment of ischemic cardiovascular disease through the promotion of cardioprotection. The vector, shown in FIG. 7, will confer expression of human erythropoietin (EPO, GenBank Accession No.: CAA26095.1, SEQ ID NO:22) upon administration of ligand, under hypoxic conditions which occur in ischemic tissue. Erythropoietin has been shown to function in cardioprotection and anti-remodeling, in response to ischemia.

```
SEQ ID NO: 22:
MGVHECPAWLWLLLSLLSLPLGLPVLGAPPRLICDSRVLQRYLLEAKEAEN

ITTGCAEHCSLNENITVPDTKVNEYAWKRMEVGQQAVEVWQGLALLSEAVL

RGQALLVNSSQPWEPLQLHVDKAVSGLRSLTTLLRALGAQKEAISPPDAAS

AAPLRTITADTFRKLFRVYSNFLRGKLKLYTGEACRTGDR
```

Figure 7:
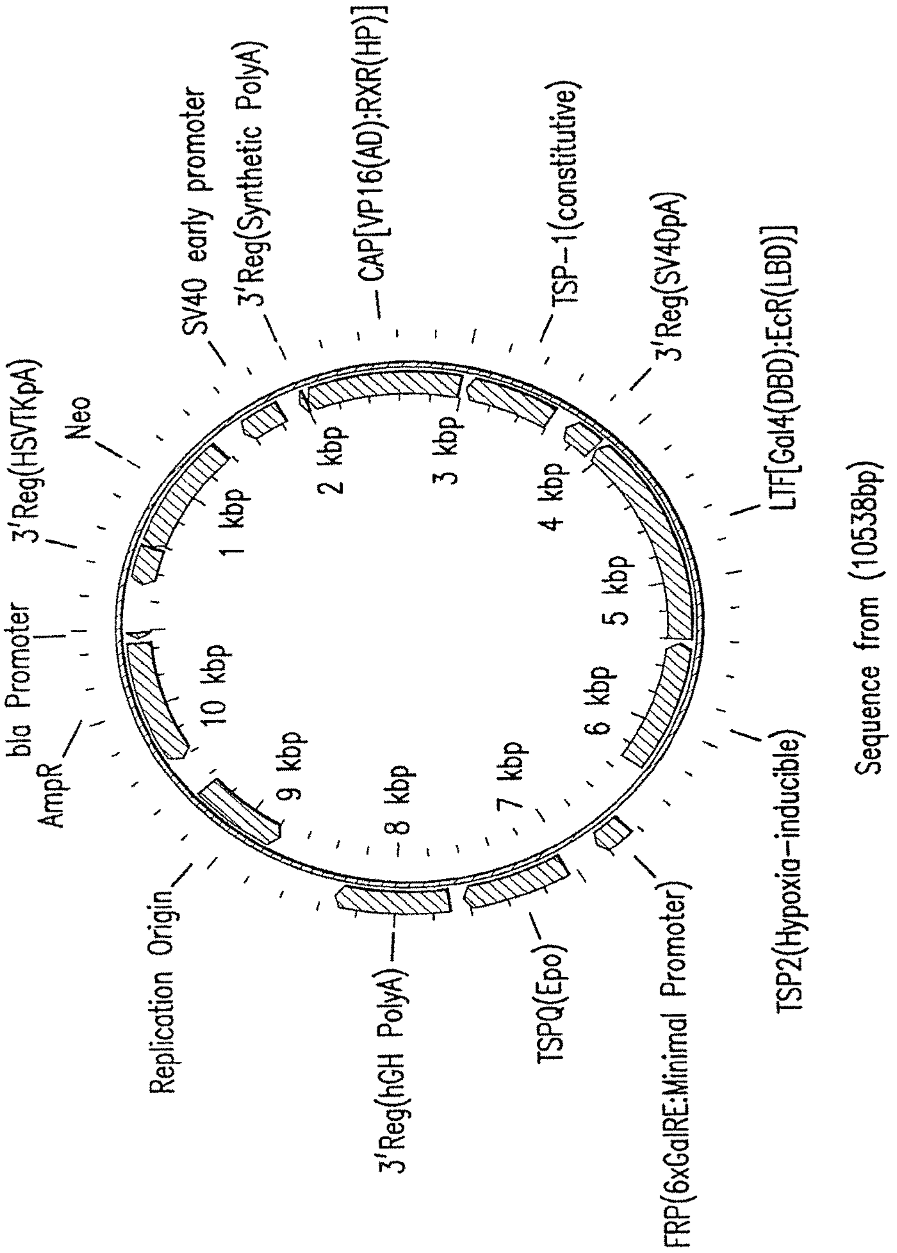
FIG. 7 is a diagram of a vector constructed under the scheme shown in FIG. 2, and engineered to express erythropoietin (EPO) under hypoxic conditions such as cardiac ischemia.

The complete nucleotide sequence of the construct shown in FIG. 7 is presented as SEQ ID NO:9. The nucleotide coordinates for salient elements of the construct are shown in Table 6.

TABLE 6

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP2(Hypoxia-inducible) | reverse | 870 | 5446 | 6315 |
| FRP(6x GalRE:minimal promoter) | forward | 189 | 6648 | 6836 |
| TSPQ(Epo) | forward | 582 | 7050 | 7631 |
| 3'Reg(hGH PolyA) | forward | 627 | 7704 | 8330 |
| Replication Origin | reverse | 589 | 8764 | 9352 |
| AmpR | reverse | 858 | 9597 | 10454 |
| bla Promoter | reverse | 39 | 10488 | 10526 |

The vector shown in FIG. 7 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible therapeutic switch promoter used in this vector is the hypoxia-inducible control promoter-1.

The coding region for the therapeutic product, EPO, is operably associated with a FRP which is activated upon contact with the LDTFC in the presence of ligand.

The construct shown in FIG. 7 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and LTF encoded by the vector will be expressed under hypoxic conditions associated with, e.g., cardiac ischemia. Ligand will be administered to the subject to be treated which will combine with the expressed LDTFC to drive expression of EPO under control of the FRP. EPO expression in turn promotes targeted cardioprotection in the ischemic tissue.

Example 4

This example describes a bioreactor/cell therapy vector useful for the treatment of ischemic cardiovascular disease through the promotion of antiogenesis and hemodynamics. The vector, shown in FIG. 8, will confer expression of human brain natriuretic factor (BNP, GenBank Accession No.: NP_002512, SEQ ID NO:23) upon administration of ligand, under hypoxic conditions which occur in ischemic tissue. BNP, as well as other natriuretic peptides, such as relaxin, ANF, CNP and adrenomodulin, has been shown to function in cardioprotection, vasodilation and anti-remodeling, in the heart. For this purpose, an example of inducible expression of BNP, in response to ischemia is given.

```
SEQ ID NO: 23:
MDPQTAPSRALLLLLFLHLAFLGGRSHPLGSPGSASDLETSGLQEQRNHL

QGKLSELQVEQTSLEPLQESPRPTGVWKSREVATEGIRGHRKMVLYTLRA

PRSPKMVQGSGCFGRKMDRISSSSGLGCKVLRRH
```

Figure 8:
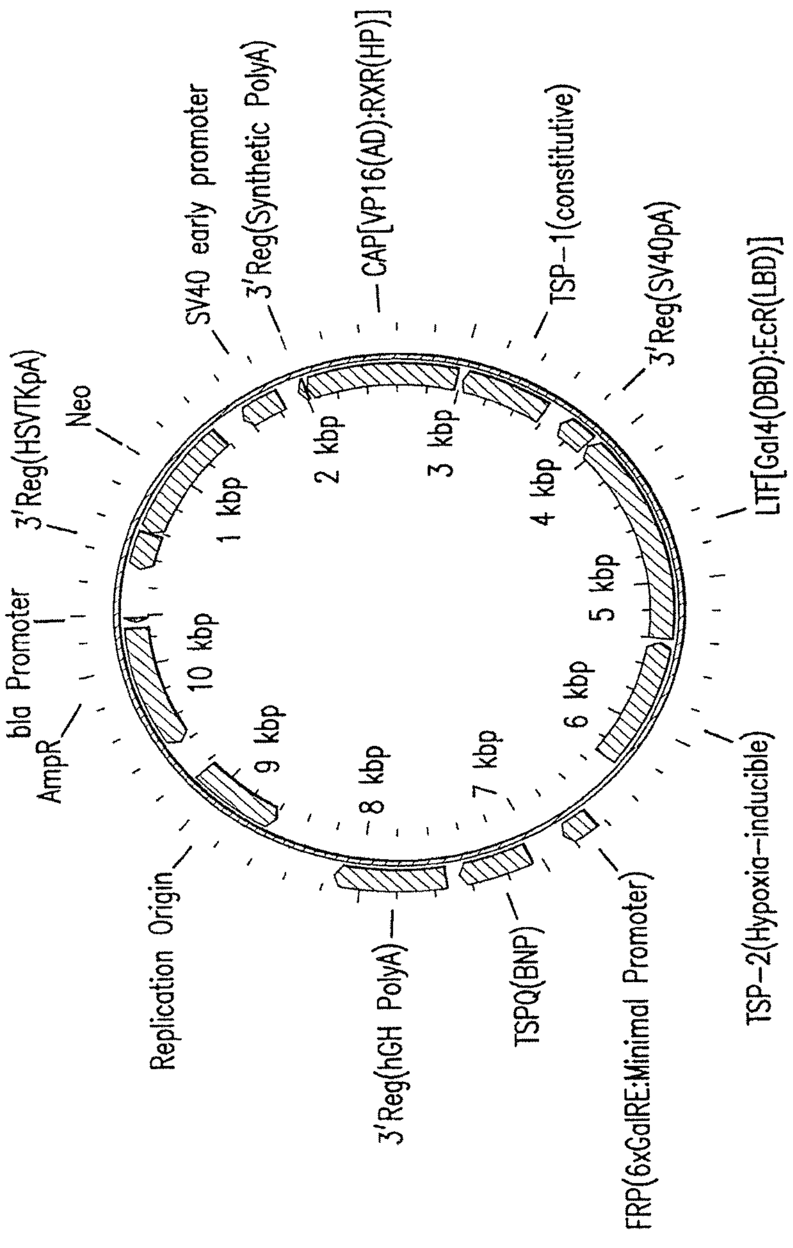
FIG. 8 is is a diagram of a vector constructed under the scheme shown in FIG. 2, and engineered to express human B-type natriuretic peptide (BNP) under hypoxic conditions such as cardiac ischemia.

The complete nucleotide sequence of the construct shown in FIG. 8 is presented as SEQ ID NO:10. The nucleotide coordinates for salient elements of the construct are shown in Table 7.

TABLE 7

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |
| LTF[GAL4(DBD):EcR(LBD)] | reverse | 1467 | 3946 | 5412 |
| TSP-2(Hypoxia-inducible) | reverse | 870 | 5446 | 6315 |
| FRP(6x GalRE:Minimal Promoter) | forward | 189 | 6648 | 6836 |
| TSPQ(BNP) | forward | 405 | 7050 | 7454 |
| 3'Reg(hGH PolyA) | forward | 627 | 7527 | 8153 |
| Replication Origin | reverse | 589 | 8587 | 9175 |
| AmpR | reverse | 858 | 9420 | 10277 |
| bla Promoter | reverse | 39 | 10311 | 10349 |

The vector shown in FIG. 8 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible TSP-2 used in this vector is the hypoxia-inducible control promoter-1.

The coding region for the therapeutic product, BNP, is operably associated with a FRP which is activated upon contact with the LDTFC in the presence of ligand.

The construct shown in FIG. 8 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a biorcactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed under hypoxic conditions associated with, e.g., cardiac ischemia. Ligand will be administered to the subject to be treated which will combine with the expressed LDTFC to drive expression of BNP under control of the FRP. BNP expression in turn promotes targeted cardioprotection, vasodilation and anti-remodeling in the ischemic tissue.

Example 5

This example describes a bioreactor/cell therapy vector useful for the treatment of ischemic cardiovascular disease through the breakdown of fibrin deposition in the heart. The vector, shown in FIG. 9, will confer expression of human tissue plasminogen activator (tPA, GenBank Accession No.: AA034406, SEQ ID NO:24) upon administration of ligand, under inflammatory conditions which occur in ischemic tissue. Tissue plasminogen activator is a serine protease that catalyzes the conversion of plasminogen to the activated enzyme plasmin, that degrades fibrin. The use of recombinant tPA has been proven effective as a thrombolytic, for the breakdown of fibrin clots, in diseases such as pulmonary embolism, myocardial infarction and stroke. In addition to clot formation, excess fibrin deposition in the heart and vasculature is associated with insulin resistant diabetes, atherosclerosis and myocardial infarction in response to inflammation. For this purpose, an example of inducible expression of tPA, in response to ischemia is given.

```
SEQ ID NO: 24:
MDAMKRGLCCVLLLCGAVFVSPSQEIHARFRRGARSYQVICRDEKTQMIY

QQHQSWLRPVLRSNRVEYCWCNSGRAQCHSVPVKSCSEPRCFNGGTCQQA

LYFSDFVCQCPEGFAGKCCEIDTRATCYEDQGISYRGTWSTAESGAECTN

WNSSALAQKPYSGRRPDAIRLGLGNHNYCRNPDRDSKPWCYVFKAGKYSS

EFCSTPACSEGNSDCYFGNGSAYRGTHSLTESGASCLPWNSMILIGNVYT

AQNPSAQALGLGKHNYCRNPDGDAKPWCHVLKNRRLTWEYCDVPSCSTCG

LRQYSQPQFRIKGGLFADIASHPWQAAIFAKHRRSPGERFLCGGILISSC

WILSAAHCFQERFPPHHLTVILGRTYRVVPGEEEQKFEVEKYIVHKEFDD

DTYDNDIALLQLKSDSSRCAQESSVVRTVCLPPADLQLPDWTECELSGYG

KHEALSPFYSERLKEAHVRLYPSSRCTSQHLLNRTVTDNMLCAGDTRSGG

PQANLHDACQGDSGGPLVCLNDGRMTLVGIISWGLGCGQKDVPGVYTKVT

NYLDWIRDNMRP
```

Figure 9:
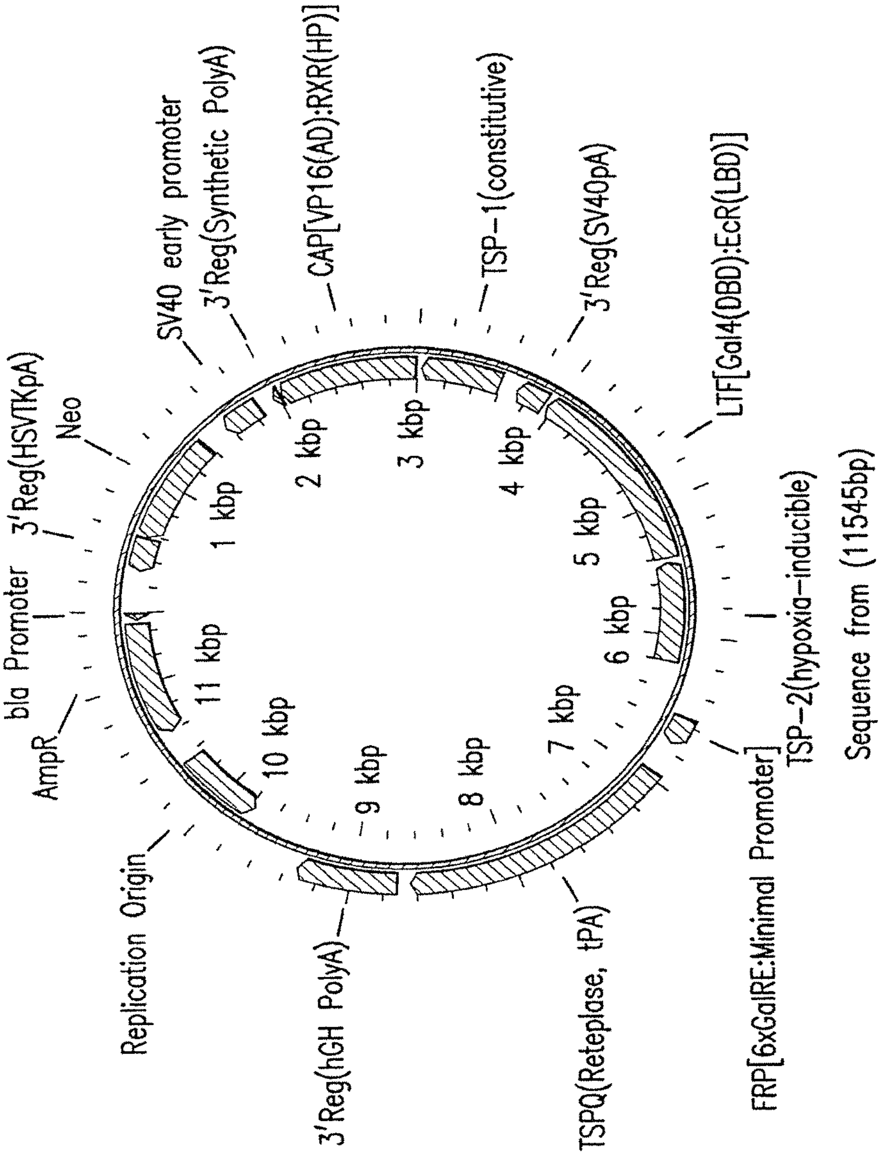
FIG. 9 is is a diagram of a vector constructed under the scheme shown in FIG. 2, and engineered to express tissue plasminogen activator (tPA) under inflammatory conditions such as cardiac ischemia.

The complete nucleotide sequence of the construct shown in FIG. 9 is presented as SEQ ID NO:11. The nucleotide coordinates for salient elements of the construct are shown in Table 8.

TABLE 8

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1 (constitutive) | reverse | 571 | 3026 | 3596 |
| 3'Reg(SV40pA) | reverse | 221 | 3719 | 3939 |
| LTF[GAL4(DBD):EcR(LBD)] | reverse | 1467 | 3946 | 5412 |
| TSP-2 (hypoxia inducible) | reverse | 770 | 5446 | 6215 |
| FRP[6xGalRE:Minimal Promoter] | forward | 189 | 6548 | 6736 |
| TPSQ (Reteplase, tPA) | forward | 1689 | 6950 | 8638 |
| 3'Reg(hGH PolyA) | forward | 627 | 8711 | 9337 |

TABLE 8-continued

| Label | Direction | Length | Start | End |
|---|---|---|---|---|
| Replication Origin | reverse | 589 | 9771 | 10359 |
| AmpR | reverse | 858 | 10604 | 11461 |
| bla Promoter | reverse | 39 | 11495 | 11533 |

The vector shown in FIG. 9 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible therapeutic switch promoter used in this vector is the human Plexin D1 promoter.

The coding region for the therapeutic product, tPA, is operably associated with a FRP which is activated upon contact with the LDTFC in the presence of ligand.

The construct shown in FIG. 9 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a biorcactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed in the event of an inflammatory response associated with, e.g., cardiac ischemia. Ligand will be administered to the subject to be treated which will combine with the expressed LDTFC to drive expression of tPA under control of the FRP. tPA expression in turn promotes targeted break-up of fibrin deposition in the ischemic tissue.

Example 6

This example describes a bioreactor/cell therapy vector useful for the treatment of ischemic cardiovascular disease through the promotion of cardioprotection, antiogenesis and hemodynamics. The vector, shown in FIG. 10, will confer expression of two therapeutic polypeptides, human relaxin (GenBank Accession No.: NP_604390.1, SEQ ID NO:25) and human hepatocyte growth factor (HGF, GenBank Accession No.: NP_000592.3, SEQ ID NO:26) upon administration of ligand, under inflammatory conditions and/or hypoxia, respectively, both of which occur in ischemic tissue. Relaxin is a potent vasodilator of the systemic and coronary circulation by a mechanism of action involving nitric oxide, and influences cardiac beating rate. HGF provides a pro-angiogenic effect, a cardioprotective anti-apoptotic effect, an anti-fibrotic effect, and is a type I collagen regenerative factor in ischemic myocardium. For this purpose, an example of separately controlled inducible expression of relaxin and HGF in response to ischemia is given.

```
SEQ ID NO: 25:
MPRLEFFHLLGVCLLLNQFSRAVADSWMEEVIKLCGRELVRAQIAICGMS

TWSKRSLSQEDAPQTPRPVAEIVPSFINKDTETINMMSEEVANLPQELKL

TLSEMQPALPQLQQHVPVLKDSSLLFEEFKKLIRNRQSEAADSSPSELKY

LGLDTHSRKKRQLYSALANKCCHVGCTKRSLARFC

SEQ ID NO: 26:
MWVTKLLPALLLQHVLLHLLLLPIAIPYAEGQRKRRNTIHEFKKSAKTTL

IKIDPALKIKTKKVNTADQCANRCTRNKGLPFTCKAFVFDKARKQCLWFP

FNSMSSGVKKEFGHEFDLYENKDYIRNCIIGKGRSYKGTVSITKSGIKCQ

PWSSMIPHEHSFLPSSYRGKDLQENYCRNPRGEEGGPWCFTSNPEVRYEV

CDIPQCSEVECMTCNGESYRGLMDHTESGKICQRWDHQTPHRHKFLPERY

PDKGEDDNYCRNPDGQPRPWCYTLDPHTRWEYCAIKTCADNTMNDTDVPL

ETTECIQGQGEGYRGTVNTIWNGIPCQRWDSQYPHEHDMTPENEKCKDLR

ENYCRNPDGSESPWCETTDPNIRVGYCSQIPNCDMSHGQDCYRGNGKNYM

GNLSQTRSGLTCSMWDKNMEDLHRHIFWEPDASKLNENYCRNPDDDAHGP

WCYTGNPLIPWDYCPISRCEGDTTPTIVNLDHPVISCAKTKQLRVVNGIP

TRTNIGWMVSLRYRNKHICGGSLIKESWVLTARQCFPSRDLKDYEAWLGI

HDVHGRGDEKCKQVLNVSQLVYGPEGSDLVLMKLARPAVLDDEVSTIDLP

NYGCTIPEKTSCSVYGWGYTGLINYDGLLRVAHLYIMGNEKCSQHHRGKV

TLNESEICAGAEKIGSGPCEGDYGGPLVCEQHKMRMVLGVIVPGRGCAIP

NRPGIFVRVAYYAKWIHKIILTYKVPQS
```

Figure 10:
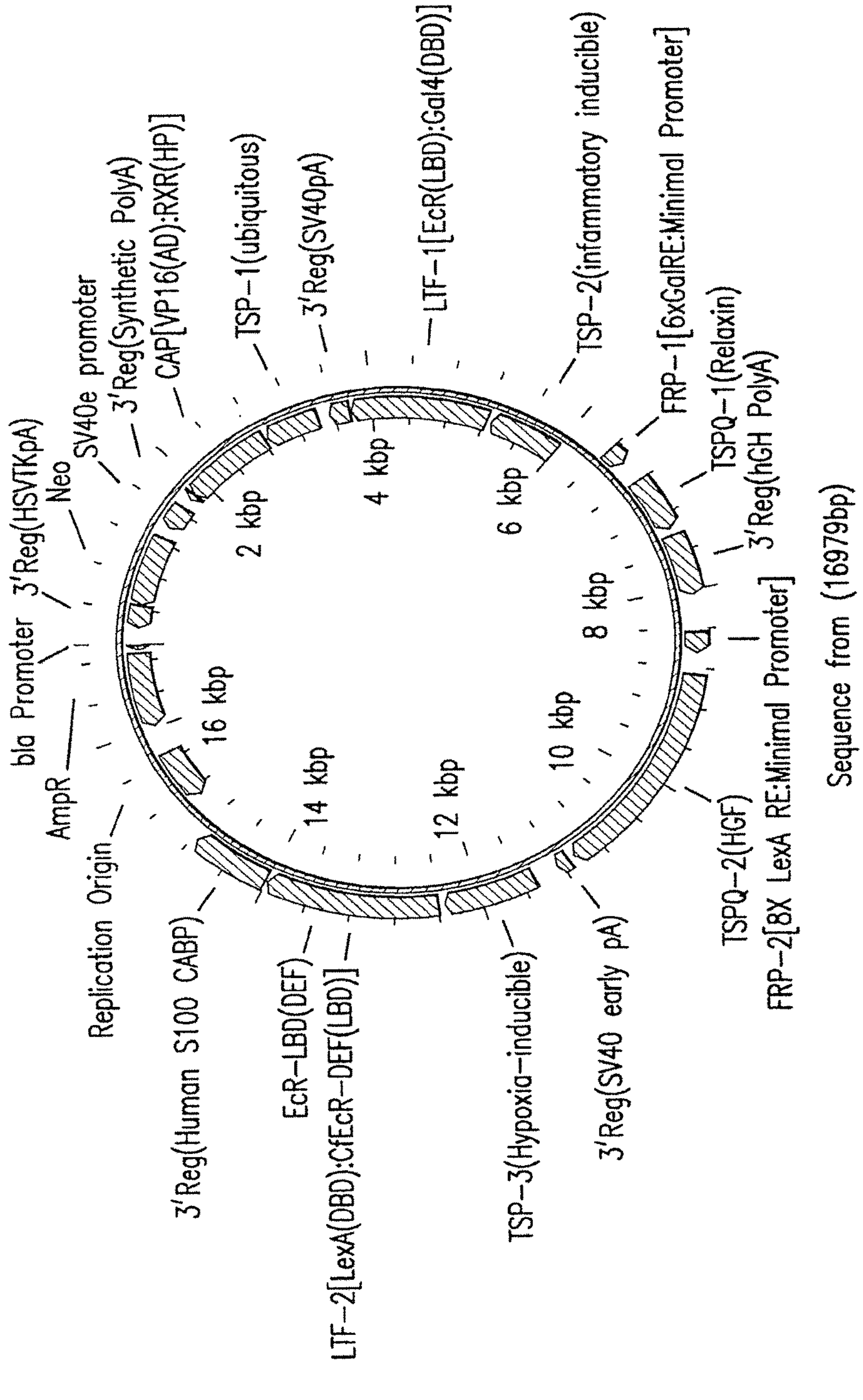
FIG. 10 is is a diagram of a vector constructed under the scheme shown in FIG. 3, and engineered to express relaxin under inflammatory conditions and/or hepatocyte growth factor under hypoxic conditions, both conditions being associated with cardiac ischemia.

The complete nucleotide sequence of the construct shown in FIG. 10 is presented as SEQ ID NO:13. The nucleotide coordinates for salient elements of the construct are shown in Table 9.

TABLE 9

| Label | Direction | Length | Start | End |
|---|---|---|---|---|
| 3'Reg(HSVTKpA) | reverse | 259 | 197 | 455 |
| NEO | reverse | 804 | 462 | 1265 |
| SV40e Promoter | reverse | 280 | 1385 | 1664 |
| 3'Reg(Synthetic PolyA) | reverse | 49 | 1782 | 1830 |
| CAP[VP16(AD):RxR(HP)] | reverse | 975 | 1837 | 2811 |
| TSP-1(ubiquitous) | reverse | 571 | 2845 | 3415 |
| 3'Reg(SV40pA) | reverse | 221 | 3538 | 3758 |
| LTF-1[EcR(LBD):Gal4(DBD)] | reverse | 1467 | 3765 | 5231 |
| TSP-2(inflammatory inducible) | reverse | 770 | 5265 | 6034 |
| FRP-1[6x GalRE:Minimal Promoter] | forward | 189 | 6405 | 6593 |
| TPSQ-1(Relaxin) | forward | 558 | 6807 | 7364 |
| 3'Reg(hGH PolyA) | forward | 627 | 7437 | 8063 |
| FRP-2[8X LexA RE:Minimal Promoter] | forward | 216 | 8437 | 8652 |
| TPSQ-2(HGF) | forward | 2187 | 8866 | 11052 |
| 3'Reg(SV40 early pA) | forward | 135 | 11112 | 11246 |
| TSP-3(Hypoxia-inducible) | forward | 870 | 11478 | 12347 |
| LTF-2[LexA(DBD) CfEcR-DEF(LBD)] | forward | 1629 | 12381 | 14009 |
| EcR-LBD (DEF) | forward | 1014 | 12996 | 14009 |
| 3'Reg(Human S100 CABP) | forward | 765 | 14016 | 14780 |
| Replication Origin | reverse | 589 | 15114 | 15702 |
| AmpR | reverse | 858 | 16038 | 16895 |
| bla Promoter | reverse | 39 | 16929 | 16967 |

The vector shown in FIG. 10 is modeled according to the gene switch system shown in FIG. 3. Under this system, the CAP subunit of the LDTFC is expressed through operable association with a first, constitutive therapeutic switch promoter (TSP-1), a first LTF (LTF-1) subunit is expressed through operable association with a second, inducible therapeutic switch promoter (TSP-2), and a second LTF (LTF-2) subunit is expressed through operable association with a third, inducible therapeutic switch promoter (TSP-3). TSP-2 in this vector is the human Plexin D1 promoter and TSP-3 in this vector is the hypoxia-inducible control promoter 1.

The coding region for the first therapeutic product, relaxin, is operably associated with a first FRP (FRP-1) having response elements which recognize the first DNA binding domain DBD-A of LTF-1, and the coding region for the second therapeutic product, HGF, is operably associated with a second FRP (FRP-2) having response elements which recognize the second DNA binding domain (DBD-B) of LTF-2. Both FRPs are activated upon contact with the respective LDTFC in the presence of ligand.

The construct shown in FIG. 10 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF-1 and/or LTF-2 will be expressed in the event of an inflammatory response and/or hypoxia associated with, e.g., cardiac ischemia. One or more ligands will be administered to the subject to be treated which will combine with the expressed LDTFC(s) to drive expression of relaxin and/or HGF under control of FRPs.

Example 7

This example describes a bioreactor/cell therapy vector useful for the treatment of ischemic cardiovascular disease through the promotion of cardiac repair and cardioprotection. The vector, shown in FIG. 11, will confer expression of human EPO (see Example 3) upon administration of ligand, under hypoxic conditions which occur in ischemic tissue. EPO has been shown to function in cardioprotection and anti-remodeling, in response to ischemic. In this example, EPO expression is specifically limited to cardiac tissue.

Figure 11:
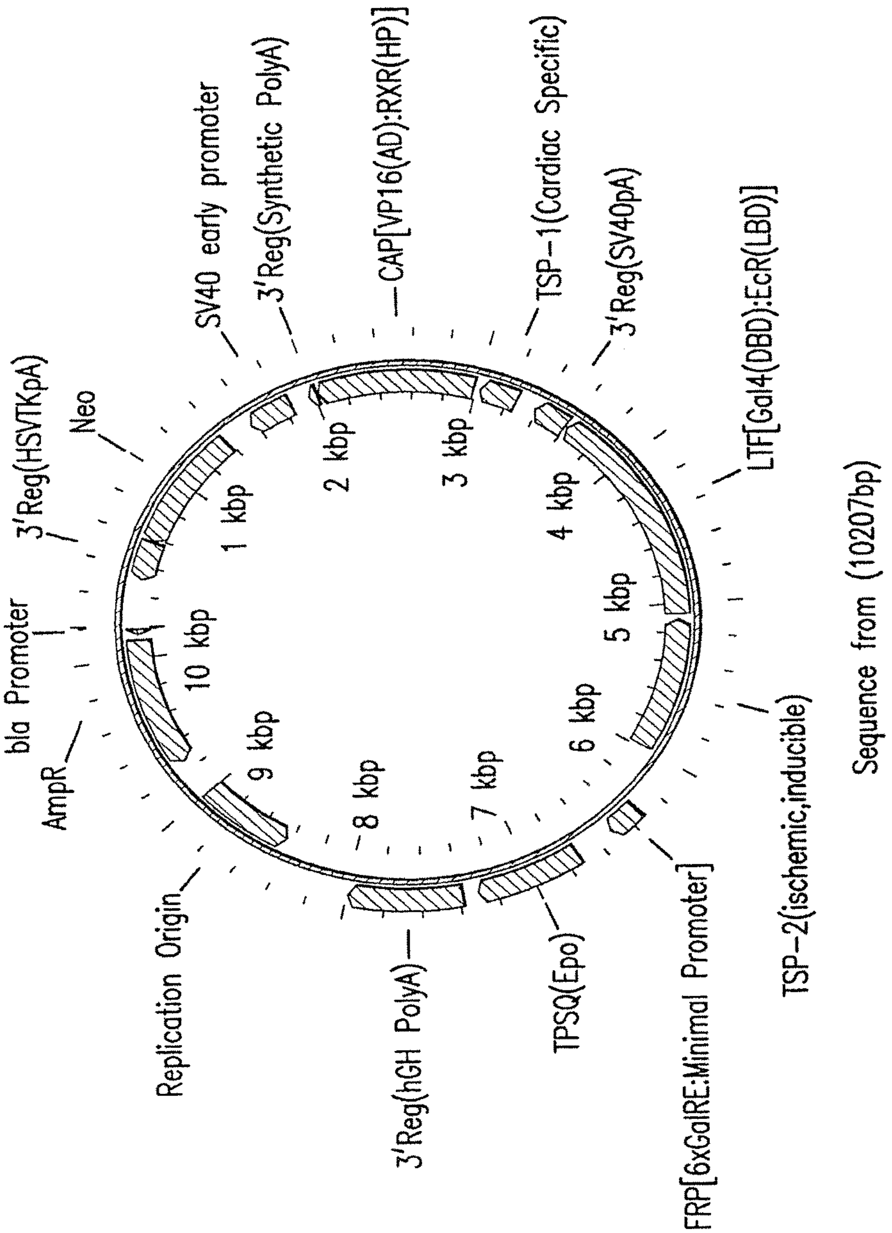
FIG. 11 is is a diagram of a vector constructed under the scheme shown in FIG. 2, and engineered to express EPO under hypoxic conditions such as cardiac ischemia with expression being limited to cardiac myocytes.

The vector shown in FIG. 11 is modeled according to the gene switch system shown in FIG. 2. Under this system, the CAP subunit is expressed through operable association with a promoter which is specific for cardiac tissue (Nxcl cardiomyocyte-specific promoter), and the LTF subunit is expressed through operable association with the hypoxia-inducible control promoter-1.

The coding region for the therapeutic product, EPO, is operably associated with a FRP which is activated upon contact with the LDTFC in the presence of ligand.

The complete nucleotide sequence of the construct shown in FIG. 11 is presented as SEQ ID NO:12. The nucleotide coordinates for salient elements of the construct are shown in Table 10.

TABLE 10

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(Cardiac Specific) | reverse | 240 | 3026 | 3265 |
| 3'Reg(SV40pA) | reverse | 221 | 3388 | 3608 |
| LTF[Gal4(DBD):EcR(LBD)] | reverse | 1467 | 3615 | 5081 |
| TSP-2(ischemic, inducible) | reverse | 870 | 5115 | 5984 |
| FRP[6x GalRE:Minimal Promoter] | forward | 189 | 6317 | 6505 |
| TPSQ (Epo) | forward | 582 | 6719 | 7300 |
| 3'Reg(hGH PolyA) | forward | 627 | 7373 | 7999 |
| Replication Origin | reverse | 589 | 8433 | 9021 |
| AmpR | reverse | 858 | 9266 | 10123 |
| bla Promoter | reverse | 39 | 10157 | 10195 |

The construct shown in FIG. 11 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the LDTFC may be expressed under the appropriate physiological conditions. The LDTFC encoded by the vector will be expressed specifically in cardiomyocytes under hypoxic conditions associated with, e.g., cardiac ischemia. Ligand will be administered to the subject to be treated which will combine with the expressed LDTFC to drive expression of EPO under control of the FRP. EPO expression in turn promotes targeted cardioprotection in the ischemic tissue.

Example 8

This example describes a gene therapy vector useful for the treatment of ischemic heart disease through the promotion of cardiac repair and angiogenesis. The vector, shown in FIG. 12, will confer expression of human IGF-1 (see Example 1) upon administration of ligand, under either hypoxic conditions in an inflammatory response, both of which may occur in ischemic tissue. For this purpose, an example of inducible IGF-1 expression, in response to hypoxia and/or an inflammatory response is given. In this example, inducible expression if IGF-1 is specifically limited to cardiomyocytes.

Figure 12:
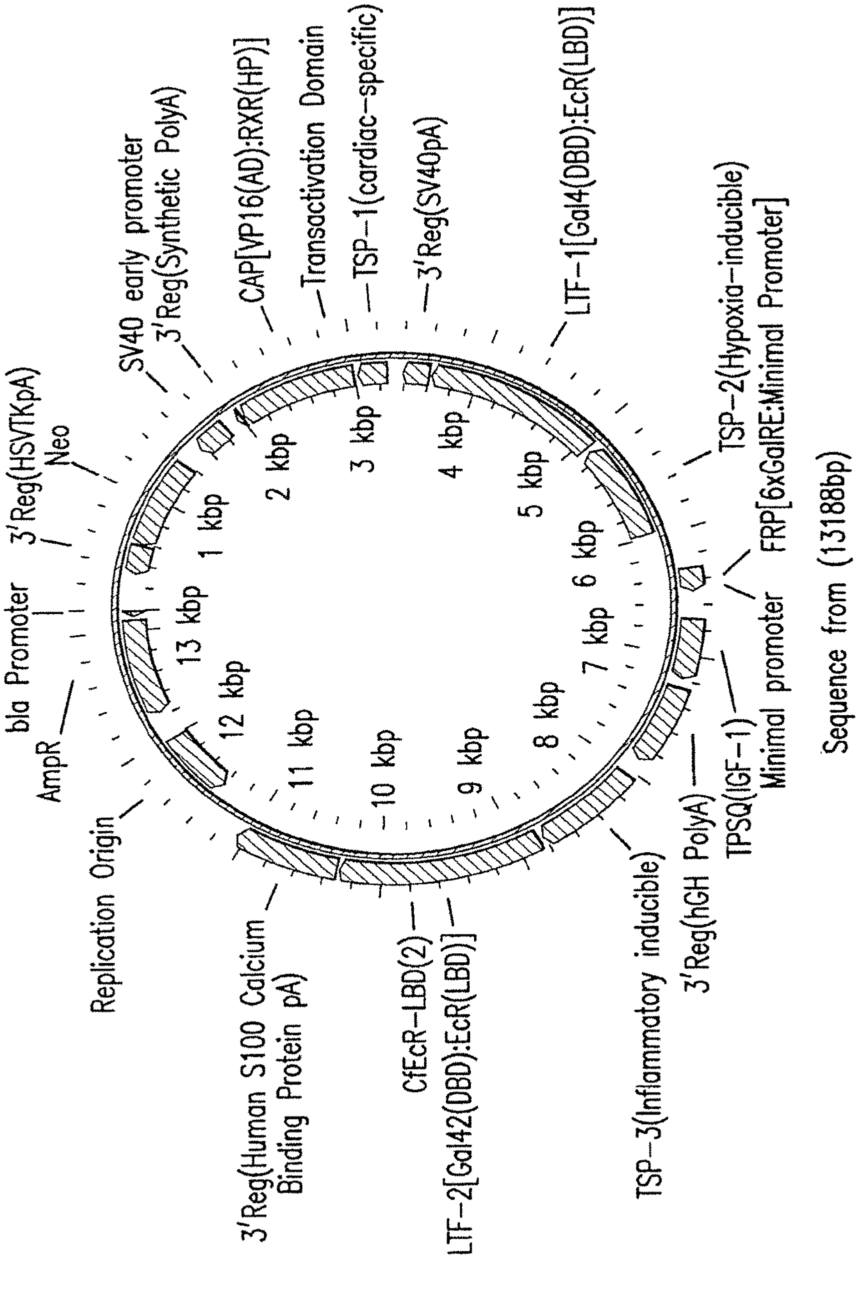
FIG. 12 is is a diagram of a vector constructed under the scheme shown in FIG. 4, and engineered to express IGF-1 under either inflammatory conditions or hypoxic conditions such as cardiac ischemia with expression being limited to cardiac myocytes.

The vector shown in FIG. 12 is modeled according to the gene switch system shown in FIG. 4. Under this system, the CAP subunit is expressed through operable association with a promoter which is specific for cardiac tissue (Nxcl cardiomyocyte-specific promoter), and LTF subunits (LTF-1 and LTF-2) of the LDTFC are expressed through either of two inducible TSPs, the first through operable association with the hypoxia-inducible control promoter-1, and the second through operable association with the human plexin D1 promoter.

The coding region for the therapeutic product, IGF-1, is operably associated with a FRP which is activated upon contact with the LDTFC in the presence of ligand.

The complete nucleotide sequence of the construct shown in FIG. 12 is presented as SEQ ID NO:14. The nucleotide coordinates for salient elements of the construct are shown in Table 11.

TABLE 11

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| Transactivation Domain | reverse | 261 | 2732 | 2992 |
| TSP-1(cardiac-specific) | reverse | 240 | 3026 | 3265 |
| 3'Reg(SV40pA) | reverse | 221 | 3388 | 3608 |
| LTF-1[Gal4(DBD):EcR(LBD)] | reverse | 1467 | 3615 | 5081 |
| TSP-2(Hypoxia-inducible) | reverse | 870 | 5115 | 5984 |
| FRP[6xGalRE:Minimal promoter] | forward | 189 | 6317 | 6505 |
| Minimal promoter | forward | 60 | 6446 | 6505 |
| TPSQ (IGF-1) | forward | 477 | 6719 | 7195 |
| 3'Reg(hGH PolyA) | forward | 627 | 7268 | 7894 |
| TSP-3(Inflammatory inducible) | forward | 770 | 8040 | 8809 |
| LTF-2[Gal42(DBD):EcR(LBD)] | forward | 1467 | 8843 | 10309 |
| CfEcR-LBD(2) | forward | 1014 | 9296 | 10309 |
| 3'Reg(Human S100 Calcium Binding Protein pA) | forward | 765 | 10316 | 11080 |
| Replication Origin | reverse | 589 | 11414 | 12002 |
| AmpR | reverse | 858 | 12247 | 13104 |
| bla Promoter | reverse | 39 | 13138 | 13176 |

The construct shown in FIG. 12 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the LDTFC may be expressed under the appropriate physiological conditions. The LDTFC encoded by the vector will be expressed specifically in cardiomyocytes under hypoxic conditions, and/or in the event of an inflammatory response, associated with, e.g., cardiac ischemia. Ligand will be administered to the subject to be treated which will combine with the expressed transcription factor to drive expression of IGF-1 under control of the FRP. IGF-1 expression in turn promotes targeted angiogenesis in the ischemic tissue.

Example 9

This example describes a bioreactor/cell therapy vector useful for the treatment of rheumatoid arthritis, active ankylosing spondylitis or plaque psoriasis or for inhibition of structural damage by the active arthritis ("RA or related diseases"). Conventional treatment of RA and related diseases includes traditional Disease Modifying Anti-Rheumatic Drugs (DMARDs) as well as biologic DMARDs such as etanercept, infliximab, and adalimumab. For example, etanercept (Enbrel®), manufactured by Amgen, is a fusion protein that contains two extracellular domains of human TNF-alpha receptor 2 fused to a Fc portion by a hinge peptide. See U.S. Pat. No. 7,276,477 (incorporated herein by reference in its entirety). Etanercept should be administered s.c. once or twice a week. Use of the etanercept gene switch system utilizing inflammation or cytokine response promoters may therefore increase convenience and safety by limiting any production of etanercept in the absence of TNF activation.

Figure 13:
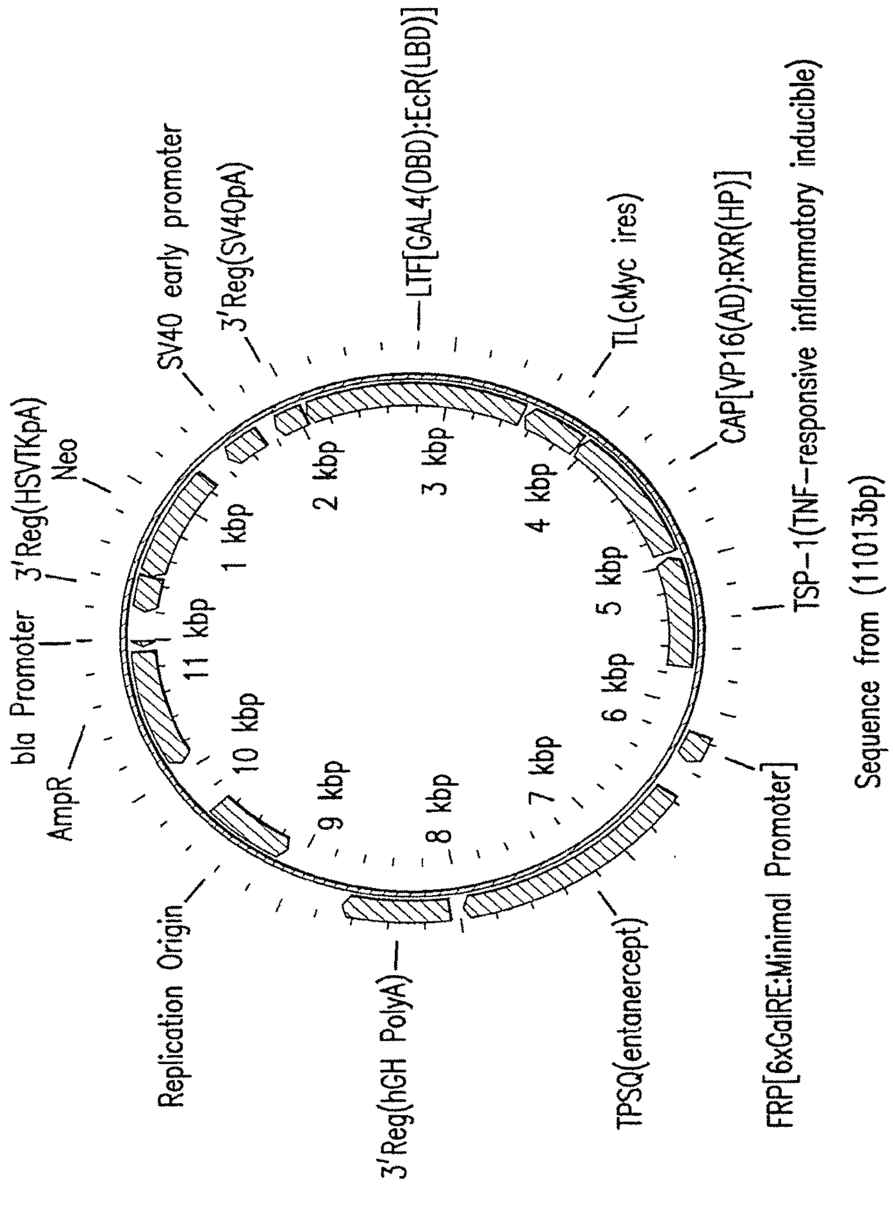
FIG. 13 is a diagram of a vector constructed under the scheme shown in FIG. 1, and engineered to express tumor necrosis factor binding protein 2 (Enbrel®) under inflammatory conditions such as rheumatoid arthritis.

The complete nucleotide sequence of the construct shown in FIG. 13 is presented as SEQ ID NO: 16. The nucleotide coordinates for salient elements of the construct are shown in Table 12.

TABLE 12

| Label | Direction | Length | Start | End |
|---|---|---|---|---|
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[GAL4(DBD):EcR(LBD)] | reverse | 1467 | 2057 | 3523 |
| TL(cMyc ires) | reverse | 408 | 3536 | 3943 |
| CAP[VP16(AD):RxR(HP)] | reverse | 975 | 3950 | 4924 |
| TSP-1(TNF-responsive inflammatory inducible) | reverse | 800 | 4958 | 5757 |
| FRP[6x GalRE:Minimal Promoter] | forward | 189 | 6168 | 6356 |
| TPSQ(entanercept) | forward | 1407 | 6570 | 7976 |
| 3'Reg(hGH PolyA) | forward | 627 | 8049 | 8675 |
| Replication Origin | reverse | 589 | 9109 | 9697 |
| AmpR | reverse | 858 | 10072 | 10929 |
| bla Promoter | reverse | 39 | 10963 | 11001 |

The vector shown in FIG. 13 is modeled according to the gene switch system shown in FIG. 1. Under this system, both the CAP subunit and the LTF subunit of the LDTFC are expressed through operable association with a single TSP-1 via use of an internal ribosome entry site (IRES). The promoter utilized in this system is a vascular cell adhesion molecule (VCAM1) promoter, which is activated by TNF-alpha. Another example of the TNF-alpha regulated promoters that may be used for the invention is human pentraxin 3(PTX3) promoter, which is responsive to TNF-alpha or Interleukin (IL)-1 beta. See Basile et al., *J. Biol. Chem.* 272(13): 8172 (1997).

The coding region for the therapeutic product, etanercept, is operably associated with a FRP which is activated upon contact with the LDTFC in the presence of ligand.

The construct shown in FIG. 13 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Systemic and/or local administration of gene therapy cells are well known in the art. Upon delivery of the cells, the LDTFC may be expressed under the appropriate physiological conditions. The LDTFC encoded by the vector will be expressed in the presence of TNF-alpha associated with, e.g., RA. Ligand will be administered to the subject to be treated which will combine with the expressed LDTFC to drive expression of etanercept under control of the TNF-alpha regulated promoter. Etanercept expression in turn captures TNF-alpha and reduces the TNF-alpha concentration in the tissues.

Example 10

This example describes a bioreactor/cell therapy vector useful for the treatment of RA and related disease through reducing the TNF-alpha level. The vector shown in FIG. 14 will confer expression of etanercept upon administration of ligand, under either the presence of TNF-alpha and/or severe inflammation, both of which may occur in RA or related diseases. For this purpose, an example of inducible etanercept expression, in response to the presence of TNF-alpha and/or an inflammatory response is given.

Figure 14:
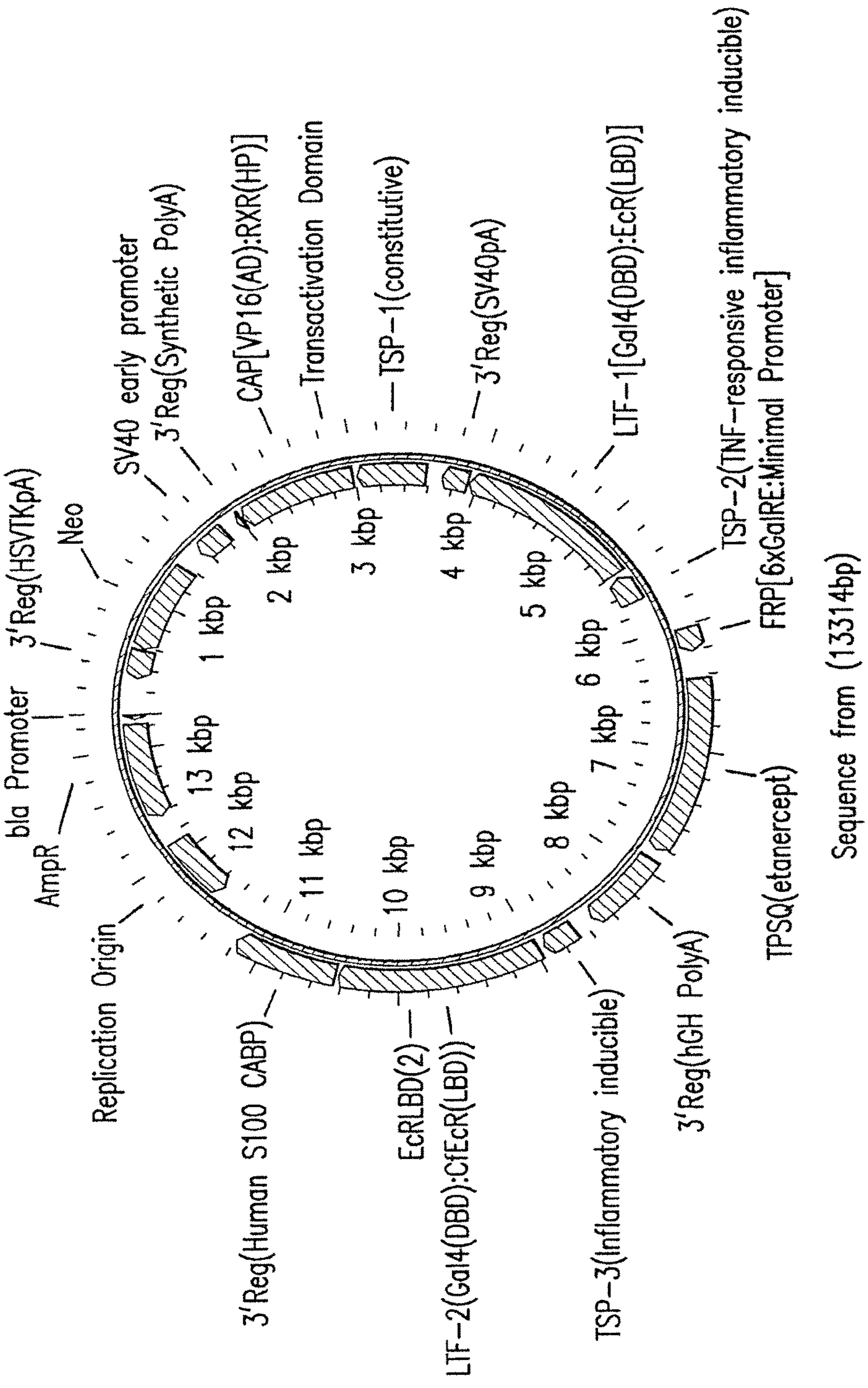
FIG. 14 is is a diagram of a vector constructed under the scheme shown in FIG. 4, and engineered to express tumor necrosis factor binding protein 2 (Enbrel®) either in reponse to TNF alpha expression or under inflammatory conditions, both conditions associated with rheumatoid arthritis.

The vector shown in FIG. 14 is modeled according to the gene switch system shown in FIG. 4. Under this system, the CAP subunit is expressed through operable association with a constitutive promoter (TSP-1), and a LTF subunit of a LDTFC is expressed by either of two inducible transcription cassettes, the first (LTF-1) through operable association with human plasminogen activator inhibitor type-2 (PAI2) promoter (TSP-2), and the second (LTF-2) through operable association with the human scrum amyloid A1 (SAA1) promoter (TSP-3). The human PAI2 promoter is activated in the presence of TNF-alpha. See Mahony et al. *Eur. J. Biochem.* 263(3) (1999) and Matsuo et al., *Biochem. J.* 405: 605 (2007). The SAA1 promoter is upregulated not directly by proinflammatory cytokines such as TNF-alpha, but by other acute inflammatory signals such as glucocorticoid. See Kumon et al., *Scandinavian J. Immunol.* 56: 504 (2002).

The coding region for the therapeutic product, etanercept, is operably associated with a FRP which is activated upon contact with the LDTFC in the presence of ligand.

The complete nucleotide sequence of the construct shown in FIG. 14 is presented as SEQ ID NO: 15. The nucleotide coordinates for salient elements of the construct are shown in Table 13.

TABLE 13

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| Transactivation Domain | reverse | 261 | 2732 | 2992 |
| TSP-1(constitutive) | reverse | 571 | 3026 | 3596 |
| 3'Reg(SV40pA) | reverse | 221 | 3719 | 3939 |
| LTF-1[Gal4(DBD):EcR(LBD)] | reverse | 1467 | 3946 | 5412 |
| TSP-2(TNF-responsive Inflammatory inducible) | reverse | 252 | 5446 | 5697 |
| FRP[6x GalRE:Minimal Promoter] | forward | 189 | 6030 | 6218 |
| TPSQ(etanercept) | forward | 1407 | 6432 | 7838 |
| 3'Reg(hGH PolyA) | forward | 627 | 7911 | 8537 |
| TSP-3(Inflammatory inducible) | forward | 253 | 8683 | 8935 |
| LTF-2(Gal4(DBD):CfEcR(LBD)) | forward | 1467 | 8969 | 10435 |
| EcRLBD(2) | forward | 1014 | 9422 | 10435 |
| 3'Reg(Human S100 CABP) | forward | 765 | 10442 | 11206 |
| Replication Origin | reverse | 589 | 11540 | 12128 |
| AmpR | reverse | 858 | 12373 | 13230 |
| bla Promoter | reverse | 39 | 13264 | 13302 |

The construct shown in FIG. 14 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Methods for systemic and/or local administration of gene therapy cells are well known in the art. Upon delivery of the cells, the LDTFC may be expressed under the appropriate physiological conditions. The LDTFC encoded by the vector will be expressed specifically in the administered cells under the presence of TNF-alpha and/or severe inflammation. Ligand will be administered to the subject to be treated which will combine with the expressed LDTFC to drive expression of etanercept under control of the FRP. Etanercept expression in turn captures TNF-alpha and reduces the TNF-alpha concentration in the tissues.

Example 11

This example describes a bioreactor/cell therapy vector useful for the treatment of RA. The vector will confer expression of two therapeutic polypeptides, etanercept and human erythropoietin (EPO) upon administration of ligand, under the presence of TNF-alpha and/or inflammatory conditions, respectively, both of which occur in RA patients. EPO induces erythrogenesis in anemic RA patients. See Mercuriali et al. *Transfusion* 34(6): 501 (2003). For this purpose, an example of separately controlled inducible expression of etanercept and EPO in response to RA and anemia, respectively, is given.

Figure 15:
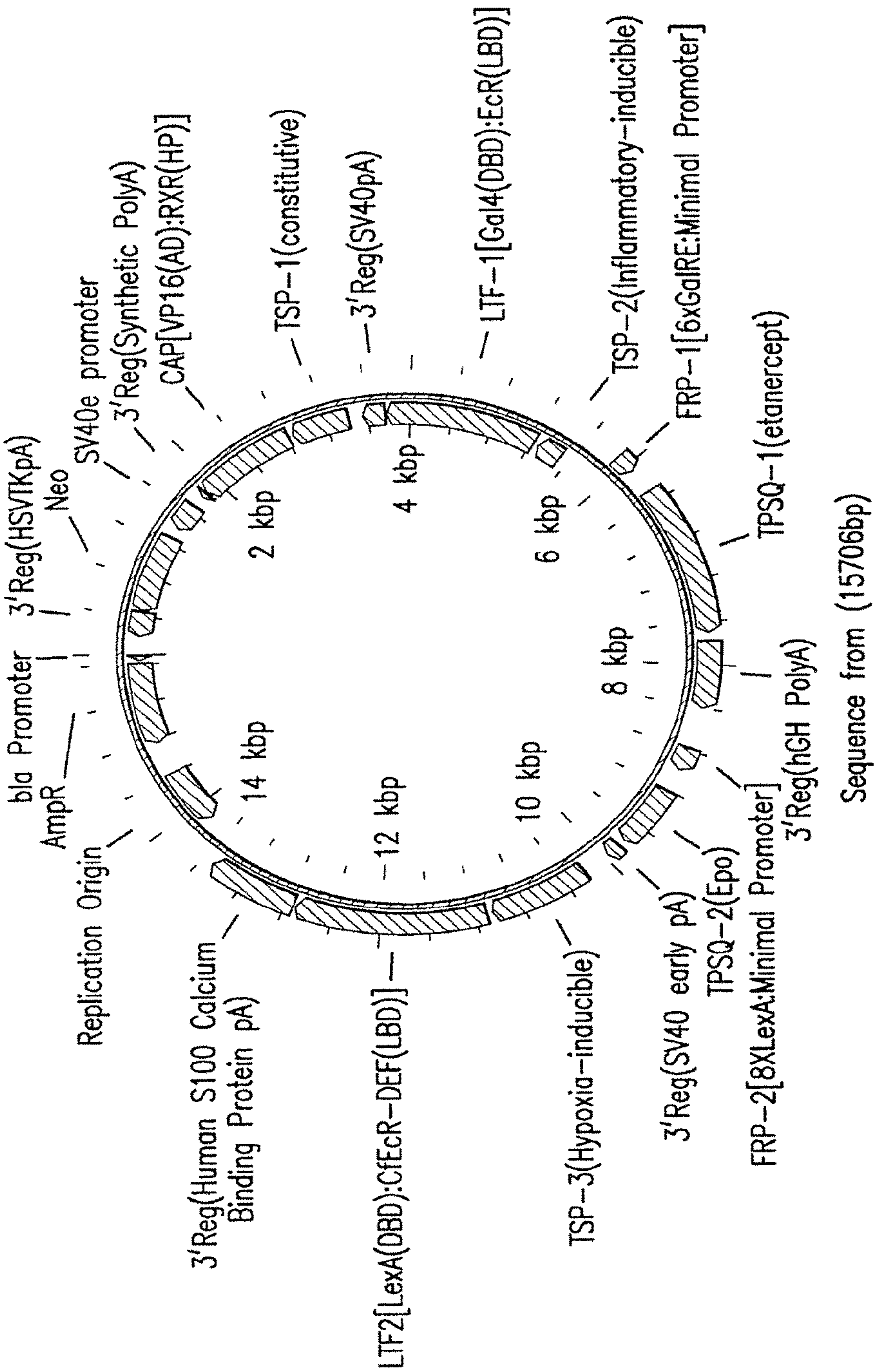
FIG. 15 is is a diagram of a vector constructed under the scheme shown in FIG. 3, and engineered to express tumor necrosis factor binding protein 2 (Enbrel®) under inflammatory conditions and/or EPO under HIF-driven hypoxic conditions, both conditions being associated with rheumatoid arthritis.

The complete nucleotide sequence of the construct shown in FIG. 15 is presented as SEQ ID NO: 17. The nucleotide coordinates for salient elements of the construct are shown in Table 14.

TABLE 14

| Label | Direction | Length | Start | End |
|---|---|---|---|---|
| 3'Reg(HSVTKpA) | reverse | 259 | 197 | 455 |
| NEO | reverse | 804 | 462 | 1265 |
| SV40e Promoter | reverse | 280 | 1385 | 1664 |
| 3'Reg(Synthetic PolyA) | reverse | 49 | 1782 | 1830 |
| CAP[VP16(AD):RxR(HP)] | reverse | 975 | 1837 | 2811 |
| TSP-1(constitutive) | reverse | 571 | 2845 | 3415 |
| 3'Reg(SV40pA) | reverse | 221 | 3538 | 3758 |
| LTF-1[Gal4(DBD):EcR(LBD)] | reverse | 1467 | 3765 | 5231 |
| TSP-2(Inflammatory-inducible) | reverse | 253 | 5265 | 5517 |
| FRP-1[6x GalRE:Minimal promoter] | forward | 189 | 5888 | 6076 |
| TPSQ-1(etanercept) | forward | 1407 | 6290 | 7696 |
| 3'Reg(hGH PolyA) | forward | 627 | 7769 | 8395 |
| FRP-2[8X LexA:Minimal Promoter] | forward | 216 | 8769 | 8984 |
| TPSQ-2(Epo) | forward | 582 | 9198 | 9779 |
| 3'Reg(SV40 early pA) | forward | 135 | 9839 | 9973 |
| TSP-3(Hypoxia-inducible) | forward | 870 | 10205 | 11074 |
| LTF2[LexA(DBD):CfEcR-DEF(LBD)] | forward | 1629 | 11108 | 12736 |
| 3'Reg(Human S100 Calcium Binding Protein pA) | forward | 765 | 12743 | 13507 |
| Replication Origin | reverse | 589 | 13841 | 14429 |
| AmpR | reverse | 858 | 14765 | 15622 |
| bla Promoter | reverse | 39 | 15656 | 15694 |

The vector shown in FIG. 15 is modeled according to the gene switch system shown in FIG. 3. Under this system, the CAP subunit of the LDTFC is expressed through operable association with a first, constitutive TSP-1, a first LTF subunit of a LDTFC (LTF-1) is expressed through operable association with a second, inducible TSP-2, and a second LTF subunit of a LDTFC (LTF-2) is expressed through operable association with a third, inducible TSP-3. The second inducible TSP-2 used in this vector is the human serum amyloid A1 (SAA1) promoter and the third inducible TSP-3 used in this vector is the hypoxia-inducible control promoter 1.

The coding region for the first therapeutic product, etanercept, is operably associated with a first FPR-1 having response elements which recognize the first DNA binding domain (DBD-A) associated with LTF-1, and the coding region for the second therapeutic product, EPO, is operably associated with a second FPR-2 having response elements which recognize the second DNA binding domain (DBD-B) associated with LTF-2. Both factor-regulated promoters are activated upon contact with the respective LDTFC in the presence of ligand.

The construct shown in FIG. 15 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Methods for systemic and/or local administration of gene therapy cells are well known in the art. Upon delivery of the cells, the LDTFC(s) may be expressed under the appropriate condition. One or more ligands will be administered to the subject to be treated which will combine with the expressed LDTFC(s) to drive expression of etanercept and/or EPO under control of FRP-1 or FRP-2. Etanercept expression in turn captures TNF-alpha and reduces the TNF-alpha concentration in the tissues, and EPO expression induces erythrogenesis and improves anemia.

Example 12

Figure 16:
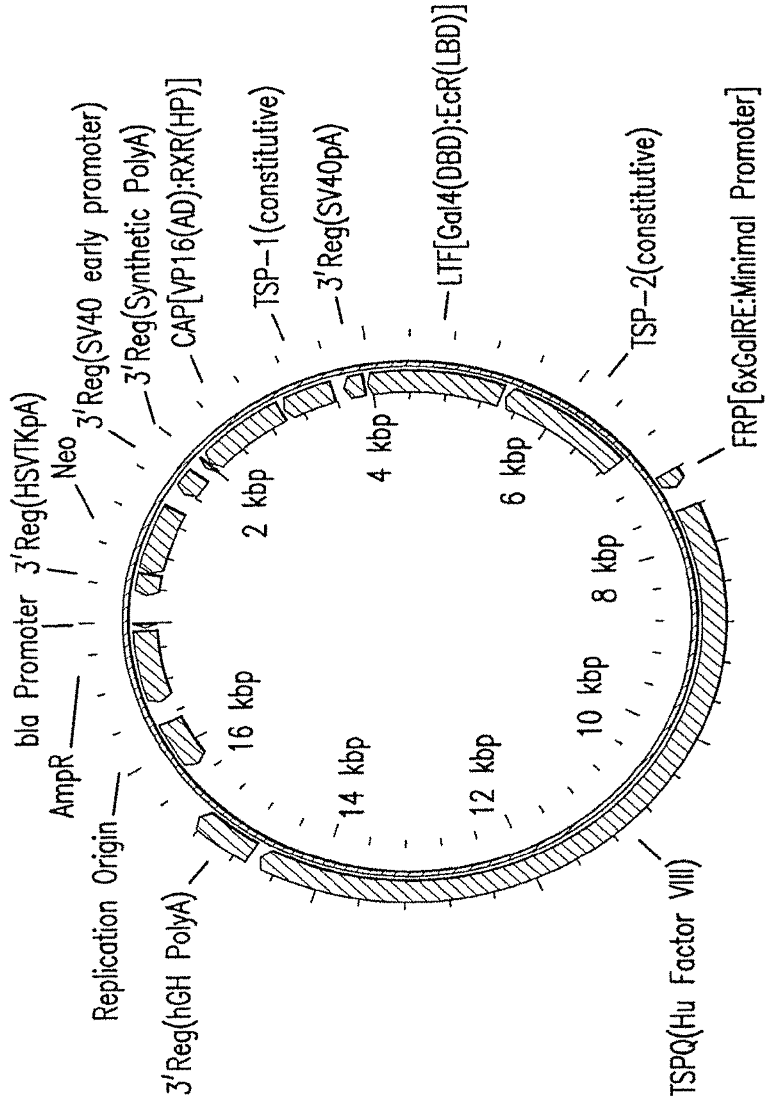
FIG. 16 is a diagram of a vector constructed under the scheme shown in FIG. 1, and engineered to express human factor VIII:C constitutively.

This example describes a bioreactor/cell therapy vector useful for the treatment of hemophilia. Hemophilia is caused by lack of either Factor VIII or Factor IX. Deficiency of Factor VIII is called hemophilia A, and deficiency of Factor IX is called hemophilia B. Hemophilia A or B may be treated by administering recombinantly produced Factor VIII or IX, respectively. See Garcia-Martin et al., *J. Gene Med.* 4(2): 215 (2002). For example, recombinantly produced Factor VIII that may be used in the present invention includes, without limitation, full length Factor VIII such as Recombinate® (markted by Baxter), Bioclate® (marketed by Aventis), Kogenate® (marketed by Bayer), Helixate® (marketed by Aventis), or Advate® (marketed by Baxter), B-domain deleted Factor VIII such as Refacto® and Xyntha® (both marked by Genetics Institute and Wyeth), or Factor VIII and von Willebrand Factor complex such as Alphanate® (marketed by Grifols Biologicals, Inc.). For this purpose, an example of inducible Alphanate® expression for a bioreactor/cell therapy in response to administration of ligand is shown in FIG. 16. Use of bioreactor/cell therapy improves problems of stability and continuous infusion. See Pipe S. W., *J. Thromb. Haemost.* 3(8): 1692 (2005).

The complete nucleotide sequence of the construct shown in FIG. 16 is presented as SEQ ID NO: 18. The nucleotide coordinates for salient elements of the construct are shown in Table 15.

TABLE 15

| Label | Direction | Length | Start | End |
|---|---|---|---|---|
| 3'Reg(HSVTKpA) | reverse | 259 | 318 | 576 |
| Neo | reverse | 795 | 583 | 1377 |
| 3'Reg(SV40 early promoter) | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP-2(constitutive) | reverse | 1417 | 5446 | 6862 |
| FRP[6xGalRE:Minimal promoter] | forward | 189 | 7195 | 7383 |
| TSPQ(Hu Factor VIII) | forward | 7002 | 7597 | 14598 |
| 3'Reg(hGH PolyA) | forward | 627 | 14671 | 15297 |
| Replication Origin | reverse | 589 | 15731 | 16319 |
| AmpR | reverse | 858 | 16564 | 17421 |
| bla Promoter | reverse | 39 | 17455 | 17493 |

The vector shown in FIG. 16 is modeled according to the gene switch system shown in FIG. 2. Under this system, the CAP subunit is expressed through operable association with a first, constitutive promoter (TSP-1), and the LTF subunit of the LDTFC is expressed through operable association with a second, constitutive promoter (TSP-2). The promoter utilized for the first constitutive promoter is UbC (short) promoter, and the promoter utilized for the second constitutive promoter is UbB (short) promoter.

The coding region for the therapeutic product, Alphanate®, is operably associated with a FRP which is activated upon contact with the LDTFC in the presence of ligand.

The construct shown in FIG. 16 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for hemophilia.

The cells may be delivered to a subject systemically, for example, via intravenous infusion. Systemic and/or local administration of gene therapy cells are well known in the art. Upon delivery the cells, the LDTFC may be expressed constitutively. Ligand will be administered to the subject to be treated which will combine with the expressed LDTFC to drive expression of Alphanate® under control of the factor regulated promoter. Alphanate® expression in turn treats the symptoms of hemophilia.

Example 13

Figure 17:
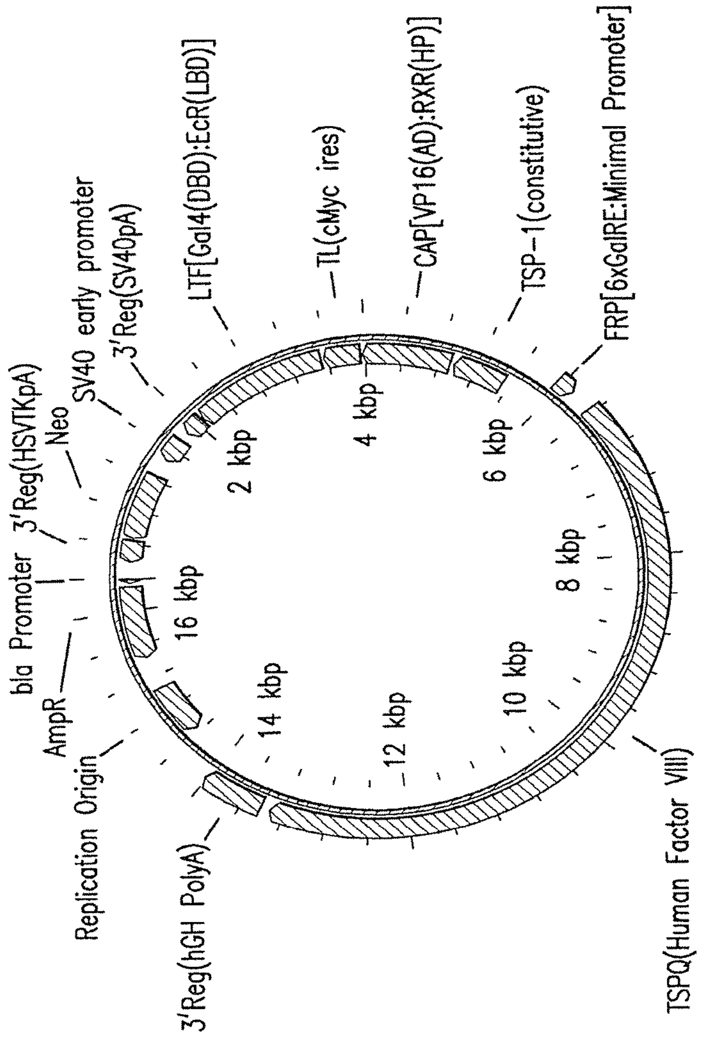
FIG. 17 is is a diagram of a vector constructed under the scheme shown in FIG. 2, and engineered to express human factor VIII:C under hypoxic conditions associated with hemophilia.

This example describes a bioreactor/cell therapy vector useful for the treatment of hemophilia. The vector shown in FIG. 17 is modeled according to the gene switch system shown in FIG. 1. Under this system, both CAP subunit, and the LTF subunit of the LDTFC are expressed through operable association with a single constitutive promoter (TSP-1) via use of an internal ribosome entry site (IRES). The constitutive promoter is UbC (short) promoter.

The coding region for the therapeutic product, ALPHANATE®, is operably associated with a FRP which is activated upon contact with the LDTFC in the presence of ligand.

The complete nucleotide sequence of the construct shown in FIG. 17 is presented as SEQ ID NO: 19. The nucleotide coordinates for salient elements of the construct are shown in Table 16.

TABLE 16

(MOD 8361)

| Label | Direction | Length | Start | End |
|---|---|---|---|---|
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[Gal4(DBD):EcR(LBD)] | reverse | 1467 | 2057 | 3523 |
| TL(cMyc ires) | reverse | 408 | 3536 | 3943 |
| CAP[VP16(AD):RxR(HP)] | reverse | 975 | 3950 | 4924 |
| TSP-1(constitutive) | reverse | 571 | 4958 | 5528 |
| FRP[6x GalRE:Minimal Promoter] | forward | 189 | 5939 | 6127 |
| TSPQ(Human Factor VIII) | forward | 7002 | 6341 | 13342 |
| 3'Reg(hGH PolyA) | forward | 627 | 13415 | 14041 |
| Replication Origin | reverse | 589 | 14475 | 15063 |
| AmpR | reverse | 858 | 15438 | 16295 |
| bla Promoter | reverse | 39 | 16329 | 16367 |

The construct shown in FIG. 17 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for hemophilia.

The cells may be delivered to a subject systemically, for example, via intravenous infusion. Systemic and/or local administration of gene therapy cells are well known in the art. Upon delivery the cells, the LDTFC may be expressed constitutively. Ligand will be administered to the subject to be treated which will combine with the expressed LDTFC to drive expression of ALPHANATE® under control of the factor regulated promoter. ALPHANATE®) expression in turn treats the symptoms of hemophilia.

Additional embodiments of the invention include the following:

E1. A method for treating, ameliorating, or preventing a disease or disorder in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce modified cells; and (b) administering ligand to said subject to induce expression of said therapeutic polypeptide or therapeutic polynucleotide;

wherein said therapeutic polypeptide or therapeutic polynucleotide is expressed at a level sufficient to treat, ameliorate, or prevent said disease or disorder.

E2. A method for expressing a therapeutic polypeptide or therapeutic polynucleotide in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce modified cells; and (b) administering ligand to said subject to induce expression of said therapeutic polypeptide or therapeutic polynucleotide.

E3. The method of E1 or E2, wherein said polynucleotides are introduced into cells that have been isolated from said subject to produce modified cells, and the modified cells are re-introduced into said subject.

E4. The method of E1 or E2, wherein said method is carried out in vivo.

E5. The method of E1 or E2, wherein said gene switch is an ecdysone receptor (EcR)-based gene switch.

E6. The method of E5, wherein said ligand binds to the EcR ligand binding domain.

E7. The method of E6, wherein said ligand is a diacylhydrazine.

E8. The method of E7, wherein said ligand is selected from the group consisting of RG-115819, RG-115932, and RG-115830.

E9. The method of E6, wherein said ligand is an amidoketone or oxadiazoline.

E10. The method of E1 or E2, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E11. The method of E10, wherein said first therapeutic switch promoter and said second therapeutic switch promoter are different.

E12. The method of E10, wherein said first therapeutic switch promoter and said second therapeutic switch promoter are the same.

E13. The method of E10, wherein said first transcription factor sequence encodes a protein comprising a heterodimer partner and a transactivation domain.

E14. The method of E10, wherein said second transcription factor sequence encodes a protein comprising a DNA-binding domain and a ligand-binding domain.

E15. The method of E1 or E2, wherein one of said polynucleotides further encodes a lethal polypeptide operably linked to an inducible promoter.

E16. A method for expressing a therapeutic polypeptide or therapeutic polynucleotide in a cell, comprising:

(a) introducing into said cell (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce a modified cell; and (b) administering ligand to said modified cell to induce expression of said therapeutic polypeptide or therapeutic polynucleotide.

E17. The method of E16, wherein said method is carried out in vitro.

E18. The method of E16, wherein said method is carried out ex vivo in a cell that has been isolated from a subject.

E19. The method of E16, wherein said method is carried out in vivo.

E20. The method of E16, wherein said gene switch is an EcR-based gene switch.

E21. The method of E20, wherein said ligand binds to the EcR ligand binding domain.

E22. The method of E21, wherein said ligand is a diacylhydrazine.

E23. The method of E22, wherein said ligand is selected from the group consisting of RG-115819, RG-115932, and RG-115830.

E24. The method of E21, wherein said ligand is an amidoketone or oxadiazoline.

E25. The method of E16, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E26. The method of E25, wherein said first therapeutic switch promoter and said second therapeutic switch promoter are different.

E27. The method of E25, wherein said first therapeutic switch promoter and said second therapeutic switch promoter are the same.

E28. The method of E25, wherein said first transcription factor sequence encodes a protein comprising a heterodimer partner and a transactivation domain.

E29. The method of E25, wherein said second transcription factor sequence encodes a protein comprising a DNA-binding domain and a ligand-binding domain.

E30. The method of E16, wherein one of said polynucleotides further encodes a lethal polypeptide operably linked to an inducible promoter.

E31. A polynucleotide encoding a gene switch, said gene switch comprising at least one transcription factor sequence, wherein said at least one transcription factor sequence encodes a ligand-dependent transcription factor, operably linked to a therapeutic switch promoter, wherein the activity of the promoter is modulated during said disease or disorder.

E32. The polynucleotide of E31, further encoding a reporter gene linked to a promoter which is activated by said ligand-dependent transcription factor.

E33. The polynucleotide of E31, wherein said gene switch is an EcR-based gene switch.

E34. The polynucleotide of E31, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E35. The polynucleotide of E34, wherein said first therapeutic switch promoter and said second therapeutic switch promoter are different.

E36. The polynucleotide of E34, wherein said first therapeutic switch promoter and said second therapeutic switch promoter are the same.

E37. The polynucleotide of E34, wherein said first transcription factor sequence encodes a protein comprising a heterodimer partner and a transactivation domain.

E38. The polynucleotide of E34, wherein said second transcription factor sequence encodes a protein comprising a DNA-binding domain and a ligand-binding domain.

E39. The polynucleotide of E31, wherein said polynucleotide further encodes a lethal polypeptide operably linked to an inducible promoter.

E40. A vector comprising the polynucleotide of E31.

E41. The vector of E40, which is a plasmid vector.

E42. The vector of E40, which is a viral vector.

E43. A kit comprising the polynucleotide of E31.

E44. A kit comprising the vector of E42.

The present invention further relates to instructions for performing one or more methods of the invention. Such instructions can instruct a user of conditions suitable for performing methods of the invention. Instructions of the invention can be in a tangible form, for example, written instructions (e.g., typed on paper), or can be in an intangible form, for example, accessible via a computer disk or over the internet.

It will be recognized that a full text of instructions for performing a method of the invention or, where the instructions are included with a kit, for using the kit, need not be provided. One example of a situation in which a kit of the invention, for example, would not contain such full length instructions is where the provided directions inform a user of the kits where to obtain instructions for practicing methods for which the kit can be used. Thus, instructions for performing methods of the invention can be obtained from internet web pages, separately sold or distributed manuals or other product literature, etc. The invention thus includes kits that direct a kit user to one or more locations where instructions not directly packaged and/or distributed with the kits can be found. Such instructions can be in any form including, but not limited to, electronic or printed forms.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A composition comprising: (1) a first polynucleotide encoding a gene switch, said gene switch comprising at least one transcription factor sequence, wherein said at least one transcription factor sequence encodes a ligand-dependent transcription factor in operable association with a hypoxia-inducible promoter, wherein the hypoxia-inducible promoter is a nucleic acid sequence at least 95% identical to the sequence from nucleotide 5446 to nucleotide 6315 of SEQ ID NO: 8, and (2) a second polynucleotide encoding a therapeutic polypeptide or therapeutic polynucleotide operably associated with a transcription factor-regulated promoter which is activated by said ligand-dependent transcription factor, wherein a ligand is capable of inducing expression of said therapeutic polypeptide or therapeutic polynucleotide.

2. The composition of claim 1, wherein said first and second polynucleotides are part of one larger polynucleotide.

3. The composition of claim 1, wherein the ligand capable of inducing expression of said therapeutic polypeptide or therapeutic polynucleotide is a diacylhydrazine.

4. The composition of claim 1, wherein the ligand capable of inducing expression of said therapeutic polypeptide or therapeutic polynucleotide is selected from the group consisting of RG-115819, RG-115932, and RG-115830.

* * * * *